United States Patent
Marquess et al.

(10) Patent No.: US 6,420,354 B1
(45) Date of Patent: Jul. 16, 2002

(54) SODIUM CHANNEL DRUGS AND USES

(75) Inventors: Daniel Marquess, Half Moon Bay; Seok-Ki Choi, Palo Alto; David T. Beattie, Belmont; John H. Griffin, Atherton; Scott Armstrong, San Francisco; Timothy J. Church, San Mateo; Thomas E. Jenkins, La Honda, all of CA (US)

(73) Assignee: Advanced Medicine, Inc., South San Francisco, CA (US)

( * ) Notice: Subject to any disclaimer, the term of this patent is extended or adjusted under 35 U.S.C. 154(b) by 0 days.

(21) Appl. No.: 09/458,107

(22) Filed: Dec. 8, 1999

Related U.S. Application Data

(63) Continuation-in-part of application No. 09/325,563, filed on Jun. 4, 1999, now abandoned.
(60) Provisional application No. 60/093,068, filed on Jul. 16, 1998, and provisional application No. 60/088,465, filed on Jun. 8, 1998.

(51) Int. Cl.$^7$ ............ C07D 245/02; C07D 211/70; C07D 333/12; A61K 31/33; A61K 31/44
(52) U.S. Cl. ............ 514/183; 514/357; 514/438; 514/651; 540/470; 546/334; 549/75; 564/353
(58) Field of Search ............ 514/183, 357, 514/438, 651; 540/470; 546/334; 549/75; 564/353

(56) References Cited

U.S. PATENT DOCUMENTS

| | | | |
|---|---|---|---|
| 3,845,770 A | 11/1974 | Theeuwes et al. | 128/260 |
| 4,326,525 A | 4/1982 | Swanson et al. | 128/260 |
| 4,902,514 A | 2/1990 | Barclay et al. | 424/473 |
| 4,992,445 A | 2/1991 | Lawter et al. | 514/279 |
| 5,001,139 A | 3/1991 | Lawter et al. | 514/344 |
| 5,011,472 A | 4/1991 | Aebischer et al. | 604/50 |
| 5,023,252 A | 6/1991 | Hseih | 514/183 |
| 5,571,827 A | 11/1996 | Barberich, et al. | 514/356 |
| 5,616,345 A | 4/1997 | Geoghegan et al. | 424/497 |
| 5,686,495 A | 11/1997 | Goldin et al. | 514/632 |
| 5,688,830 A | 11/1997 | Berger et al. | 514/651 |
| 5,738,996 A | 4/1998 | Hodges et al. | 435/7.1 |
| 5,846,839 A | 12/1998 | Gallop et al. | 436/518 |
| 5,891,643 A | 4/1999 | Fesik et al. | 435/7.1 |
| 5,985,933 A | * 11/1999 | Zeitlin | 514/651 |

FOREIGN PATENT DOCUMENTS

| | | |
|---|---|---|
| CA | 2240325 | 6/1998 |
| DE | 23 00 543 | 7/1974 |
| DE | 4240981 | 6/1994 |
| EP | 372934 A2 | 6/1990 |
| EP | 372934 B1 | 6/1990 |
| EP | 0459829 A1 | 12/1991 |
| EP | 0869119 A1 | 11/1998 |
| WO | WO 93/04048 * | 3/1993 |
| WO | WO 93/06121 | 4/1993 |
| WO | WO 96/20934 | 7/1996 |
| WO | WO 96/20935 | 7/1996 |
| WO | WO 97/09317 | 3/1997 |
| WO | WO 97/27169 | 7/1997 |
| WO | WO 98/38174 | 9/1998 |

OTHER PUBLICATIONS

Doig, M.V., et al. "The Use of Thermospray Liquid Chromatography–Mass Spectrometry to Aid in the Indentification of Urinary Metabolites of a Novel Antiepileptic Drug Lamotrigine." *J. Chrom.* (Elsevier Science Publishers, B.B. Amsterdam) 554(1/02): 181–189 (1991).

Bernatowics, et al. "Urethan Protected Derivatives of 1–Guanylpyrazole for the Mild and Efficient Preparation of Guanidines." *Tetrahedron Letters*. 34(21):3389–3392 (1993).

Bossert, et al. "4–Aryldihydropyridines, a New Class of Highly Active Calcium Antagonists." *Angew, Chem. Int. Ed.* 20:762–769 (1981).

Brenner, et al. "Encoded Combinatorial Chemistry." *Proc. Nat'l Acad. Sci., USA*. 89:5381–5383 (1992).

Choi et al. "Glutamate Neurotoxicity in Cortical Cell Culture." *J. Neurosci*. 7(2):357–68 (1987).

Choi et al. "Ionic Dependence of Glutamate Neurotoxicity." *J. Neurosci*. 7(2): 369–79 (1987).

Cole, et al. "Discovery of Chiral Catalysts through Ligand Diversity: Ti–Catalyzed Enantioselective Addition of TMSCN to meso Epoxides." *Angew. Chem. Int'l. Ed. Engl.* 35(15): 1668–1671 (1996).

Costall, B., et al. "Actions of Sulpiride and Tiapride in a Simple Model of Anxiety in Mice." *Neuropharmacol.* 26:195 (1987).

Dalby, N., et al. "Comparison of the preclinical anticonvulsant profiles of tioagabine, lamotrigine, gabapentin and vigabatrin" *Epilepsy Research*. 28:63 (1997).

Davis, et al. "Drug leads from Combinatorieal Phosphodiester Libraries." *J. Med. Chem*. 38(22) (4363–4366 (1995).

Denyer, et al. "HTS Approaches to Voltage–Gated Ion Channel Drug Discovery." *Drug Discovery Today*. 3(7): 323–332 (1998).

Doggrell, et al. Ion Channel Modulators as Potential Positive Ionotropic Compounds for Treatment of Heart Failure.: Clinical and Experimental Pharmacology and Physiology, 21: 833–843 (1994).

DubuissonD., et al. "The Formalin Test: A Quantitative Study of the Analgesic Effects of Morphine, Meperidine, and Brain Stem Stimulation in Rats and Cats." *Pain*. 4:161 (1977).

(List continued on next page.)

Primary Examiner—Mukund J. Shah
Assistant Examiner—Deepak Rao
(74) Attorney, Agent, or Firm—David E. Boone; Jeffrey A. Hagenah; Roberta P. Saxon

(57) ABSTRACT

The compounds of this invention comprise 2–10 ligands covalently connected, each of the ligands being capable of binding to a ligand binding site in a Na$^+$ channel, thereby modulating the biological activities thereof.

13 Claims, 25 Drawing Sheets

OTHER PUBLICATIONS

Gee, et al. "Cyclic Peptides as Non–carboxyl–terminal Ligands of Syntrophin PDZ Domains." *J. Biol. Chem.* 273(34): 21980–21987 (1994).

Heuttner, JE., et al. "Primary Culture of Identified Neurons from the Visual Cortex of Postnatal Rats." *J. Neurosci.* 6:3044 (1986).

Hunter, J.C., et al. "The effect of novel anti–epileptic drugs in rat experimental models of acute and chronic pain." *Eur. J. Pharmacol.* 324(153) (1997).

HunterJ.C., et al. "Voltage–Gated Sodium Channel Blockers for the Treatment of Chronic Pain." *Current Opinion in CPNS Investigational Drugs.* 1(1): 72–81 (1999).

Kuo, et al. "A Common Anticonvulsant Binding site for Phenyltoin, Carbamazepire and Lamiotrigine in Neuronal NA+Channels." *Mol. Pharmacology.* 54: 712–721 (1998).

Kuo, et al. "Characterization of lamotrigine inhibition of $Na^+$ channel in rat hippocampal neurones." *Br. J. Pharm.* 121: 1231–1238 (1997).

Liang, et al. "Parallel Synthesis and Screening of a Solid Phase Carbohydrate Library." *Science.* 274: 1520–1522 (1996).

Loughhead, et al. "Synthesis of Mexiletine Steroisomers and Related Compounds via $S_N$Ar Neucleophilic Substitution of $Cr(CO)_8$–Complexed Aromatic Fluoride." *J. Org. Chem.* 64:3373–3375 (1999).

Melchiorre, C., et al. "Polymethylene tetramines as Muscarinic Receptor Probes." *Trends Pharmacol. Sci.* 10(Suppl)::55–59 (1989).

Menger, et al. "Phosphatase Catalysis developed via Combinatorial Organic Chemistry." *J. Org. Chem.* 60: 6666–6667 (1995).

O'Neill, M.J. et al. "Effects of $Ca^{2+}$ and $Na^+$channel inhibitors in vitro and in global cerebral ischaemia in vivo." *Eur. J. Pharmacol.* 332:121 (1997).

Portughese, Philip S. "The Role of Concepts in STructure—Activity Relationship Studies of Opioid Ligands." *J. Med. Chem.* 35(11): 1927–1937 (1992).

Shepheard, SL, et al. "Comparison of the Effects of Sumatriptan and the $NK_1$ Antagonist CP–99,994 on Plasma Extravasation in Dura Mater and c–fos mRNA Expression in Trigeminal Nucleus Caudalis of Rats." *Neuropharmacology.*, 34(3): 255 (19995).

Shuker, et al. "Discovering High Affinity Ligands for Proteins: SAR by NMR." *Science.* 274, 1531–1534 (1996).

Southam, E., et al. "Lamotrigine inhibits monoamine uptake in vitro and modulates 5–hydroxytypatamine uptake in rats." *Eur. J. Pharmacol.* 358:19 (1998).

Ther. L., et al. "Zue pharmakodynamischen Wirkiiung der optischen isomeren des methadons." *Dtsh Apoth Zig*, 103:514 (1963). (Summary in English).

Whalley, et al., "Basic Concepts in Cellular Cardiac Electrophysiology: Part II: Block of Ion Channels by Antiarrhythmic Drugs." *PACE*, 18(Part I): 1686–1704 (1995).

* cited by examiner

FIG. 3A
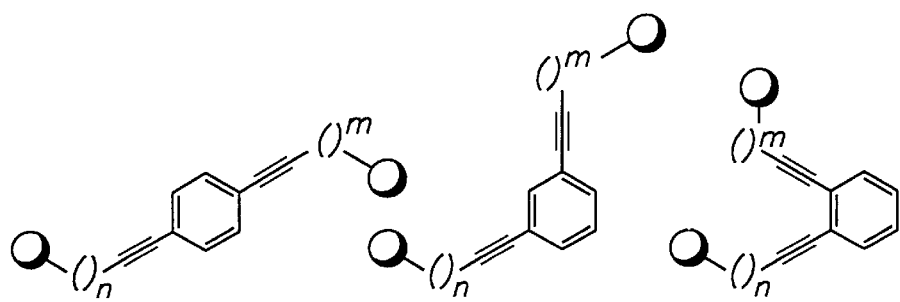
◯ = ligand
n+m+core<100 atoms
FIG. 3B
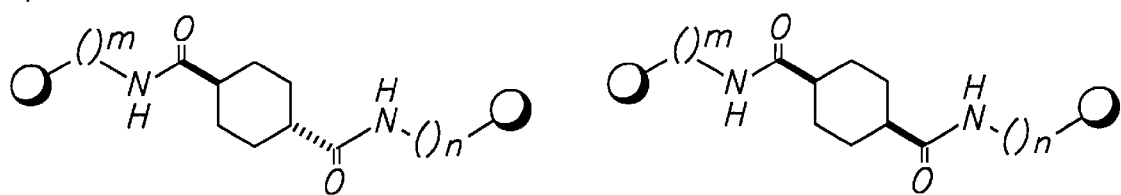
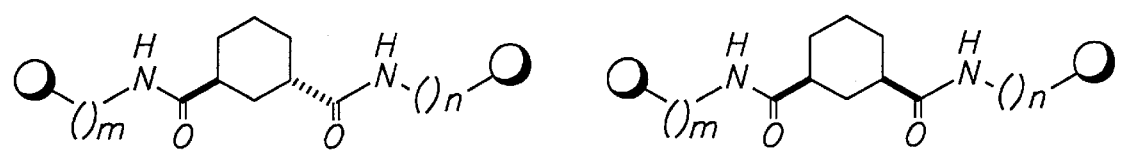
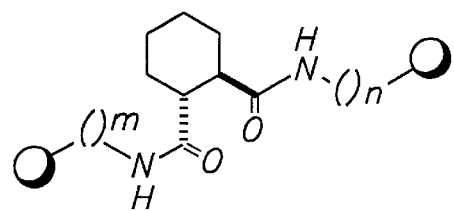

*Scheme A*
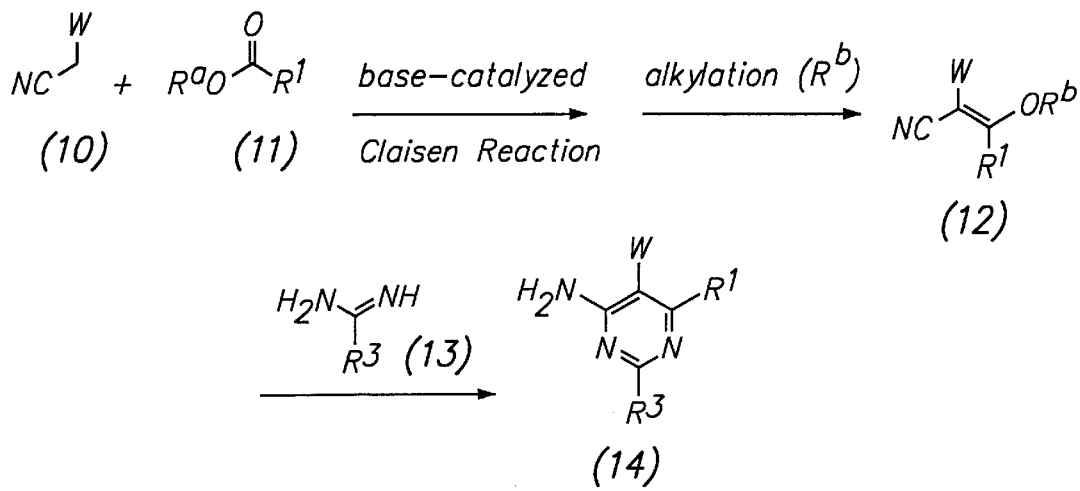
*Scheme B*
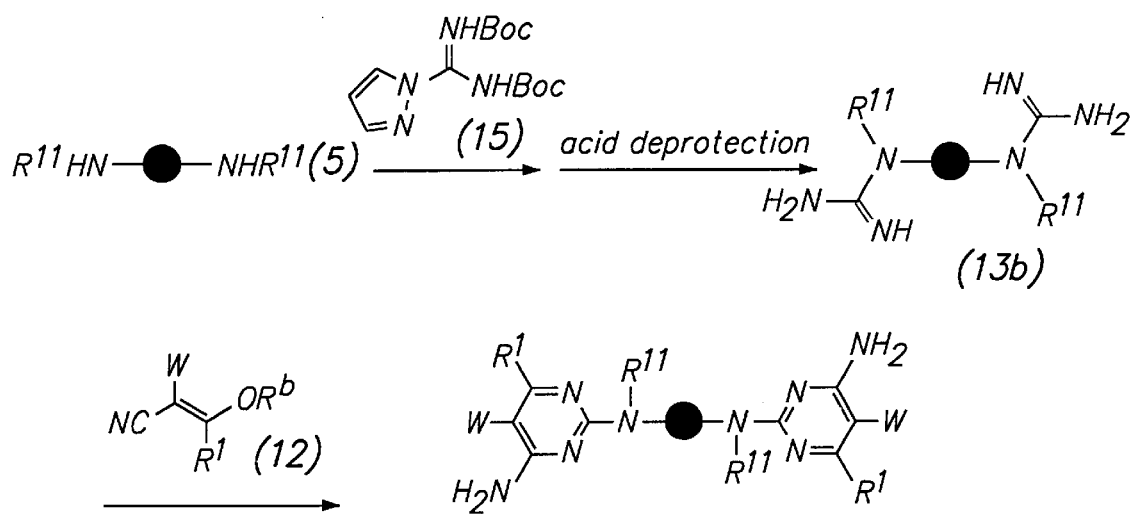
Formula 1
*Example 1*
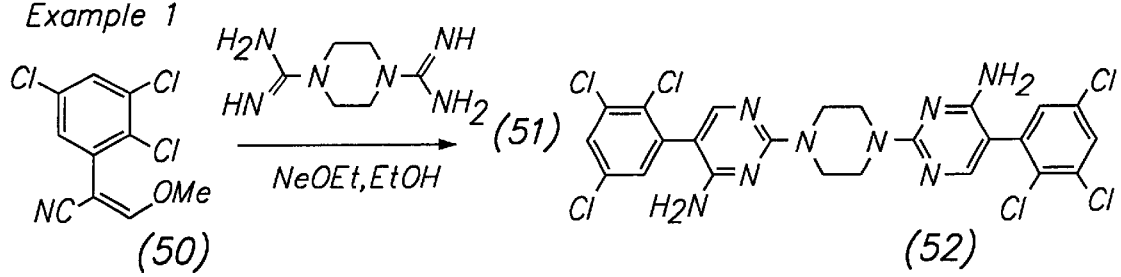
FIG. 8A

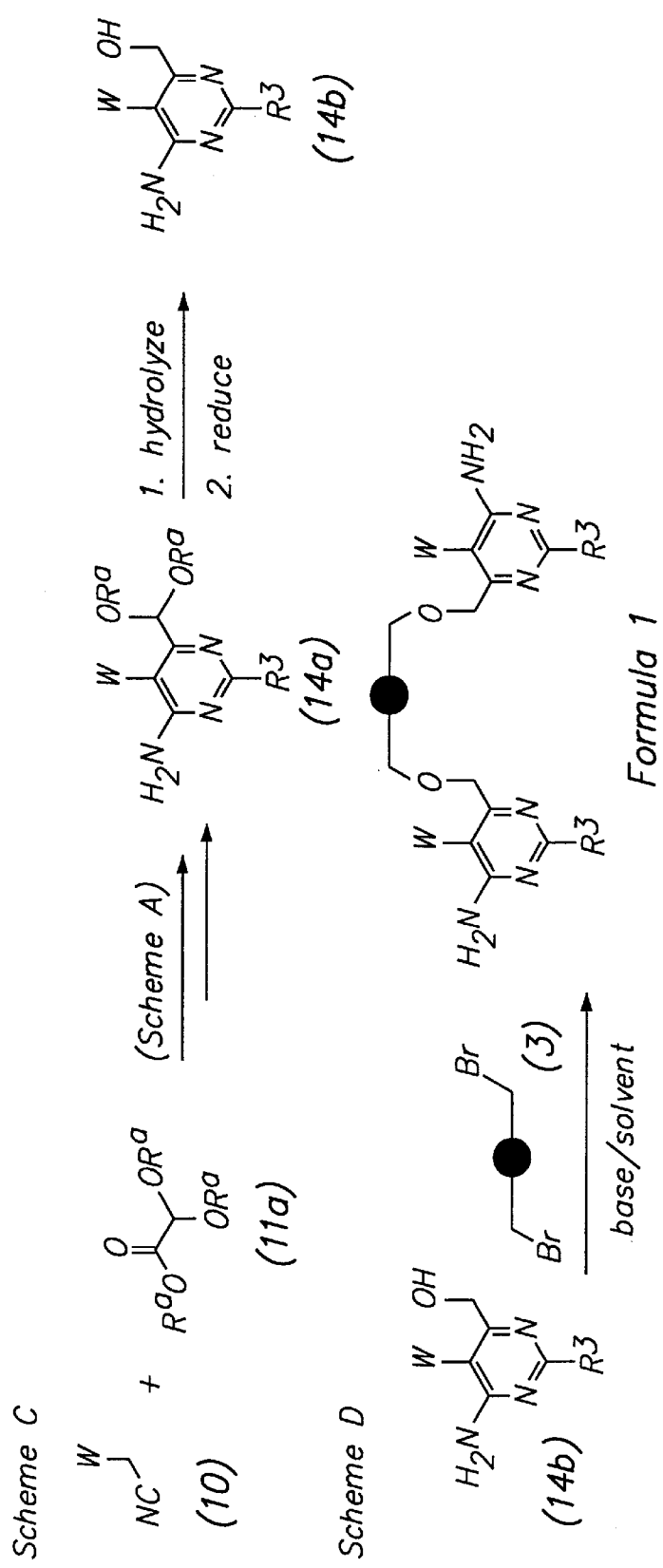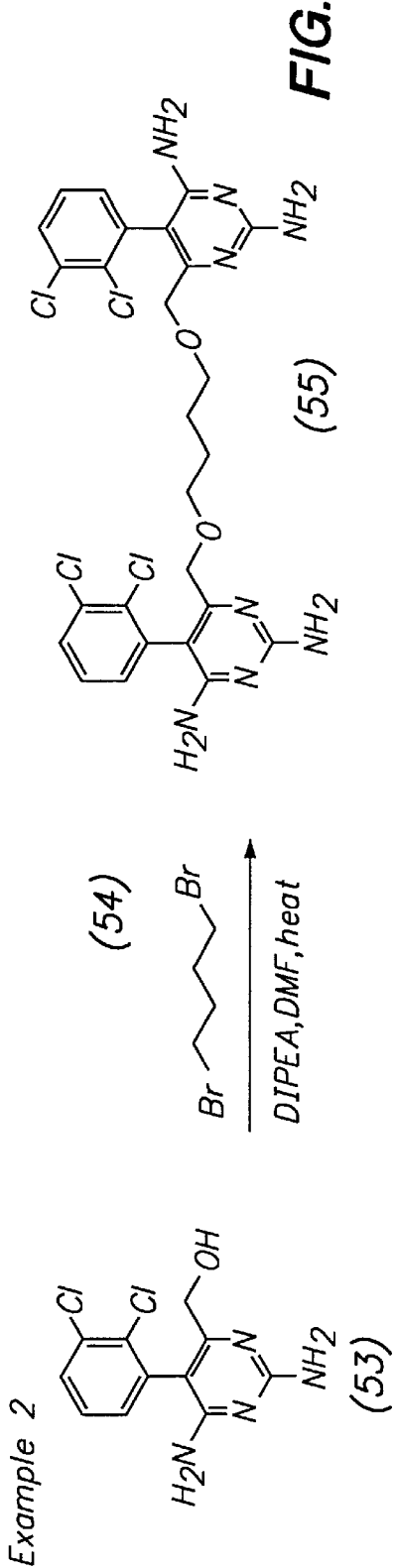
FIG. 8B

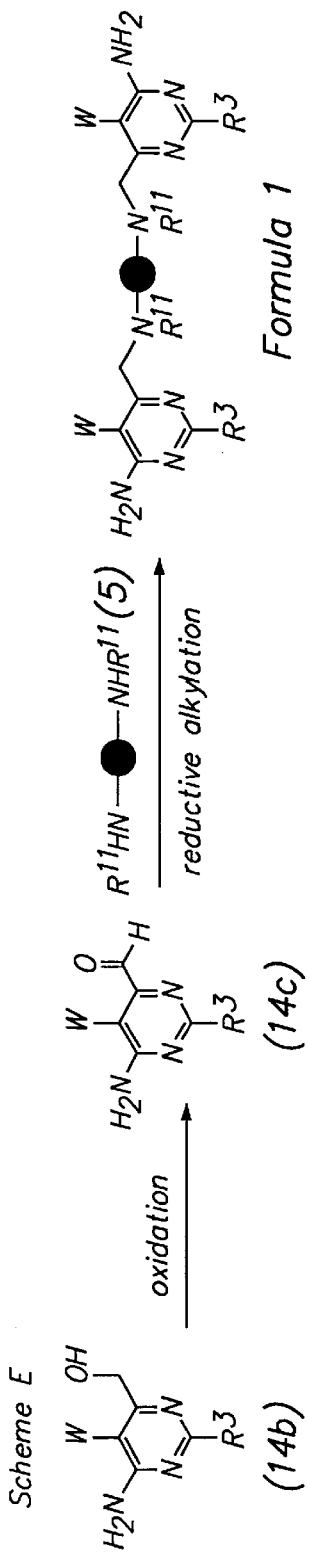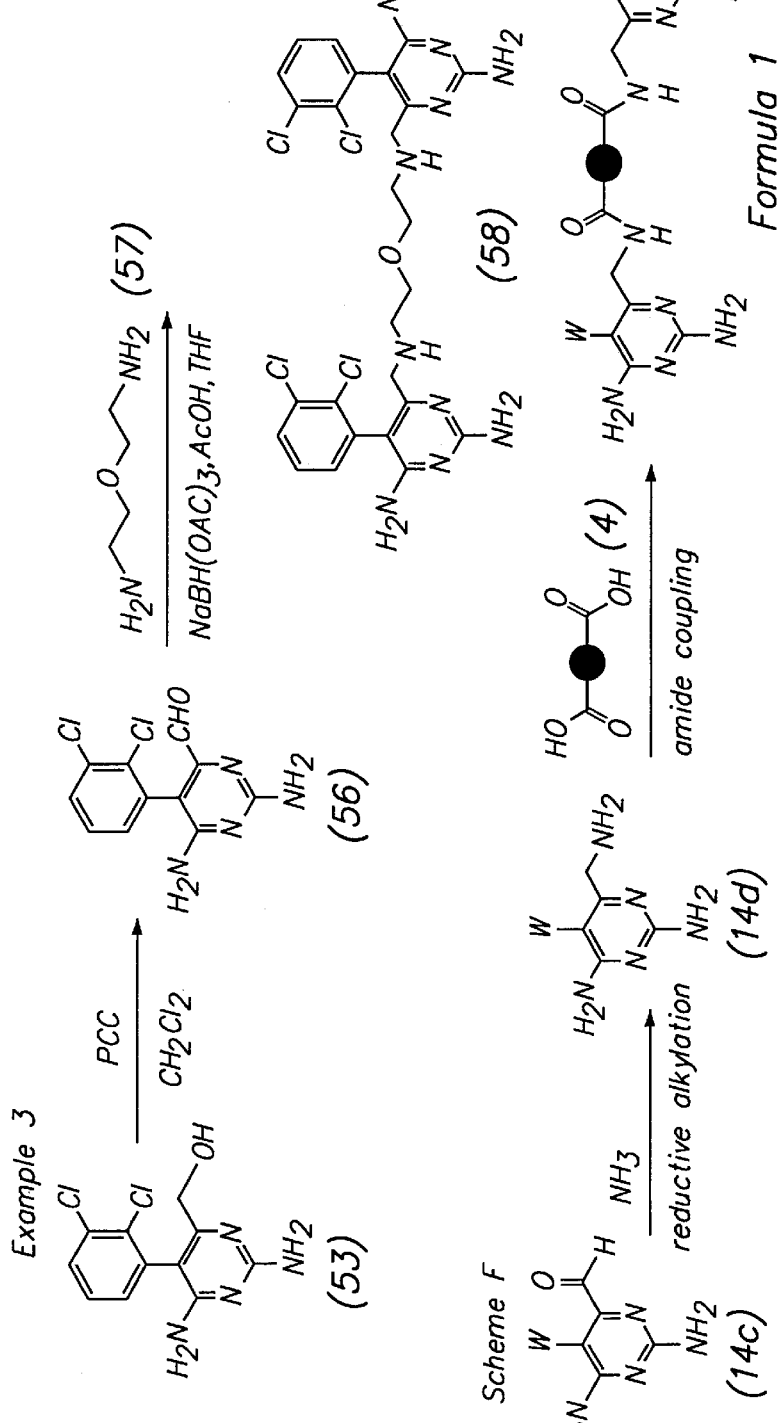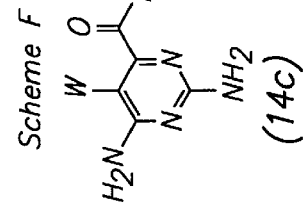
FIG. 8C

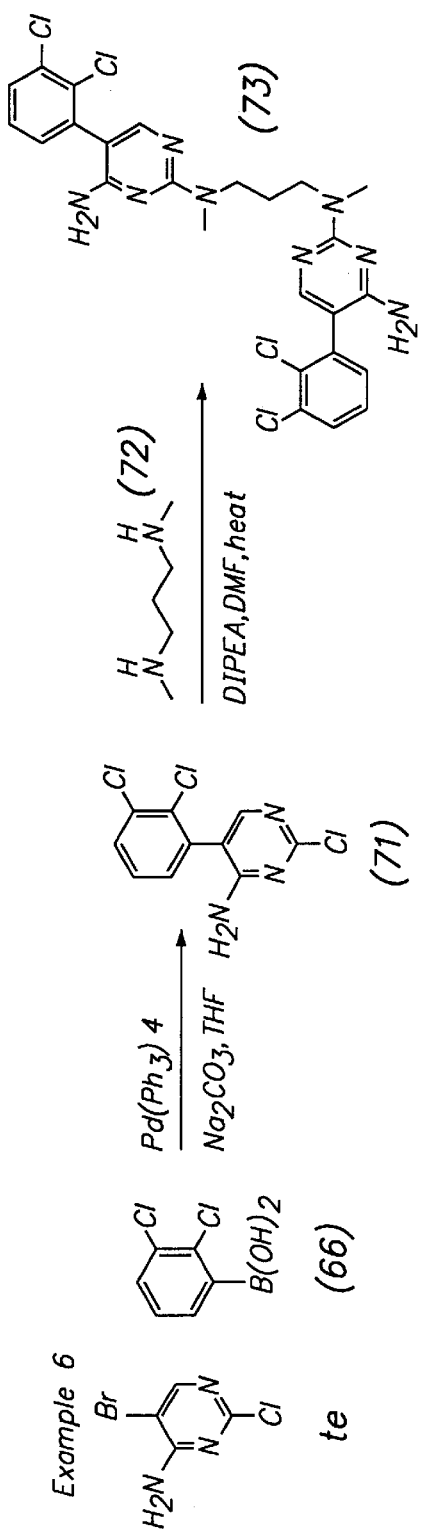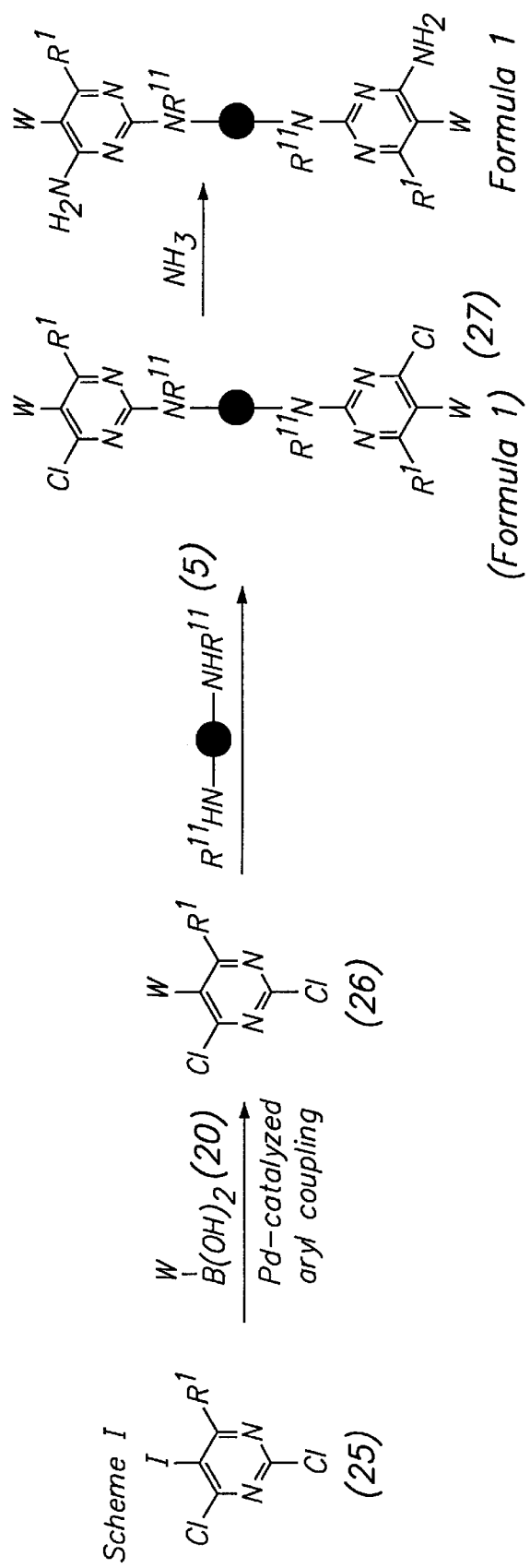
FIG. 8F

Scheme L
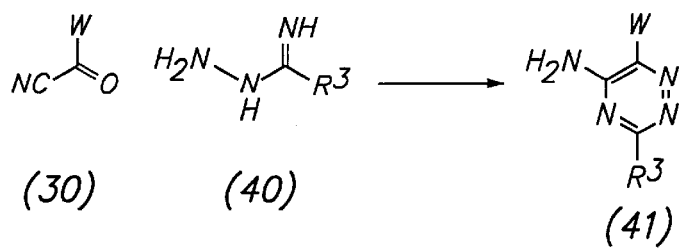
Scheme M
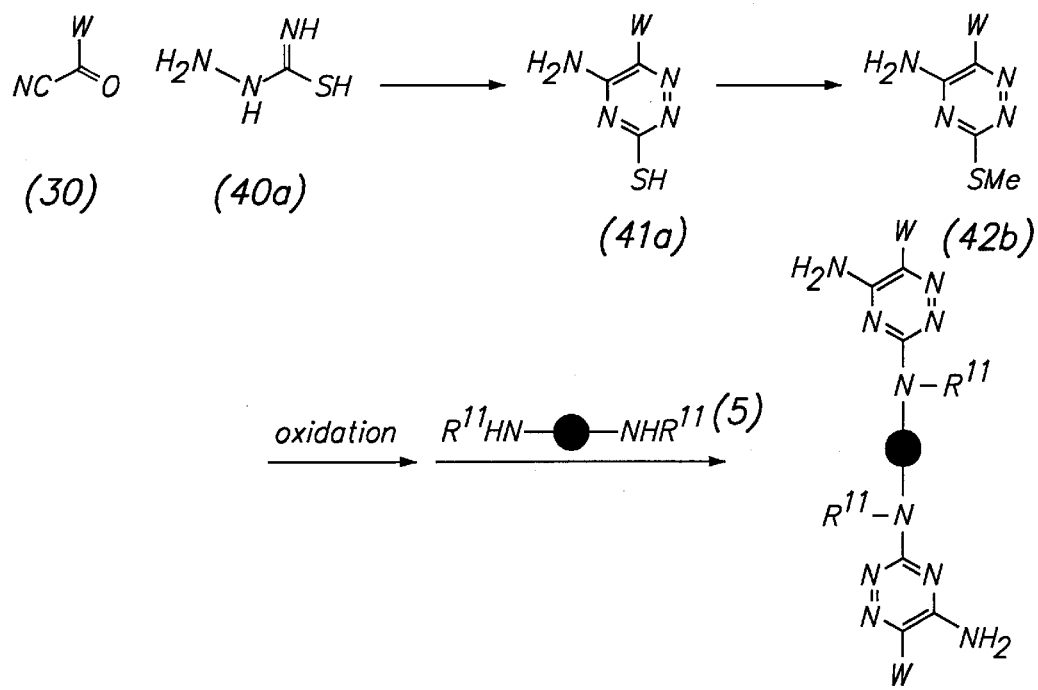
FIG. 8I
Formula 1
Example 10
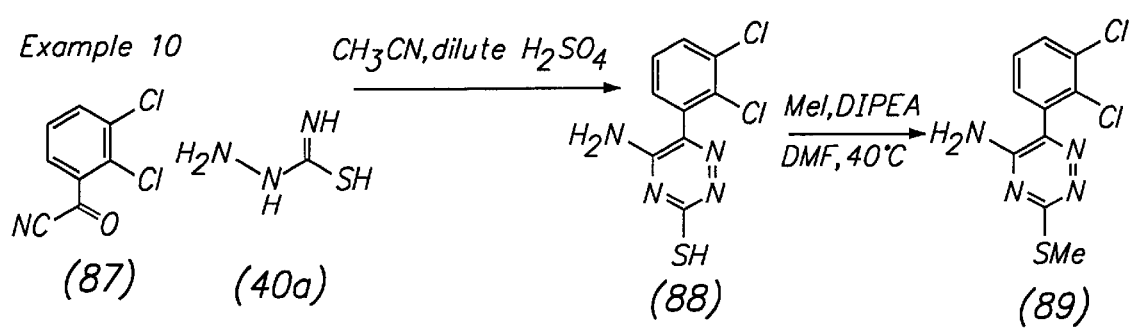
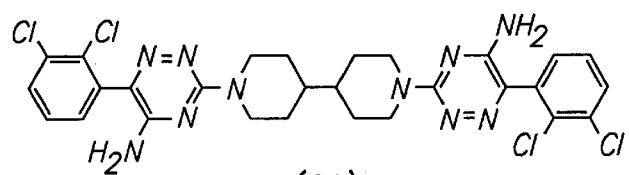

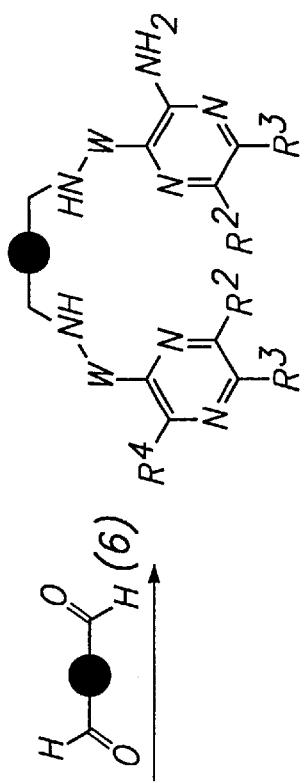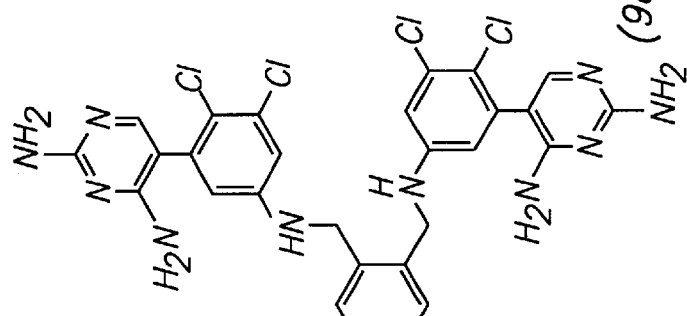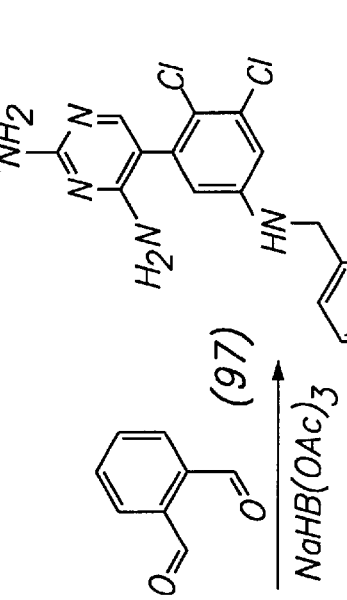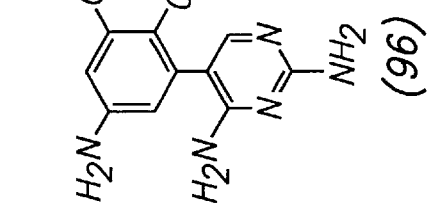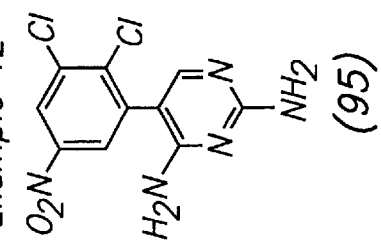
FIG. 8K

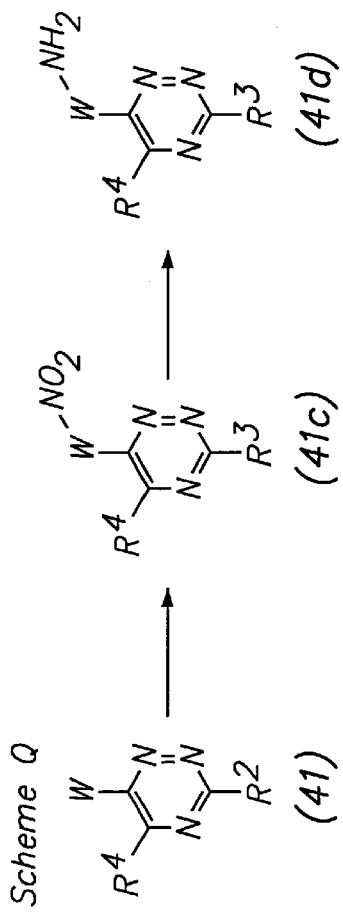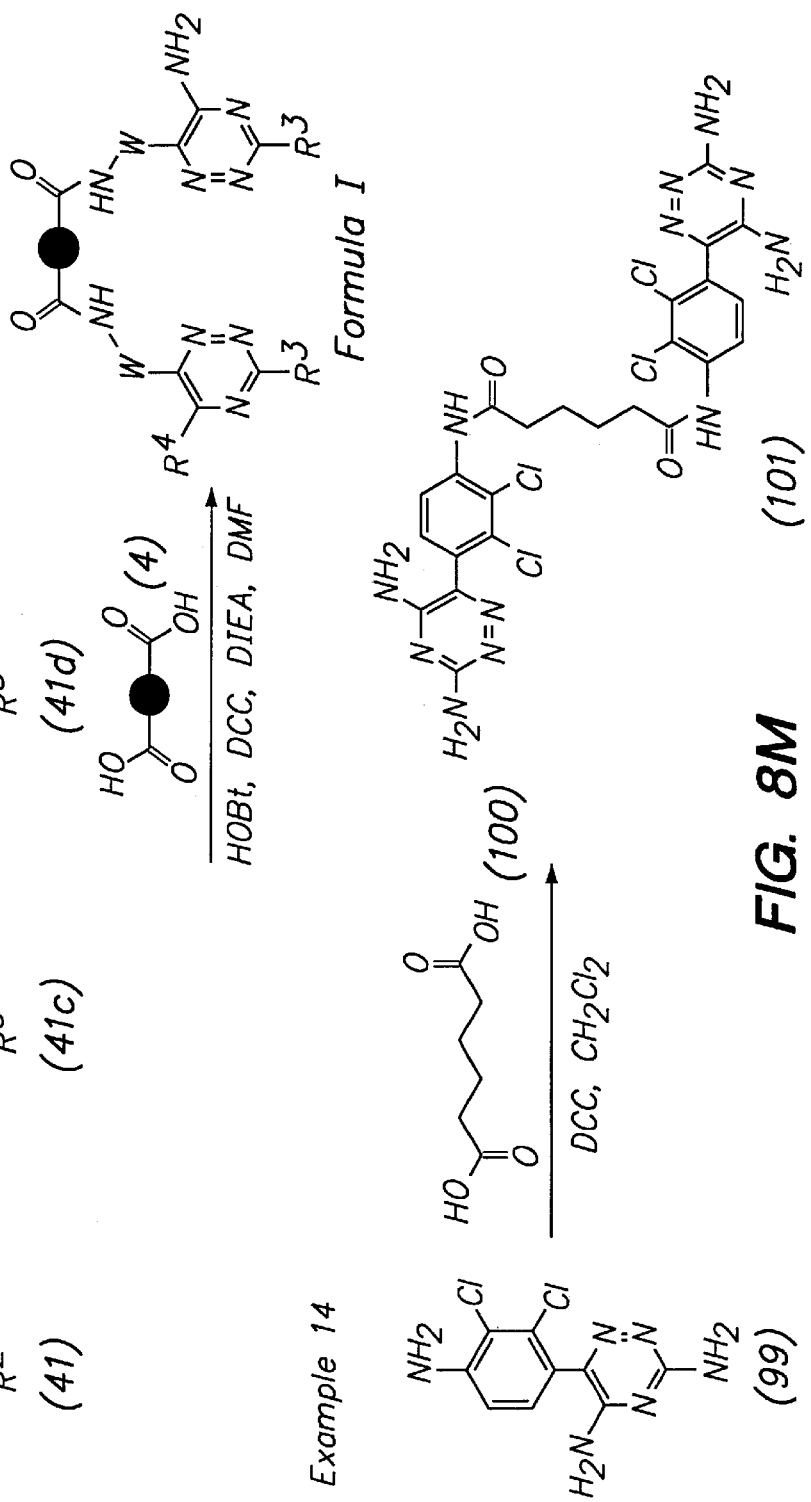
FIG. 8M

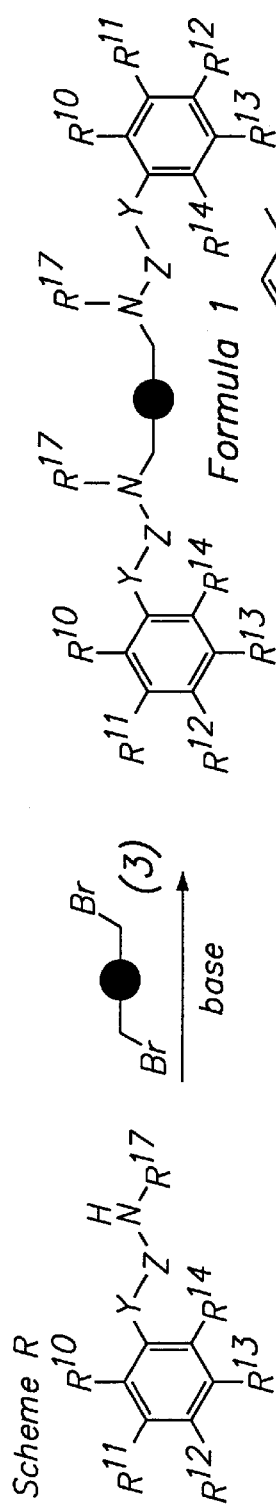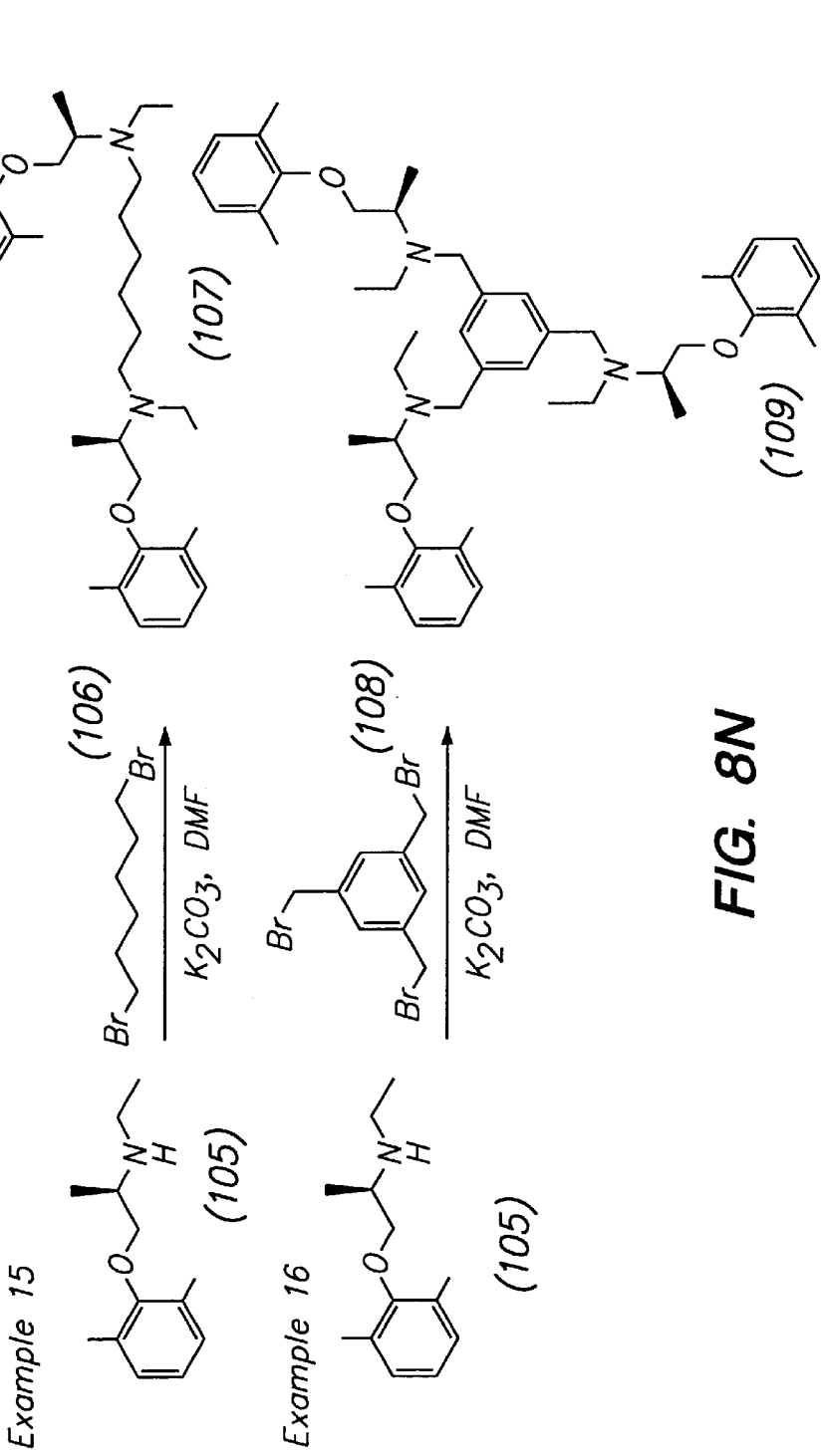
FIG. 8N

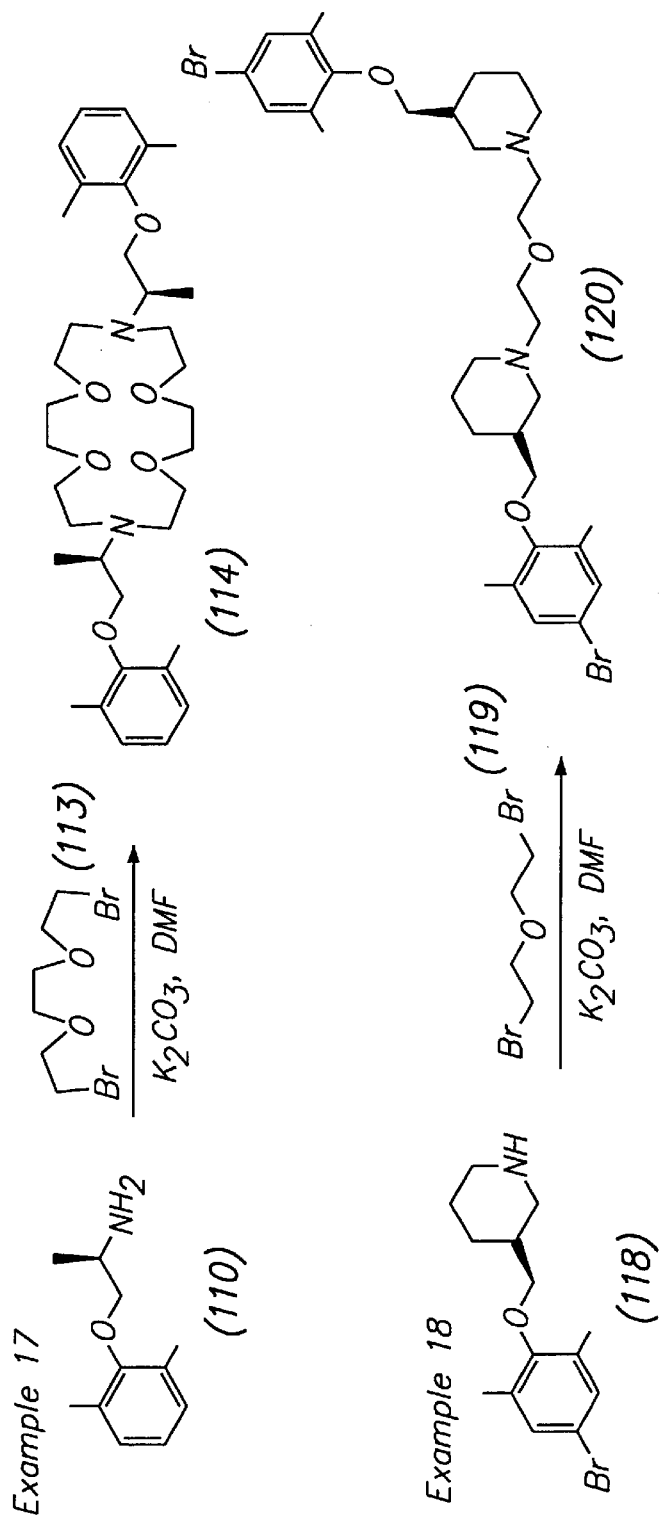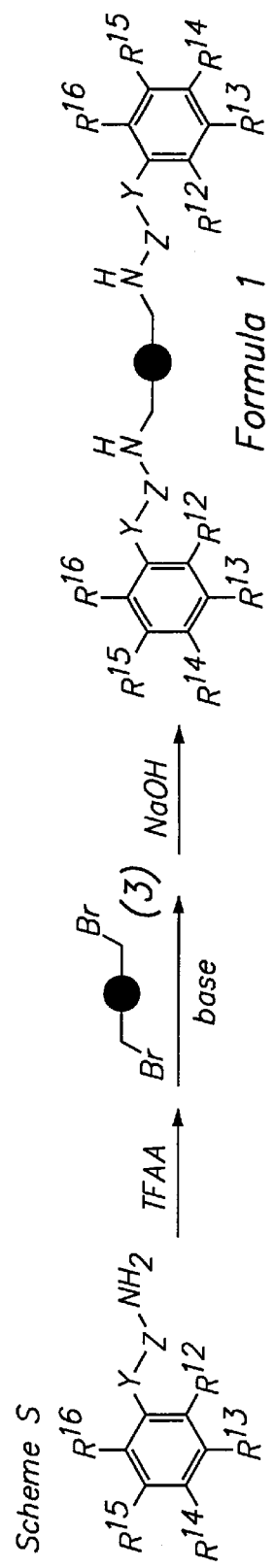
FIG. 80

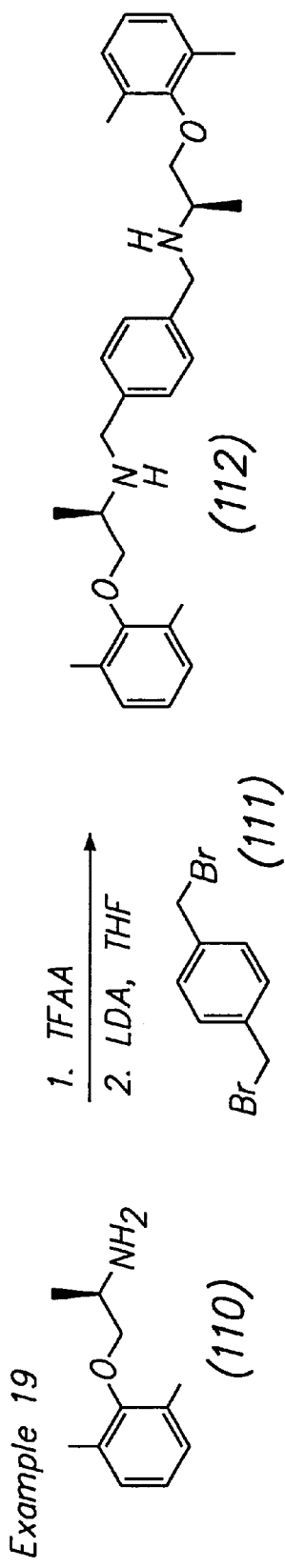
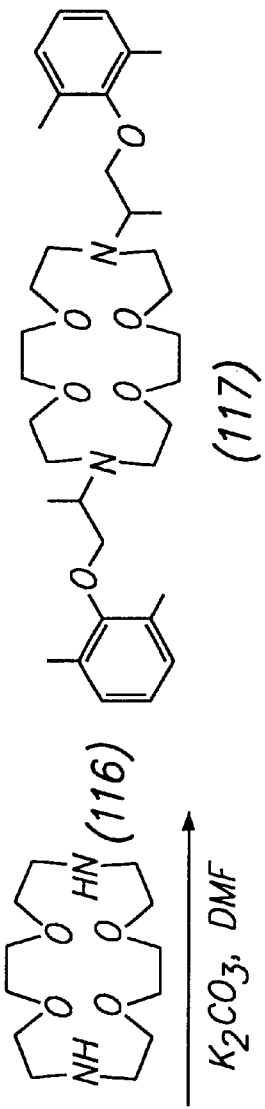
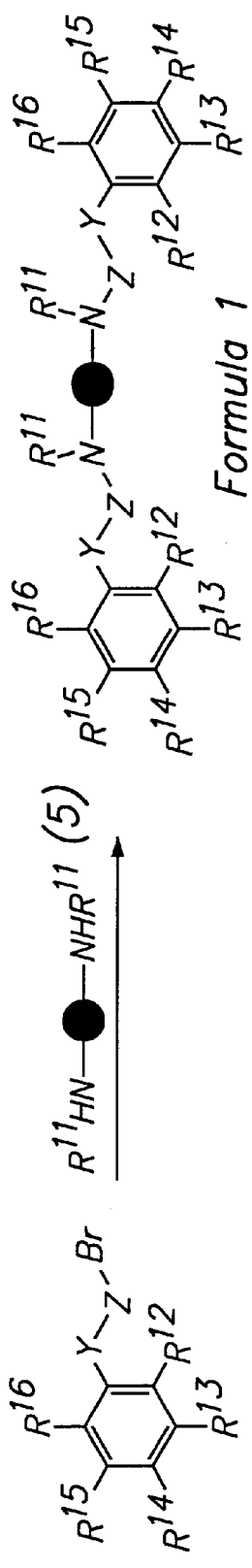
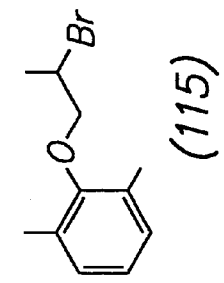
FIG. 8P

FIG. 8Q
Example 21
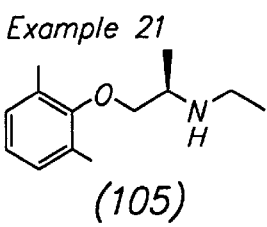 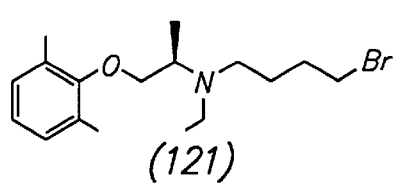
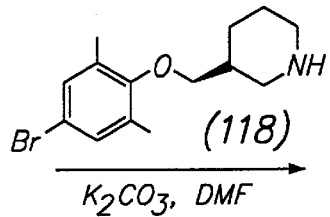 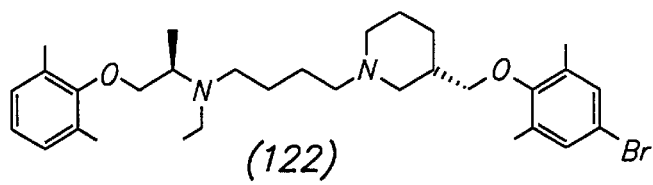
Example 22
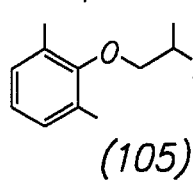 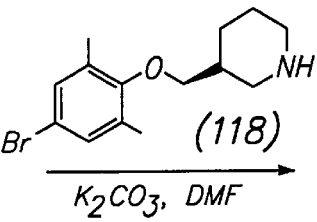 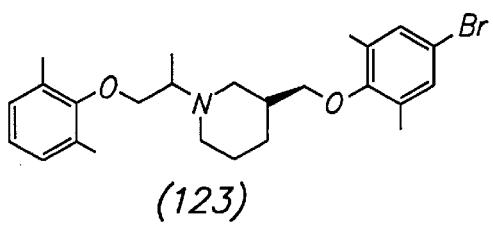
Example 23
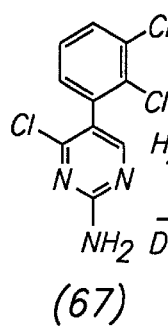 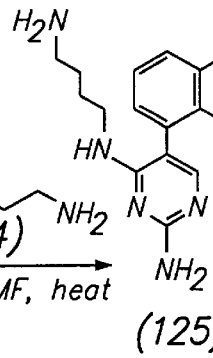 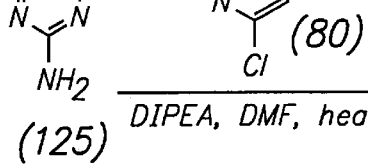 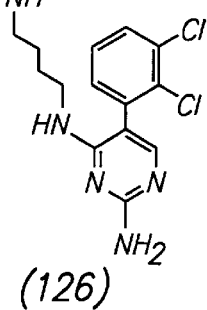
Example 24
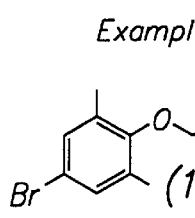 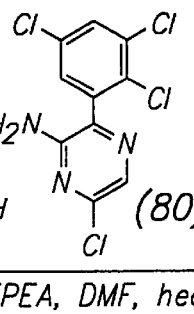 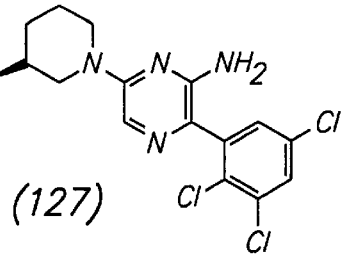

SODIUM CHANNEL DRUGS AND USES

This is a continuation-in-part application of application U.S. Ser. No. 09/325,563, filed Jun. 4, 1999 and now abandoned, which claims the benefit of U.S. Provisional Application No. 60/088,465 filed Jun. 8, 1998 and No. 60/093,068 filed Jul. 16, 1998, the entire contents of which are incorporated herein by reference.

BACKGROUND

1. Field of the Invention

This invention relates to novel multibinding compounds that bind to sodium ($Na^+$) channels and modulate their activity. The compounds of this invention comprise 2–10 $Na^+$ channel ligands covalently connected by a linker or linkers, wherein the ligands in their monovalent (i.e., unlinked) state bind to and are capable of modulating the activity of one or more types of $Na^+$ channel. The manner of linking the ligands together is such that the multibinding agents thus formed demonstrate an increased biologic and/or therapeutic effect as compared to the same number of unlinked ligands made available for binding to the $Na^+$ channel. The invention also relates to methods of using such compounds and to methods of preparing them.

The compounds of this invention are particularly useful for treating diseases and conditions of mammals that are mediated by $Na^+$ channels. Accordingly, this invention also relates to pharmaceutical compositions comprising a pharmaceutically acceptable excipient and an effective amount of a compound of this invention.

2. State of the Art

Voltage-gated ion channels play a critical role in shaping the electrical activity of neuronal and muscle cells, and in controlling the secretion of neurotransmitters and hormones through the gating of calcium ion entry. Large families of voltage-gated sodium ($Na^+$), potassium ($K^+$) and calcium ($Ca^{2+}$) ion channels have been defined using electrophysiological, pharmacological and molecular techniques; they are named according to their selective permeability for a particular cation with reference to their voltage dependence, kinetic behavior or molecular identity.

Although the structures of $Na^+$, $K^+$ and $Ca^{2+}$ channels are quite different, there are common functional elements represented in each. The channels are all transmembrane proteins with an ion-selective aqueous pore that, when open, extends across the membrane. Channel opening and closing (gating) is controlled by a voltage-sensitive region of the protein containing charged amino acids that move within the electric field. The movement of these charged groups leads to conformational changes in the structure of the channel resulting in conducting (open/activated) or nonconducting (closed/inactivated) states.

Voltage-gated $Na^+$ channels mediate regenerative inward currents that are responsible for the initial depolarization of action potentials in brain neurons. $Na^+$ channels are large glycoproteins that consist of various subunits, the principal one being the alpha ($\alpha$) subunit. $Na^+$ channels exist as dimers in cardiac and skeletal muscles and exist as heterotrimers in neuronal cells. FIG. 1A shows that the $\alpha$ subunit has a modular architecture; it consists of four internally homologous domains (labeled I–IV), each of which contains six transmembrane segments. Prominant phosphorylation sites of the $\alpha$ subunit are also shown. The four domains fold together so as to create a central pore whose structural constituents determine the selectivity and conductance properties of the channel as shown in FIG. 1B. Auxiliary beta ($\beta$) subunits are important modulators of $Na^+$ channel function. Biochemical studies reveal the existence of two distinct $\beta$ subunits ($\beta1$ and $\beta2$) associated with the brain $Na^+$ channel. It should be understood that, for purposes of simplification, other subunits that may be involved in or required for transporter activity have been omitted from the diagrams.

$Na^+$ channels can exist in multiple ion conducting (open) and nonconducting (closed/inactivated) conformations. FIG. 2A illustrates how $Na^+$ channels open and then rapidly inactivate following voltage stimulation. Transitions between these states occurs in a voltage and time-dependent manner. The time course and voltage dependency of $Na^+$-channel activity can be described by separate activation and inactivation gating processes. Activation takes place upon depolarization of the membrane ($\Delta V_m$) and the channel adopts an open pore conformation allowing $Na^+$ influx. Inactivation processes then change the channel conformation to a nonconducting, non-activatable state. Repolarization returns the channels from inactivated to resting conformations. FIG. 2B illustrates how $Na^+$ channel opening may be prolonged by toxin binding. Toxins such as veratridine and batrachotoxin are activators that can bind to channels in the open conformation and stabilize the channel in a modified conducting state. This in effect removes or slows down the inactivation process allowing ion flux to continue from minutes to hours. Conversely, toxins such as tetrodotoxin (TTX) are blockers that can bind to the channel in the inactivated conformations. One method of distinguishing different $Na^+$ channels is whether they are TTX-sensitive or TTX-resistant. (See, for example, Denyer, et al., "HTS Approaches to Voltage-Gated Ion Channel Drug Discovery", *DDT*, 3, No. 7, 323–332 (1998); Whalley, et al. "Basic Concepts in Cellular Cardiac Electrophysiology: Part II: Block of Ion Channels by Antiarrhythmic Drugs", *PACE*, 18, Part I, 1686–1704 (1995); Goodman & Gilban's "The Pharmacological Basis of Therapeutics" McGraw-Hill, Ninth Ed. Ch. 35, 851–856; and Doggrell, et al., "Ion channel Modulators as Potential Positive Inotropic Compounds for Treatment of Heart Failure", *Clinical and Experimental Pharmacology and Physiology*, 21833–843, 1994.)

Sodium channel blockers/modulators are employed to alleviate various disease conditions including, but not limited to, epilepsy, pain, anaesthesia, neuroprotection, arrhythmia, and migraine. (See, for example, PCT Publication WO 96/20935, European Patent Application EP 0869119, PCT Publication WO 97/27169, U.S. Pat. No. 5,688,830, Hunter & Loughhead "Voltage-Gated Sodium Channel Blockers for the Treatment of Chronic Pain", *Current Opinion in CPNS investigational Drugs*, 1999, vol. 1, no. 1, 72–81 and Loughhead et al., "Synthesis of Mexiletine Stereoisomers and Related Compounds via $S_NAr$ Nucleophilic Substitution of a $Cr(CO)_8$-Complexed Aromatic Fluoride" *J. Org. Chem.* 1999, 64, 3373–3375.) Antiepileptic agents, include, for example, phenytoin, carbamazepine, and lamotrigine. Phenytoin is the prototypic antiepileptic sodium channel blocker and is efficacious in treating partial and generalized tonic-clonic seizures in humans. One important property of phenytoin is that it is capable of preventing seizures without producing sedation. Thus, phenytoin was the first antiepileptic to approach the therapeutic ideal of inhibiting abnormal brain activity characteristic of seizures without appreciably interfering with normal brain activity.

Carbamazepine, an iminostilbene derivative of tricyclic antidepressants, exhibits a spectrum of anticonvulsant activity very similar to that of phenytoin. In humans, it is effective against partial and generalized tonic-clonic seizures, but not against absence seizures. Lamotrigine has been used for treating partial and generalized tonic-clonic seizure.

Topiramate is a sulfamate-substituted monosaccharide, with a phenytoin-like profile in the maximal electroshock and pentylenetetrazol tests. These studies have also shown that it can control seizures in some genetic epilepsy models, in amygdala-kindled rats and in animals with ischemia-induced epilepsy. Clinical studies have shown that topiramate is effective as an add-on drug for treating simple or complex partial seizures with or without secondary generalization, even when administrered as monotherapy.

The clinical shortcomings of drugs in current usage are considerable. For example, lamotrigine causes rash and sedation and topiramate, phenytoin, and carbamazepine causes central nervous system side effects.

Thus, there continues to exist a need for novel compounds having improved therapeutic activities (e.g., increased potency, greater tissue selectivity, increased efficacy, reduced side effects and a more favorable duration of action.)

SUMMARY OF THE INVENTION

This invention is directed to novel multibinding compounds that bind to $Na^+$ channels in mammalian tissues and can be used to treat diseases and conditions mediated by such channels.

Accordingly, in one of its composition aspects, this invention is directed to a multibinding compound and salts thereof comprising 2 to 10 ligands which may be the same or different and which are covalently attached to a linker or linkers, which may be the same or different, each of said ligands comprising a ligand domain capable of binding to a $Na^+$ channel.

The multibinding compounds of this invention are preferably represented by formula I:

$$(L)_p(X)_q \quad \quad (I)$$

where each L is a ligand that may be the same or different at each occurrence; X is a linker that may be the same or different at each occurrence; p is an integer of from 2 to 10; and q is an integer of from 1 to 20; wherein each of said ligands comprises a ligand domain capable of binding to a $Na^+$ channel. Preferably q is less than p.

Preferably, the binding of the multibinding compound to a $Na^+$ channel or channels in a mammal modulates diseases and conditions mediated by the $Na^+$ channel or channels.

In another of its composition aspects, this invention is directed to a pharmaceutical composition comprising a pharmaceutically acceptable excipient and a therapeutically effective amount of one or more multibinding compounds (or pharmaceutically acceptable salts thereof) comprising 2 to 10 ligands which may be the same or different and which are covalently attached to a linker or linkers, which may be the same or different, each of said ligands comprising a ligand domain capable of binding to a $Na^+$ channel of a cell mediating mammalian diseases or conditions, thereby modulating the diseases or conditions.

In still another of its composition aspects, this invention is directed to a pharmaceutical composition comprising a pharmaceutically acceptable excipient and a therapeutically effective amount of one or more multibinding compounds represented by formula I, $$(L)_p(X)_q \quad \quad (I)$$

or pharmaceutically acceptable salts thereof, where each L is a ligand that may be the same or different at each occurrence; X is a linker that may be the same or different at each occurrence; p is an integer of from 2 to 10; and q is an integer of from 1 to 20; wherein each of said ligands comprises a ligand domain capable of binding to a $Na^+$ channel of a cell mediating mammalian diseases or conditions, thereby modulating the diseases or conditions. Preferably q is less than p.

In one of its method aspects this invention is directed to a method for modulating the activity of a $Na^+$ channel in a biologic tissue, which method comprises contacting a tissue having a $Na^+$ channel with a multibinding compound (or pharmaceutically acceptable salts thereof) under conditions sufficient to produce a change in the activity of the channel in said tissue, wherein the multibinding compound comprises 2 to 10 ligands which may be the same or different and which are covalently attached to a linker or linkers, which may be the same or different, each of said ligands comprising a ligand domain capable of binding to a $Na^+$ channel.

In another of its method aspects, this invention is directed to a method for treating a disease or condition in a mammal resulting from an activity of a $Na^+$ channel, which method comprises administering to said mammal a therapeutically effective amount of a pharmaceutical composition comprising a pharmaceutically acceptable excipient and one or more multibinding compounds (or pharmaceutically acceptable salts thereof) comprising 2 to 10 ligands which may be the same or different and which are covalently attached to a linker or linkers, which may be the same or different, each of said ligands comprising a ligand domain capable of binding to a $Na^+$ channel of a cell mediating mammalian diseases or conditions.

In yet another of its method aspects, this invention is directed to a method for treating a disease or condition in a mammal resulting from an activity of a $Na^+$ channel, which method comprises administering to said mammal a therapeutically effective amount of a pharmaceutical composition comprising a pharmaceutically acceptable excipient and one or more multibinding compounds represented by formula I, $$(L)_p(X)_q \quad \quad (I)$$

and pharmaceutically acceptable salts thereof, where each L is a ligand that may be the same or different at each occurrence; X is a linker that may be the same or different at each occurrence; p is an integer of from 2 to 10; and q is an integer of from 1 to 20; wherein each of said ligands comprises a ligand domain capable of binding to a $Na^+$ channel of a cell mediating mammalian diseases or conditions. Preferably q is less than p.

In a further aspect, this invention provides processes for preparing the multibinding agents of Formula I.

This invention is further directed to general synthetic methods for generating large libraries of diverse multimeric compounds which multimeric compounds are candidates for possessing multibinding properties. The diverse multimeric compound libraries provided by this invention are synthesized by combining a linker or linkers with a ligand or ligands to provide for a library of multimeric compounds wherein the linker and ligand each have complementary functional groups permitting covalent linkage. The library of linkers is preferably selected to have diverse properties such as valency, linker length, linker geometry and rigidity, hydrophilicity or hydrophobicity, amphiphilicity, acidity, basicity and polarization. The library of ligands is preferably selected to have diverse attachment points on the same ligand, different functional groups at the same site of otherwise the same ligand, and the like.

This invention is also directed to libraries of diverse emultimeric compounds which multimeric compounds are candidates for possessing multibinding properties. These libraries are prepared via the methods described above and permit the rapid and efficient evaluation of what molecular constraints impart multibinding properties to a ligand or a class of ligands targeting a receptor.

Accordingly, in one of its method aspects, this invention is directed to a method for identifying multimeric ligand compounds possessing multibinding properties which method comprises:

(a) identifying a ligand or a mixture of ligands wherein each ligand contains at least one reactive functionality;

(b) identifying a library of linkers wherein each linker in said library comprises at least two functional groups having complementary reactivity to at least one of the reactive functional groups of the ligand;

(c) preparing a multimeic ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands; and (d) assaying the multimeric ligand compounds produced in (c) above to identify multimeric ligand compounds possessing multibinding properties.

In another of its method aspects, this invention is directed to a method for identifying multimeric ligand compounds possessing multibinding properties which method comprises:

(a) identifying a library of ligands wherein each ligand contains at least one reactive functionality;

(b) identifying a linker or mixture of linkers wherein each linker comprises at least two functional groups having complementary reactivity to at least one of the reactive functional groups of the ligand;

(c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands; and (d) assaying the multimeric ligand compounds produced in (c) above to identify multimeric ligand compounds possessing multibinding properties.

The preparation of the multimeric ligand compound library is achieved by either the sequential or concurrent combination of the two or more stoichiometric equivalents of the ligands identified in (a) with the linkers identified in (b). Sequential addition is preferred when a mixture of different ligands is employed to ensure heterodimeric or multimeric compounds are prepared. Concurrent addition of the ligands occurs when at least a portion of the multimer compounds prepared are homomultimeric compounds.

The assay protocols recited in (d) can be conducted on the multimeric ligand compound library produced in (c) above, or preferably, each member of the library is isolated by preparative liquid chromatography mass spectrometry (LCMS).

In one of its composition aspects, this invention is directed to a library of multimeric ligand compounds which may possess multivalent properties which library is prepared by the method comprising:

(a) identifying a ligand or a mixture of ligands wherein each ligand contains at least one reactive functionality;

(b) identifying a library of linkers wherein each linker in said library comprises at least two functional groups having complementary reactivity to at least one of the reactive functional groups of the ligand; and (c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands.

In another of its composition aspects, this invention is directed to a library of multimeric ligand compounds which may possess multivalent properties which library is prepared by the method comprising:

(a) identifying a library of ligands wherein each ligand contains at least one reactive functionality;

(b) identifying a linker or mixture of linkers wherein each linker comprises at least two functional groups having complementary reactivity to at least one of the reactive functional groups of the ligand; and (c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands.

In a preferred embodiment, the library of linkers employed in either the methods or the library aspects of this invention is selected from the group comprising flexible linkers, rigid linkers, hydrophobic linkers, hydrophilic linkers, linkers of different geometry, acidic linkers, basic linkers, linkers of different polarization and amphiphilic linkers. For example, in one embodiment, each of the linkers in the linker library may comprise linkers of different chain length and/or having different complementary reactive groups. Such linker lengths can preferably range from about 2 to 100 Å.

In another preferred embodiment, the ligand or mixture of ligands is selected to have reactive functionality at different sites on said ligands in order to provide for a range of orientations of said ligand on said multimeric ligand compounds. Such reactive functionality includes, by way of example, carboxylic acids, carboxylic acid halides, carboxyl esters, amines, halides, isocyanates, vinyl unsaturation, ketones, aldehydes, thiols, alcohols, anhydrides, and precursors thereof. It is understood, of course, that the reactive functionality on the ligand is selected to be complementary to at least one of the reactive groups on the linker so that a covalent linkage can be formed between the linker and the ligand.

In other embodiments, the multimeric ligand compound is homomeric (i.e., each of the ligands is the same, although it may be attached at different points) or heterodimeric (i.e., at least one of the ligands is different from the other ligands).

In addition to the combinatorial methods described herein, this invention provides for an interative process for rationally evaluating what molecular constraints impart multibinding properties to a class of multimeric compounds or ligands targeting a receptor. Specifically, this method aspect is directed to a method for identifying multimeric ligand compounds possessing multibinding properties which method comprises:

(a) preparing a first collection or iteration of multimeric compounds which is prepared by contacting at least two stoichiometric-equivalents of the ligand or mixture of ligands which target a receptor with a linker or mixture of linkers wherein said ligand or mixture of ligands comprises at least one reactive functionality and said linker or mixture of linkers comprises at least two functional groups having complementary reactivity to at least one of the reactive functional groups of the ligand wherein said contacting is conducted under conditions wherein the complementary functional groups react to form a covalent linkage between said linker and at least two of said ligands;

(b) assaying said first collection or iteration of multimeric compounds to assess which if any of said multimeric compounds possess multibinding properties;

(c) repeating the process of (a) and (b) above until at least one multimeric compound is found to possess multibinding properties;

(d) evaluating what molecular constraints imparted multibinding properties to the multimeric compound or compounds found in the first iteration recited in (a)–(c) above;

(e) creating a second collection or iteration of multimeric compounds which elaborates upon the particular molecular constraints imparting multibinding properties to the multimeric compound or compounds found in said first iteration;

(f) evaluating what molecular constraints imparted enhanced multibinding properties to the multimeric compound or compounds found in the second collection or iteration recited in (e) above;

(g) optionally repeating steps (e) and (f) to further elaborate upon said molecular constraints.

Preferably, steps (e) and (f) are repeated at least two times, more preferably at from 2–50 times, even more preferably from 3 to 50 times, and still more preferably at least 5–50 times.

BRIEF DESCRIPTION OF THE DRAWINGS

FIG. 3 illustrates a method for optimizing the linker geometry for presentation of ligands (filled circles) in bivalent compounds:

A. phenyldiacetylene core structure
B. cyclohexane dicarboxylic acid core structure

DETAILED DESCRIPTION OF THE INVENTION

Figure 1A:
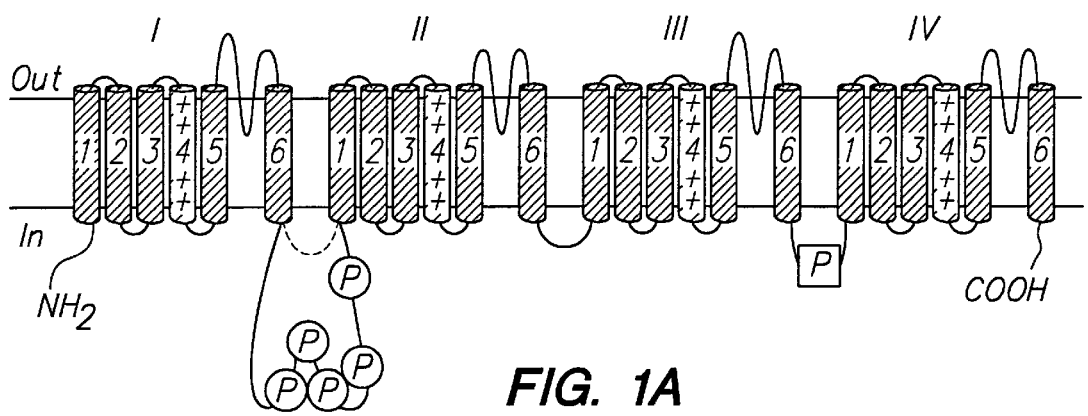
FIGS. 1A and 1B are highly schematic illustrations of the transmembrane organization.
Figure 1B:
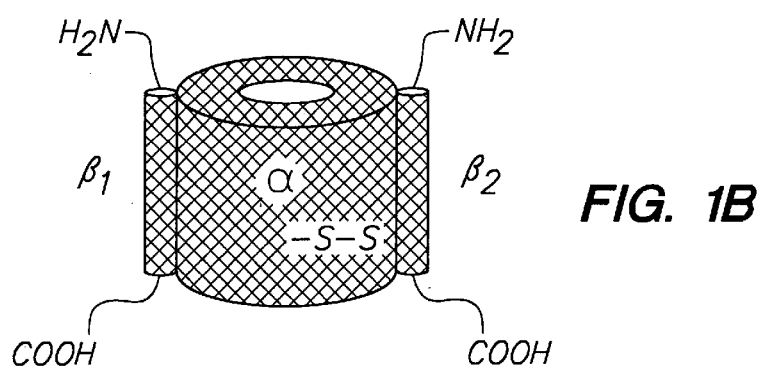
Figure 2A:
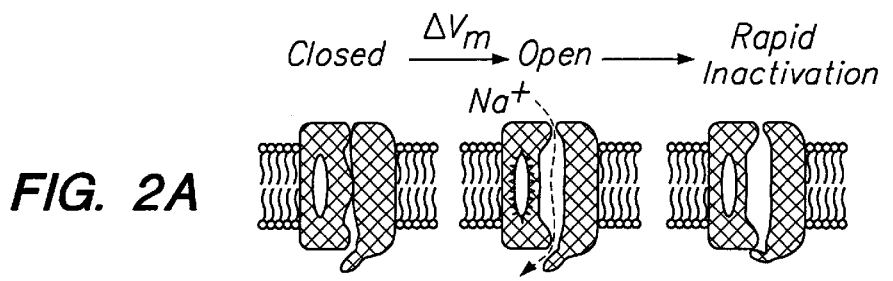
FIGS. 2A and 2B illustrate the multiple ion conducting (open) and nonconducting (closed/inactivated) conformations.
Figure 2B:
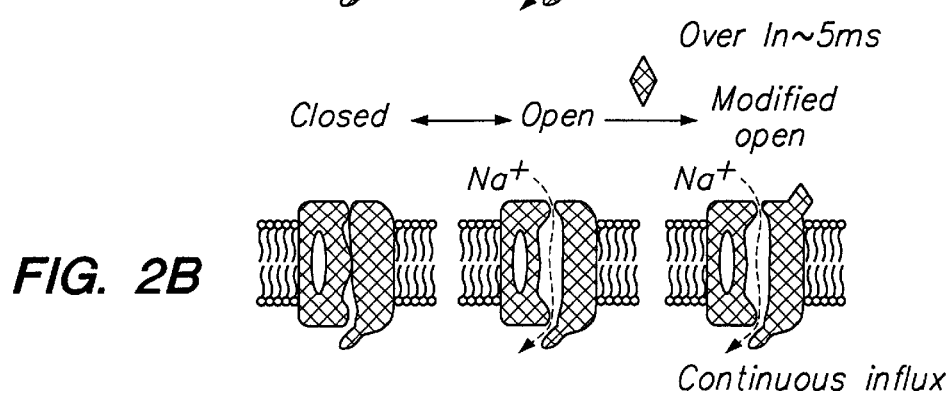

Biological systems in general are controlled by molecular interactions between bioactive ligands and their receptors, in which the receptor "recognizes" a molecule or a portion thereof (i.e., a ligand domain) to produce a biological effect. The $Na^+$ channels are considered to be pharmacological receptors: they possess specific binding sites for ligands having agonist and antagonist activities; the binding of ligands to such sites modulates $Na^+$ flux through the channel; the channel properties (i.e., gating and ion selectivity) are regulatable. Accordingly, diseases or conditions that involve, or are mediated by, $Na^+$ channels can be treated with pharmacologically active ligands that interact with such channels to initiate, modulate or abrogate transporter activity.

The interaction of a $Na^+$ channel and a $Na^+$ channel-binding ligand may be described in terms of "affinity" and "specificity"; The "affinity" and "specificity" of any given ligand-$Na^+$ channel interaction is dependent upon the complementarity of molecular binding surfaces and the energetic costs of complexation (i.e., the net difference in free energy between bound and free states). Affinity may be quantified by the equilibrium constant of complex formation, the ratio of on/off rate constants, and/or by the free energy of complex formation. Specificity relates to the difference in binding affinity of a ligand for different receptors.

The net free energy of interaction of such ligand with a $Na^+$ channel is the difference between energetic gains (enthalpy gained through molecular complementarity and entropy gained through the hydrophobic effect) and energetic costs (enthalpy lost through decreased solvation and entropy lost through reduced translational, rotational and conformational degrees of freedom).

The compounds of this invention comprise 2 to 10 $Na^+$ channel-binding ligands covalently linked together and capable of acting as multibinding agents. Without wishing to be bound by theory, the enhanced activity of these compounds is believed to arise at least in part from their ability to bind in a multivalent manner with multiple ligand binding sites on a $Na^+$ channel or channels, which gives rise to a more favorable net free energy of binding. Multivalent interactions differ from collections of individual monovalent (univalent) interactions by being capable of providing enhanced biologic and/or therapeutic effect. Multivalent binding can amplify binding affinities and differences in binding affinities resulting in enhanced binding specificity as well as affinity.

DEFINITIONS

As used herein:

The term "alkyl" refers to a monoradical branched or unbranched saturated hydrocarbon chain, preferably having from 1 to 40 carbon atoms, preferably 1–10 carbon atoms, more preferably 1–6 carbon atoms; such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated.

The term "substituted alkyl" refers to an alkyl group as, defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and and are chosen from hydrogen, optionally substituted alkyl, cycloalkyl, alkenyl, cycloalkenyl, alkynyl, aryl, heteroaryl and heterocyclic.

The term "alkylene" refers to a diradical of a branched or unbranched saturated hydrocarbon chain, preferably having from 1 to 40 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to: (1) An alkylene group as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocyclooxy, nitro, and —NR$_a$R$_b$, wherein R$_a$ and R$_b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group; (2) An alkylene group as defined above that is interrupted by 1–20 atoms independently chosen from oxygen, sulfur and NR$_a$—, where R$_a$ is chosen from hydrogen, optionally substituted alkyl, cycloalkyl, alkenyl, cycloalkenyl, alkenyl, cycloalkenyl, alkynyl, aryl, heteroaryl and heterocyclic, or groups selected from carbonyl, carboxyester, carboxyamide and sulfonyl; and (3) An alkylene group as defined above that has both from 1 to 5 substituents as defined above and is also interrupted by 1–20 atoms as defined above. Examples of substituted alkylenes are chloromethylene (—CH(Cl)—), aminoethylene (—CH(NH$_2$)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "alkaryl" or "aralkyl" refers to the groups -alkylene-aryl and -substituted alkylene-aryl in which alkylene and aryl are as defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Examples of such groups are methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioakoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

"Alkenyl" refers to a monoradical of a branched or unbranched unsaturated hydrocarbon preferably having from 2 to 40 carbon atoms, preferably 2–10 carbon atoms, more preferably 2–6 carbon atoms, and preferably having 1–6 double bonds. This term is further exemplified by such radicals as vinyl, prop-2-enyl, pent-3-enyl, hex-5-enyl, 5-ethlyldodec-3,6-dienyl, and the like.

The term "substituted alkenyl" refers to an alkenyl group as defined above having from 1 to 5 substituents selected from the group consisting of alkoxy, substituted alkoxy, acyl, acylamino, acyloxy, amino, aminoacyl, aminoacyloxy, oxyaminoacyl, azido, cyano, halogen, hydroxyl, keto, thioketo, carboxyl, carboxylalkyl, thiol, thioalkoxy, substituted thioalkoxy, aryl, heteroaryl, heterocyclic, aryloxy, thioaryloxy, heteroaryloxy, thioheteroarylosy, heterocyclooxy, thioheterocyclooxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and, —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

"Alkenylene" refers to a diradical of an unsaturated hydrocarbon, preferably having from 2 to 40 carbon atoms, preferably 2–10 carbon atoms, more preferably 2–6 carbon atoms, and preferably having 1–6 double bonds. This term is further exemplified by such radicals as 1,2-ethenyl, 1,3-prop-2-enyl, 1,5-pent-3-enyl, 1,4-hex-5-enyl, 5-ethyl-1,12-dodec-3,6-dienyl, and the like.

The term "substituted alkenylene" refers to an alkenylene group as defined above having from 1 to 5 substituents, selected from the group consisting of alkoxy, substituted alkoxy, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocyclooxy, nitro, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

"Alkynyl" refers to a monoradical of an unsaturated hydrocarbon, preferably having from 2 to 40 carbon atoms, preferably 2–10 carbon atoms, more preferably 2–6 carbon atoms, and preferably having 1–6 triple bonds. This term is further exemplified by such radicals as acetylenyl, prop-2-ynyl, pent-3-ynyl, hex-5-ynyl, 5-ethyldodec-3,6-diynyl, and the like.

The term "substituted alkenylene" refers to an alkenylene group as defined above having from 1 to 5 substituents, selected from the group consisting of alkoxy, substituted alkoxy, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocycloxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, SO$_2$-heterocyclic, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

"Alkynylene" refers to a diradical of an unsaturated hydrocarbon radical, preferably having from 2 to 40 carbon atoms, preferably 2–10 carbon atoms, more preferably 2–6 carbon atoms, and preferably having 1–6 triple bonds. This term is further exemplified by such radicals as 1,3-prop-2-ynyl, 1,5-pent-3-ynyl, 1,4-hex-5-ynyl, 5-ethyl-1,12-dodec-3,6-diynyl, and the like.

The term "acyl" refers to the groups —CHO, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" refers to the group —C(O)NRR where each R is independently hydrogen, alkyl, substituted alkyl, aryl, heteroaryl, heterocyclic or where both R groups are joined to form a heterocyclic group (e.g., morpholine) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl).

Unless otherwise constrained by the definition for the aryl substituent, such aryl groups can optionally be substituted with from 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —S$_2$-alkyl, —SO$_2$-substituted alkyl, —SO$_2$-aryl, —SO$_2$-heteroaryl, trihalomethyl, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to a diradical derived from aryl or substituted aryl as defined above, and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, alkynyl, substituted alkynyl, aryl, heteroaryl and heterocyclic provided that both R's are not hydrogen.

The term "carboxyalkyl" refers to the group "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl where alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents selected from the group consisting of alkoxy, substituted alkoxy, cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "cycloalkenyl" refers to cyclic alkenyl groups of from 4 to 20 carbon atoms having a single cyclic ring or fused rings and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl; —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "halo" or "halogen" refers to fluoro, chloro, bromo and iodo.

"Haloalkyl" refers to alkyl as defined above substituted by 1–4 halo groups as defined above, which may be the same or different, such as 3-fluorododecyl, 12,12,12-trifluorododecyl, 2-bromooctyl, -3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, mono-and di-alkylamino, mono- and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Preferred heteroaryls include pyridyl, pyrrolyl and furyl.

The term "heteroaryloxy" refers to the group heteroaryl-O—.

The term "heteroarylene" refers to the diradical group derived from heteroaryl or substituted heteroaryl as defined above, and is exemplified by the groups 2,6-pyridylene, 2,4-pyridiylene, 1,2-quinolinylene, 1,8-quinolinylene, 1,4-benzofuranylene, 2,5-pyridiylene, 1,3-morpholinylene, 2,5-indolenyl and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, cyano; halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Such heterocyclic groups can have a single ring or multiple condensed rings.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridie, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, incline, morpholino, piperidinyl, tetrahydrofuranyl, and the like as well as N-alkoxy-nitrogen containing heterocycles.

A preferred class of heterocyclics include "crown compounds" which refers to a specific class of heterocyclic compounds having one or more repeating units of the formula [—(CH$_2$—)$_m$Y—] where m is equal to or greater than 2, and Y at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$—NH)$_2$] and the like. Typically such crown compounds can have from 4 to 10 heteroatoms and 8 to 40 carbon atoms.

The term "heterocyclooxy" refers to the group heterocyclic-O—.

The term "thioheterocyclooxy" refers to the group heterocyclic-S—.

The term "heterocyclene" refers to the diradical group derived from a heterocycle as defined herein, and is exemplified by the groups 2,6-morpholino, 2,5-morpholino and the like.

The term "oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

"Alkyl optionally interrupted by 1–5 atoms chosen from O, S, or N" refers to alkyl as defined above in which the carbon chain is interrupted by O, S, or N. Within the scope are ethers, sulfides, and amines, for example 1-methoxydecyl, 1-pentyloxynonane, 1-(2-isopropoxyethoxy)-4-methylnonane, 1-(2-ethoxyethoxy) dodecyl, 2-(t-butoxy)heptyl, 1-pentylsulfanylnonane, nonylpentylamine, and the like.

"Heteroarylalkyl" refers to heteroaryl as defined above linked to alkyl as defined above, for example pyrid-2-ylmethyl, 8-quinolinylpropyl, and the like.

"Optional" or "optionally" means that the subsequently described event or circumstance may or may not occur, and that the description includes instances where said event or circumstance occurs and instances in which it does not. For example, optionally substituted alkyl means that alkyl may or may not be substituted by those groups enumerated in the definition of substituted alkyl.

The term "pharmaceutically acceptable salt" refers to salts which retain the biological effectiveness and properties of the multibinding compounds of this invention and which are not biologically or otherwise undesirable. In many cases, the multibinding compounds of this invention are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amities, trialkenyl amines, substituted alkenyl amines, di(substituted alkenyl) amines, tri(substituted alkenyl) amines, cycloalkyl amines, di(cycloalkyl) amines, tri (cycloalkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri (iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "protecting group" or "blocking group" refers to any group which when bound to one or more hydroxyl, thiol, amino or carboxyl groups of the compounds prevents reactions from occurring at these groups and which protecting group can be removed by conventional chemical or enzymatic steps to reestablish the hydroxyl, thiol, amino or carboxyl group. See, generally, T. W. Greene & P. G. M. Wuts, *Protective Groups in Organic Synthesis*, $2^{nd}$ Ed., 1991, John Wiley and Sons, N.Y.

The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxyl protecting groups include esters such as methyl, ethyl propyl, t-butyl etc. which can be removed by mild hydrolysis conditions compatible with the nature of the product.

As used herein, the terms "inert organic solvent" or "inert solvent" mean a solvent inert under the conditions of the reaction being described in conjunction therewith including, for example, benzene, toluene, acetonitrile, tetrahydrofuran, dimethylformamide, chloroform, methylene chloride (or dichloromethane), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

The term "$Na^+$ channel" refers to a structure comprised of integral membrane proteins that functions to allow $Na^+$ to equilibrate across a membrane according to its electrochemical gradient and at rates that are diffusion limited.

"Ligand" as used herein denotes a compound that is a binding partner for a $Na^+$ channel receptor, and is bound thereto, for example, by complementarity. The specific region or regions of the ligand molecule that is recognized by the ligand binding site of a $Na^+$ channel receptor is designated as the "ligand domain". A ligand may be either capable of binding to a receptor by itself, or may require the presence of one or more non-ligand components for binding (e.g. ions, a lipid molecule, a solvent molecule, and the like). The linker can be either a chiral or achiral molecule.

The ligands and linkers which comprise the multibinding agents of the invention and the multibinding compounds themselves may have various steroisomeric forms, including enantiomers and diastereomers. It is to be understood that the invention contemplates all possible stereoisomeric forms of multibinding compounds, and mixtures thereof.

Ligands useful in this invention comprise Na$^+$ channel modulators such as, for example, carbamazepine, felbamate, fosphenytoin, lamotrigine, permenol, topiramate, vipocitine, phenytoin, ADC1, alprafenone, trophix, AWD-140-190, berlafenone, BRB-I-28, CI-953, CNS-5151, Co-102862, E-047/1, GE-68, GW273227, GW286103, GW273293, iodoamiloride, lidocaine, PNU-151774E, PD-85639, RP-66055, RSD-921, RS-2135, SL-90.0571, sipatrigine, topiramate, QX-314, ZM-227189, 534U87, 4030W92, 202W92 mexilitene, N-ethylmexilitene, flecainide, RS 132943, and tocainide and their analogues. Table 1 sets forth the indications treated by the Na$^+$ channel modulators. It should be noted that beyond the primary indications listed in the table, many of the Na$^+$ channel blockers such as, for example, mexilitene, lamotrigine, amitriptyline, and other anti-seizure compounds are used to treat pain as well.

TABLE 1

| Drug | Indication(s) |
| --- | --- |
| Carbamazepine | Epilepsy |
| Felbamate | Epilepsy |
| Fosphenytoin | Epilepsy |
| Lamotrigine | Epilepsy, ischemia, seizures |
| Permenol | Arrythmia |
| Topiramate | Epilepsy, seizures |
| Vipocitine | Epilepsy, depression |
| Phenytoin | Seizures |
| ADC1 | Ischemia, epilepsy, seizure |
| Alprafenone | Arrhythmia |
| Trophix | Pain |
| AWD-140-190 | Epilepsy, CNS disease |
| Berlafenone | Arrhythmia |
| BRB-I-28 | Arrhythmia |
| CI-953 | Ischemia |
| CNS-5151 | Ischemia |
| Co-102862 | Pain, epilepsy |
| E-047/1 | Arrythmia |
| GE-68 | Arrythmia |
| GW273227 | |
| GW286103 | |
| GW273293 | Epilepsy, pain |
| Iodoamiloride | Cystic fibrosis |
| Lidocaine | Arrhythmia |
| PNU-151774E | Pain, epilepsy |
| PD-85639 | Arrythmia |
| RP-66055 | Cerebral infarction, cerebrovascular ischemia, epilepsy |
| RSD-921 | Arrhythmia |
| RS-2135 | Arrhythmia |
| SL-90.0571 | Epilepsy |
| Sipatrigine | Stroke |
| Topiramate | Epilepsy (children) |
| QX-314 | pain/urinary tract disease |
| ZM-227189 | Arrythmia, tachycardia |
| 534U87 | Epilepsy |
| 4030W92 | Epilepsy, pain, depression |
| 202W92 | Stroke |
| mexilitene | Pain |
| N-ethylmexilitene | |
| Flecainide | Pain |
| RS 132943 | Pain |
| Tocainide | |
| Amitriptyline | Pain |

While it is contemplated that many sodium channel ligands that are currently known can be used in the preparation of multibinding compounds of this invention, it should be understood that portions of the ligand structure that are not essential for molecular recognition and binding activity (i.e., that are not part of the ligand domain) may be varied substantially, replaced with unrelated structures and, in some cases, omitted entirely without affecting the binding interaction. Accordingly, it should be understood that the term "ligand" is not intended to be limited to compounds known to be useful as Na$^+$ channel receptor-binding compounds (e.g., known drugs), in that ligands that exhibit marginal activity or lack useful activity as monomers can be highly active as multibinding compounds, because of the biological benefit conferred by multivalency. The primary requirement for a ligand as defined herein is that it has a ligand domain, as defined above, which is available for binding to a recognition site on a Na$^+$ channel.

For purposes of the present invention, the term "ligand" or "legands" is intended to include the racemic ligands as well as the individual stereoisomers of the ligands, including pure enantiomers and non-raceunic mixtures thereof. The scope of the invention as described and claimed encompasses the racemic forms of the ligands as well as the individual enantiomers and non-racemic mixtures thereof.

The term "ligand binding site" as used herein denotes a site on a Na$^+$ channel receptor that recognizes a ligand domain and provides a binding partner for the ligand. The ligand binding site may be defined by monomeric or multimeric structures. This interaction may be capable of producing a unique biological effect, for example agonism, antagonism, modulation, or may maintain an ongoing biological event, and the like.

It should be recognized that the ligand binding sites of Na$^+$ channel receptors that participate in biological multivalent binding interactions are constrained to varying degrees by their intra- and intermolecular associations. For example, Na$^+$ channel ligand binding sites may be covalently joined in a single structure, noncovalently associated in one or more multimeric structures, embedded in a membrane or biopolymer matrix, and so on, and therefore have less translational and rotational freedom than if the same sites were present as monomers in solution.

The terms "agonism" and "antagonism" are well known in the art. As used herein, the term "agonist" refers to a ligand that when bound to a Na$^+$ channel stimulates its activity. The term "antagonist" refers to a ligand that when bound to a Na$^+$ channel inhibits its activity. Channel block or activation may result from allosteric effects of ligand binding to the channel rather than occupancy of the channel pore. These allosteric effects may produce changes in protein conformation that affect Na$^+$ binding sites, gating mechanisms and/or the pore region (i.e., ion permeation).

As described above, a sodium channel can exist in several modes: C (closed resting state); C* (activated closed state); O (open state); and I (inactivated state). The probability that a channel will exist in one of these four states changes with voltage. A given ligand may have different binding affinities for different states, and be capable of producing agonist or antagonist activity.

The term "modulatory effect" is intended to refer to the ability of a ligand to change the activity of a Na$^+$ channel through binding to the channel.

"Multibinding agent" or "multibinding compound" refers herein to a compound that has from 2 to 10 Na$^+$ channel ligands as defined herein (which may be the same or different) covalently bound to one or more linkers (which may be the same or different), and is capable of multivalency, as defined below.

A multibinding compound provides an improved biologic an d/or therapeutic effect compared to that of the same number of unlinked ligands available for binding to the ligand binding sites on a Na$^+$ channel or channels. Examples of improved "biologic and/or therapeutic effect" include increased ligand-receptor binding interactions (e.g., increased affinity, increased ability to elicit a functional change in the target, improved kinetics), increased selectivity for the target, increased potency, increased efficacy, decreased toxicity, increased therapeutic index, improved duration of action, improved bioavailability, improved pharmacokinetics, improved activity spectrum, and the like. The multibinding compounds of this invention will exhibit at least one, and preferably more than one, of the above-mentioned effects.

The term "library" refers to at least 3, preferably from $10^2$ to $10^9$ and more preferably from $10^2$ to $10^4$ multimeric compounds. Preferably, these compounds are prepared as a multiplicity of compounds in a single solution or reaction mixture which permits facile synthesis thereof. In one embodiment, the library of multimeric compounds can be directly assayed for multibinding properties. In another embodiment, each member of the library of multimeric compounds is first isolated and, optionally, characterized. This member is then assayed for multibinding properties.

The term "collection" refers to a set of multimeric compounds which are prepared either sequentially or concurrently (e.g., combinatorially). The collection comprises at least 2 members; preferably from 2 to $10^9$ members and still more preferably from 10 to $10^4$ members.

The term "multimeric compound" refers to compounds comprising from 2 to 10 ligands covalently connected through at least one linker which compounds may or may not possess multibinding properties (as defined herein).

The term "pseudohalide" refers to functional groups which react in displacement reactions in a manner similar to a halogen. Such functional groups include, by way of example; mesyl, tosyl, azido and cyano groups.

"Univalency" or "monovalency" as used herein refers to a single binding interaction between one ligand with one ligand binding site as defined herein. It should be noted that a compound having multiple copies of a ligand (or ligands) exhibits univalency when only one ligand of that compound interacts with a ligand binding site. Examples of univalent interactions are depicted below.

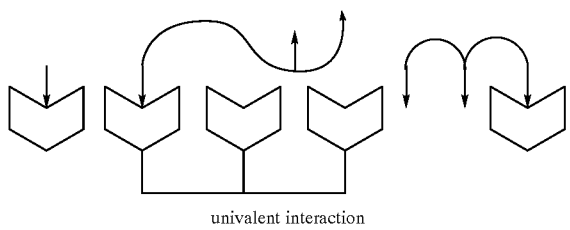

univalent interaction

"Multivalency" as used herein refers to the concurrent binding of from 2 to 10 linked ligands, which may be the same or different, and two or more corresponding ligand binding sites; which may be the same or different. An example of trivalent binding is depicted below for illustrative purposes.

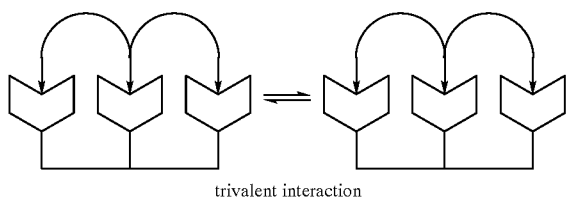

trivalent interaction

It should be understood that not all compounds that contain multiple copies of a ligand attached to a linker necessarily exhibit the phenomena of multivalency, i.e., that the biologic and/or therapeutic effect of the multibinding agent is greater than that of the same number of unlinked ligands made available for binding to the ligand binding sites. For multivalency to occur, the ligand domains of the ligands that are linked together must be presented to their cognate ligand binding sites by the linker or linkers in a specific manner in order to bring about the desired ligand-orienting result, and thus produce a multibinding interaction.

The term "linker" or "linkers" as used herein, identified where appropriate by the symbol X, refers to a group or groups that covalently link(s) from 2 to 10 ligands (as defined above) in a manner that provides a compound capable of multivalency. The linker is a ligand-orienting entity that permits attachment of multiple copies of a ligand (which may be the same or different) thereto.

The term "linker" includes everything that is not considered to be part of the ligand, e.g., ancillary groups such as solubilizing groups, lipophilic groups, groups that alter pharmacodynamics or pharmacokinetics, groups that modify the diffusability of the multibinding compound, spacers that attach the ligand to the linker, groups that aid the ligand-orienting function of the linker, for example, by imparting flexibility or rigidity to the linker as a whole, or to a portion thereof, and so on. The term "linker" does not, however, cover solid inert supports such as beads, glass particles, rods, and the like, but it is to be understood that the multibinding compounds of this invention can be attached to a solid support if desired, for example, for use in separation and purification processes and for similar applications.

The extent to which the previously discussed enhanced activity of multibinding compounds is realized in this invention depends upon the efficiency with which the linker or linkers that joins the ligands presents them to their array of ligand binding sites. Beyond presenting these ligands for multivalent interactions with ligand binding sites, the linker spatially constrains these interactions to occur within dimensions defined by the linker.

The linkers used in this invention are selected to allow multivalent binding of ligands to any desired ligand binding sites of a $Na^+$ channel, whether such sites are located within the cell membrane, interiorly (e.g., within a channel/translocation pore), both interiorly and on the periphery of a channel, at the boundary region between the lipid bilayer and the channel, or at any intermediate position thereof. The preferred linker length will vary depending on the distance between adjacent ligand binding sites, and the geometry, flexibility and composition of the linker. The length of the linker will preferably be in the range of about 2 Å to about 100 Å, more preferably from about 2 Å to about 50 Å and even more preferably from about 3 Å to about 20 Å.

Figure 7:
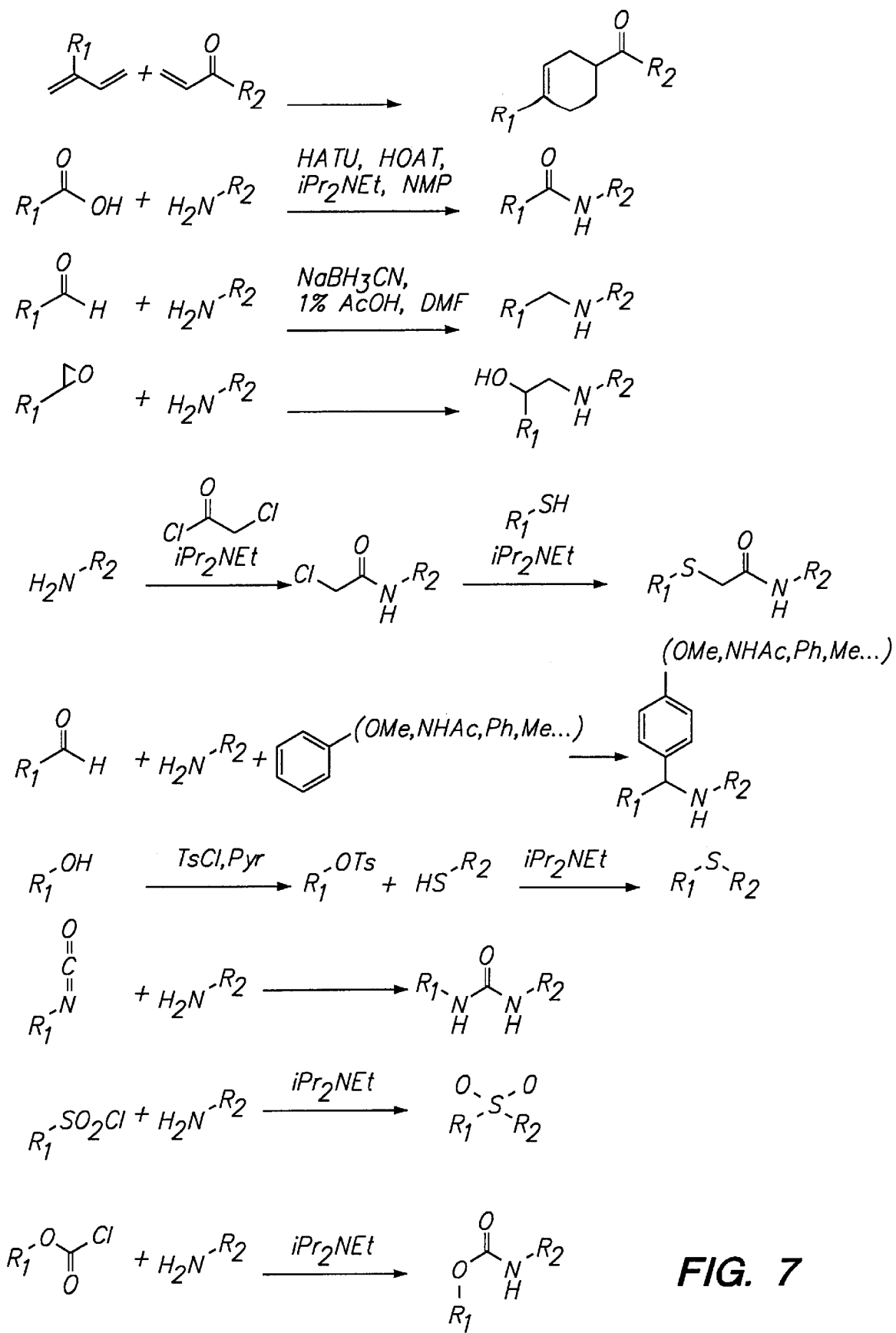
FIG. 7 illustrates numerous reactive functional groups and the resulting bonds formed by reaction therebetween.
Figure 8D:
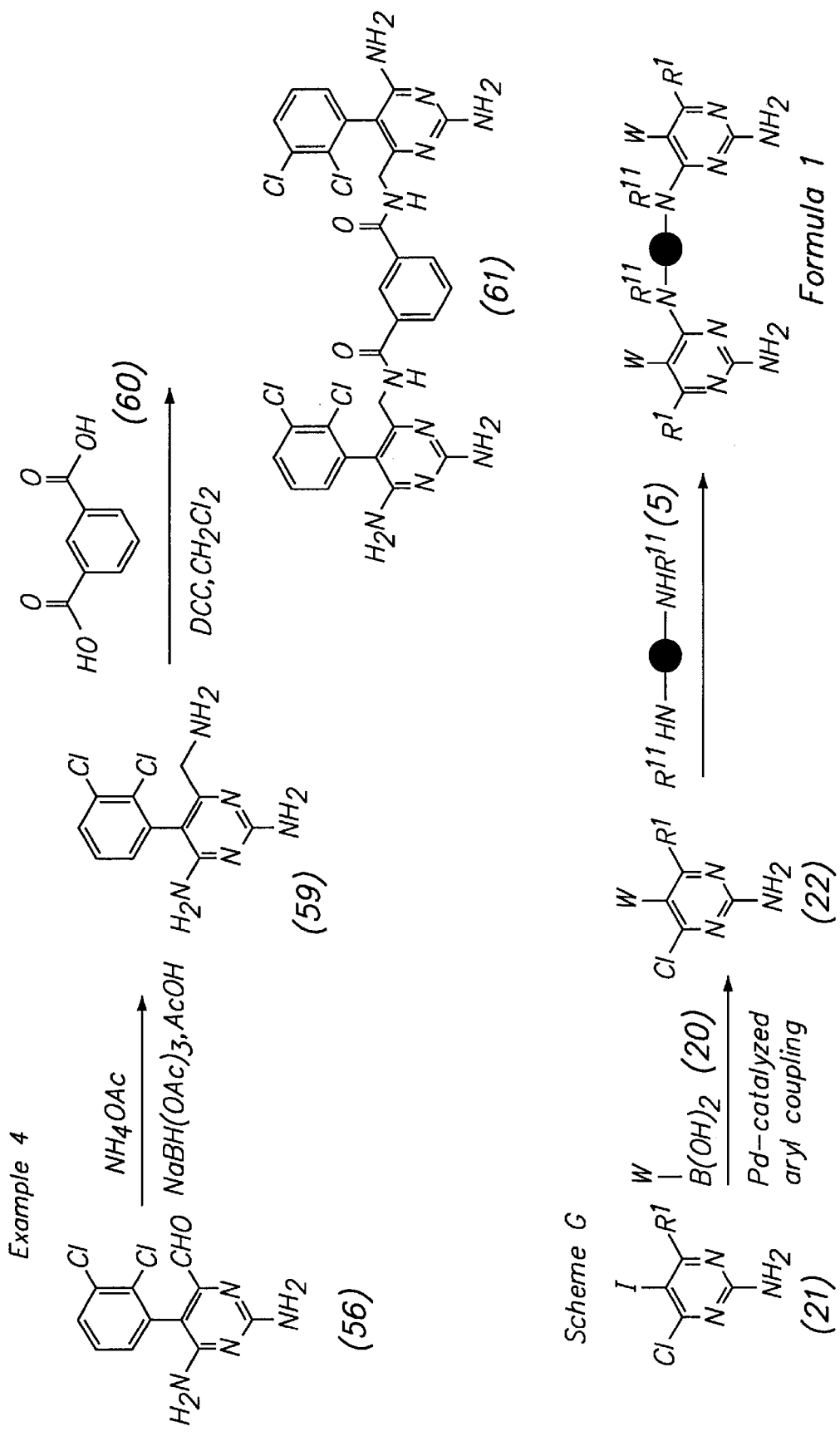
FIGS. 8A–8Q illustrate convenient methods for preparing the multibinding compounds of this invention.
Figure 8E:
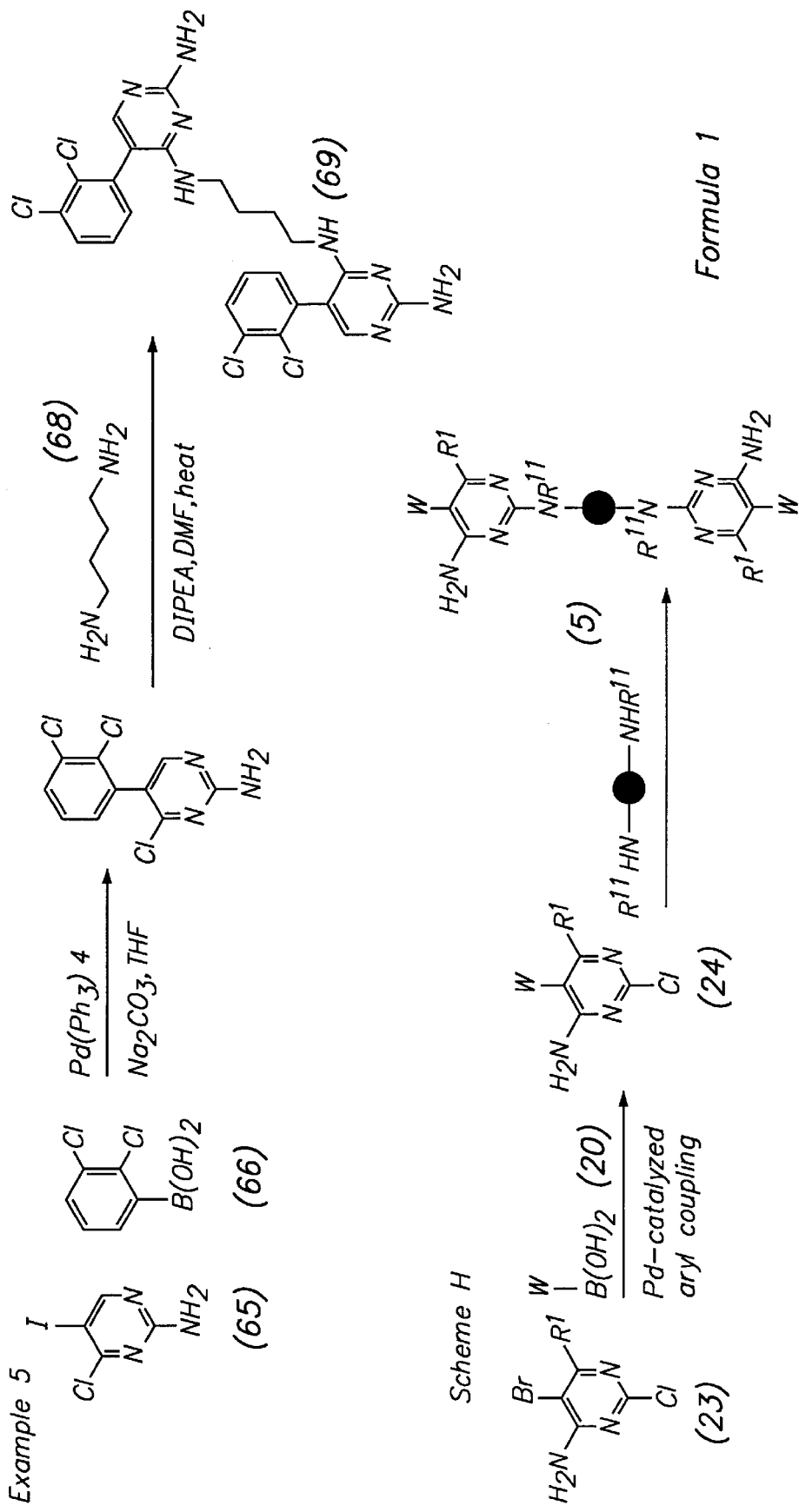
Figure 8G:
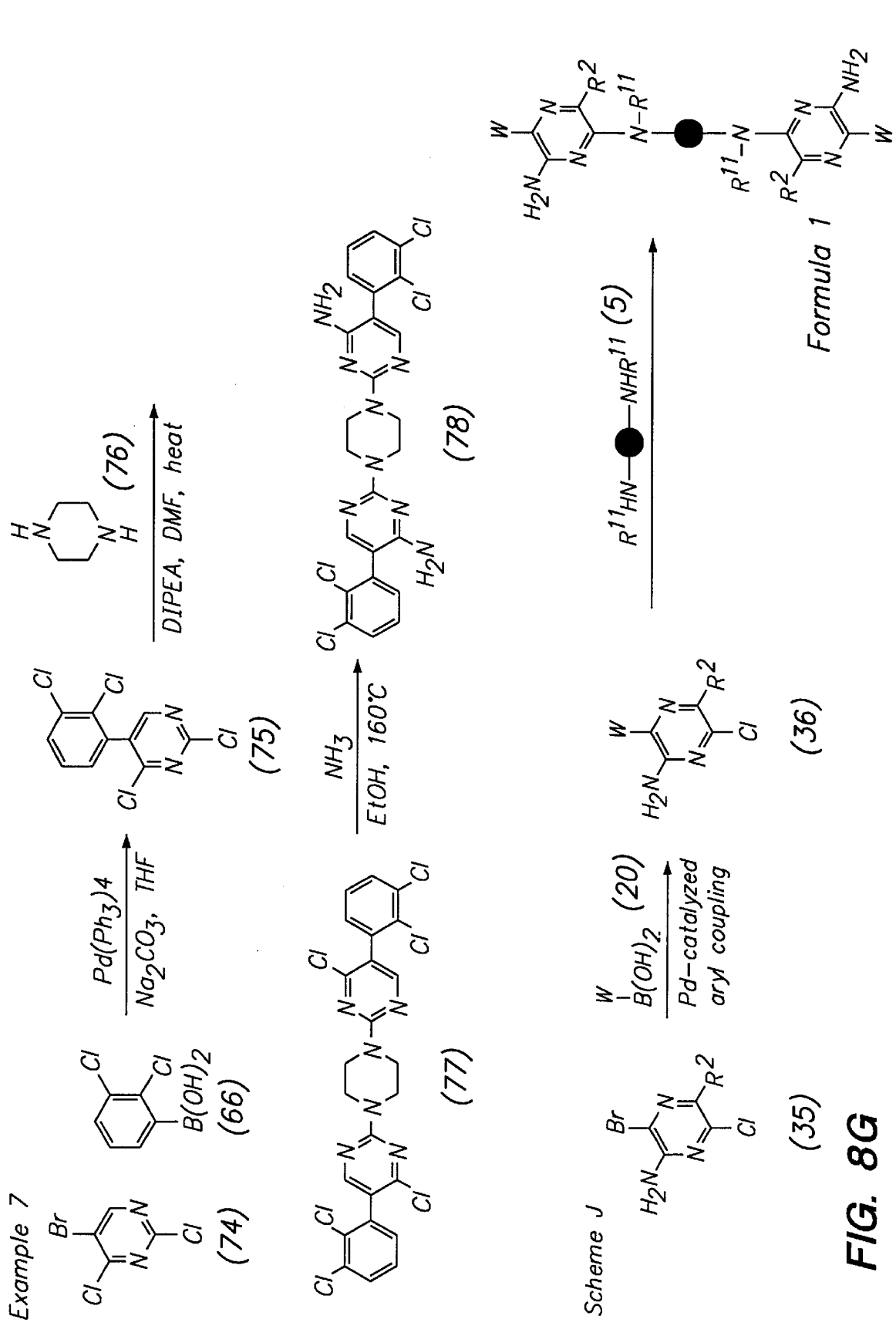
Figure 8H:
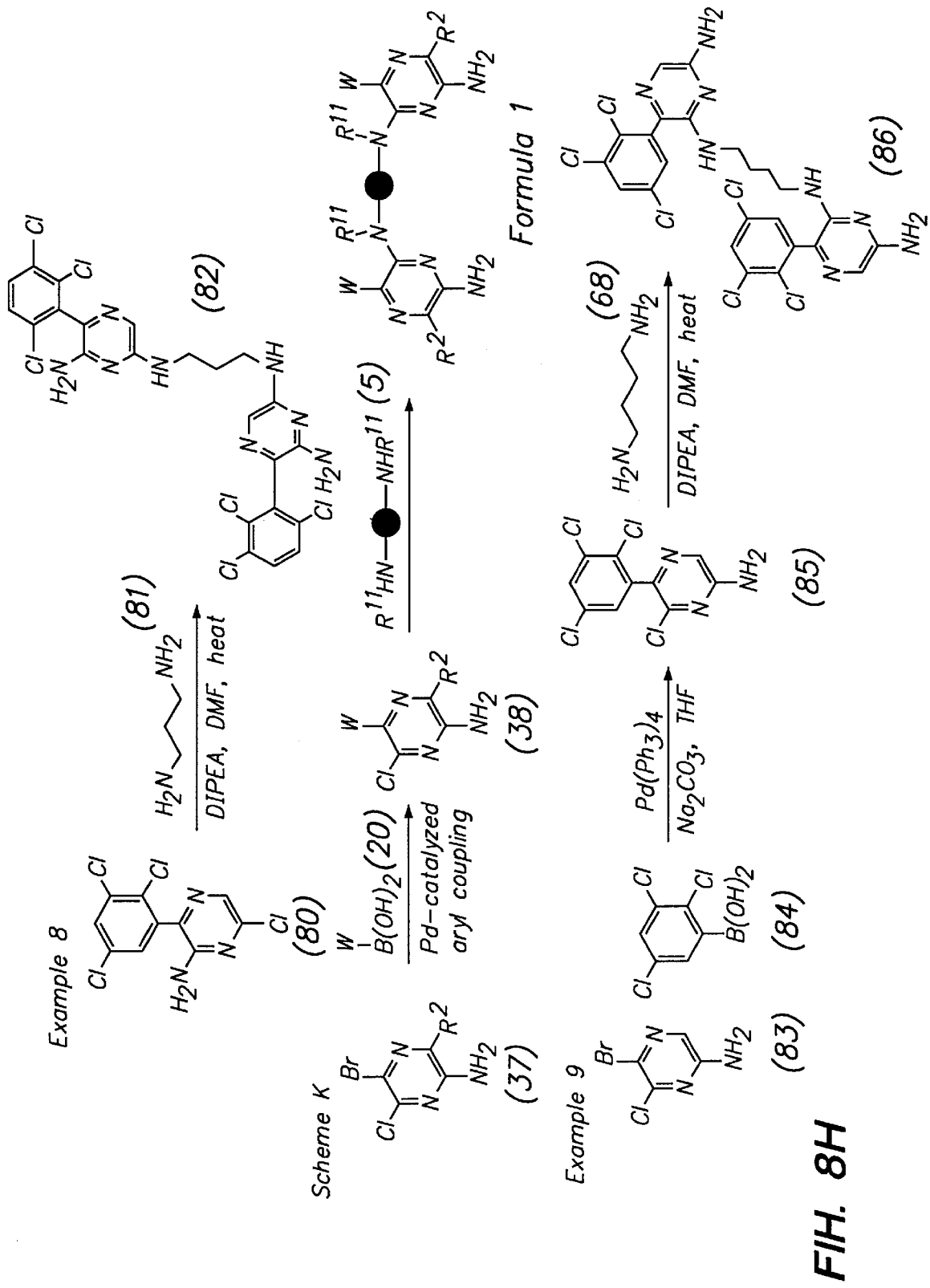
Figure 8J:
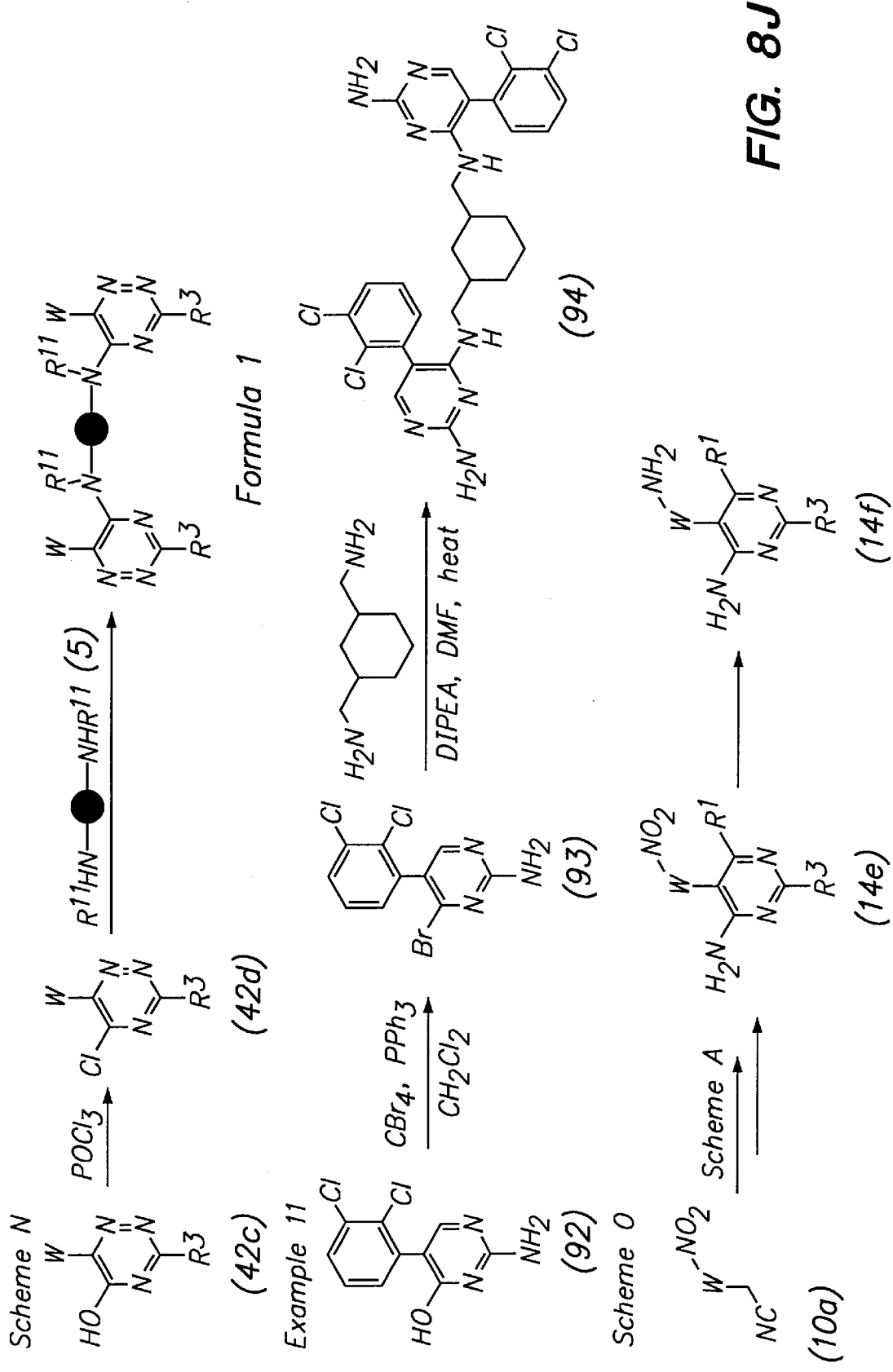
Figure 8L:
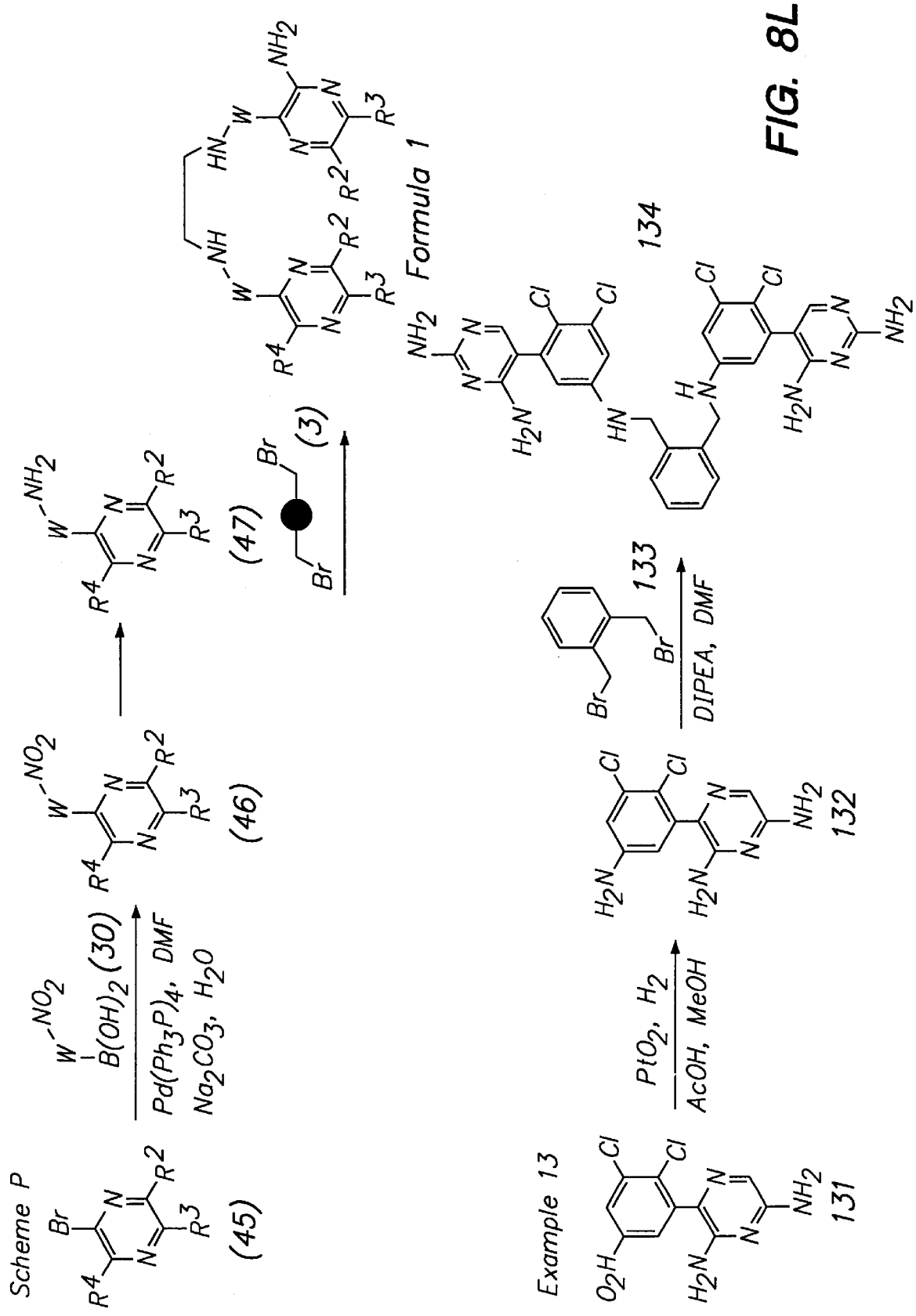

The ligands are covalently attached to the linker or linkers using conventional chemical techniques. The reaction chemistries resulting in such linkage are well known in the art and involve the use of reactive functional groups present on the linker and ligand. Preferably, the reactive functional groups on the linker are selected relative to the functional groups available on the ligand for coupling, or which can be introduced onto the ligand for this purpose. Again, such reactive functional groups are well known in the art. For example, reaction between a carboxylic acid of either the linker or the ligand and a primary or secondary amine of the ligand or the linker in the presence of suitable well-known activating agents results in formation of an amide bond covalently linking the ligand to the linker; reaction between an amine group of either the linker or the ligand and a sulfonyl halide of the ligand or the linker results in formation of a sulfonamide bond covalently linking the ligand to the linker; and reaction between an alcohol or phenol group of either the linker or the ligand and an alkyl or aryl halide of the ligand or the linker results in formation of an ether bond covalently linking the ligand to the linker. FIG. 7 illustrates numerous reactive functional groups and the resulting bonds formed by reaction therebetween. Where functional groups are lacking, they can be created by suitable chemistries that are described in standard organic chemistry texts such as J. March, *Advanced Organic Chemistry*, 4$^{th}$ Ed., (Wiley-Interscience, N.Y., 1992).

The linker is attached to the ligand at a position that retains ligand domain-ligand binding site interaction and specifically which permits the ligand domain of the ligand to orient itself to bind to the ligand binding site. Such positions and synthetic protocols for linkage are well known in the art. The term linker embraces everything that is not considered to be part of the ligand.

The relative orientation in which the ligand domains are displayed depends both on the particular point or points of attachment of the ligands to the linker, and on the framework geometry. The determination of where acceptable substitutions can be made on a ligand is typically based on prior knowledge of structure-activity relationships (SAR) of the ligand and/or congeners and/or structural information about ligand-receptor complexes (e.g. X-ray crystallography, NMR, and the like). Such positions and synthetic protocols for linkage are well known in the art and can be determined by those with ordinary skill in the art (see Methods of Preparation.) Following attachment of a ligand to the linker or linkers, or to a significant portion thereof (e.g., 2–10 atoms of linker), the linker-ligand conjugate may be tested for retention of activity in a relevant assay system (see Utility and Testing below for representative assays).

At present, it is preferred that the multibinding compound is a bivalent compound in which two ligands are covalently linked, or a trivalent compound, in which three ligands are covalently linked. Linker design is further discussed under Methods of Preparation.

"Potency" as used herein refers to the minimum concentration at which a ligand is able to achieve a desirable biological or therapeutic effect. The potency of a ligand is typically proportional to its affinity for its receptor. In some cases, the potency may be non-linearly correlated with its affinity. In comparing the potency of two drugs, e.g., a multibinding agent and the aggregate of its unlinked ligand, the dose-response curve of each is determined under identical test conditions (e.g., in an in vitro or in vivo assay, in an appropriate animal model). The finding that the multibinding agent produces an equivalent biologic or therapeutic effect at a lower concentration than the aggregate unlinked ligand (e.g., on a per weight, per mole or per ligand basis) is indicative of enhanced potency.

"Selectivity" or "specificity" is a measure of the binding preferences of a ligand for different receptors. The selectivity of a ligand with respect to its target receptor relative to another receptor is given by the ratio of the respective values of $K_d$ (i.e., the dissociation constants for each ligand-receptor complex) or, in cases where a biological effect is observed below the $K_d$, the ratio of the respective $EC_{50}$s or $IC_{50}$s (i.e., the concentrations that produce 50% of the maximum response for the ligand interacting with the two distinct receptors).

The term "treatment" refers to any treatment of a disease or condition in a mammal, particularly a human, and includes:

(i) preventing the disease or condition from occurring in a subject which may be predisposed to the condition but has not yet been diagnosed with the condition and, accordingly, the treatment constitutes prophylactic treatment for the pathologic condition;

(ii) inhibiting the disease or condition, i.e., arresting its development;

(iii) relieving the disease or condition, i.e., causing regression of the disease or condition; or (iv) relieving the symptoms resulting from the disease or condition without addressing the underlying disease or condition, e.g., relieving symptoms of epilepsy, seizures, pain, stroke, ischemia, arrhythmia and depression, but not an underlying cause.

The phrase "disease or condition which is modulated by treatment with a multibinding Na$^+$ channel ligand" covers all disease states and/or conditions that are generally acknowledged in the art to be usefully treated with a ligand for a Na$^+$ channel in general, and those disease states and/or conditions that have been found to be usefully treated by a specific multibinding compound of our invention, i.e., the compounds of Formula I. Such disease states include, by way of example only, pathophysiological disorders, including hypertension, cardiac arrhythmogenesis, insulin-dependent diabetes, non-insulin dependent diabetes mellitus, diabetic neuropathy, seizures, tachycardia, ischemic heart disease, cardiac failure, angina, myocardial infarction, transplant rejection, autoimmune disease, sickle cell anemia, muscular dystrophy, gastrointestinal disease, mental disorder, sleep disorder, anxiety disorder, eating disorder, neurosis, alcoholism, inflammation, cerebrovascular ischemia, CNS diseases, epilepsy, Parkinson's disease, asthma, incontinence, urinary dysfunction, micturition disorder, irritable bowel syndrome, restenosis, subarachnoid hemorrhage, Alzheimers disease, drug dependence/addiction, schizophrenia, Huntington's chorea, tension-type headache, trigeminal neuralgia, cluster headache, migraine (acute and prophylaxis), inflammatory pain, neuropathic pain and depression.

The term "therapeutically effective amount" refers to that amount of multibinding compound that is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable excipient" is intended to include vehicles and carriers capable of being coadministered with a multibinding compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multibinding compounds also falls within the scope of the present invention.

Combinatorial Libraries

The methods described above lend themselves to combinatorial approaches for identifying multimeric compounds which possess multibinding properties. Specifically, factors such as the proper juxtaposition of the individual ligands of a multibinding compound with respect to the relevant array of binding sites on a target or targets is important, in optimizing the interaction of the multibinding compound with its target(s) and to maximize the biological advantage through multivalency. One approach is to identify a library of candidate multibinding compounds with properties spanning the multibinding parameters that are relevant for a particular target. These parameters include: (1) the identity of ligand(s), (2) the orientation of ligands, (3) the valency of the construct, (4) linker length, (5) linker geometry, (6) linker physical properties, and (7) linker chemical functional groups.

Libraries of multimeric compounds potentially possessing multibinding properties (i.e., candidate multibinding compounds) and comprising a multiplicity of such variables are prepared and these libraries are then evaluated via conventional assays corresponding to the ligand selected and the multibinding parameters desired. Considerations relevant to each of these variables are set forth below:

Selection of ligand(s)

A single ligand or set of ligands is (are) selected for incorporation into the libraries of candidate multibinding compounds which library is directed against a particular biological target or targets. The only requirement for the ligands chosen is that they are capable of interacting with the selected target(s). Thus, ligands may be known drugs, modified forms of known drugs, substructures of known drugs or substrates of modified forms of known drugs (which are competent to interact with the target), or other compounds. Ligands are preferably chosen based on known favorable properties that may be projected to be carried over to or amplified in multibinding forms. Favorable properties include demonstrated safety and efficacy in human patients, appropriate PK/ADME profiles, synthetic accessibility, and desirable physical properties such as solubility, logP, etc. However, it is crucial to note that ligands which display an unfavorable property from among the previous list may obtain a more favorable property through the process of multibinding compound formation; i.e., ligands should not necessarily be excluded on such a basis. For example, a ligand that is not sufficiently potent at a particular target so as to be efficacious in a human patient may become highly potent and efficacious when presented in multibinding form. A ligand that is potent and efficacious but not of utility because of a non-mechanism-related toxic side effect may have increased therapeutic index (increased potency relative to toxicity) as a multibinding compound. Compounds that exhibit short in vivo half-lives may have extended half-lives as multibinding compounds. Physical properties of ligands that limit their usefulness (e.g. poor bioavailability due to low solubility, hydrophobicity, hydrophilicity) may be rationally modulated in multibinding forms, providing compounds with physical properties consistent with the desired utility.

Orientation: selection of ligand attachment points and linking chemistry

Several points are chosen on each ligand at which to attach the ligand to the linker. The selected points on the ligand/linker for attachment are functionalized to contain complementary reactive functional groups. This permits probing the effects of presenting the ligands to their receptor(s) in multiple relative orientations, an important multibinding design parameter. The only requirement for choosing attachment points is that attaching to at least one of these points does not abrogate activity of the ligand. Such points for attachment can be identified by structural information when available. For example, inspection of a co-crystal structure of a protease inhibitor bound to its target allows one to identify one or more sites where linker attachment will not preclude the enzyme:inhibitor interaction. Alternatively, evaluation of ligand/target binding by nuclear magnetic resonance will permit the identification of sites non-essential for ligand/target binding. See, for example, Fesik, et al., U.S. Pat. No. 5,891,643. When such structural information is not available, utilization of structure-activity relationships (SAR) for ligands will suggest positions where substantial structural variations are and are not allowed. In the absence of both structural and SAR information, a library is merely selected with multiple points of attachment to allow presentation of the ligand in multiple distinct orientations. Subsequent evaluation of this library will indicate what positions are suitable for attachment.

It is important to emphasize that positions of attachment that do abrogate the activity of the monomeric ligand may also be advantageously included in candidate multibinding compounds in the library provided that such compounds bear at least one ligand attached in a manner which does not abrogate intrinsic activity. This selection derives from, for example, heterobivalent interactions within the context of a single target molecule. For example, consider a receptor antagonist ligand bound to its target receptor, and then consider modifying this ligand by attaching to it a second copy of the same ligand with a linker which allows the second ligand to interact with the same receptor molecule at sites proximal to the antagonist binding site, which include elements of the receptor that are not part of the formal antagonist binding site and/or are elements of the matrix surrounding the receptor such as the membrane. Here, the most favorable orientation for interaction of the second ligand molecule with the receptor/matrix may be achieved by attaching it to the linker at a position which abrogates activity of the ligand at the formal antagonist binding site. Another way to consider this is that the SAR of individual ligands within the context of a multibinding structure is often different from the SAR of those same ligands in momomeric form.

The foregoing discussion focused on bivalent interactions of dimeric compounds bearing two copies of the same ligand joined to a single linker through different attachment points, one of which may abrogate the binding/activity of the monomeric ligand. It should also be understood that bivalent advantage may also be attained with heterodimeric constructs bearing two different ligands that bind to common or different targets.

For example, an $Na^+$ channel blocker and an opioid agonist may be joined to a linker through attachment points which do not abrogate the binding affinity of the monomeric ligands for their respective receptor sites. Both target receptors are present on CNS nerve cells. If the opioid agonist unit enhances the activity of $Na^+$ channel blocker at the most important $Na^+$ channels, and the $Na^+$ channel blocker enhances the activity of the opioid agonist at the appropriate opioid receptors, the activity will be above and beyond that of the combination of the monomeric species.

Once the ligand attachment points have been chosen, one identifies the types of chemical linkages that are possible at those points. The most preferred types of chemical linkages are those that are compatible with the overall structure of the ligand (or protected forms of the ligand) readily and generally formed, stable and intrinsically inocuous under typical chemical and physiological conditions, and compatible with a large number of available linkers. Amide bonds, ethers, amines, carbamates, ureas, and sulfonamides are but a few examples of preferred linkages.

Linkers: spanning relevant multibinding parameters through selection of valency, linker length, linker geometry, rigidity, physical properties, and chemical functional groups In the library of linkers employed to generate the library of candidate multibinding compounds, the selection of linkers employed in this library of linkers takes into consideration the following factors:

Valency. In most instances the library of linkers is initiated with divalent linkers. The choice of ligands and proper juxtaposition of two ligands relative to their binding sites permits such molecules to exhibit target binding affinities and specificities more than sufficient to confer biological advantage. Furthermore, divalent linkers or constructs are also typically of modest size such that they retain the desirable biodistribution properties of small molecules.

Linker length. Linkers are chosen in a range of lengths to allow the spanning of a range of inter-ligand distances that encompass the distance preferable for a given divalent interaction. In some instances the preferred distance can be estimated rather precisely from high-resolution structural information of targets, typically enzymes and soluble receptor targets. In other instances where high-resolution structural information is not available (such as 7TM G-protein coupled receptors), one can make use of simple models to estimate the maximum distance between binding sites either on adjacent receptors or at different locations on the same receptor. In situations where two binding sites are present on the same target (or target subunit for multisubunit targets), preferred linker distarices are 2–20 Å, with more preferred linker distances of 3–12 Å. In situations where two binding sites reside on separate (e.g., protein) target sites, preferred linker distances are 20–100 Å, with more preferred distances of 30–70 Å.

Linker geometry and rigidity. The combination of ligand attachment site, linker length, linker geometry, and linker rigidity determine the possible ways in which the ligands of candidate multibinding compounds may be displayed in three dimensions and thereby presented to their binding sites. Linker geometry and rigidity are nominally determined by chemical composition and bonding pattern, which may be controlled and are systematically varied as another spanning function in a multibinding array. For example, linker geometry is varied by attaching two ligands to the ortho, meta, and para positions of a benzene ring, or in cis- or trans-arrangements at the 1,1- vs. 1,2- vs. 1,3- vs. 1,4- positions around a cyclohexane core or in cis- or trans-arrangements at a point of ethylene unsaturation. Linker rigidity is varied by controlling the number and relative energies of different conformational states possible for the linker. For example, a divalent compound bearing two ligands joined by 1,8-octyl linker has many more degrees of freedom, and is therefore less rigid than a compound in which the two ligands are attached to the 4,4' positions of a biphenyl linker.

Linker physical properties. The physical properties of linkers are nominally determined by the chemical constitution and bonding patterns of the linker, and linker physical properties impact the overall physical properties of the candidate multibinding compounds in which they are included. A range of linker compositions is typically selected to provide a range of physical properties (hydrophobicity, hydrophilicity, amphiphilicity, polarizability, acidity, and basicity) in the candidate multibinding compounds. The particular choice of linker physical properties is made within the context of the physical properties of the ligands they join and preferably the goal is to generate molecules with favorable PK/ADME properties. For example, linkers can be selected to avoid those that are too hydrophilic or too hydrophobic to be readily absorbed and/or distributed in vivo.

Linker chemical functional groups. Linker chemical functional groups are selected to be compatible with the chemistry chosen to connect linkers to the ligands and to impart the range of physical properties sufficient to span initial examination of this parameter.

Combinatorial synthesis

Having chosen a set of n ligands (n being determined by the sum of the number of different attachment points for each ligand chosen) and m linkers by the process outlined above, a library of (n!)m candidate divalent multibinding compounds is prepared which spans the relevant multibinding design parameters for a particular target. For example, an array generated from two ligands, one which has two attachment points (A1, A2) and one which has three attachment points (B1, B2, B3) joined in all possible combinations provide for at least 15 possible combinations of multibinding compounds:

| A1-A1 | A1-A2 | A1-B1 | A1-B2 | A1-B3 | A2-A2 | A2-B1 | A2-B2 |
|---|---|---|---|---|---|---|---|
| A2-B3 | B1-B1 | B1-B2 | B1-B3 | B2-B2 | B2-B3 | B3-B3 | |

When each of these combinations is joined by 10 different linkers, a library of 150 candidate multibinding compounds results.

Given the combinatorial nature of the library, common chemistries are preferably used to join the reactive functionalities on the ligands with complementary reactive functionalities on the linkers. The library therefore lends itself to efficient parallel synthetic methods. The combinatorial library can employ solid phase chemistries well known in the art wherein the ligand and/or linker is attached to a solid support. Alternatively and preferably, the combinatorial libary is prepared in the solution phase. After synthesis, candidate multibinding compounds are optionally purified before assaying for activity by, for example, chromatographic methods (e.g., HPLC).

Analysis of array by biochemical analytical, pharmacological, and computational methods Various methods are used to characterize the properties and activities of the candidate multibinding compounds in the library to determine which compounds possess multibinding properties. Physical constants such as solubility under various solvent conditions and logD/clogD values are determined. A combination of NMR spectroscopy and computational methods is used to determine low-energy conformations of the candidate multibinding compounds in fluid media. The ability of the members of the library to bind to the desired target and other targets is determined by various standard methods, which include radioligand displacement assays for receptor and ion channel targets, and kinetic inhibition analysis for many enzyme targets. In vitro efficacy, such as for receptor agonists and antagonists, ion channel blockers, and antimicrobial activity, are also determined. Pharmacological data, including oral absorption, everted gut penetration, other pharmacokinetic parameters and efficacy data are determined in appropriate models. In this way, key structure-activity relationships are obtained for multibinding design parameters which are then used to direct future work.

The members of the library which exhibit multibinding properties, as defined herein, can be readily determined by conventional methods. First those members which exhibit multibinding properties are identified by conventional methods as described above including conventional assays (both in vitro and in vivo.

Second, ascertaining the structure of those compounds which exhibit multibinding properties can be accomplished via art recognized procedures. For example, each member of the library can be encrypted or tagged with appropriate information allowing determination of the structure of relevant members at a later time. See: for example, Dower, et al., International Patent Application Publication No. WO 93/06121; Brenner, et al. , Proc. Natl. Acad. Sci., USA, 89:5181 (1992); Gallop, et al., U.S. Pat. No. 5,846,839; each of which are incorporated herein by reference in its entirety. Alternatively, the structure of relevant multivalent compounds can also be determined from soluble and untagged libaries of candidate multivalent compounds by methods known in the art such as those described by Hindsgaul, et al., Canadian Patent Application No. 2,240,325 which was published on Jul. 11, 1998. Such methods couple frontal affinity chromatography with mass spectroscopy to determine both the structure and relative binding affinities of candidate multibinding compounds to receptors.

The process set forth above for dimeric candidate multibinding compounds can, of course, be extended to trimeric candidate compounds and higher analogs thereof.

Follow-up synthesis and analysis of additional array(s)

Based on the information obtained through analysis of the initial library, an optional component of the process is to ascertain one or more promising multibinding "lead" compounds as defined by particular relative ligand orientations, linker lengths, linker geometries, etc. Additional libraries are then generated around these leads to provide for further information regarding structure to activity relationships, These arrays typically bear more focused variations in linker structure to further optimize target affinity and/or activity at the target (antagonism, partial agoinism, etc.), and/or alter physical properties. By iterative redesign/analysis using the novel principles of multibinding design along with classical medicinal chemistry, biochemistry, and pharmacrology approaches, one is able to prepare and identify optimal multibinding compounds that exhibit biological advantage towards their targets and as therapeutic agents.

To further elaborate upon this procedure, suitable divalent linkers include, by way of example only, those derived from dicarboxylic acids, disulfonylhalides, dialdehydes, diketones, dihalides, diisocyanates, diamines, diols, mixtures of carboxylic acids, sulfonylhalides, aldehydes, ketones, halides, isocyanates, amines and diols. In each case, the carboxylic acid, sulfonylhalide, aldehyde, ketone, halide, isocyanate, amine and diol functional group is reacted with a complementary functionality on the ligand to form a covalent linkage. Such complementary functionality is well known in the art as illustrated in the following table:

| COMPLEMENTARY BINDING CHEMISTRIES | | |
|---|---|---|
| First Reactive Group | Second Reactive Group | Linkage |
| hydroxyl | isocyanate | urethane |
| amine | epoxide | β-aminohydroxy |
| sulfonyl halide | amine | sulfonamide |
| carboxyl acid | amine | amide |
| hydroxyl | alkyl/aryl halide | ether |
| aldehyde | amine/NaCNBH$_3$ | amine |
| ketone | amine/NaCNBH$_3$ | amine |
| amine | isocyanate | urea |

The following table illustrates, by way of example, starting materials (identified as X-1 through X-418) that can be used to prepare linkers incorporated in the multibinding compounds of this invention utilizing the chemistry described above. For example, 1,10-decanedicarboxylic acid, X1, can be reacted with 2 equivalents of a ligand carrying an amino group in the presence of a coupling reagent such as DCC to provide a bivalent multibinding compound of formula (I) wherein the ligands are linked via a 1,10-decanediamido linking group.

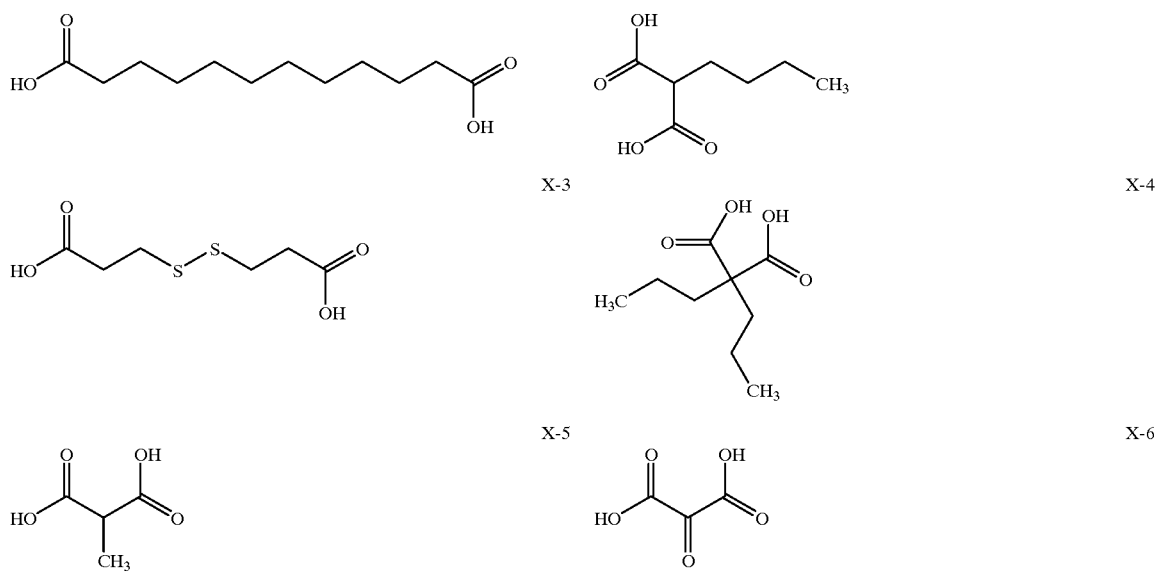

-continued
X-7
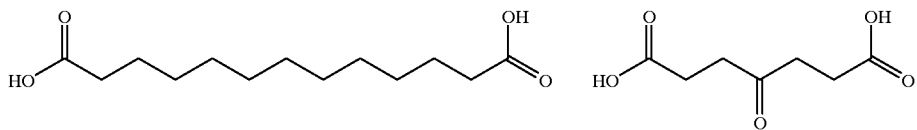
X-8
X-9
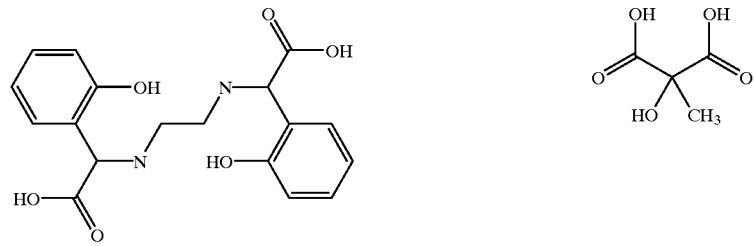
X-10
X-11
X-12
X-13
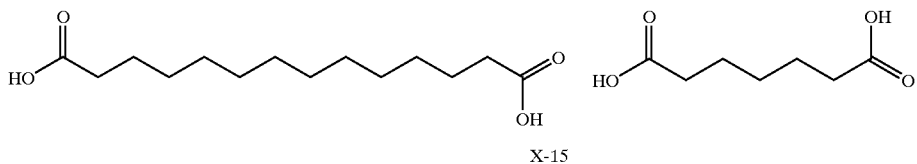
X-14
X-15
X-16
X-17
X-18
X-19
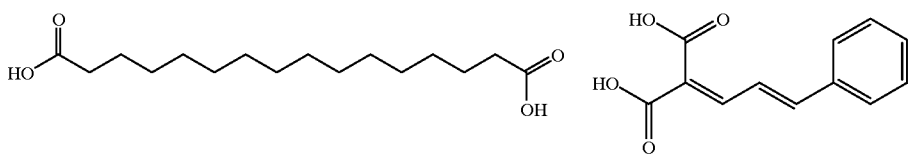
X-20
X-21
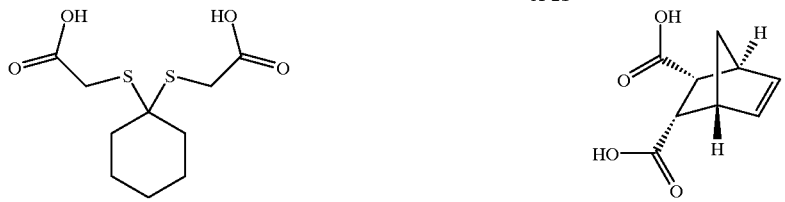
X-22

-continued
X-23
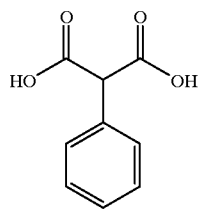
X-24
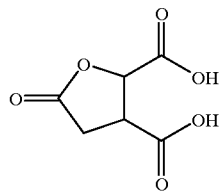
X-25
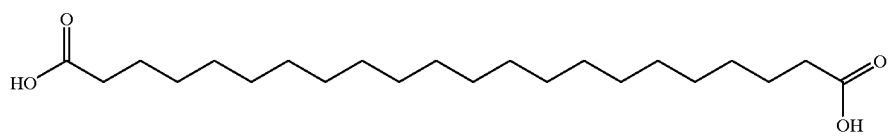
X-26
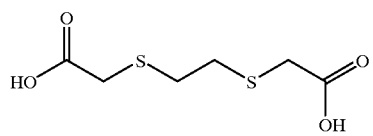
X-27
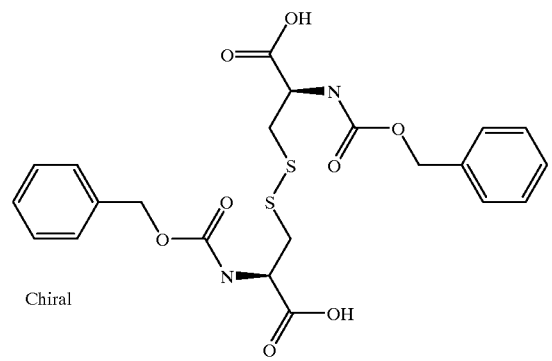
X-28
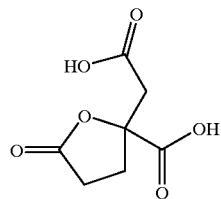
X-29
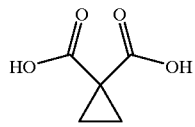
X-30
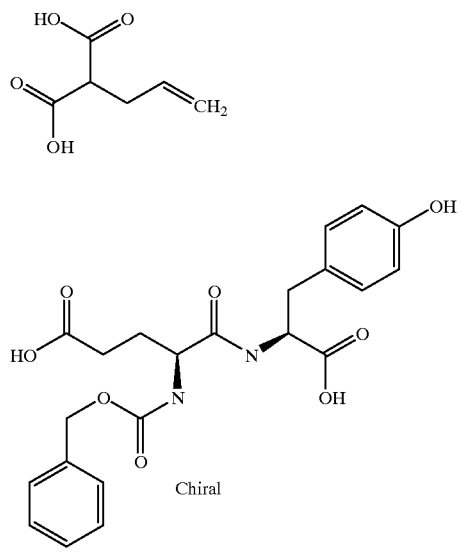
X-31
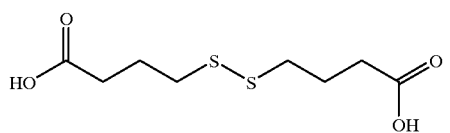
X-32
X-33
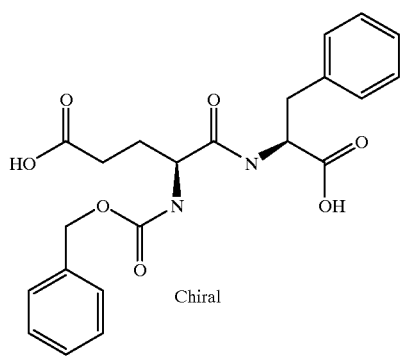

-continued
X-34 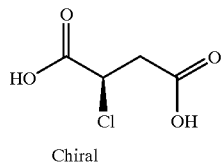 X-35 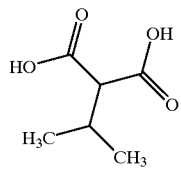
X-36 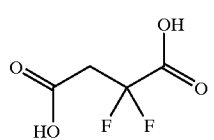 X-37 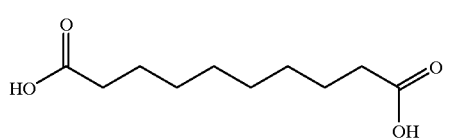
X-38 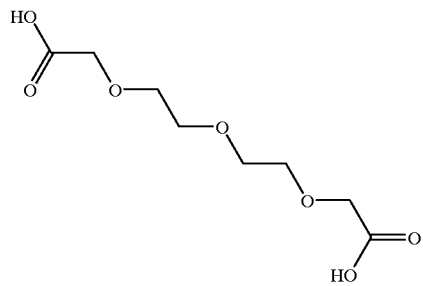 X-39 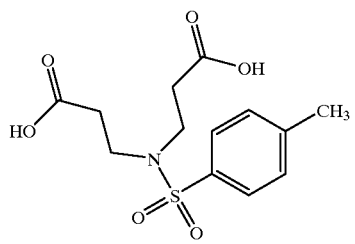
X-40 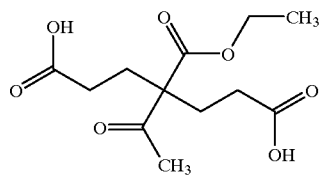 X-41 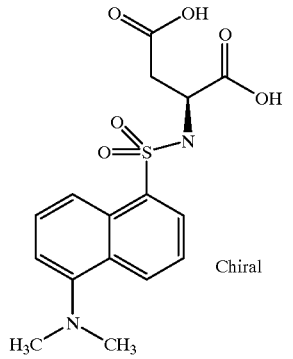
X-42 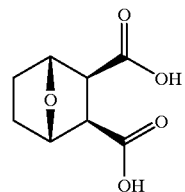 X-43 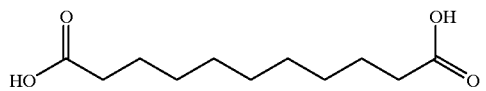
X-44 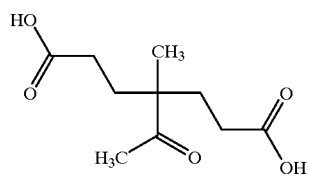 X-45 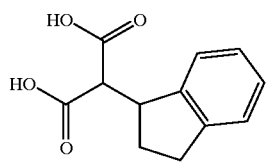

-continued
X-46
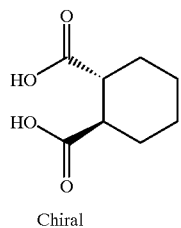
Chiral
X-47
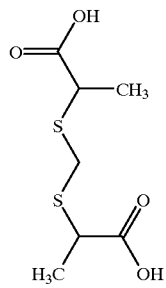
X-48
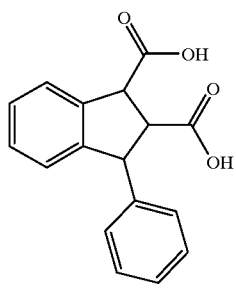
X-49
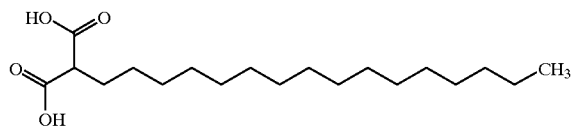
X-50
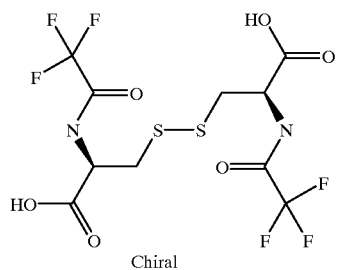
Chiral
X-51
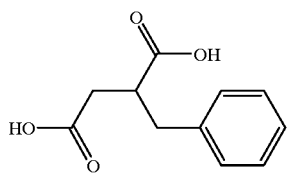
X-52
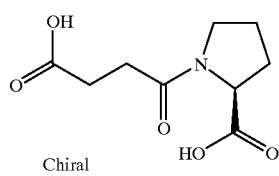
Chiral
X-53
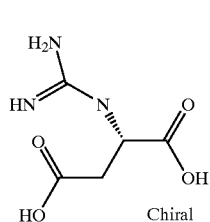
Chiral
X-54
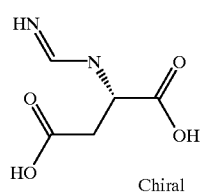
Chiral
X-55
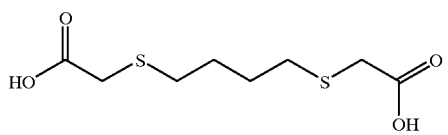
X-56
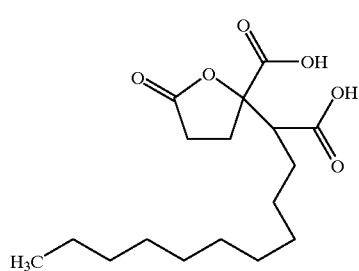
X-57
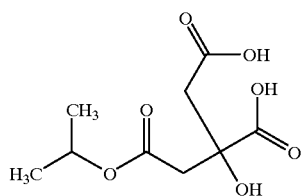

-continued
X-58
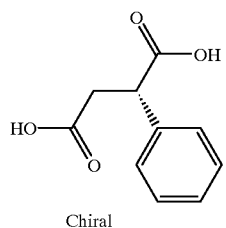
Chiral
X-59
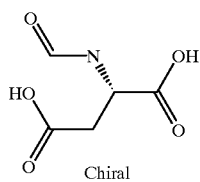
Chiral
X-60
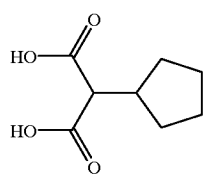
X-61
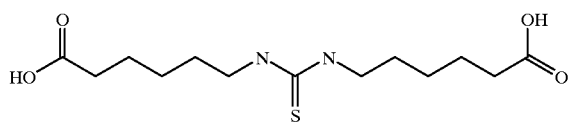
X-62
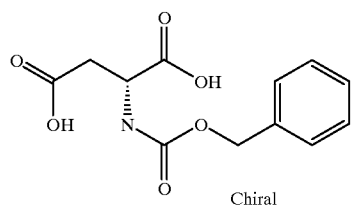
Chiral
X-63
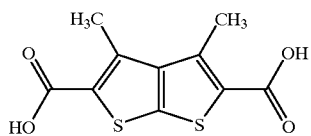
X-64
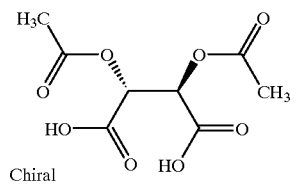
Chiral
X-65
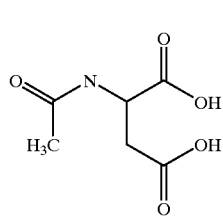
X-66
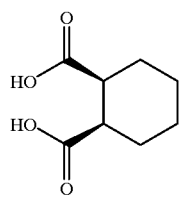
X-67
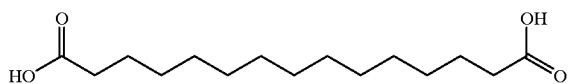
X-68
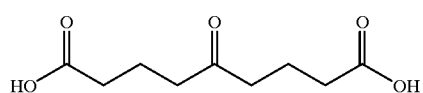
X-69
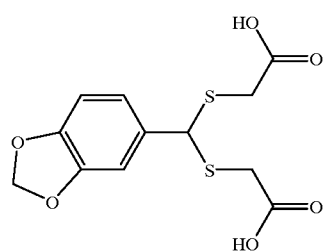

-continued
X-70
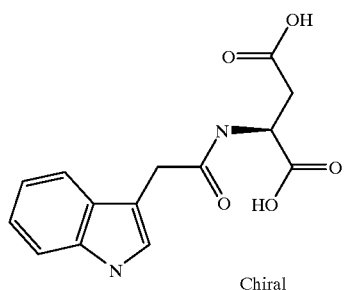
Chiral
X-71
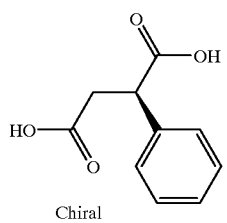
Chiral
X-72
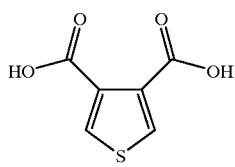
X-73
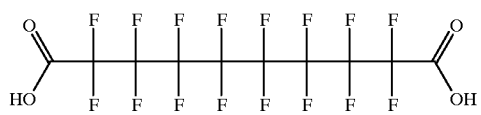
X-74
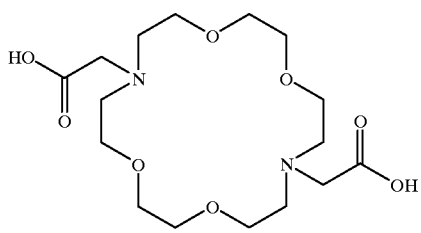
X-75
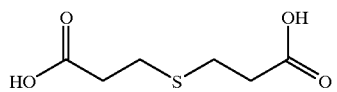
X-76
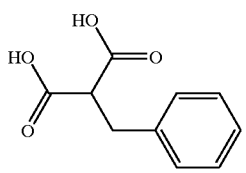
X-77
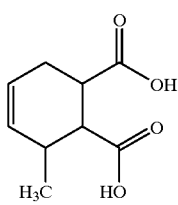
X-78
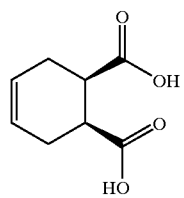
X-79
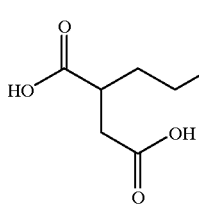
X-80
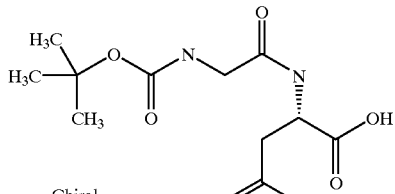
Chiral
X-81
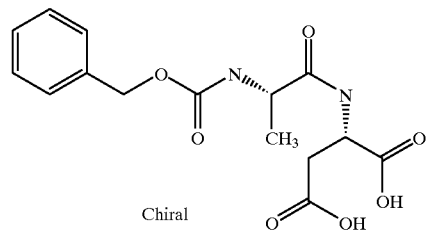
Chiral -continued
X-82
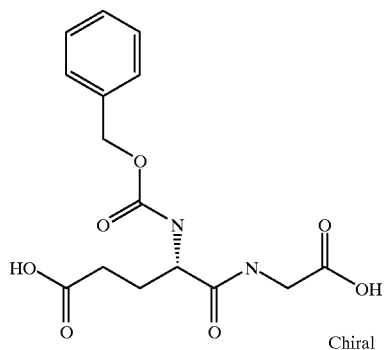
Chiral
X-83
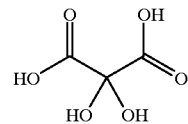
X-84
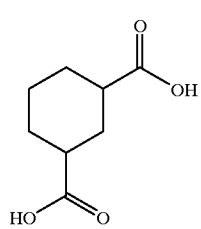
X-85
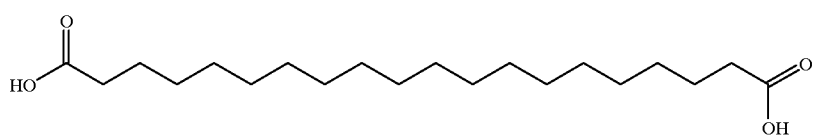
X-86
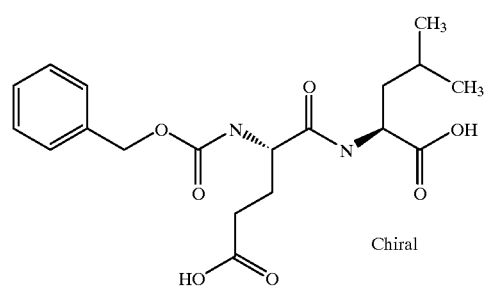
Chiral
X-87
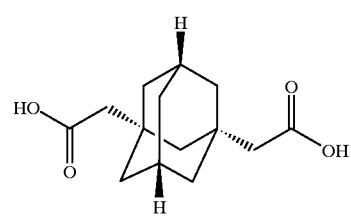
X-88
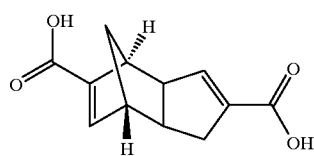
X-89
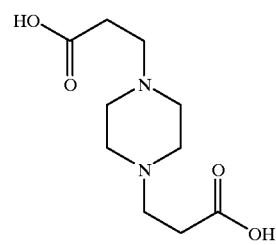
X-90
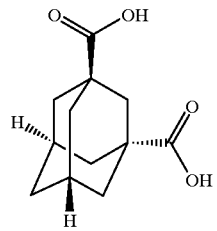
X-91
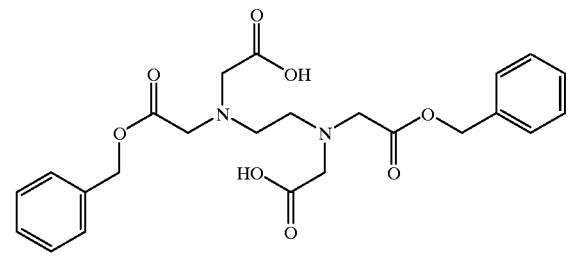

-continued
X-92 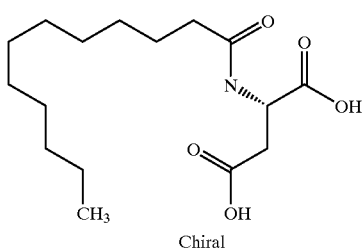
Chiral
X-93 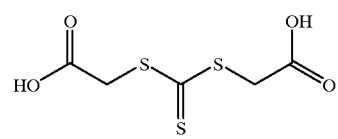
X-94 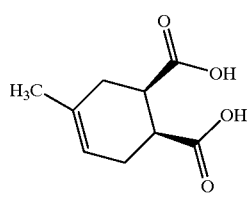
X-95 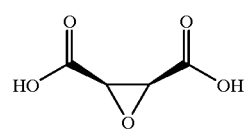
X-96 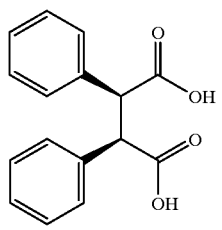
X-97 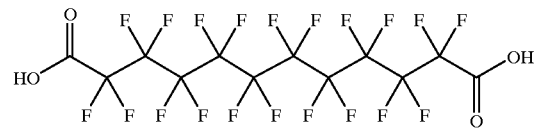
X-98 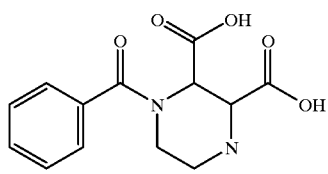
X-99 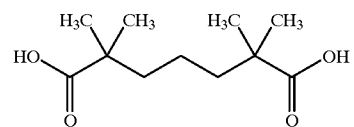
X-100 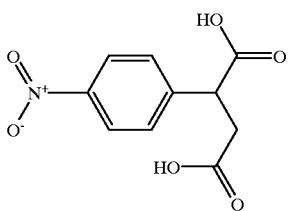
X-101 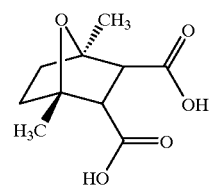
X-102 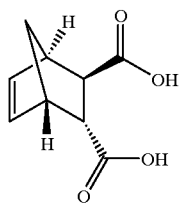
X-103 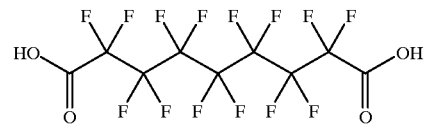
X-104 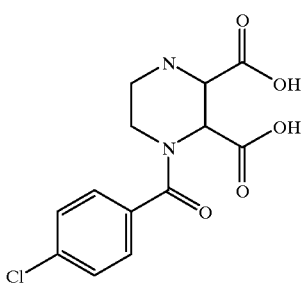
X-105 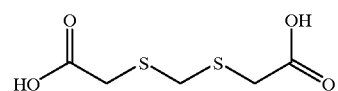

-continued
X-106
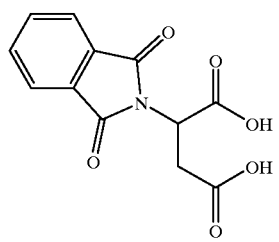
X-107
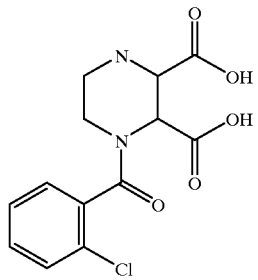
X-108
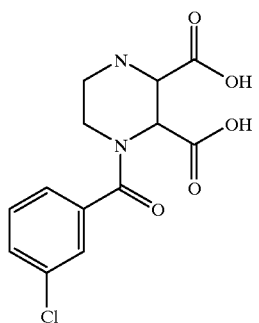
X-109
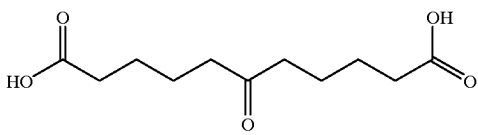
X-110
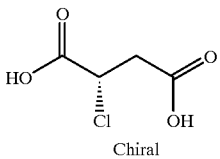
X-111
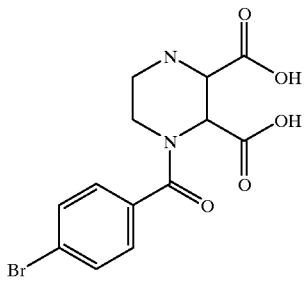
X-112
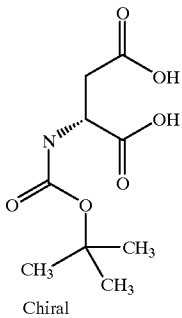
X-113
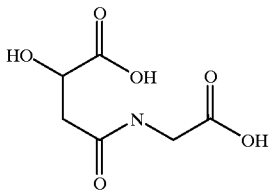
X-114
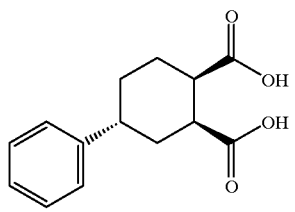
X-115
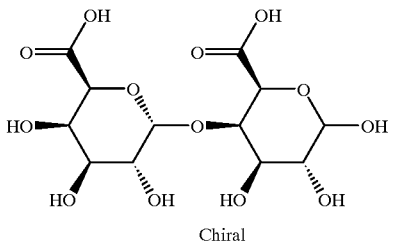

-continued
X-116
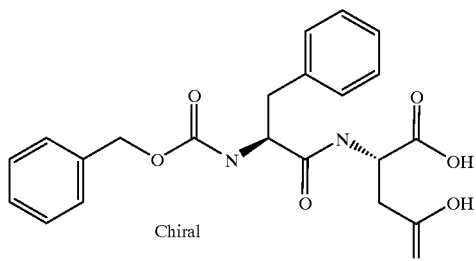
X-117
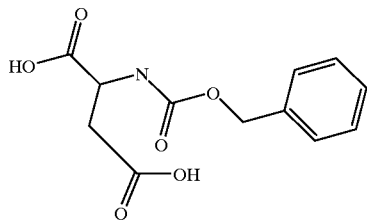
X-118
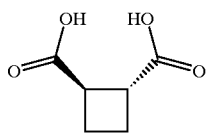
X-119
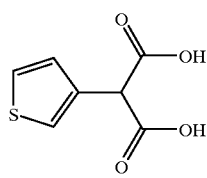
X-120
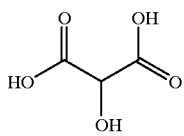
X-121
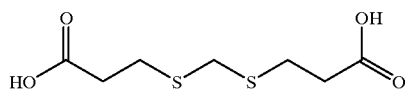
X-122
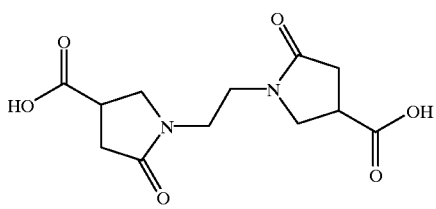
X-123
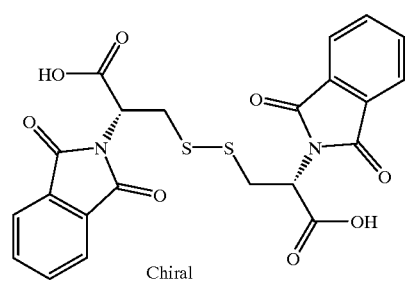
X-124
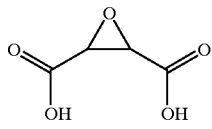
X-125
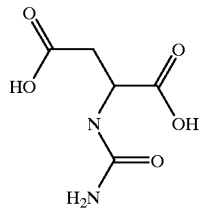
X-126
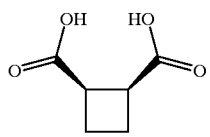
X-127
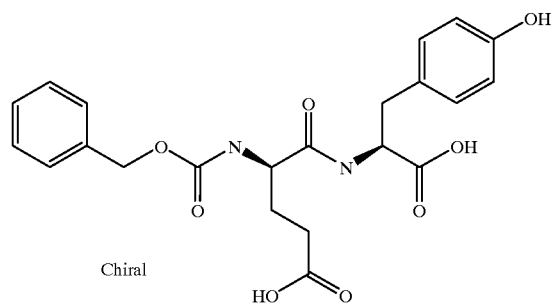
X-128
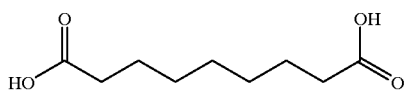
X-129
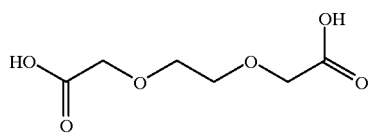

-continued

X-130

X-131

X-132

Disulfonyl Halides

X-133

X-134

X-135

X-136

X-137

X-138

X-139

X-140

X-141

X-142

-continued

Dialdehydes

-continued
X-157 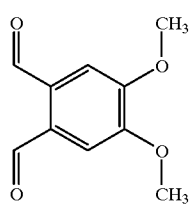
X-158 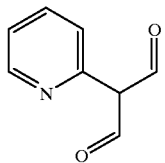
X-159 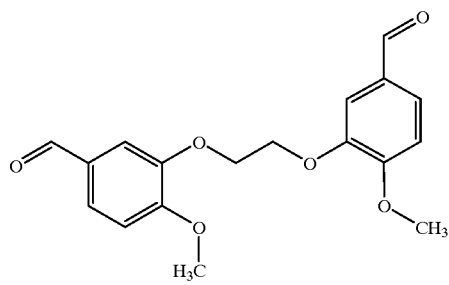
X-160 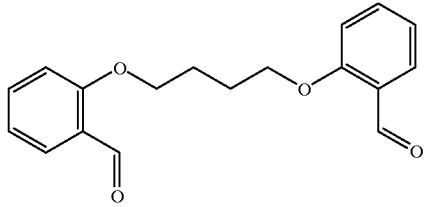
X-161 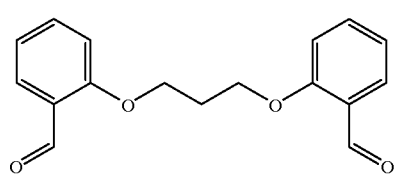
X-162 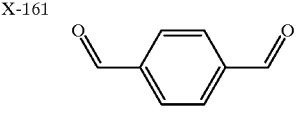
X-163 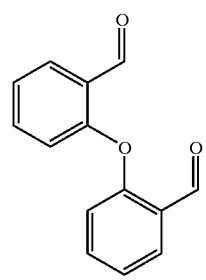
X-164 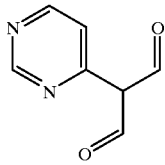
X-165 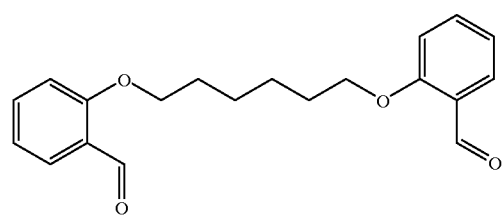
X-166 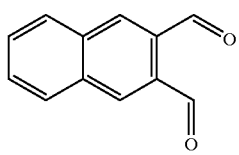
X-167 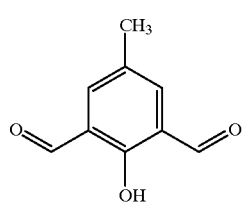
X-168 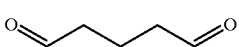
X-169 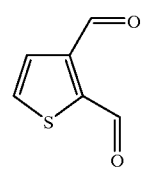
X-170 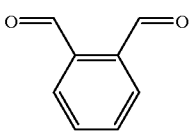

-continued
X-171 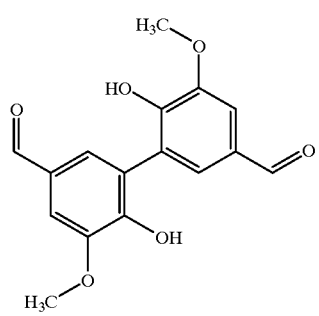
X-172 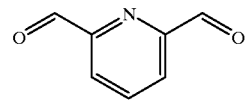
X-173 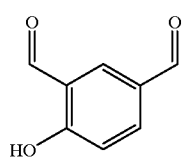
X-174 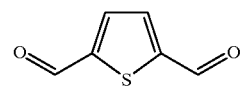
Dihalides
X-175 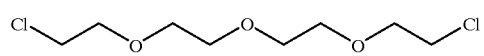
X-176 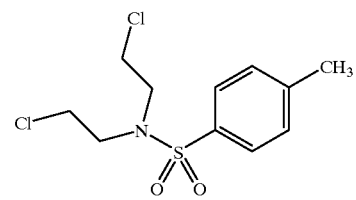
X-177 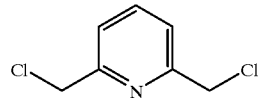
X-178 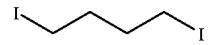
X-179 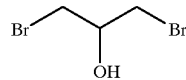
X-180 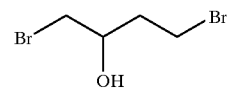
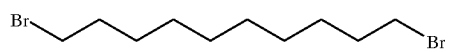
X-181 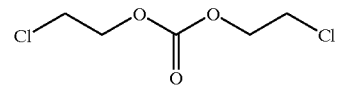
X-183 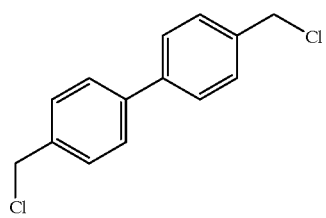
X-184 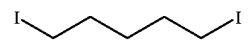
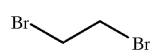
X-185 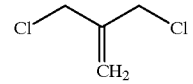
X-187 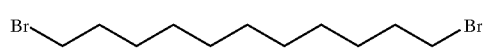
X-188 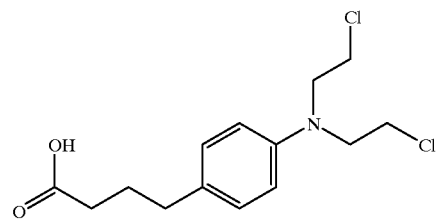

-continued
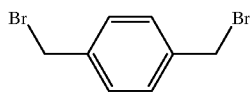
X-189
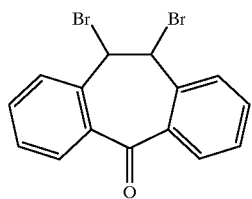
X-190
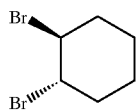
X-191
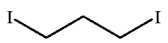
X-192
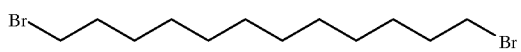
X-193
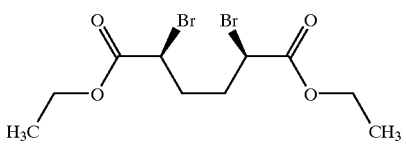
X-194
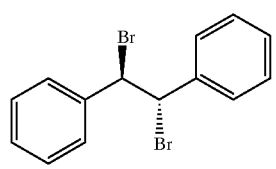
X-195
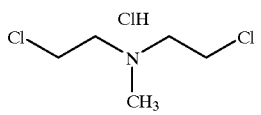
X-196
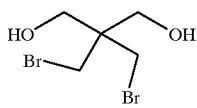
X-197
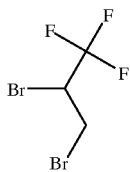
X-198
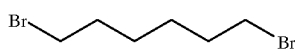
X-199
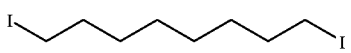
X-200
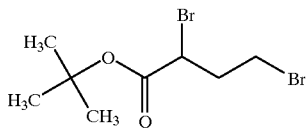
X-201
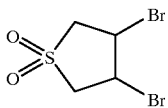
X-202
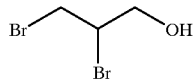
X-203
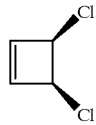
X-204
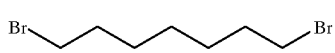
X-205
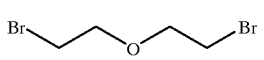
X-206
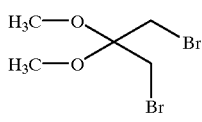
X-207
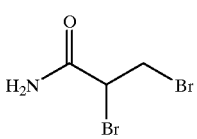
X-208
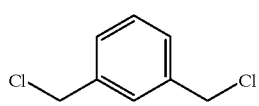
X-209
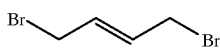
X-210

-continued
X-211 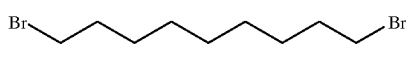
X-212 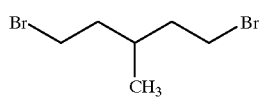
X-213 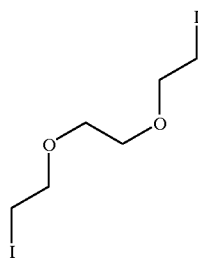
X-214 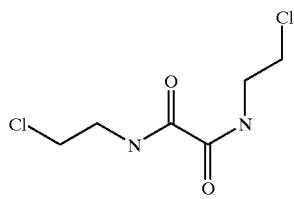
Diisocyanates
X-215 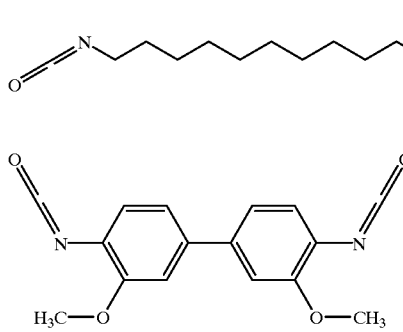
X-216 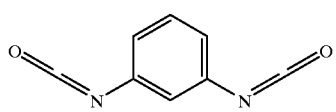
X-217 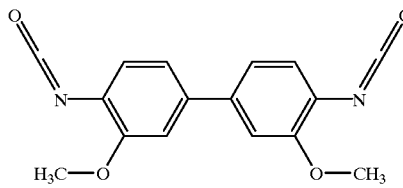
X-218 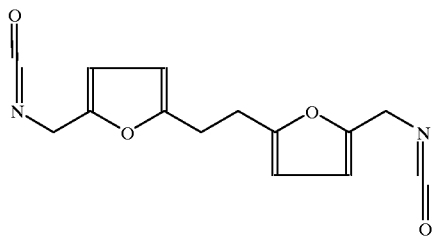
X-219 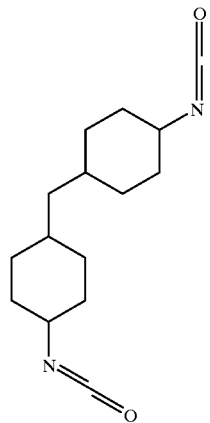
X-220 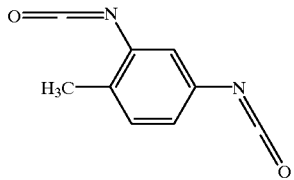
X-221 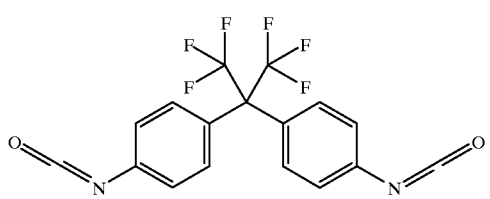
X-222 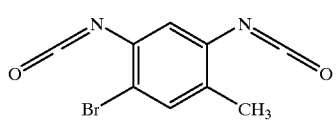

X-223
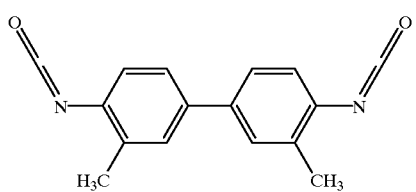
X-224
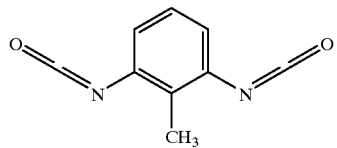
X-225
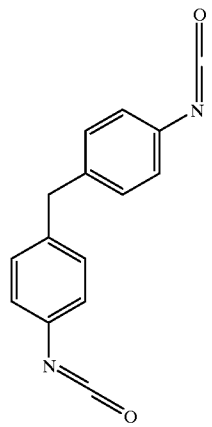
X-226
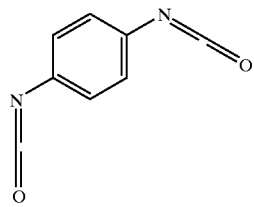
X-227
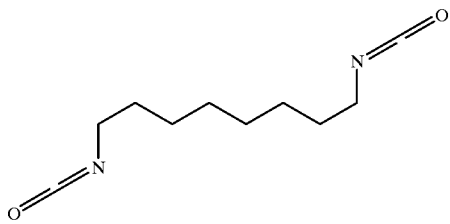
X-228
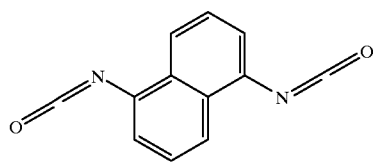
X-229
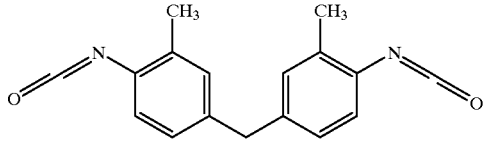
X-230
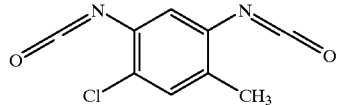
X-231
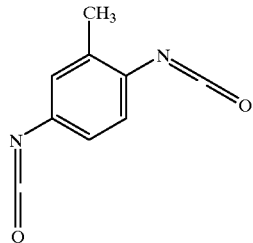
X-232
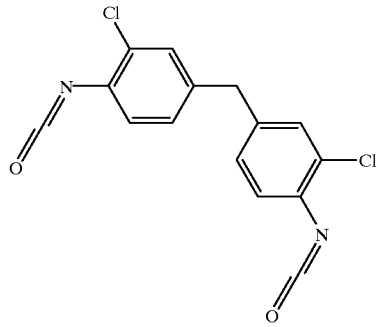
X-233
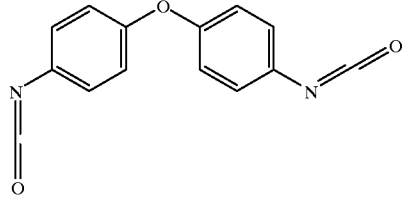
X-234
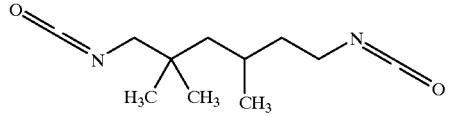

-continued
X-235
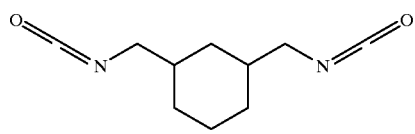
X-236
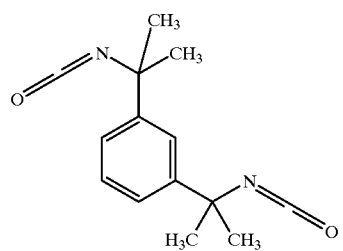
X-237
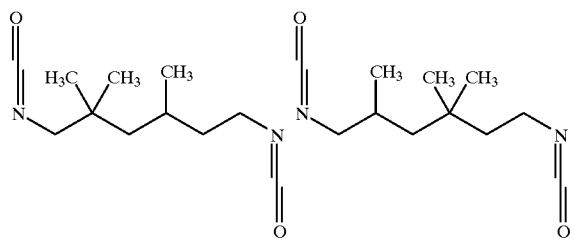
X-238
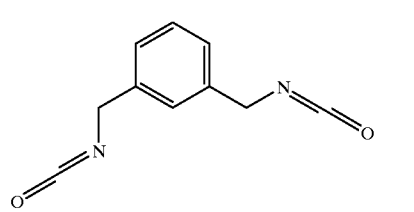
X-239
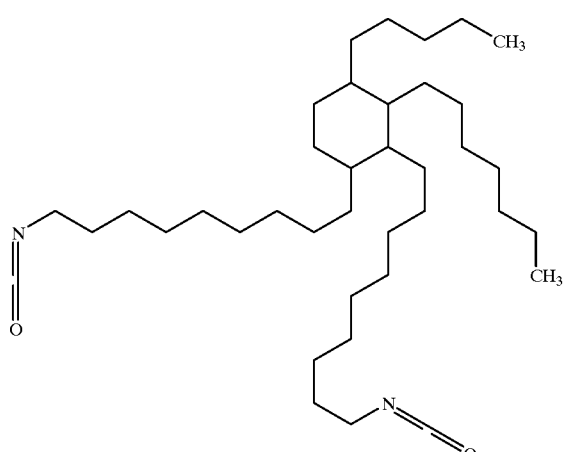
X-240
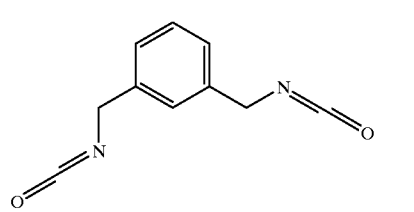
X-241
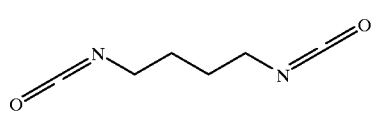
X-242
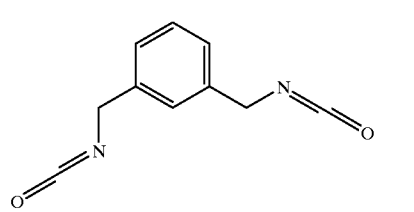
X-243
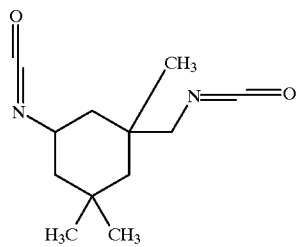
X-244
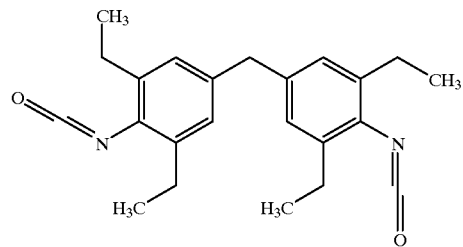
X-245
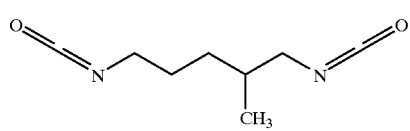
X-246
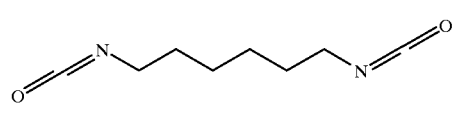

-continued
X-247 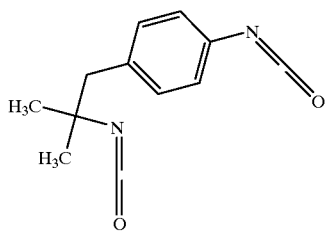
X-248 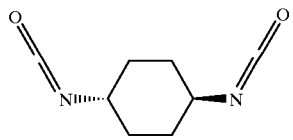
Diamines
X-249 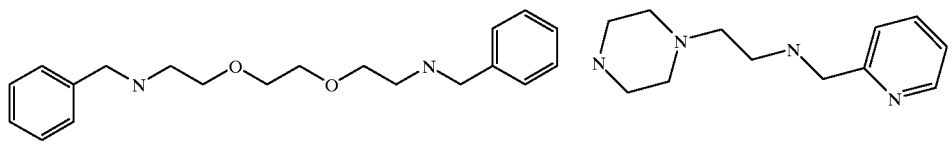
X-250
X-251 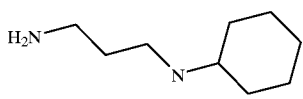
X-252 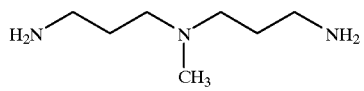
X-253 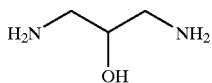
X-254 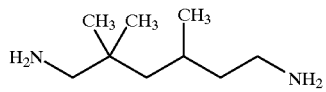
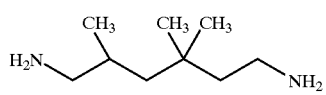
X-255 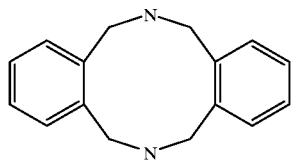
X-256 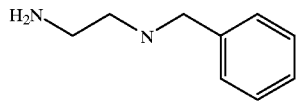
X-257 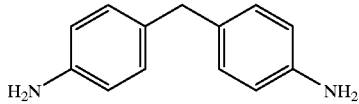
X-258 
X-259 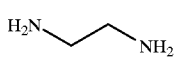
X-260 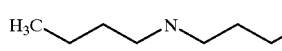
X-261 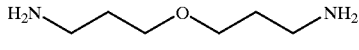
X-262 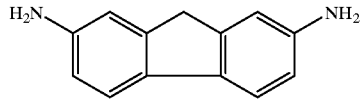
X-263 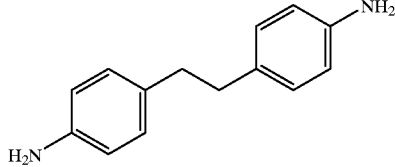
X-264 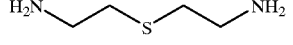
X-265

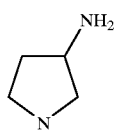
X-266
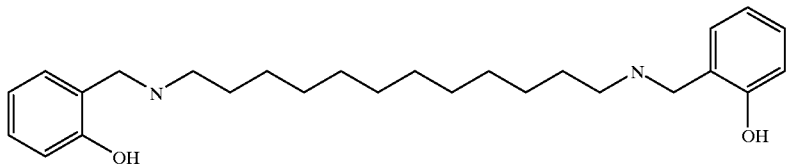
X-267
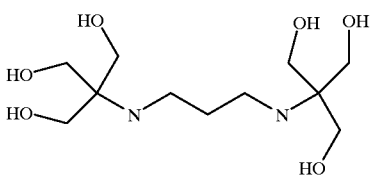
X-268
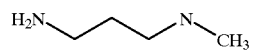
X-269
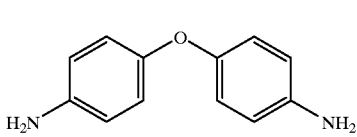
X-270
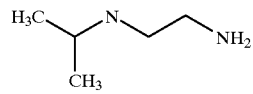
X-271
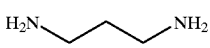
X-272
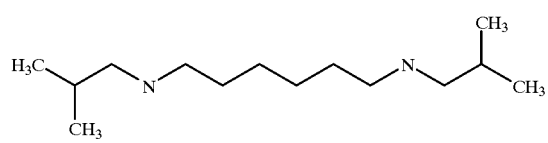
X-273
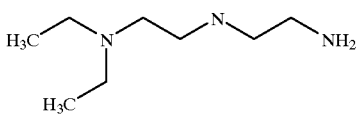
X-274
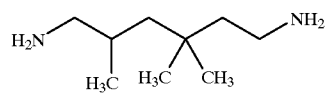
X-275
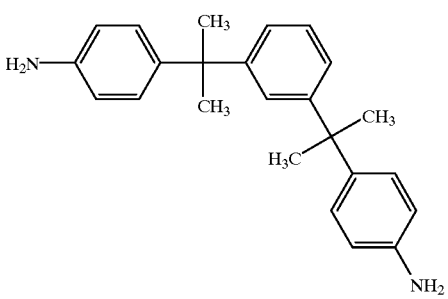
X-276
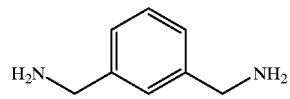
X-277
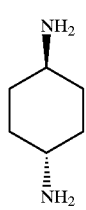
X-278
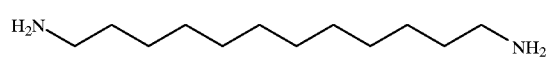
X-279
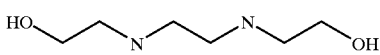
X-280
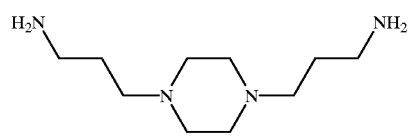
X-281

-continued
X-282
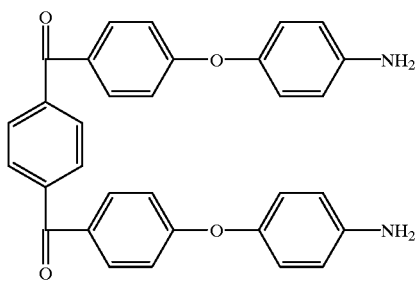
X-283
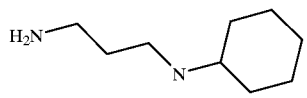
X-284
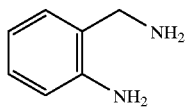
X-285
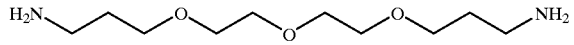
X-286
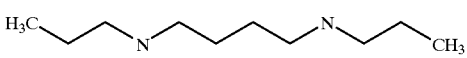
X-287
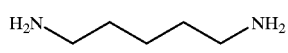
X-288
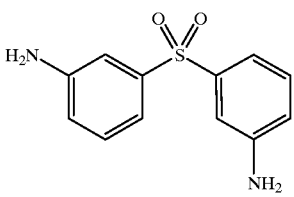
X-289
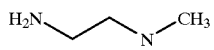
X-290
X-291
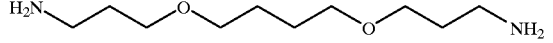
X-292
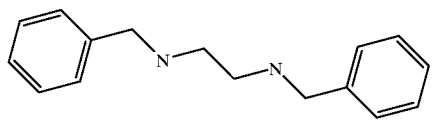
X-293
X-294
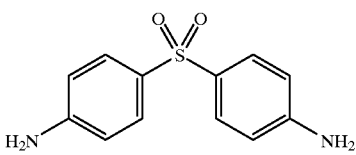
X-295
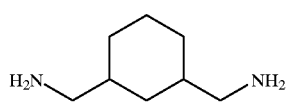
X-296
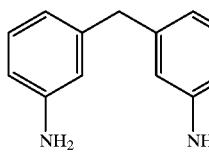
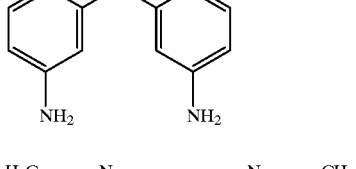
X-297
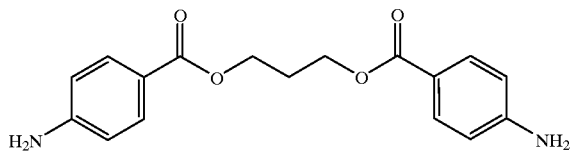
X-298
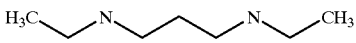
X-299
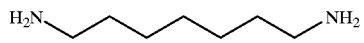
X-300
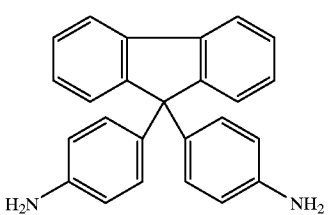
X-301

X-302
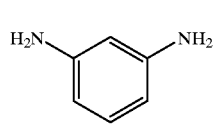
X-303
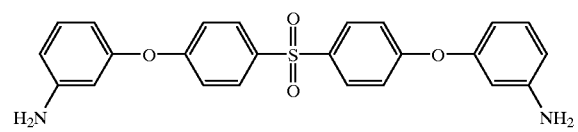
X-304
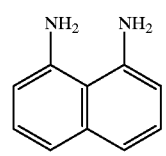
X-305
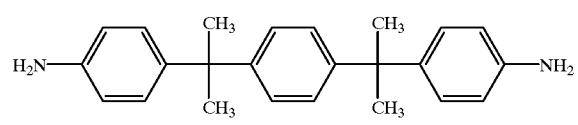
X-306
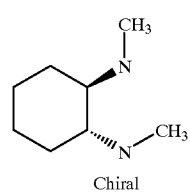
X-307
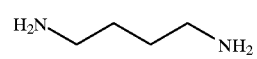
X-308
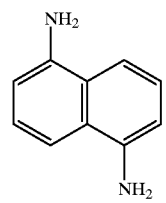
X-309
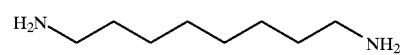
X-310
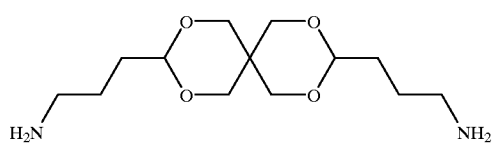
X-311
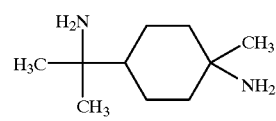
X-312
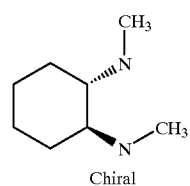
X-313
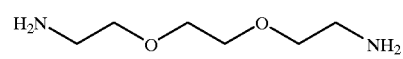
X-314
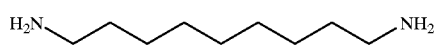
X-315
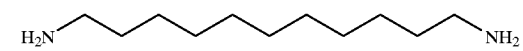
X-316
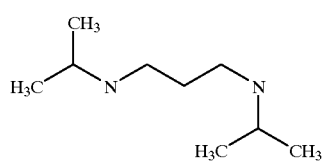
X-317
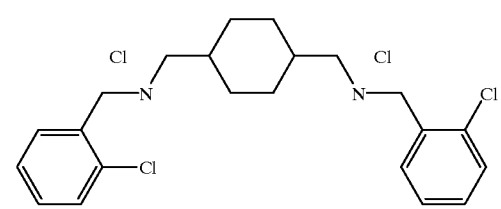

X-318
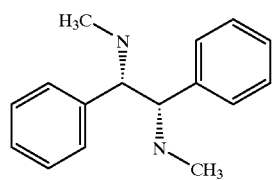
Chiral
X-319
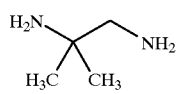
X-320
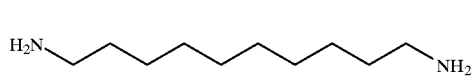
X-321
X-322
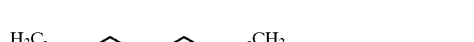
X-323
X-324
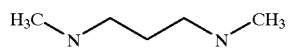
X-325
Diols
X-326
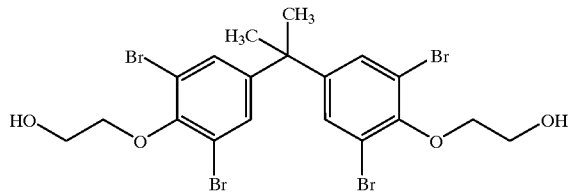
X-327
X-328
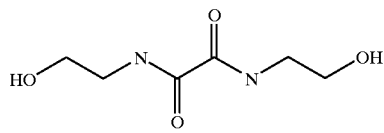
X-329
X-330
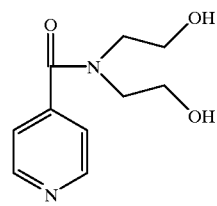
X-331
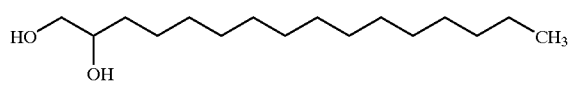
X-332
X-333
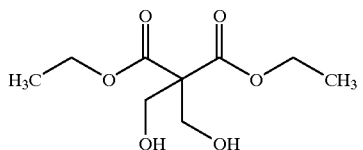

-continued
X-334 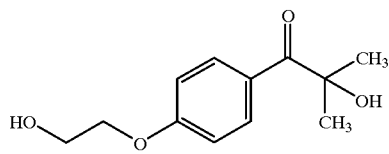 X-335 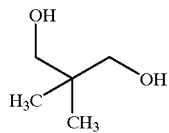
X-336 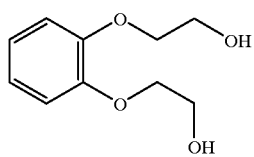 X-337 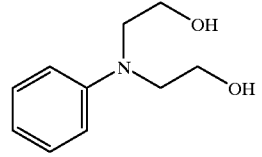
X-338 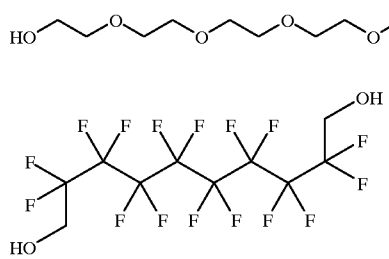 X-339 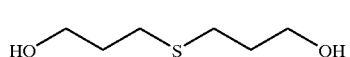
X-340 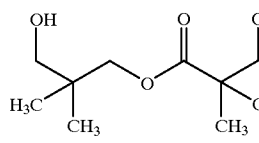 X-341 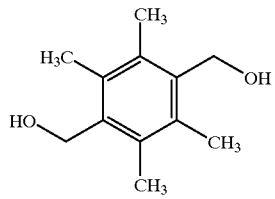
X-342 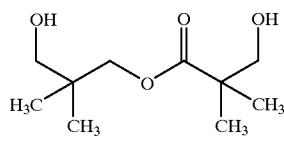 X-343 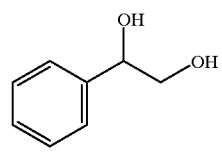
X-344 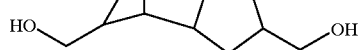 X-345 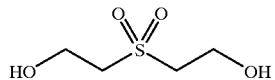
X-346 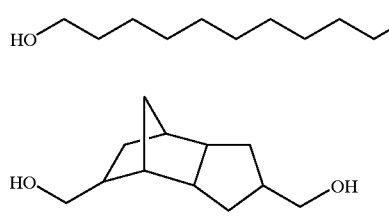 X-347 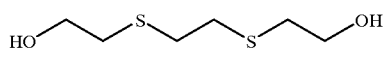
X-348 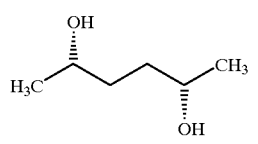 X-349 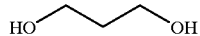
X-350 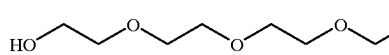 X-351 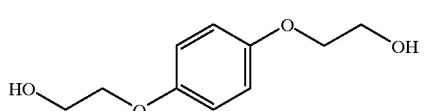
X-352 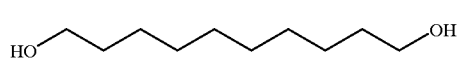 X-353 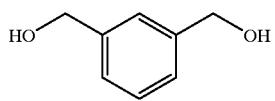

-continued
X-354 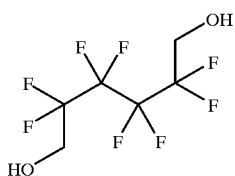 X-355 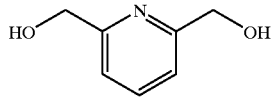
X-356 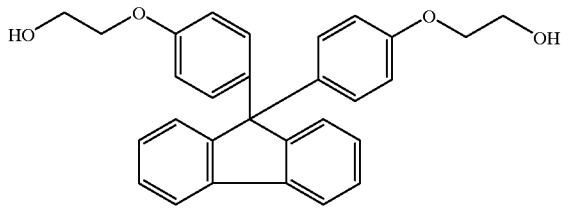 X-357 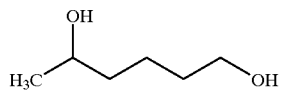
X-358 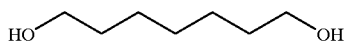 X-359 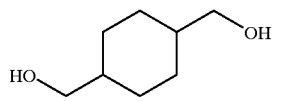
X-360 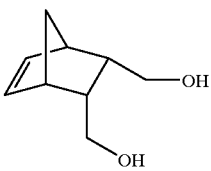 X-361 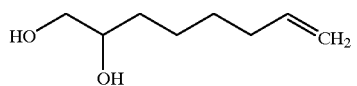
X-362 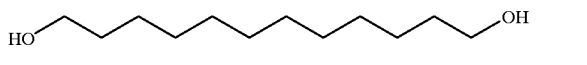 X-363 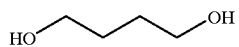
X-364 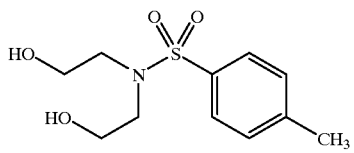 X-365 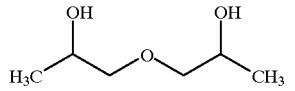
X-366 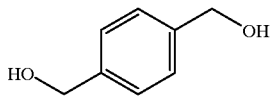 X-367 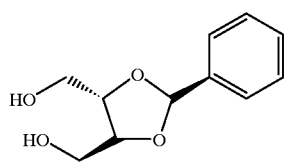
X-368 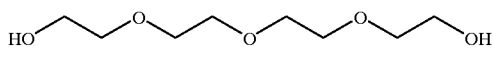 X-369
X-370 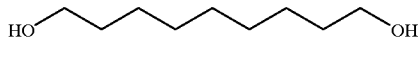 X-371 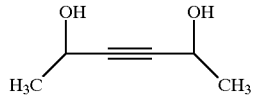

-continued
X-372
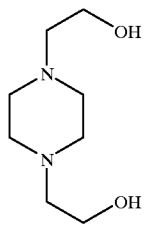
X-373
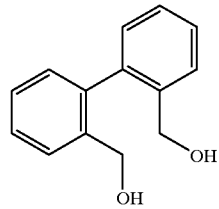
X-374
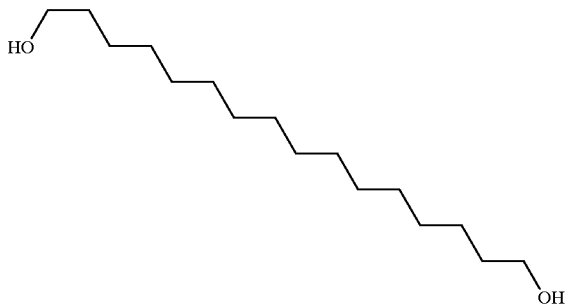
X-375
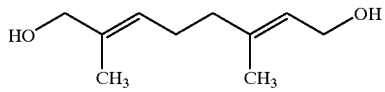
X-376
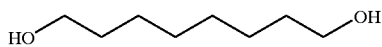
X-377
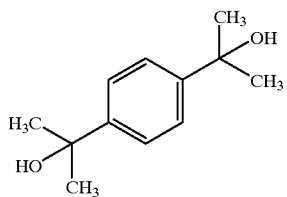
X-378
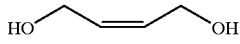
X-379
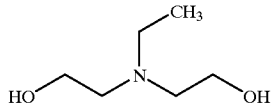
X-380
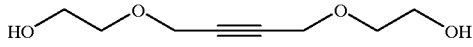
X-381
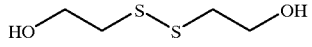
X-382
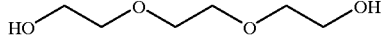
X-383
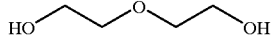
X-384
X-385
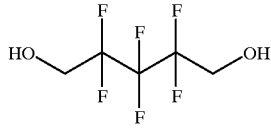
Dithiols
X-386
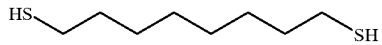
X-387
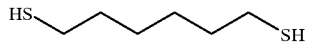
X-388
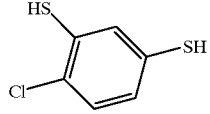
X-389
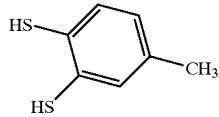

-continued
X-390
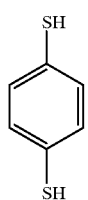
X-391
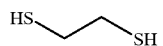
X-392
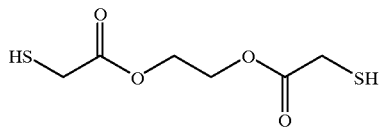
X-393
X-394
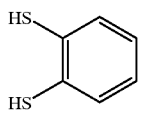
X-395
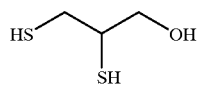
X-396
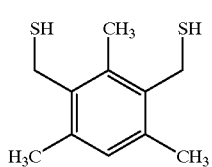
X-397
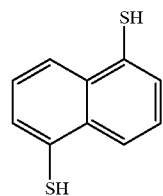
X-398
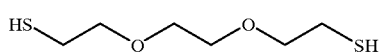
X-399
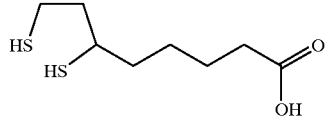
X-400
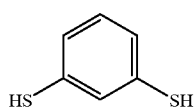
X-401
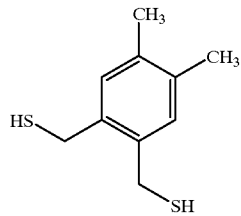
X-402
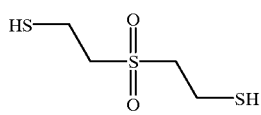
X-403
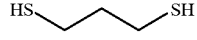
X-404
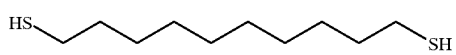
X-405
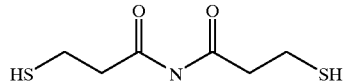
X-406
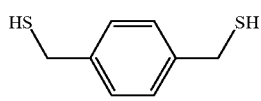
X-407
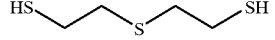
X-408
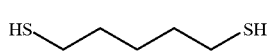
X-409
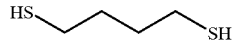
X-410
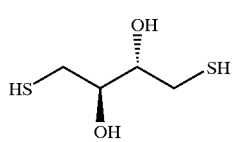
X-411
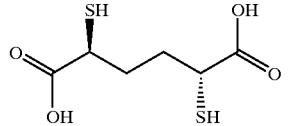

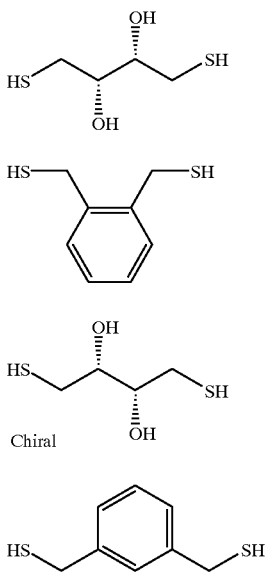

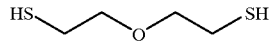
X-413

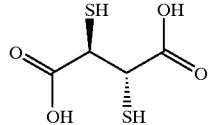
X-415

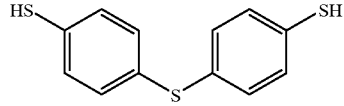
X-417

X-418

Representative ligands for use in this invention include, by way of example, those described above.

For example, L-1 can be an anti-seizure compound (e.g., lamotrigine, compounds 36 of Scheme J (described herein), carbamazepine and 4030W92);

L-2 can be a local anesthetic (e.g., lidocaine, and QX-314); and

L3 can be an anti-arrhythmic compound (e.g., mexilitene, tocainide, and flecainide).

Combinations of ligands (L) and linkers (X) per this invention include, by way example only, homo- and heterodimers wherein a first ligand is selected from L-1 through L-3 above and the second ligand and linker is selected from the following:

| | | | | | |
|---|---|---|---|---|---|
| L-1/X-1- | L-1/X-2- | L-1/X-3- | L-1/X-4- | L-1/X-5- | L-1/X-6- |
| L-1/X-7- | L-1/X-8- | L-1/X-9- | L-1/X-10- | L-1/X-11- | L-1/X-12- |
| L-1/X-13- | L-1/X-14- | L-1/X-15- | L-1/X-16- | L-1/X-17- | L-1/X-18- |
| L-1/X-19- | L-1/X-20- | L-1/X-21- | L-1/X-22- | L-1/X-23- | L-1/X-24- |
| L-1/X-25- | L-1/X-26- | L-1/X-27- | L-1/X-28- | L-1/X-29- | L-1/X-30- |
| L-1/X-31- | L-1/X-32- | L-1/X-33- | L-1/X-34- | L-1/X-35- | L-1/X-36- |
| L-1/X-37- | L-1/X-38- | L-1/X-39- | L-1/X-40- | L-1/X-41- | L-1/X-42- |
| L-1/X-43- | L-1/X-44- | L-1/X-45- | L-1/X-46- | L-1/X-47- | L-1/X-48- |
| L-1/X-49- | L-1/X-50- | L-1/X-51- | L-1/X-52- | L-1/X-53- | L-1/X-54- |
| L-1/X-55- | L-1/X-56- | L-1/X-57- | L-1/X-58- | L-1/X-59- | L-1/X-60- |
| L-1/X-61- | L-1/X-62- | L-1/X-63- | L-1/X-64- | L-1/X-65- | L-1/X-66- |
| L-1/X-67- | L-1/X-68- | L-1/X-69- | L-1/X-70- | L-1/X-71- | L-1/X-72- |
| L-1/X-73- | L-1/X-74- | L-1/X-75- | L-1/X-76- | L-1/X-77- | L-1/X-78- |
| L-1/X-79- | L-1/X-80- | L-1/X-81- | L-1/X-82- | L-1/X-83- | L-1/X-84- |
| L-1/X-85- | L-1/X-86- | L-1/X-87- | L-1/X-88- | L-1/X-89- | L-1/X-90- |
| L-1/X-91- | L-1/X-92- | L-1/X-93- | L-1/X-94- | L-1/X-95- | L-1/X-96- |
| L-1/X-97- | L-1/X-98- | L-1/X-99- | L-1/X-100- | L-1/X-101- | L-1/X-102- |
| L-1/X-103- | L-1/X-104- | L-1/X-105- | L-1/X-106- | L-1/X-107- | L-1/X-108- |
| L-1/X-109- | L-1/X-110- | L-1/X-111- | L-1/X-112- | L-1/X-113- | L-1/X-114- |
| L-1/X-115- | L-1/X-116- | L-1/X-117- | L-1/X-118- | L-1/X-119- | L-1/X-120- |
| L-1/X-121- | L-1/X-122- | L-1/X-123- | L-1/X-124- | L-1/X-125- | L-1/X-126- |
| L-1/X-127- | L-1/X-128- | L-1/X-129- | L-1/X-130- | L-1/X-131- | L-1/X-132- |
| L-1/X-133- | L-1/X-134- | L-1/X-135- | L-1/X-136- | L-1/X-137- | L-1/X-138- |
| L-1/X-139- | L-1/X-140- | L-1/X-141- | L-1/X-142- | L-1/X-143- | L-1/X-144- |
| L-1/X-145- | L-1/X-146- | L-1/X-147- | L-1/X-148- | L-1/X-149- | L-1/X-150- |
| L-1/X-151- | L-1/X-152- | L-1/X-153- | L-1/X-154- | L-1/X-155- | L-1/X-156- |
| L-1/X-157- | L-1/X-158- | L-1/X-159- | L-1/X-160- | L-1/X-161- | L-1/X-162- |
| L-1/X-163- | L-1/X-164- | L-1/X-165- | L-1/X-166- | L-1/X-167- | L-1/X-168- |
| L-1/X-169- | L-I/X-170- | L-1/X-171- | L-1/X-172- | L-1/X-173- | L-1/X-174- |
| L-1/X-175- | L-1/X-176- | L-1/X-177- | L-1/X-178- | L-1/X-179- | L-1/X-180- |
| L-1/X-181- | L-1/X-182- | L-1/X-183- | L-1/X-184- | L-1/X-185- | L-1/X-186- |
| L-1/X-187- | L-1/X-188- | L-1/X-189- | L-1/X-190- | L-1/X-191- | L-1/X-192- |
| L-1/X-193- | L-1/X-194- | L-1/X-195- | L-1/X-196- | L-1/X-197- | L-1/X-198- |
| L-1/X-199- | L-1/X-200- | L-1/X-201- | L-1/X-202- | L-1/X-203- | L-1/X-204- |
| L-1/X-205- | L-1/X-206- | L-1/X-207- | L-1/X-208- | L-1/X-209- | L-1/X-210- |
| L-1/X-211- | L-1/X-212- | L-1/X-213- | L-1/X-214- | L-1/X-215- | L-1/X-216- |

-continued

| | | | | | |
|---|---|---|---|---|---|
| L-1/X-217- | L-1/X-218- | L-1/X-219- | L-1/X-220- | L-1/X-221- | L-1/X-222- |
| L-1/X-223- | L-1/X-224- | L-1/X-225- | L-1/X-226- | L-1/X-227- | L-1/X-228- |
| L-1/X-229- | L-1/X-230- | L-1/X-231- | L-1/X-232- | L-1/X-233- | L-1/X-234- |
| L-1/X-235- | L-1/X-236- | L-1/X-237- | L-1/X-238- | L-1/X-239- | L-1/X-240- |
| L-1/X-241- | L-1/X-242- | L-1/X-243- | L-1/X-244- | L-1/X-245- | L-1/X-246- |
| L-1/X-247- | L-1/X-248- | L-1/X-249- | L-1/X-250- | L-1/X-251- | L-1/X-252- |
| L-1/X-253- | L-1/X-254- | L-1/X-255- | L-1/X-256- | L-1/X-257- | L-1/X-258- |
| L-1/X-259- | L-1/X-260- | L-1/X-261- | L-1/X-262- | L-1/X-263- | L-1/X-264- |
| L-1/X-265- | L-1/X-266- | L-1/X-267- | L-1/X-268- | L-1/X-269- | L-1/X-270- |
| L-1/X-271- | L-1/X-272- | L-1/X-273- | L-1/X-274- | L-1/X-275- | L-1/X-276- |
| L-1/X-277- | L-1/X-278- | L-1/X-279- | L-1/X-280- | L-1/X-281- | L-1/X-282- |
| L-1/X-283- | L-1/X-284- | L-1/X-285- | L-1/X-286- | L-1/X-287- | L-1/X-288- |
| L-1/X-289- | L-1/X-290- | L-1/X-291- | L-1/X-292- | L-1/X-293- | L-1/X-294- |
| L-1/X-295- | L-1/X-296- | L-1/X-297- | L-1/X-298- | L-1/X-299- | L-1/X-300- |
| L-1/X-301- | L-1/X-302- | L-1/X-303- | L-1/X-304- | L-1/X-305- | L-1/X-306- |
| L-1/X-307- | L-1/X-308- | L-1/X-309- | L-1/X-310- | L-1/X-311- | L-1/X-312- |
| L-1/X-313- | L-1/X-314- | L-1/X-315- | L-1/X-316- | L-1/X-317- | L-1/X-318- |
| L-1/X-319- | L-1/X-320- | L-1/X-321- | L-1/X-322- | L-1/X-323- | L-1/X-324- |
| L-1/X-325- | L-1/X-326- | L-1/X-327- | L-1/X-328- | L-1/X-329- | L-1/X-330- |
| L-1/X-331- | L-1/X-332- | L-1/X-333- | L-1/X-334- | L-1/X-335- | L-1/X-336- |
| L-1/X-337- | L-1/X-338- | L-1/X-339- | L-1/X-340- | L-1/X-341- | L-1/X-342- |
| L-1/X-343- | L-1/X-344- | L-1/X-345- | L-1/X-346- | L-1/X-347- | L-1/X-348- |
| L-1/X-349- | L-1/X-350- | L-1/X-351- | L-1/X-352- | L-1/X-353- | L-1/k-354- |
| L-1/X-355- | L-1/X-356- | L-1/X-357- | L-1/X-358- | L-1/X-359- | L-1/X-360- |
| L-1/X-361- | L-1/X-362- | L-1/X-363- | L-1/X-364- | L-1/X-365- | L-1/X-366- |
| L-1/X-367- | L-1/X-368- | L-1/X-369- | L-1/X-370- | L-1/X-371- | L-1/X-372- |
| L-1/X-373- | L-1/X-374- | L-1/X-375- | L-1/X-376- | L-1/X-377- | L-1/X-378- |
| L-1/X-379- | L-1/X-380- | L-1/X-381- | L-1/X-382- | L-I/X-383- | L-1/X-384- |
| L-1/X-385- | L-1/X-386- | L-1/X-387- | L-1/X-388- | L-1/X-389- | L-1/X-390- |
| L-1/X-391- | L-1/X-392- | L-1/X-393- | L-1/X-394- | L-1/X-395- | L-1/X-396- |
| L-1/X-397- | L-1/X-398- | L-1/X-399- | L-1/X-400- | L-1/X-401- | L-1/X-402- |
| L-1/X-403- | L-1/X-404- | L-1/X-405- | L-1/X-406- | L-1/X-407- | L-1/X-408- |
| L-1/X-409- | L-1/X-410- | L-1/X-411- | L-1/X-412- | L-1/X-413- | L-1/X-414- |
| L-1/X-415- | L-1/X-416- | L-1/X-417- | L-1/X-418- | | |
| L-2/X-1- | L-2/X-2- | L-2/X-3- | L-2/X-4- | L-2/X-5- | L-2/X-6- |
| L-2/X-7- | L-2/X-8- | L-2/X-9- | L-2/X-10- | L-2/X-11- | L-2/X-12- |
| L-2/X-13- | L-2/X-14- | L-2/X-15- | L-2/X-16- | L-2/X-17- | L-2/X-18- |
| L-2/X-19- | L-2/X-20- | L-2/X-21- | L-2/X-22- | L-2/X-23- | L-2/X-24- |
| L-2/X-25- | L-2/X-26- | L-2/X-27- | L-2/X-28- | L-2/X-29- | L-2/X-30- |
| L-2/X-31- | L-2/X-32- | L-2/X-33- | L-2/X-34- | L-2/X-35- | L-2/X-36- |
| L-2/X-37- | L-2/X-38- | L-2/X-39- | L-2/X-40- | L-2/X-41- | L-2/X-42- |
| L-2/X-43- | L-2/X-44- | L-2/X-45- | L-2/X-46- | L-2/X-47- | L-2/X-48- |
| L-2/X-49- | L-2/X-50- | L-2/X-51- | L-2/X-52- | L-2/X-53- | L-2/X-54- |
| L-2/X-55- | L-2/X-56- | L-2/X-57- | L-2/X-58- | L-2/X-59- | L-2/X-60- |
| L-2/X-61- | L-2/X-62- | L-2/X-63- | L-2/X-64- | L-2/X-65- | L-2/X-66- |
| L-2/X-67- | L-2/X-68- | L-2/X-69- | L-2/X-70- | L-2/X-71- | L-2/X-72- |
| L-2/X-73- | L-2/X-74- | L-2/X-75- | L-2/X-76- | L-2/X-77- | L-2/X-78- |
| L-2/X-79- | L-2/X-80- | L-2/X-81- | L-2/X-82- | L-2/X-83- | L-2/X-84- |
| L-2/X-85- | L-2/X-86- | L-2/X-87- | L-2/X-88- | L-2/X-89- | L-2/X-90- |
| L-2/X-91- | L-2/X-92- | L-2/X-93- | L-2/X-94- | L-2/X-95- | L-2/X-96- |
| L-2/X-97- | L-2/X-98- | L-2/X-99- | L-2/X-100- | L-2/X-101- | L-2/X-102- |
| L-2/X-103- | L-2/X-104- | L-2/X-105- | L-2/X-106- | L-2/X-107- | L-2/X-108- |
| L-2/X-109- | L-2/X-110- | L-2/X-111- | L-2/X-112- | L-2/X-113- | L-2/X-114- |
| L-2/X-115- | L-2/X-116- | L-2/X-117- | L-2/X-118- | L-2/X-119- | L-2/X-120- |
| L-2/X-121- | L-2/X-122- | L-2/X-123- | L-2/X-124- | L-2/X-125- | L-2/X-126- |
| L-2/X-127- | L-2/X-128- | L-2/X-129- | L-2/X-130- | L-2/X-131- | L-2/X-132- |
| L-2/X-133- | L-2/X-134- | L-2/X-135- | L-2/X-136- | L-2/X-137- | L-2/X-138- |
| L-2/X-139- | L-2/X-140- | L-2/X-141- | L-2/X-142- | L-2/X-143- | L-2/X-144- |
| L-2/X-145- | L-2/X-146- | L-2/X-147- | L-2/X-148- | L-2/X-149- | L-2/X-150- |
| L-2/X-151- | L-2/X-152- | L-2/X-153- | L-2/X-154- | L-2/X-155- | L-2/X-156- |
| L-2/X-157- | L-2/X-158- | L-2/X-159- | L-2/X-160- | L-2/X-161- | L-2/X-162- |
| L-2/X-163- | L-2/X-164- | L-2/X-165- | L-2/X-166- | L-2/X-167- | L-2/X-168- |
| L-2/X-169- | L-2/X-170- | L-2/X-171- | L-2/X-172- | L-2/X-173- | L-2/X-174- |
| L-2/X-175- | L-2/X-176- | L-2/X-177- | L-2/X-178- | L-2/X-179- | L-2/X-180- |
| L-2/X-181- | L-2/X-182- | L-2/X-183- | L-2/X-184- | L-2/X-185- | L-2/X-186- |
| L-2/X-187- | L-2/X-188- | L-2/X-189- | L-2/X-190- | L-2/X-191- | L-2/X-192- |
| L-2/X-193- | L-2/X-194- | L-2/X-195- | L-2/X-196- | L-2/X-197- | L-2/X-198- |
| L-2/X-199- | L-2/X-200- | L-2/X-201- | L-2/X-202- | L-2/X-203- | L-2/X-204- |
| L-2/X-205- | L-2/X-206- | L-2/X-207- | L-2/X-208- | L-2/X-209- | L-2/X-210- |
| L-2/X-211- | L-2/X-212- | L-2/X-213- | L-2/X-214- | L-2/X-215- | L-2/X-216- |
| L-2/X-217- | L-2/X-218- | L-2/X-219- | L-2/X-220- | L-2/X-221- | L-2/X-222- |
| L-2/X-223- | L-2/X-224- | L-2/X-225- | L-2/X-226- | L-2/X-227- | L-2/X-228- |
| L-2/X-229- | L-2/X-230- | L-2/X-231- | L-2/X-232- | L-2/X-233- | L-2/X-234- |
| L-2/X-235- | L-2/X-236- | L-2/X-237- | L-2/X-238- | L-2/X-239- | L-2/X-240- |
| L-2/X-241- | L-2/X-242- | L-2/X-243- | L-2/X-244- | L-2/X-245- | L-2/X-246- |
| L-2/X-247- | L-2/X-248- | L-2/X-249- | L-2/X-250- | L-2/X-251- | L-2/X-252- |
| L-2/X-253- | L-2/X-254- | L-2/X-255- | L-2/X-256- | L-2/X-257- | L-2/X-258- |
| L-2/X-259- | L-2/X-260- | L-2/X-261- | L-2/X-262- | L-2/X-263- | L-2/X-264- |
| L-2/X-265- | L-2/X-266- | L-2/X-267- | L-2/X-268- | L-2/X-269- | L-2/X-270- |

-continued

| | | | | | |
|---|---|---|---|---|---|
| L-2/X-271- | L-2/X-272- | L-2/X-273- | L-2/X-274- | L-2/X-275- | L-2/X-276- |
| L-2/X-277- | L-2/X-278- | L-2/X-279- | L-2/X-280- | L-2/X-281- | L-2/X-282- |
| L-2/X-283- | L-2/X-284- | L-2/X-285- | L-2/X-286- | L-2/X-287- | L-2/X-288- |
| L-2/X-289- | L-2/X-290- | L-2/X-291- | L-2/X-292- | L-2/X-293- | L-2/X-294- |
| L-2/X-295- | L-2/X-296- | L-2/X-297- | L-2/X-298- | L-2/X-299- | L-2/X-300- |
| L-2/X-301- | L-2/X-302- | L-2/X-303- | L-2/X-304- | L-2/X-305- | L-2/X-306- |
| L-2/X-307- | L-2/X-308- | L-2/X-309- | L-2/X-310- | L-2/X-311- | L-2/X-312- |
| L-2/X-313- | L-2/X-314- | L-2/X-315- | L-2/X-316- | L-2/X-317- | L-2/X-318- |
| L-2/X-319- | L-2/X-320- | L-2/X-321- | L-2/X-322- | L-2/X-323- | L-2/X-324- |
| L-2/X-325- | L-2/X-326- | L-2/X-327- | L-2/X-328- | L-2/X-329- | L-2/X-330- |
| L-2/X-331- | L-2/X-332- | L-2/X-333- | L-2/X-334- | L-2/X-335- | L-2/X-336- |
| L-2/X-337- | L-2/X-338- | L-2/X-339- | L-2/X-340- | L-2/X-341- | L-2/X-342- |
| L-2/X-343- | L-2/X-344- | L-2/X-345- | L-2/X-346- | L-2/X-347- | L-2/X-348- |
| L-2/X-349- | L-2/X-350- | L-2/X-351- | L-2/X-352- | L-2/X-353- | L-2/X-354- |
| L-2/X-355- | L-2/X-356- | L-2/X-357- | L-2/X-358- | L-2/X-359- | L-2/X-360- |
| L-2/X-361- | L-2/X-362- | L-2/X-363- | L-2/X-364- | L-2/X-365- | L-2/X-366- |
| L-2/X-367- | L-2/X-368- | L-2/X-369- | L-2/X-370- | L-2/X-371- | L-2/X-372- |
| L-2/X-373- | L-2/X-374- | L-2/X-375- | L-2/X-376- | L-2/X-377- | L-2/X-378- |
| L-2/X-379- | L-2/X-380- | L-2/X-381- | L-2/X-382- | L-2/X-383- | L-2/X-384- |
| L-2/X-385- | L-2/X-386- | L-2/X-387- | L-2/X-388- | L-2/X-389- | L-2/X-390- |
| L-2/X-391- | L-2/X-392- | L-2/X-393- | L-2/X-394- | L-2/X-395- | L-2/X-396- |
| L-2/X-397- | L-2/X-398- | L-2/X-399- | L-2/X-400- | L-2/X-401- | L-2/X-402- |
| L-2/X-403- | L-2/X-404- | L-2/X-405- | L-2/X-406- | L-2/X-407- | L-2/X-408- |
| L-2/X-409- | L-2/X-410- | L-2/X-411- | L-2/X-412- | L-2/X-413- | L-2/X-414- |
| L-2/X-415- | L-2/X-416- | L-2/X-417- | L-2/X-418- | | |
| L-3/X-1- | L-3/X-2- | L-3/X-3- | L-3/X-4- | L-3/X-5- | L-3/X-6- |
| L-3/X-7- | L-3/X-8- | L-3/X-9- | L-3/X-10- | L-3/X-11- | L-3/X-12- |
| L-3/X-13- | L-3/X-14- | L-3/X-15- | L-3/X-16- | L-3/X-17- | L-3/X-18- |
| L-3/X-19- | L-3/X-20- | L-3/X-21- | L-3/X-22- | L-3/X-23- | L-3/X-24- |
| L-3/X-25- | L-3/X-26- | L-3/X-27- | L-3/X-28- | L-3/X-29- | L-3/X-30- |
| L-3/X-31- | L-3/X-32- | L-3/X-33- | L-3/X-34- | L-3/X-35- | L-3/X-36- |
| L-3/X-37- | L-3/X-38- | L-3/X-39- | L-3/X-40- | L-3/X-41- | L-3/X-42- |
| L-3/X-43- | L-3/X-44- | L-3/X-45- | L-3/X-46- | L-3/X-47- | L-3/X-48- |
| L-3/X-49- | L-3/X-50- | L-3/X-51- | L-3/X-52- | L-3/X-53- | L-3/X-54- |
| L-3/X-55- | L-3/X-56- | L-3/X-57- | L-3/X-58- | L-3/X-59- | L-3/X-60- |
| L-3/X-61- | L-3/X-62- | L-3/X-63- | L-3/X-64- | L-3/X-65- | L-3/X-66- |
| L-3/X-67- | L-3/X-68- | L-3/X-69- | L-3/X-70- | L-3/X-71- | L-3/X-72- |
| L-3/X-73- | L-3/X-74- | L-3/X-75- | L-3/X-76- | L-3/X-77- | L-3/X-18- |
| L-3/X-79- | L-3/X-80- | L-3/X-81- | L-3/X-82- | L-3/X-83- | L-3/X-84- |
| L-3/X-85- | L-3/X-86- | L-3/X-87- | L-3/X-88- | L-3/X-89- | L-3/X-90- |
| L-3/X-91- | L-3/X-92- | L-3/X-93- | L-3/X-94- | L-3/X-95- | L-3/X-96- |
| L-3/X-97- | L-3/X-98- | L-3/X-99- | L-3/X-100- | L-3/X-101- | L-3/X-102- |
| L-3/X-103- | L-3/X-104- | L-3/X-105- | L-3/X-106- | L-3/X-107- | L-3/X-108- |
| L-3/X-109- | L-3/X-110- | L-3/X-111- | L-3/X-112- | L-3/X-113- | L-3/X-114- |
| L-3/X-115- | L-3/X-116- | L-3/X-117- | L-3/X-118- | L-3/X-119- | L-3/X-120- |
| L-3/X-121- | L-3/X-122- | L-3/X-123- | L-3/X-124- | L-3/X-125- | L-3/X-126- |
| L-3/X-127- | L-3/X-128- | L-3/X-129- | L-3/X-130- | L-3/X-131- | L-3/X-132- |
| L-3/X-133- | L-3/X-134- | L-3/X-135- | L-3/X-136- | L-3/X-137- | L-3/X-138- |
| L-3/X-139- | L-3/X-140- | L-3/X-141- | L-3/X-142- | L-3/X-143- | L-3/X-144- |
| L-3/X-145- | L-3/X-146- | L-3/X-147- | L-3/X-148- | L-3/X-149- | L-3/X-150- |
| L-3/X-151- | L-3/X-152- | L-3/X-153- | L-3/X-154- | L-3/X-155- | L-3/X-156- |
| L-3/X-157- | L-3/X-158- | L-3/X-159- | L-3/X-160- | L-3/X-161- | L-3/X-162- |
| L-3/X-163- | L-3/X-164- | L-3/X-165- | L-3/X-166- | L-3/X-167- | L-3/X-168- |
| L-3/X-169- | L-3/X-170- | L-3/X-171- | L-3/X-172- | L-3/X-173- | L-3/X-174- |
| L-3/X-175- | L-3/X-176- | L-3/X-177- | L-3/X-178- | L-3/X-179- | L-3/X-180- |
| L-3/X-181- | L-3/X-182- | L-3/X-183- | L-3/X-184- | L-3/X-185- | L-3/X-186- |
| L-3/X-187- | L-3/X-188- | L-3/X-189- | L-3/X-190- | L-3/X-191- | L-3/X-192- |
| L-3/X-193- | L-3/X-194- | L-3/X-195- | L-3/X-196- | L-3/X-197- | L-3/X-198- |
| L-3/X-199- | L-3/X-200- | L-3/X-201- | L-3/X-202- | L-3/X-203- | L-3/X-204- |
| L-3/X-205- | L-3/X-206- | L-3/X-207- | L-3/X-208- | L-3/X-209- | L-3/X-210- |
| L-3/X-211- | L-3/X-212- | L-3/X-213- | L-3/X-214- | L-3/X-215- | L-3/X-216- |
| L-3/X-217- | L-3/X-218- | L-3/X-219- | L-3/X-220- | L-3/X-221- | L-3/X-222- |
| L-3/X-223- | L-3/X-224 | L-3/X-225- | L-3/X-226- | L-3/X-227- | L-3/X-228- |
| L-3/X-229- | L-3/X-230- | L-3/X-231- | L-3/X-232- | L-3/X-233- | L-3/X-234- |
| L-3/X-235- | L-3/X-236- | L-3/X-237- | L-3/X-238- | L-3/X-239- | L-3/X-240- |
| L-3/X-241- | L-3/X-242- | L-3/X-243- | L-3/X-244- | L-3/X-245- | L-3/X-246- |
| L-3/X-247- | L-3/X-248- | L-3/X-249- | L-3/X-250- | L-3/X-251- | L-3/X-252- |
| L-3/X-253- | L-3/X-254- | L-3/X-255- | L-3/X-256- | L-3/X-257- | L-3/X-258- |
| L-3/X-259- | L-3/X-260- | L-3/X-261- | L-3/X-262- | L-3/X-263- | L-3/X-264- |
| L-3/X-265- | L-3/X-266- | L-3/X-267- | L-3/X-268- | L-3/X-269- | L-3/X-270- |
| L-3/X-271- | L-3/X-272- | L-3/X-273- | L-3/X-274- | L-3/X-275- | L-3/X-276- |
| L-3/X-277- | L-3/X-278- | L-3/X-279- | L-3/X-280- | L-3/X-281- | L-3/X-282- |
| L-3/X-283- | L-3/X-284- | L-3/X-285- | L-3/X-286- | L-3/X-287- | L-3/X-288- |
| L-3/X-289- | L-3/X-290- | L-3/X-291- | L-3/X-292- | L-3/X-293- | L-3/X-294- |
| L-3/X-295- | L-3/X-296- | L-3/X-297- | L-3/X-298- | L-3/X-299- | L-3/X-300- |
| L-3/X-301- | L-3/X-302- | L-3/X-303- | L-3/X-304- | L-3/X-305- | L-3/X-306- |
| L-3/X-307- | L-3/X-308- | L-3/X-309- | L-3/X-310- | L-3/X-311- | L-3/X-312- |
| L-3/X-313- | L-3/X-314- | L-3/X-315- | L-3/X-316- | L-3/X-317- | L-3/X-318- |
| L-3/X-319- | L-3/X-320- | L-3/X-321- | L-3/X-322- | L-3/X-323- | L-3/X-324- |

-continued

| | | | | | |
|---|---|---|---|---|---|
| L-3/X-325- | L-3/X-326- | L-3/X-327- | L-3/X-328- | L-3/X-329- | L-3/X-330- |
| L-3/X-331- | L-3/X-332- | L-3/X-333- | L-3/X-334- | L-3/X-335- | L-3/X-336- |
| L-3/X-337- | L-3/X-338- | L-3/X-339- | L-3/X-340- | L-3/X-341- | L-3/X-342- |
| L-3/X-343- | L-3/X-344- | L-3/X-345- | L-3/X-346- | L-3/X-347- | L-3/X-348- |
| L-3/X-349- | L-3/X-350- | L-3/X-351- | L-3/X-352- | L-3/X-353- | L-3/X-354- |
| L-3/X-355- | L-3/X-356- | L-3/X-357- | L-3/X-358- | L-3/X-359- | L-3/X-360- |
| L-3/X-361- | L-3/X-362- | L-3/X-363- | L-3/X-364- | L-3/X-365- | L-3/X-366- |
| L-3/X-367- | L-3/X-368- | L-3/X-369- | L-3/X-370- | L-3/X-371- | L-3/X-372- |
| L-3/X-373- | L-3/X-374- | L-3/X-375- | L-3/X-376- | L-3/X-377- | L-3/X-378- |
| L-3/X-379- | L-3/X-380- | L-3/X-381- | L-3/X-382- | L-3/X-383- | L-3/X-384- |
| L-3/X-385- | L-3/X-386- | L-3/X-387- | L-3/X-388- | L-3/X-389- | L-3/X-390- |
| L-3/X-391- | L-3/X-392- | L-3/X-393- | L-3/X-394- | L-3/X-395- | L-3/X-396- |
| L-3/X-397- | L-3/X-398- | L-3/X-399- | L-3/X-400- | L-3/X-401- | L-3/X-402- |
| L-3/X-403- | L-3/X-404- | L-3/X-405- | L-3/X-406- | L-3/X-407- | L-3/X-408- |
| L-3/X-409- | L-3/X-410- | L-3/X-411- | L-3/X-412- | L-3/X-413- | L-3/X-414- |
| L-3/X-415- | L-3/X-416- | L-3/X-417- | L-3/X-418- | | |
| and so on | | | | | |

METHODS OF PREPARATION

Linkers

The linker or linkers, when covalently attached to multiple copies of the ligands, provides a biocompatible, substantially non-immunogenic multibinding compound. The biological activity of the multibinding $Na^+$ channel compound is highly sensitive to the geometry, composition, size, length, flexibility or rigidity, the presence or absence of anionic or cationic charge, the relative hydrophobicity/hydrophilicity, and similar properties of the linker. Accordingly, the linker is preferably chosen to maximize the biological activity of the compound. The linker may be biologically "neutral," i.e., not itself contribute any additional biological activity to the multibinding compound, or it may be chosen to further enhance the biological activity of the compound. In general, the linker may be chosen from any organic molecule construct that orients two or more ligands for binding to the receptors to permit multivalency. In this regard, the linker can be considered as a "framework" on which the ligands are arranged in order to bring about the desired ligand-orienting result, and thus produce a multibinding compound.

For example, different orientations of ligands can be achieved by varying the geometry of the framework (linker) by use of mono- or polycyclic groups, such as aryl and/or heteroaryl groups, or structures incorporating one or more carbon—carbon multiple bonds (alkenyl, alkenylene, alkynyl or alkynylene groups). The optimal geometry and composition of frameworks (linkers) used in the multibinding compounds of this invention are based upon the properties of their intended receptors. For example, it is preferred to use rigid cyclic groups (e.g., aryl, heteroaryl), or non-rigid cyclic groups (e.g., cycloalkyl or crown groups) to reduce conformational entropy when such may be necessary to achieve energetically coupled binding.

Different hydrophobic/hydrophilic characteristics of the linker as well as the presence or absence of charged moieties can readily be controlled by the skilled artisan. For example, the hydrophobic nature of a linker derived from hexamethylene diamine ($H_2N(CH_2)_6NH_2$) or related polyamines can be modified to be substantially more hydrophilic by replacing the alkylene group with a poly(oxyalkylene) group such as found in the commercially available "Jeffamines" (class of surfactants).

Different frameworks can be designed to provide preferred orientations of the ligands. The identification of an appropriate framework geometry for ligand domain presentation is an important first step in the construction of a multi binding agent with enhanced activity. Systematic spatial searching strategies can be used to aid in the identification of preferred frameworks through an iterative process. FIGS. 3A and 3B illustrate a useful strategy for determining an optimal framework display orientation for ligand domains and can be used for preparing the bivalent compounds of this invention. Various alternative strategies known to those skilled in the art of molecular design can be substituted for the one described here.

As shown in FIGS. 3A and 3B, the ligands (shown as filled circles) are attached to a central core structure such as phenyldiacetylene (Panel A) or cyclohexane dicarboxylic acid (Panel B). The ligands are spaced apart from the core by an attaching moiety of variable lengths m and n. If the ligand possesses multiple attachment sites (see discussion below), the orientation of the ligand on the attaching moiety may be varied as well. The positions of the display vectors around the central core structures are varied, thereby generating a collection of compounds. Assay of each of the individual compounds of a collection generated as described will lead to a subset of compounds with the desired enhanced activities (e.g., potency, selectivity). The analysis of this subset using a technique such as Ensemble Molecular Dynamics will suggest a framework orientation that favors the properties desired.

The process may require the use of multiple copies of the same central core structure or combinations of different types of display cores. It is to be noted that core structures other than those shown here can be used for determining the optimal framework display orientation of the ligands. The above-described technique can be extended to trivalent compounds and compounds of higher-order valency.

A wide variety of linkers is commercially available (e.g., Chem Sources USA and Chem Sources International; the ACD electronic database; and Chemical Abstracts). Many of the linkers that are suitable for use in this invention fall into this category. Others can be readily synthesized by methods known in the art, and as described below. Examples of linkers include aliphatic moieties, aromatic moieties, steroidal moieties, peptides, and the like. Specific examples are peptides or polyamides, hydrocarbons, aromatics, heterocyclics, ethers, lipids, cationic or anionic groups, or a combination thereof.

Figure 4A:
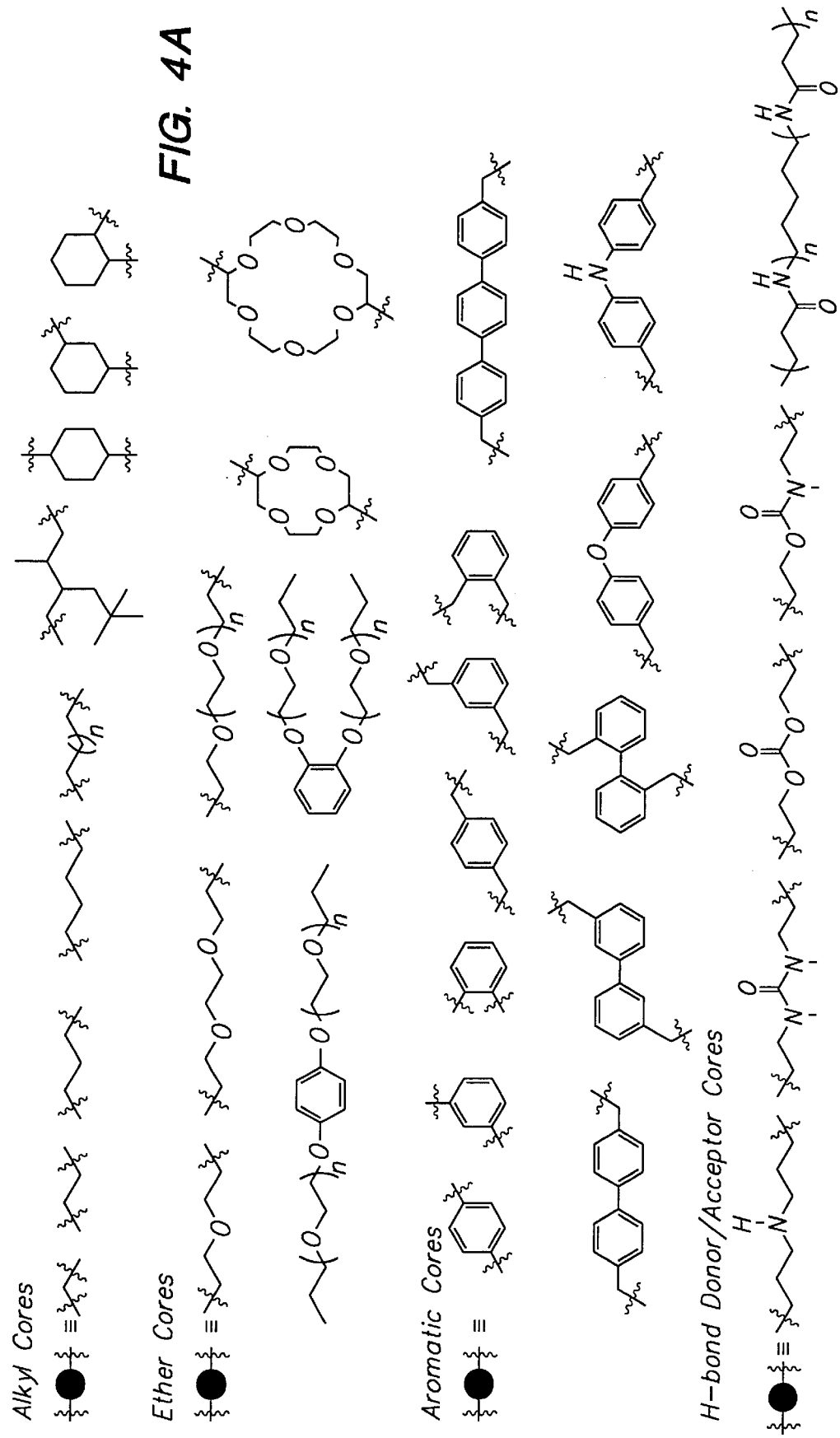
FIGS. 4A and 4B show exemplary linker "core" structures.
Figure 4B:
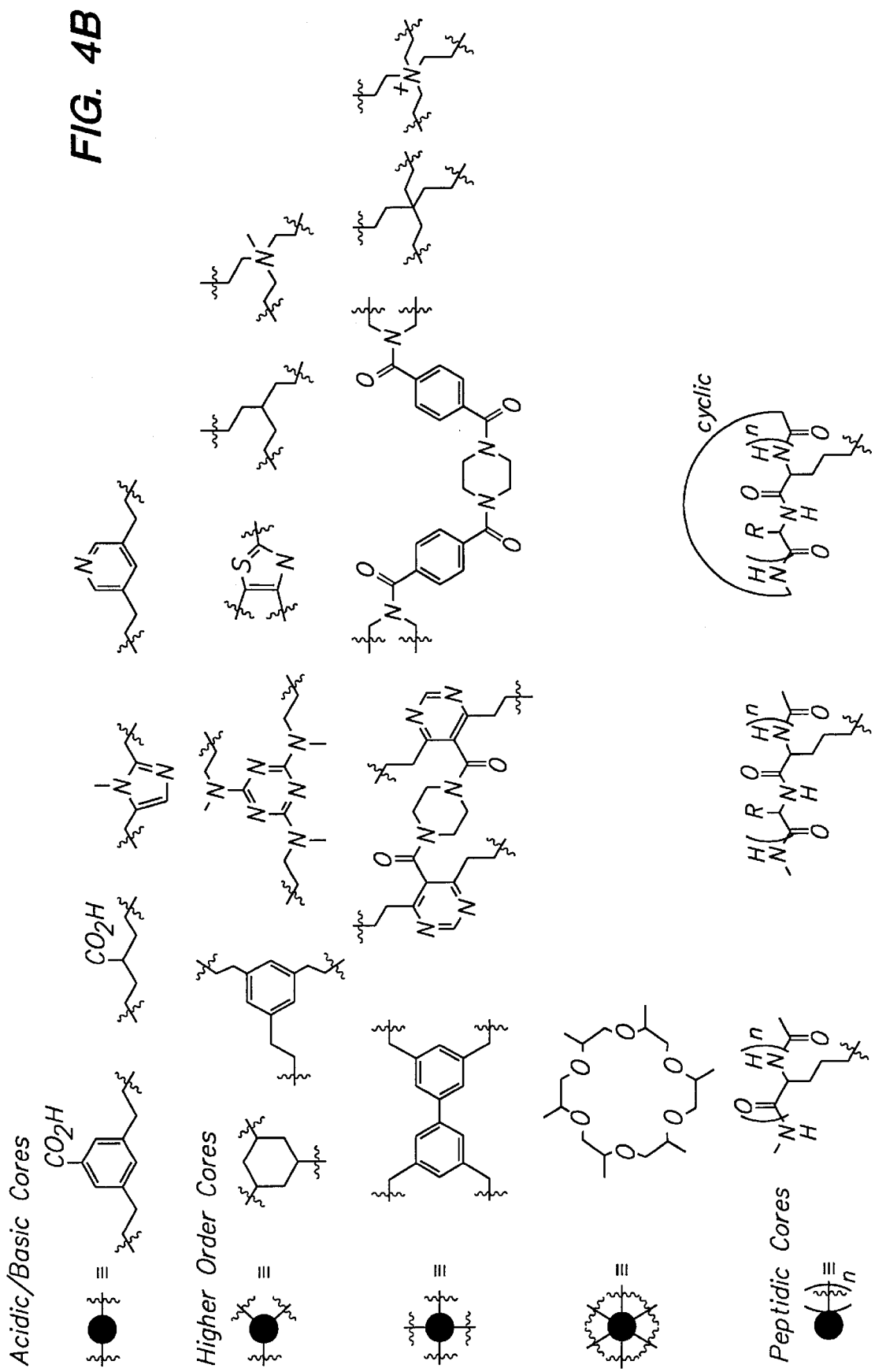
Figure 5A:
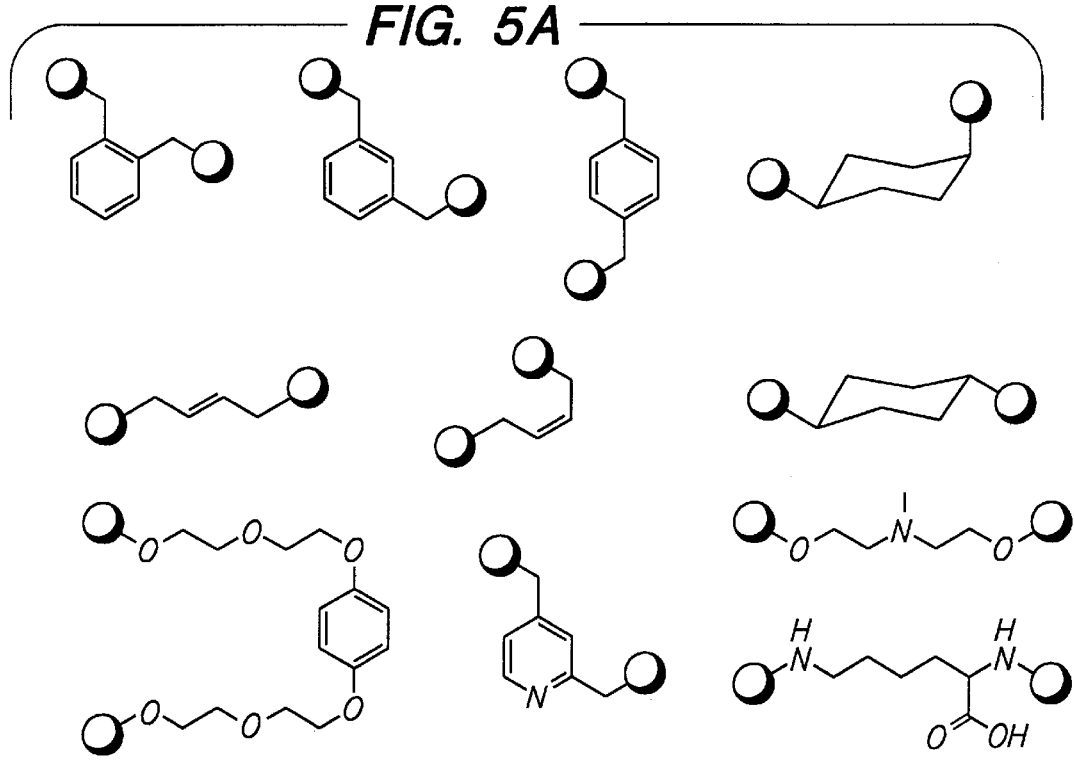
FIG. 5 illustrates examples of multi-binding compounds comprising (A) 2 ligands, (B) 3 ligands, (C) 4 ligands, and (D) >4 ligands attached in different formats to a linker.
Figure 5B:
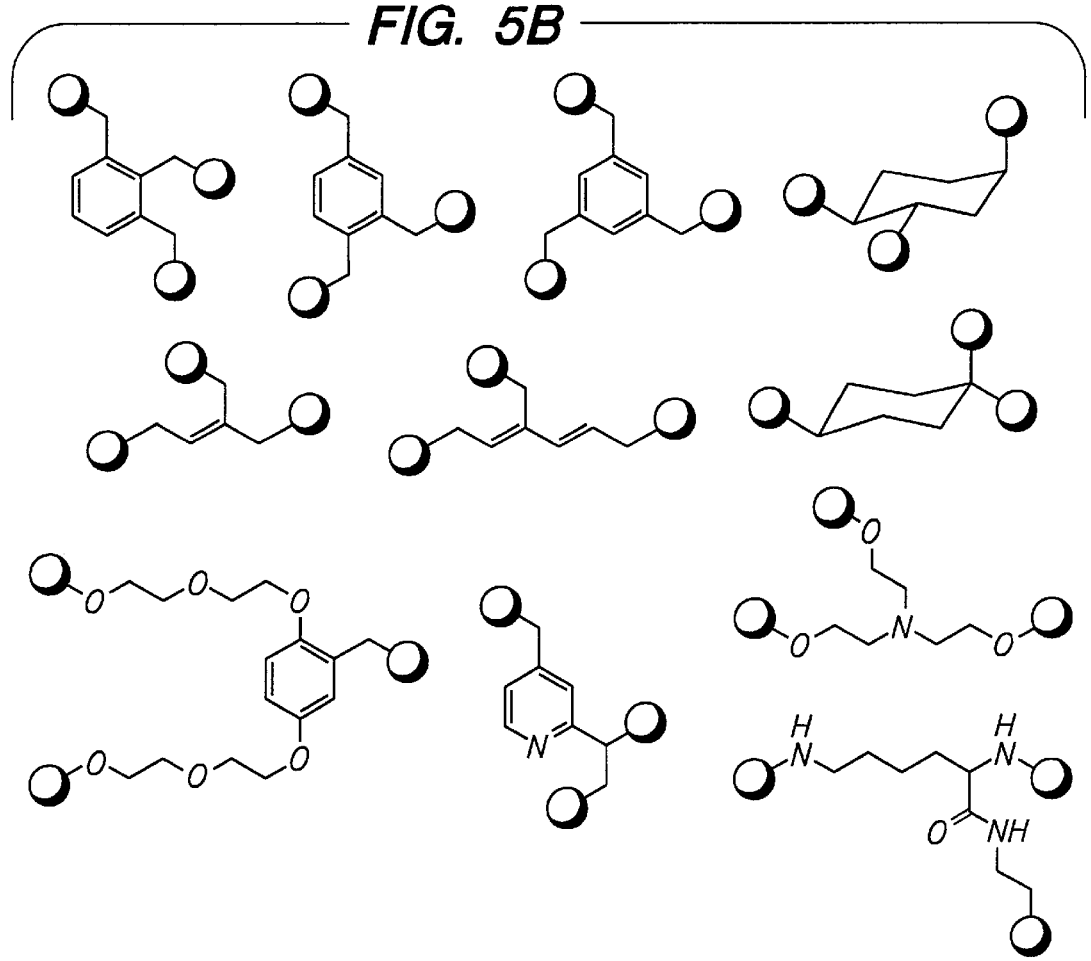
Figure 5C:
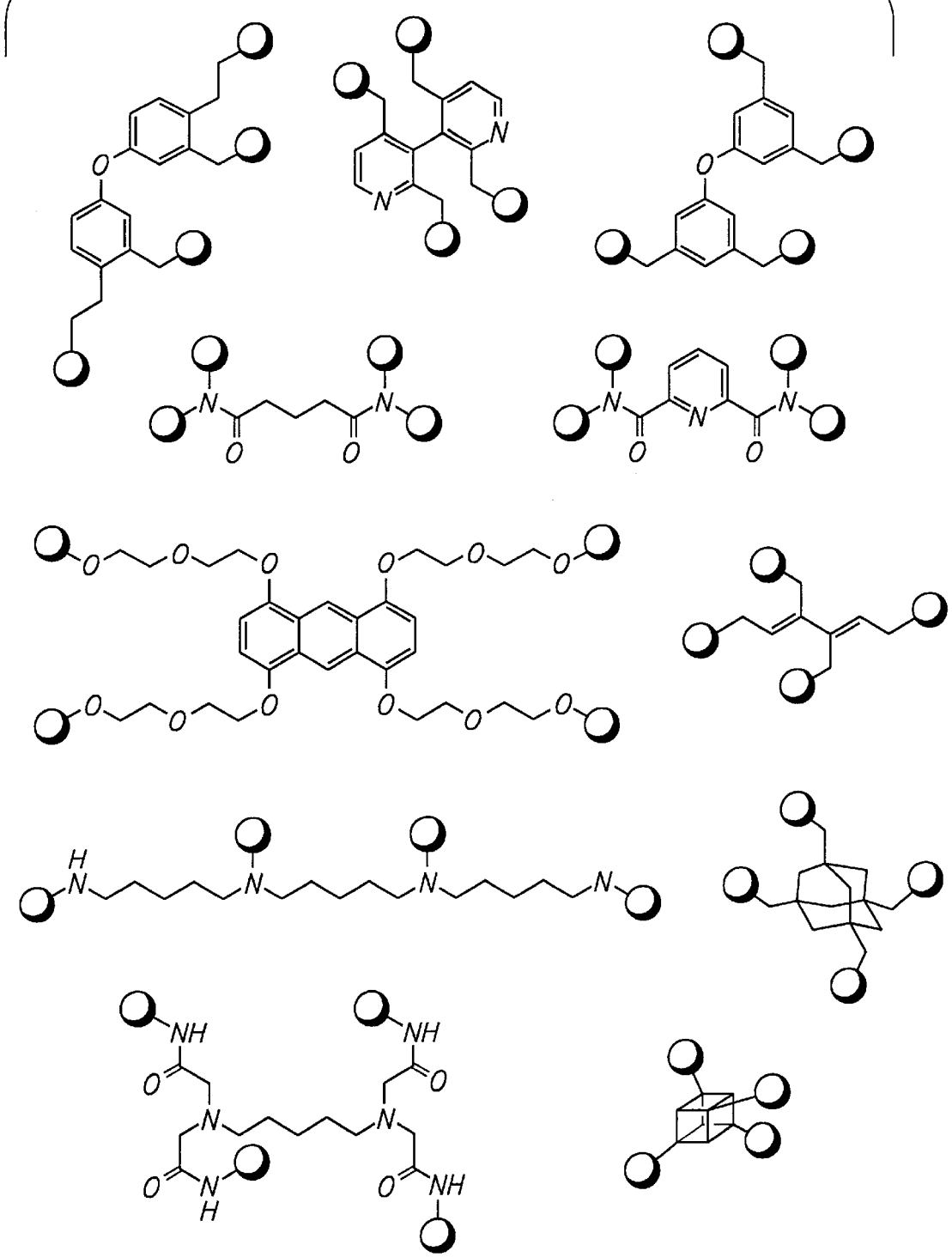
Figures 5D, 6:
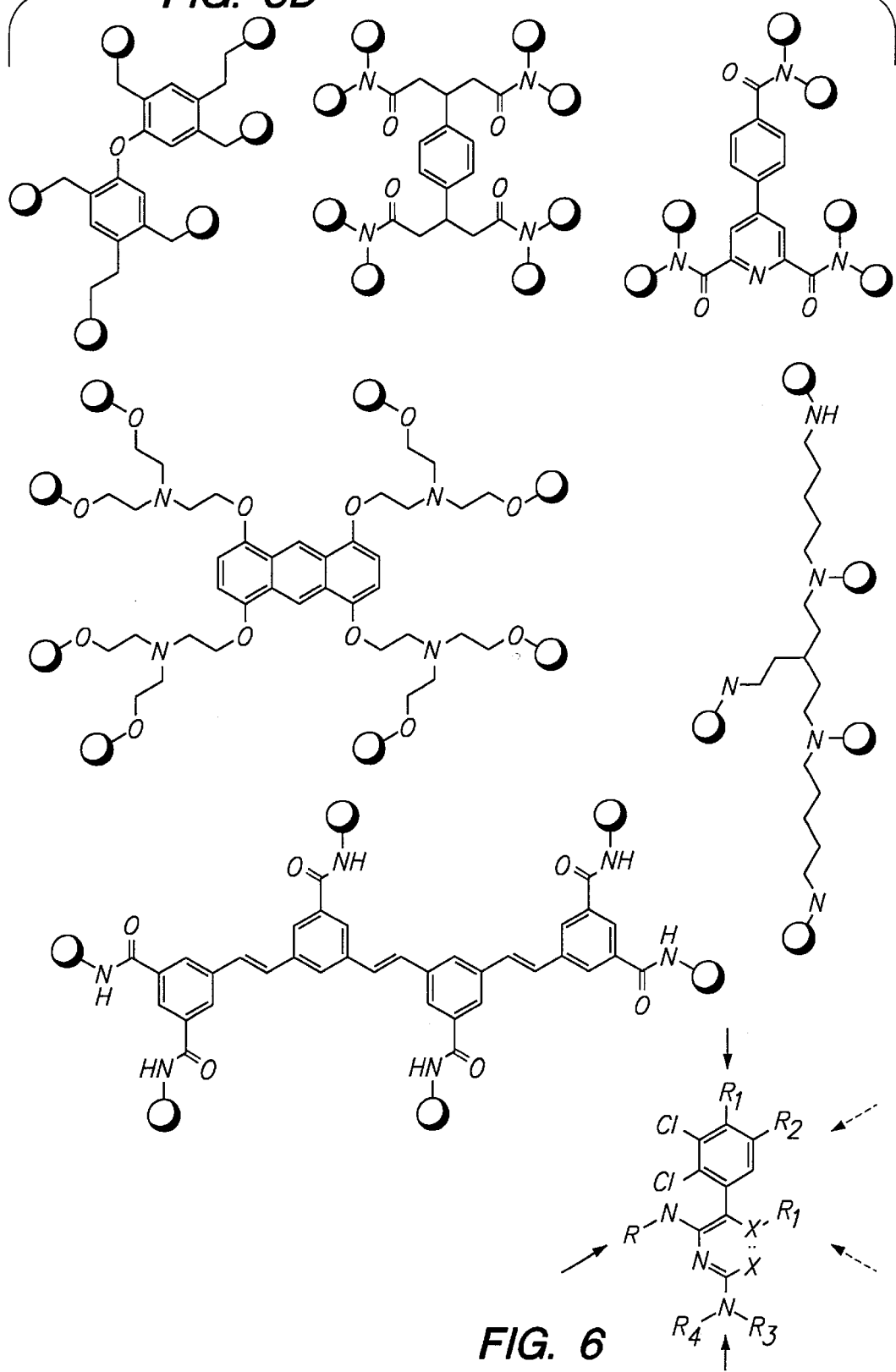
FIG. 6 illustrates a representative ligand which may be used in preparing multi-binding compounds. Potentially modifiable positions are indicated by arrows.

Examples are given below and in FIG. 4, but it should be understood that various changes may be made and equivalents may be substituted without departing from the true spirit and scope of the invention. For example, properties of the linker can be modified by the addition or insertion of ancillary groups into the linker, for example, to change the solubility of the multibinding compound (in water, fats, lipids, biological fluids, etc.), hydrophobicity, hydrophilicity, linker flexibility, antigenicity, stability, and the like. For example, the introduction of one or more poly(ethylene glycol) (PEG) groups onto the linker enhances the hydrophilicity and water solubility of the multibinding compound, increases both molecular weight and molecular size and, depending on the nature of the unPEGylated linker, may increase the in vivo retention time. Further, PEG may decrease antigenicity and potentially enhances the overall rigidity of the linker.

Ancillary groups that enhance the water solubility/hydrophilicity of the linker, and accordingly, the resulting multibinding compounds, are useful in practicing this invention. Thus, it is within the scope of the present invention to use ancillary groups such as, for example, small repeating units of ethylene glycols, alcohols, polyols, (e.g., glycerin, glycerol propoxylate, saccharides, including mono-, oligosaccharides, etc.) carboxylates (e.g., small repeating units of glutamic acid, acrylic acid, etc.), amines (e.g., tetraethylenepentamine), and the like to enhance the water solubility and/or hydrophilicity of the multibinding compounds of this invention. In preferred embodiments, the ancillary group used to improve water solubility/hydrophilicity will be a polyether. In particularly preferred embodiments, the ancillary group will contain a small number of repeating ethylene oxide (—CH$_2$CH$_2$O—) units.

The incorporation of lipophilic ancillary groups within the structure of the linker to enhance the lipophilicity and/or hydrophobicity of the compounds of Formula I is also within the scope of this invention. Lipophilic groups useful with the linkers of this invention include, but are not limited to, lower alkyl, aromatic groups and polycyclic aromatic groups. The aromatic groups may be either unsubstituted or substituted with other groups, but are at least substituted with a group which allows their covalent attachment to the linker. As used herein the term "aromatic groups" incorporates both aromatic hydrocarbons and heterocyclic aromatics. Other lipophilic groups useful with the linkers of this invention include fatty acid derivatives which may or may not form micelles in aqueous medium and other specific lipophilic groups which modulate interactions between the multibinding compound and biological membranes.

Also within the scope of this invention is the use of ancillary groups which result in the compound of Formula I being incorporated into a vesicle, such as a liposome, or a micelle. The term "lipid" refers to any fatty acid derivative that is capable of forming a bilayer or micelle such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro and other like groups well known in the art. Hydrophobicity could be conferred by the inclusion of groups that include, but are not limited to long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphoglycerides and sphingolipids, representative examples of which include phosphatidylcholine, phosphatidylethanolamine, phosphatidylserine, phosphatidylinositol, phosphatidic acid, pannitoyleoyl phosphatidylcholine, lysophosphatidylcholine, lysophosphatidyl-ethanolane, dipalimtoylphosphatidylcholine, dioleoylphosphatidyl-chohne, distearoyl-phosphatidylcholine and dilinoleoylphosphatidylcholine. Other compounds lacking phosphorus, such as sphingolipid and glycosphingolipid families, are also within the group designated as lipid. Additionally, the amphipathic lipids described above may be mixed with other lipids including triglycerides and sterols.

The flexibility of the linker can be manipulated by the inclusion of ancillary groups which are bulky and/or rigid. The presence of bulky or rigid groups can hinder free rotation about bonds in the linker, or bonds between the linker and the ancillary group(s), or bonds between the linker and the functional groups. Rigid groups can include, for example, those groups whose conformational freedom is restrained by the presence of rings and/or π-bonds, for example, aryl, heteroaryl and heterocyclic groups. Other groups which can impart rigidity include polypeptide groups such as oligo- or polyproline chains.

Rigidity can also be imparted electrostatically. Thus, if the ancillary groups are either positively or negatively charged, the similarly charged ancillary groups will force the linker into a configuration affording the maximum distance between each of the like charges. The energetic cost of bringing the like charged groups closer to each other, which is inversely related to the square of the distance between the groups, will tend to hold the linker in a configuration that maintains the separation between the like-charged ancillary groups. Further, ancillary groups bearing opposite charges will tend to be attracted to their oppositely charged counterparts and potentially may enter into both inter- and intramolecular ionic bonds. This non-covalent mechanism will tend to hold the linker in a conformation which allows bonding between the oppositely charged groups. The addition of ancillary groups which are charged, or alternatively, protected groups that bear a latent charge which is unmasked, following addition to the linker, by deprotection, a change in pH, oxidation, reduction or other mechanisms known to those skilled in the art, is within the scope of this invention.

Bulky groups can include, for example, large atoms, ions (e.g., iodine, sulfur, metal ions, etc.) or groups containing large atoms, polycyclic groups, including aromatic groups, non-aromatic groups and structures incorporating one or more carbon—carbon π-bonds (i.e., alkenes and alkynes). Bully groups can also include oligomers and polymers which are branched- or straight-chain species. Species that are branched are expected to increase the rigidity of the structure more per unit molecular weight gain than are straight-chain species.

In preferred embodiments, rigidity (entropic control) is imparted by the presence of alicyclic (e.g., cycloalkyl), aromatic and heterocyclic groups. In other preferred embodiments, this comprises one or more six-membered rings. In still further preferred embodiments, the ring is an aryl group such as, for example, phenyl or naphthyl, or a macrocyclic ring such as, for example, a crown compound.

In view of the above, it is apparent that the appropriate selection of a linker group providing suitable orientation, entropy and physico-chemical properties is well within the skill of the art.

Eliminating or reducing antigenicity of the multibinding compounds described herein is also within the scope of this invention. In certain cases, the antigenicity of a multibinding compound may be eliminated or reduced by use of groups such as, for example, poly(ethylene glycol).

The Compounds of Formula I

As explained above, the multibinding compounds described herein comprise 2–10 ligands attached covalently to a linker that links the ligands in a manner that allows their multivalent binding to ligand binding sites of Na$^+$ channels. The linker spatially constrains these interactions to occur within dimensions, defined by the linker. This and other factors increases the biologic and/or therapeutic effect of the multibinding compound as compared to the same number of ligands used in monobinding form.

The compounds of this invention are preferably represented by the empirical formula $(L)_p(X)_q$ where L, X, p and q are as defined above. This is intended to include the several ways in which the ligands can be linked together in order to achieve the objective of multivalency, and a more detailed explanation is provided below.

As noted previously, the linker may be considered as a framework to which ligands are attached. Thus, it should be recognized that the ligands can be attached at any suitable position on this framework, for example, at the termini of a linear chain or at any intermediate position thereof.

The simplest and most preferred multibinding compound is a bivalent compound which can be represented as L—X—L, where L is a ligand and is the same or different and X is the linker. A trivalent compound could also be represented in a linear fashion, i.e., as a sequence of repeated units L—X—L—X—L, in which L is a ligand and is the same or different at each occurrence, as is X. However, a trivalent compound can also comprise three ligands attached to a central core, and thus be represented as $(L)_3X$, where the linker X could include, for example, an aryl or cycloalkyl group. Tetravalent compounds can be represented in a linear array:

L—X—L—X—L—X—L, or a branched array

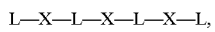

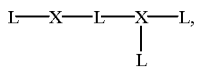

i.e., a branched construct analogous to the isomers of butane (n-butyl, iso-butyl, sec-butyl, and t-butyl) or a tetrahedral array, e.g.

where X and L are as defined herein. Alternatively, it could be represented as an alkyl, aryl or cycloalkyl derivative as described above with four (4) ligands attached to the core liner.

The same considerations apply to higher multibinding compounds of this invention containing from 5–10 ligands. However, for multibinding agents attached to a central linker such as an aryl, cycloalkyl or heterocyclyl group, or a crown compound, there is a self-evident constraint that there must be sufficient attachment sites on the linker to accommodate the number of ligands present; for example, a benzene ring could not accommodate more than 6 ligands, whereas a multi-ring linker (e.g., biphenyl) could accommodate a larger number of ligands.

The above described compounds may alternatively be represented as cyclic chains of the form:

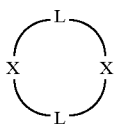

and variants thereof.

All of the above variations are intended to be within the scope of the invention defined by the formula $(L)_p(X)_q$. Examples of bivalent and higher-order valency compounds of this invention are provided in FIGS. 5A to 5D.

With the foregoing in mind, a preferred linker may be represented by the following formula:

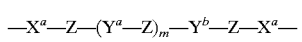

in which:

m is an integer of from 0 to 20;

$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of:

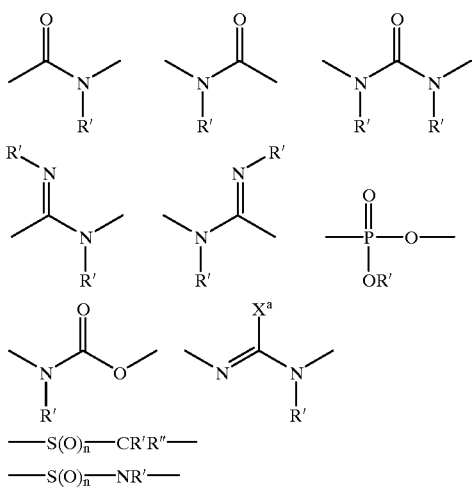

—S—S— or a covalent bond;

in which:

n is 0, 1 or 2; and

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

Additionally, tile linker moiety can be optionally substituted at any atom therein by one or more alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic group.

In anther embodiment of this invention, the linker (i.e., X, X' or X") has the formula.

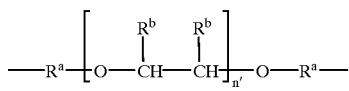

wherein
- each $R^a$ is independently selected from the group consisting of a covalent bond, alkylene, substituted alkylene and arylene;
- each $R^b$ is independently selected from the group consisting of hydrogen, alkyl and substituted alkyl; and
- n' is an integer ranging from 1 to about 20.

In view of the above description of the linker, it is understood that the term "linker" when used in combination with the term "multibinding compound" includes both a covalently contiguous single linker (e.g., L—X—L) and multiple covalently non-contiguous linkers (L—X—L—X—L) within the multibinding compound.

As was previously discussed, the linker or linkers can be attached to different positions on the ligand molecule to achieve different orientations of the ligand domains and thereby facilitate multivalency. For example, the positions that are potentially available for linking a representative ligand are indicated by arrows in the structure shown in FIG. 6. Preferred positions of attachment suggested by known SAR are illustrated in the reaction schemes described herein.

Certain $Na^+$ channel ligands may be chiral and exhibit stereoselectivity. The most active enantiomers are preferably used as ligands in the multibinding compounds of this invention. The chiral resolution of enantiomers is accomplished by well known procedures that result in the formation of diastereomeric derivatives or salts, followed by conventional separation by chromatographic procedures or by fractional crystallization (see, e.g., Bossert, et al., *Angew. Chem. Int. Ed.*, 20:762–769 (1981) and U.S. Pat. No. 5,571,827 and references cited therein). Chiral ligands are also readily available via asymmetric synthesis.

The ligands are covalently attached to the linker using conventional chemical techniques. The reaction chemistries resulting in such linkage are well known in the art and involve the coupling of reactive functional groups present on the linker and ligand. In some cases, it may be necessary to protect portions of the ligand that are not involved in linking reactions.

Preferably, the reactive functional groups on the linker are selected relative to the functional groups on the ligand that are available for coupling, or can be introduced onto the ligand for this purpose in some embodiments, the linker is coupled to ligand precursors, with the completion of ligand synthesis being carried out in a subsequent step. Where functional groups are lacking, they can be created by suitable chemistries that are described in standard organic chemistry texts such as J. March, *Advanced Organic Chemistry*, 4th Ed. (Wiley-Interscience, N.Y., 1992). Examples of the chemistry for connecting ligands by a linker are shown in FIG. 7 where $R_1$ and $R_2$ represent a ligand and/or the linking group. One skilled in the art will appreciate that synthetically equivalent coupling reactions can be substituted for the reactions illustrated herein.

The linker to which the ligands or ligand precursors are attached comprises a "core" molecule having two or more functional groups with reactivity that is complementary to that of the functional groups on the ligand. FIG. 4 illustrates the diversity of "cores" that are useful for varying the linker size, shape, length, orientation, rigidity, acidity/basicity, hydrophobicity/hydrophilicity, hydrogen bonding characteristics and number of ligands connected. This pictorial representation is intended only to illustrate the invention, and not to limit its scope to the structures shown. In the Figures and reaction schemes that follow, a solid circle is used to generically represent a core molecule. The solid circle is equivalent to a linker as defined above after reaction.

Preparation of Multibinding Compounds of the Invention

The multibinding compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Any suitable compound that binds to $Na^+$ cancels can be used as a ligand in this invention. Typically, a compound selected for use as a ligand will have at lease one functional group, such as an amino, hydroxyl, thiol or carboxyl group and the like, which allows the compound to be readily coupled to the linker.

In the examples below, the following abbreviations have the following meanings. If an abbreviation is not defined, it has its generally accepted meaning.

| | |
|---|---|
| Å | Angstroms |
| cm | centimeter |
| DCC | dicyclohexyl carbodiimide |
| DIPEA | N,N-diisopropylethylamine |
| DMA | N,N-dimethylacetamide |
| DMF | N,N-dimethylformamide |
| DMSO | dimethylsulfoxide |
| DPPA | diphenylphosphorylazide |
| EDTA | ethylenediaminetetraacetic acid |
| g | gram |
| HPLC | high performance liquid chromatography |
| MEM | minimal essential medium |
| mg | milligram |
| MIC | minimum inhibitory concentration |
| min | minute |
| mL | milliliter |
| mm | millimeter |
| mmol | millimol |
| N | normal |
| TEA | triethylamine |
| THF | tetrahydrofuran |
| µL | microliters |
| µm | microns |

The preferred co pounds of Formula I are bivalent. It should be noted, however, that the same techniques can be used to generate higher order multibinding compounds, i.e., the compounds of the invention where p is 3–10.

Reactions performed under standard amide coupling conditions are carried out in an inert polar solvent (e.g., DMF, DMA) in the presence of a hindered base (e.g., TEA, DIPEA) and standard amide coupling reagents (e.g., DPPA, PyBOP, HATU, DCC).

The following describes several methods for preparing multibinding compounds employing ligands having the following structures A and B:

Structure A

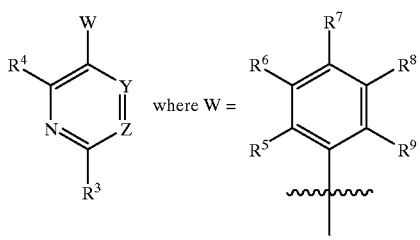

where W = wherein, Y is N or C—R$^1$; Z is N or C—R$^2$; R$^3$ and R$^4$ are each independently amino, substituted amino, halogen, hydroxyl, ether, thioether, alkyl, R$^5$,R$^6$,R$^7$,R$^8$, and R$^9$ are each independently hydrogen, halogen, amino, substituted amino, hydroxyl, ether, thioether, fluoroalkyl, allyl, W is preferably 2,3-dichlorophenyl (wherein R$^5$=R$^1$=Cl, and R$^7$=R$^8$=R$^9$=H) or 2,3,5-trichlorophenyl (wherein R$^5$=R$^6$=R$^8$=Cl, and R$^7$=R$^9$=H).

For structure A, three preferred subclasses of compounds are the pyrimidine series, the triazine series, and the pyrazine series as described as follows.

| Subclass | Structure | Illustrative Examples |
|---|---|---|
| Pyrimidine (Y = N, C—R$^1$, Z = N) | 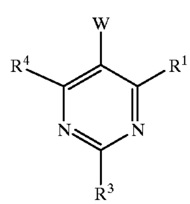 | 4030W92 (W = 2,3-dichlorophenyl (R$^1$ = CH$_2$F, and R$^3$ = R$^4$ = NH$_2$) |
| | | Sipatrigine (W = 2,3,5-trichlorophenyl, (R$^1$ = H, R$^4$ = NH$_2$, and R$^3$ = 4-methyl-piperazin-1-yl) |
| Triazine (Y = N, Z = N) | 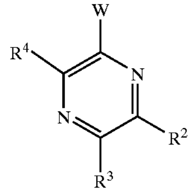 | Lamotrigine (W = 2,3-dichlorophenyl, and R$^3$ = R$^4$ = NH$_2$) |
| Pyrazine (Y = N, Z = C—R$^2$) | | GW273293 (W = 2,3,5-trichlorophenyl, and R$^3$ = R$^4$ = NH$_2$) |

Structure B

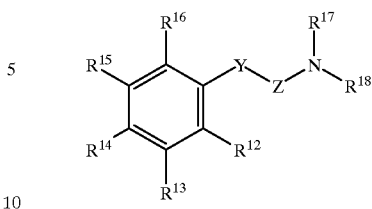

wherein R$^{12}$, R$^{13}$, R$^{14}$, R$^{15}$, R$^{16}$ and R$^{17}$ are independently hydrogen, alkyl, halogen, ether, thioether, carboyl derivatives, hydroxyl, fluoroalkyl, amino, substituted amino, Y is —(CH$_2$)$_n$— where n is an integer from 1–4, O, S, NR (where R=H or alkyl), (—R$^{101}$R$^{102}$)$_n$— where n is an integer from 1–4 and R$^{101}$ and R$^{102}$ are independently hydrogen, lower alkyl, or substituted lower alkyl and Z is —(CH)$_n$—, ((—R$^{101}$R$^{102}$)— where n is an integer from 14 and R$^{101}$ and R$^{102}$ are independently hydrogen, lower alkyl, or substituted lower alkyl.

For structure B, three preferred compounds are: (1) mexilitene: Y—O, Z—CH$_2$—CH(CH$_3$)—R$^{12}$=R$^{16}$=Me, R$^{13}$=R$^{14}$=H, R$^{17}$=R$^{18}$=H; (2) N-ethyl mexilitene: Y=O, Z=CH$_2$—CH(CH$_3$)—, R$^{12}$=R$^{16}$=Me, R$^{13}$=R$^{14}$=R$^{15}$=H, R$^{17}$=Et, R$^{18}$=H; and (3) a phenoxymethyl piperidine deriviative as described in EP 869119 A1, wherein Y=O, Z=CH$_2$—CH(R$^{19}$)—CH$_2$—, R$^{12}$=R$^{16}$=Me, R$^{13}$=R$^{15}$=H, R$^{14}$=Br, R$^{17}$=Me and R$^{18}$ and R$^{19}$, taken together, are —(CH)$_3$—.

It will be understood by those skilled in the art that the following methods may be used to prepare other multibinding compounds of this invention.

The strategies for preparing compounds of Formula I discussed above involve coupling the ligand directly to a homobifunctional core. Another strategy that can be used with all ligands, and for the preparation of both bivalent and higher order multibinding compounds, is to introduce a 'spacer' before coupling to a central core. Such a spacer can itself be selected from the same set as the possible core compounds.

Compounds of Formula I of higher order valency, i.e., p=3–10, can be prepared by simple extension of the above strategies. Specifically compounds are prepared by coupling ligands to a central core bearing multiple functional groups. The reaction conditions are the same as described above for the preparation of bivalent compounds, with appropriate adjustments made in the molar quantities of ligand and reagents.

All of the synthetic strategies described above employ a step in which the ligand, attached to spacers or not, is symmetrically linked to functionally equivalent positions on a central core. Compounds of Formula I can also be synthesized using an asymmetric linear approach. This strategy may be preferred when linking two or more ligands at different points of connectivity or when preparing heterovalomers.

Representative syntheses of ligand precursors are illustrated in the reaction schemes and examples shown in FIG. 8 and described herein.

Scheme A illustrates the synthesis of a pyrimidine class compound. As shown, compounds 10 and 11 first undergo a base-catalyzed Claisen Reaction followed by alkylation to produce compound 12 which in turn is reacted with compound 13 to yield the pyrimidine compound. This technique for synthesizing monovalent compounds and for the synthesis of compound 12 are described, for example, PCT application WO97/09317, BP372934A2, EP372934B1.

Scheme B illustrates a synthesis of a bivalent pyrimidine compound of the Formula I that adapts the method shown in scheme A wherein a dimeric guanidine compound (13b) is employed in place of the monomeric compound (13). Compounds of formula (13b) can be made by known techniques, for example, by reacting diamine linker(5) with compound (15) (see Synthesis, (6), 579–82; 1994). Alternatively, they may be synthesized by reacting diamines with cyanamide in water to yield compounds of Formula (13b), (See, for example, German Patent DE 4240981.) The preparation of compound (15) is described in Tetrahedron Lett., 34(21), 3389–92 (1993). By varying the substitution on the benzaldehyde precursor of W other compounds of formula (12) can be synthesized.

Example 1 illustrates the preparation of bivalent compound 52 of Formula I via scheme B. Specifically, to a solution of NaOEt (from 9.13 mmol of sodium) in ethanol (20 mL) is added piperazinodiformamidine dihydrochloride (51) (8.22 mmol). After stirring for a further 10 minutes, 2-(2,3,5-trichlorophenyl)-3-methoxyacrylonitrile (50) (19.2 mmol) is added and the mixture is stirred at reflux for 4 hours. The mixture is left standing at room temperature overnight and then filtered. The filtrate is concentrated and the residue is purified by chromatography to afford the title product. Compound (51) is described in CAS 17238-65-2.

Scheme C illustrates the general principle of using conventional synthetic techniques to introduce functional groups in the ligand which can then be interconverted into other functional groups or dimerized. As shown, compounds 10 and 11a produce pyrimidine 14a via the base-catalyzed Claisen Reaction and alkylation process of scheme A. In this case, $R^1$ contains an acetal which is hydrolyzed and reduced to alcohol (14b). This process is described in WO97/09317 for 2,4-diamino-5-(2,3-dichlorophenyl)-6-hydroxymethyl pyrimidine. Others of form (14b) can be made by varying substitution at W, $R^3$, following the techniques described in WO97/09317.

Scheme D illustrates the synthesis of a bivalent compound of Formula I by direct dimerization of the alcohol (14b) by a process whereby the alcohol is coupled to dihalide linker (3).

Example 2 illustrates the preparation of (55), a compound of Formula I via scheme D. Specifically, a solution of 20 mmols of (53) in DMF with 10 mmols of 1,4-dibromobutane (54) and 20 mmols of diisopropylethylamine is heated at 80° C. and the reaction followed by TLC. When judged complete, the mixture is partitioned between ethyl acetate and water and the organic phase washed with water, dried over sodium sulfate and the solvent removed in vacuo. The residue is purified by chromatography to afford the desired product. The preparation of compound (53) is also described in WO97/09317.

Scheme E illustrates the synthesis of a bivalent compound of Formula I by oxidizing of alcohol (14b) into the aldehyde (14c), followed by dimerization by reductive alkylation with diamine linker (5).

Example 3 illustrates the preparation of a compound of Formula I (58), via Scheme E. Specifically, alcohol (53) (100 mmol) is dissolved in $CH_2Cl_2$. Pyridinium chloroformate (110 mmol) is added in portions with stirring. The progress of the reaction is monitored by TLC. When judged complete, the solution is filtered through a small plug of silica gel, then evaporated under vacuum. The residue is chromatographed to afford the desired product (56).

Diamine (57) (2 mmol) is dissolved in THF (10 ml). Acetic acid (0.5 ml) is then added and the reaction is heated to reflux. Aldehyde (56) (1 mmol) dissolved in THF (10 ml) is then added dropwise to the refluxing solution over 60 minutes and the reaction is refluxed for a further 60 minutes. At this point, $NaBH(OAc)_3$ is added in portions and the reaction is stirred at reflux for a further 2 hours. The reaction is allowed to cool and then is quenched with aqueous $NH_4Cl$ solution until the pH of the solution is adjusted to pH 7.0 using either 1 M HCl or 1 M NaOH. The product is extracted from this aqueous phase with EtOAc. The organic layer is dried using $Na_2SO_4$, the drying agent is then filtered off and the solvent removed in vacuo to provide the crude product. The desired material is purified from this mixture using reverse phase HPLC.

Scheme F illustrates the synthesis of a bivalent compound of the Formula I by conversion of aldehyde 14c to the amine (14d), followed by dimerization via amide coupling to diacid linker (4).

Example 4 illustrates the preparation of a compound of Formula I (61) via Scheme F. Specifically, aldehyde (56) (1 mmol) dissolved in $CH_2Cl_2$ (10 ml) is then added dropwise over 60 minutes to a refluxing solution of ammonium acetate (3 mmol) and acetic acid and the reaction is refluxed for a further 60 minutes. At this point, $NaBH(OAc)_3$ is added in portions and the reaction is stirred at relux for a further 2 hours. The reaction is allowed to cool and then is quenched with aqueous $NH_4Cl$ solution until the pH of the solution is adjusted to pH 7.0 using either 1 M HCl or 1 M NaOH. The product is extracted from this aqueous phase with EtOAc. The organic layer is dried using $Na_2SO_4$, the drying agent is then filtered off and the solvent removed in vacuo to provide the crude product. The desired material is purified from this mixture using reverse phase HPLC.

A solution of (59) (2 mmols) and isophthalic acid (60) (1 mmol) in methylene chloride is prepared under argon in a flask equipped with magnetic stirrer and drying tube. To this solution is added dicyclohexylcarbodiimide (solid, 2.1 mmols) while stirring at room temperature. The course of the reaction is followed by thin layer chromatography. When reaction has occurred, the reaction solution is diluted with ethyl acetate and washed with water and with aqueous $Na_2CO_3$. The organic layer is dried ($NaSO_4$), filtered and concentrated under reduced pressure to give the crude product. The desired compound is obtained by purification of the crude product by use of HPLC.

Scheme G illustrates the synthesis of bivalent compounds of Formula I from monovalent compounds in the pyrimidine class. (The references cited with respect to schemes J and K for the pyrazines are applicable for schemes G, H and I.) As shown, reaction of compound 21 and 20 via a Pd-catalyzed aryl coupling reaction yields monovalent compound 22 which is then coupled to diamine (5) to form the bivalent compound.

Example 5 illustrates the preparation of (69), a compound of Formula I via Scheme G. Specifically, a mixture of (65) (30 mmol) in THF and tetrakis(triphenylphosphine) palladium(0) is stirred under nitrogen at room temperature for 10 minutes. 2M aqueous sodium carbonate is added to the mixture followed by a solution of 2,3-dichlorobenzene boronic acid (66) (30 mmol) in absolute ethanol and the mixture refluxed under nitrogen for 17 hours. A further equivalent of 2,3,5-trichlorobenzene boronic acid in absolute ethanol is added and the mixture refluxed for an additional 7.50 hours. Finally, another equivalent of 2,3,5-trichlorobenzene boronic acid in absolute ethanol is added to the mixture and continued refluxing for 17 hours. The cooled mixture is evaporated in vacuo. The residue is dissolved in chloroform, washed with aqueous saturated sodium bicarbonate and water, dried over anhydrous magnesium sulfate, filtered and the filtrate evaporated down in vacuo. The residue is purified by flash chromatography using chloroform/methanol as the eluant to afford the desired product (67).

A solution of 72 mmols of (67) in DMF with 36 mmols of 1,3-diaminopropane (68) and 20 mmols of diisopropylethylamine is heated as necessary in a sealed vessel and the reaction followed by TLC. When judged complete, the mixture is partitioned between ethyl acetate and water and the organic phase washed with water, dried over sodium sulfate and the solvent removed in vacuo. The residue is purified by chromatography to afford the desired product. Compound (65) is described in CAS 3993-80-4 and compound (66) is described in WO 98/38174.

Scheme H illustrates the synthesis of another bivalent compounds of Formula I from monovalent compounds in the pyrimidine class. As shown, reaction of compound 23 and 20 via a Pd-catalyzed aryl coupling reaction yields monovalent compound 24 which is then coupled to diamine (5) to form the bivalent compound.

Example 6 illustrates the preparation of (73), a compound of Formula I via Scheme H. Specifically, a mixture of (70) (30 mmol) in THF and tetrakis(triphenylphosphine)palladium(0) is stirred under nitrogen at room temperature for 10 minutes. 12M aqueous sodium carbonate is added to the mixture followed by a solution of 2,3-dichlorobenzene boronic acid (66) (30 mmol) in absolute ethanol and the mixture refluxed under nitrogen for 17 hours. A further equivalent of 2,3,5-trichlorobenzene boronic acid in absolute ethanol is added and the mixture refluxed for an additional 7.50 hours. Finally, another equivalent of 2,3,5-trichlorobenzene boronic acid in absolute ethanol is added to the mixture and continued refluxing for 17 hours. The cooled mixture is evaporated in vacuo. The residue is dissolved in chloroform, washed with aqueous saturated sodium bicarbonate and water, dried over anhydrous magnesium sulfate, filtered and the filtrate evaporated down in vacuo. The residue is purified by flash chromatography using chloroform/methanol as the eluant to afford the desired product (71).

A solution of 72 mmols of (71) in DMF with 36 mmols of N,N'-dimethyl-1,3-propanediamine (72) and 20 mmols of diisopropylethylamine is heated as necessary in a sealed vessel and the reaction followed by TLC. When judged complete, the mixture is partitioned between ethyl acetate and water and the organic phase washed with water, dried over sodium sulfate and the solvent removed in vacuo. The residue is purified by chromatography to afford the desired product. Compound (70) is described in CAS 205672-25-9.

Scheme I illustrates the synthesis of another bivalent compound of Formula I from monovalent compounds in the pyrimidine class. As shown, reaction of compound 25 and 20 via a Pd-catalyzed aryl coupling reaction yields monovalent compound 26 which is then coupled to diamine (5) to form the bivalent compound.

Example 7 illustrates the preparation of (78), a compound of Formula I via Scheme I. Specifically, a mixture of (74) (30 mmol) in THF and tetrakis(triphenylphosphine)palladium(0) is stirred under nitrogen at room temperature for 10 minutes. 2M aqueous sodium carbonate is added to the mixture followed by a solution of 2,3-dichlorobenzene boronic acid (66) (30 mmol) in absolute ethanol and the mixture refluxed under nitrogen for 17 hours. A further equivalent of 2,3,5-trichlorobenzene boronic acid in absolute ethanol is added and the mixture refluxed for an additional 7.50 hours. Finally, another equivalent of 2,3,5-trichlorobenzene boronic acid in absolute ethanol is added to the mixture and continued refluxing for 17 hours. The cooled mixture is evaporated in vacuo. The residue is dissolved in chloroform, washed with aqueous saturated sodium bicarbonate and water, dried over anhydrous magnesium sulfate, filtered and the filtrate evaporated down in vacuo. The residue is purified by flash chromatography using chloroform/methanol as the eluant to afford the desired product (75).

A solution of 72 mmols of (75) in DMF with 36 mmols of piperazine (76) and 20 mmols of diisopropylethylamine is heated as necessary in a sealed vessel and the reaction followed by TLC. When judged complete, the mixture is partitioned between ethyl acetate and water and the organic phase washed with water, dried over sodium sulfate and the solvent removed in vacuo. The residue is purified by chromatography to afford the desired product (77).

A suspension of (77) (72 mmol) in absolute ethanol and ammonia (375 ml) is stirred and heated in an autoclave at 160° C. and 20 atm. for 16 hours. The cooled mixture is evaporated in vacuo and extracted with hot methanol. The combined methanol extracts are evaporated in vacuo. The residue is dissolved in hot chloroform, dried over anhydrous magnesium sulfate, filtered and the filtrate evaporated in vacuo. The residue is triturated with 40–60° C. petroleum ether, filtered, and dried in vacuo to afford the desired product. Compound (74) is described in CAS 13544-44-0. (Note that ins scheme I the coupling leaves two Cls (26); selective coupling at the more reactive position gives (27)).

Scheme J illustrates the synthesis bivalent compounds of Formula I from monovalent compounds in the pyrazine class. As shown, reaction of compound 35 and 20 via a Pd-catalyzed aryl coupling reaction yields monovalent compound 36 which is then coupled to diamine (5) to form the bivalent compound. This reaction is described in WO98/38174.

Example 8 illustrates the preparation of (82), a compound of Formula I via Scheme J. Specifically, a solution of 72 mmols of 2-amino-6-chloro-3-(2,3,5-trichlorophenyl)pyrazine (80) in DMF with 36 mmols of 1,3-diaminopropane (81) and 20 mmols of diisopropylethylamine is heated as necessary in a sealed vessel and the reaction followed by TLC. When judged complete, the mixture is partitioned between ethyl acetate and water and the organic phase washed with water, dried over sodium sulfate and the solvent removed in vacuo. The residue is purified by chromatography to afford the desired product. Compound (80) is described in WO 98/38174.

Scheme K illustrates the same process as shown in Scheme J adapted to create a compound (38) with the Cl in a different position in the ring.

Note for schemes G, H, I, J, and K the preferred compounds of Formula (20) (66) and (84) are described in WO98/38174, others are accessible by conventional synthesis (from an aromatic bromo compound).

Example 9 illustrates the preparation of (86), a compound of Formula I via Scheme K. Specifically, a mixture of 2-chloro-3-bromo-6-acetamido-pyrazine (83) (30 mmol) in THF and tetrakis(triphenylphosphine)palladium(0) is stirred under nitrogen at room temperature for 10 minutes. 2M aqueous sodium carbonate is added to the mixture followed by a solution of 2,3,5-trichlorobenzene boronic acid (84) (30 mmol) in absolute ethanol and the mixture refluxed under nitrogen for 17 hours. A further equivalent of 2,3,5-trichlorobenzene boronic acid in absolute ethanol is added and the mixture refluxed for an additional 7.50 hours. Finally, another equivalent of 2,3,5-trichlorobenzene boronic acid in absolute ethanol is added to the mixture and continued refluxing for 17 hours. The cooled mixture is evaporated in vacuo. The residue is dissolved in chloroform, washed with aqueous saturated sodium bicarbonate and water, dried over anhydrous magnesium sulfate, filtered and the filtrate evaporated down in vacuo. The residue is purified by flash chromatography using chloroform/methanol as the eluant to afford the desired product (85).

A solution of 72 mmols of (85) in DMF with 36 mmols of 1,4-diaminobutane (68) and 20 mmols of diisopropylethylamine is heated as necessary in a sealed vessel and the reaction followed by TLC. When judged complete, the mixture is partitioned between ethyl acetate and water and the organic phase washed with water, dried over sodium sulfate and the solvent removed in vacuo. The residue is purified by chromatography to afford the desired product. Compound (83) is described in CAS 173253-42-4.

Schemes L and M illustrate the general principle of using conventional synthetic techniques to introduce functional groups in the ligand which can then be interconverted into other functional groups or dimerized.

As shown, in scheme L illustrates the synthesis of a triazine class compound. As shown, compounds 30 and 40 form triazine compound 41.

Scheme M illustrates the synthesis of a bivalent compound of the Formula I from monovalent triazines that encompass lamotrigine. The synthesis of lamotrigine is further described in WO96/20934. As shown, following synthesis of thiol compound 41a from 30 and 40a, the thiol compound is methylated to produce compound 42b. The product formed by oxidation of compound 42b is coupled to diamine linker (5) to produce the bivalent compound.

EXAMPLE 10

Preparation of (91), a Compound of Formula I via Scheme M

A solution of 2,3,5-trichlorbenzoyl cyanide (87) (13 mmol) is dissolved in acetonitrile and added dropwise to a suspension of (40a) (39 mmol) in dilute sulphuric acid. The temperature is maintained below 30° C. The mixture is stirred at room temperature for 3 days. The solid is filtered, washed with water and sucked dry. A suspension of the solid in a 10% solution of sodium hydroxide pellets in water is stirred at room temperature for 1 hour. The solid is filtered, washed with water and dried in vacuo. The solid is refluxed with hot n-propanol for 1.5 hours, filtered and dried in vacuo at 80° C. to afford the desired product (88).

A solution of 72 mmols of (88) in DMF with 72 mmols of methyl iodide and 72 mmols of diisopropylethylamine is heated at 40° C. for 12 hours. The reaction mixture is concentrated and chromatographed to afford the desired product (89).

A solution of 60 mmols of (89) in dichloromethane with 120 mmols of m-chloroperoxybenzoic acid is stirred at room temperature for 12 hours. The reaction mixture is concentrated and chromatographed to afford the desired product. A solution of 50 mmols of the resulting product in DN with 50 mmols diisopropylethylamine and 25 mmols of 4,4'-bipiperidine dihydrochloride (90) is heated at 120° C. for 12 hours in a sealed vessel. The reaction mixture is concentrated and chromatographed to afford the desired product. Compound (87) is reported in EP 0459829(A11).

Scheme N illustrates the synthesis of a bivalent compound of the Formula I from monovalent triazine 42d which is produced by chlorination of compound 42c.

EXAMPLE 11

Preparation of (94) a Compound of Formula I via Scheme N

Alcohol (92) (5 mmol) is dissolved in $CH_2Cl_2$ at 0° C. and $CBr_4$ (12 mmol) is added. A solution of $PPh_3$ (15 mmol) in $CH_2Cl_2$ is added. The progress of the reaction is monitored by TLC. When judged complete, the solvent is removed under vacuum and the residue is chromatographed to afford the desired product (93).

A solution of 72 mmols of (93) in DMF with 36 mmols of 1,3-cyclohexanebis(methylamine) and 20 mmols of diisopropylethylamine is heated as necessary in a sealed vessel and the reaction followed by TLC. When judged complete, the mixture is partitioned between ethyl acetate and water and the organic phase washed with water, dried over sodium sulfate and the solvent removed in vacuo. The residue is purified by chromatography to afford the desired product. Compound (92) is described in WO 96/20934.

Schemes O, P, and Q illustrate the general principle of linking through the ligand phenyl ring, with a functional group introduced in this position via several approaches. A different approach is shown for each class below.

Scheme O illustrates the synthesis of a compound of Formula I from monovalent pyrimidine ligands that are coupled by dialdehyde linker (6). The pyrimidine is produced using a nitro-substituted starting material (10a) via the process of scheme A to yield nitro-substituted (14c). Aniline compound 14(f) is produced by reduction which is then dimerized.

EXAMPLE 12

Preparation of (98), a Compound of Formula I via Scheme O

A solution of (95) (0.0007M) in acetic acid (12 ml)/methanol (1 ml) is reduced under an atmosphere of hydrogen in the presence of $PtO_2$ (0.12 g). The mixture is filtered and the filtrate is concentrated. The residue is neutralized with saturated $NaHCO_3$ solution and the product is extracted with ethylacetate, bulked, dried ($MgSO_4$) and evaporated to afford the desired product (96).

Compound (96) (2 mmol) is dissolved in THF (10 ml). Acetic acid (0.5 ml) is then added and the reaction is heated to reflux. Phthalaldehyde (1 mmol) dissolved in THF (10 ml) is then added dropwise to the refluxing solution over 60 minutes and the reaction is refluxed for a further 60 minutes. At this point, $NaBH(OAc)_3$ (1 mmol) is added in portions and the reaction is stirred at relux for a further 2 hours. The reaction is allowed to cool and then is quenched with aqueous $NH_4Cl$ solution until the pH of the solution is adjusted to pH 7.0 using either 1 M HCl or 1 M NaOH. The product is extracted from this aqueous phase with EtOAc. The organic layer is dried using $NaSO_4$, the drying agent is then filtered off and the solvent removed in vacuo to provide the crude product. The title compound is purified from this mixture using reverse phase HPLC.

Scheme P illustrates the synthesis of a compound of Formula I from monovalent pyrazine ligands that are coupled by dihalide linker(3). The pyrazine 47 is synthesized from a nitro-substituted starting material (45) via the process of Scheme J which initially yields nitro-substituted compound (46), which is then reduced and the aniline is used in dimerization.

EXAMPLE 13

Preparation of (134), a Compound of Formula I via Scheme P

A solution of (131) (0.0007M) in acetic acid (12 ml)/methanol (1 ml) is reduced under an atmosphere of hydrogen in the presence of $PtO_2$ (0.12 g). The mixture is filtered and the filtrate is concentrated. The residue is neutralized with saturated NaHCO$_3$ solution and the product is extracted with ethylacetate, bulked, dried (MgSO$_4$) and evaporated to afford the desired product (132).

Compound (132) (1 mmol) is dissolved in DMF (5 mL) and treated sequentially with 0.5 mmol α,α-bromo-o-xylene (133) and 2 mmol powdered potassium carbonate. The mixture is heated as necessary to effect reaction, which is monitored by TLC. When judged complete, the mixture is partitioned between ethyl acetate and water and the organic phase washed with water, dried over, sodium sulfate and the solvent removed in vacuo. The residue is purified by chromatography to afford the title structure.

Scheme Q illustrates the synthesis of a compound of Formula I from monovalent triazine ligands that are coupled by dicarboxylic acid linker (4). The triazine 41c is formed by nitration of compound (41). Triazine 41c is then reduced and the aniline 41d is used in dimerization.

EXAMPLE 14

Preparation of (101), a Compound of Formula I via Scheme Q

A solution of (99) (2 mmols) and adipic acid (100) (1 mmol) in methylene chloride is prepared under argon in a flask equipped with magnetic stirrer and drying tube. To this solution is added dicyclohexylcarbodiimide (solid, 2.1 mmols) while stirring at room temperature. The course of the reaction is followed by thin layer chromatography. When reaction has occurred, the reaction solution is diluted with ethyl acetate and washed with water and with aqueous Na$_2$CO$_3$. The organic layer is dried (Na$_2$SO$_4$), filtered and concentrated under reduced pressure to give the crude product. The desired compound is obtained by purification of the crude product by use of HPLC.

Schemes R, S, T, and U illustrate the synthesis of bivalent compounds of Formula I from monovalent compounds of structure B. In each case, the linkage is from the [N] group of a first ligand to the [N] group of a second ligand.

Scheme R illustrates the coupling of a monovalent compound with dihalide 3.

EXAMPLE 15

Preparation of (107), a Compound of Formula I via Scheme R

A solution of 20 mmols of (R)-N-ethyl mexiletine (105) in DMF with 10 mmols of 1,6-dibromohexane (106) and 20 mmols of potassium carbonate is heated as necessary and the reaction followed by TLC. When judged complete, the mixture is partitioned between ethyl acetate and water and the organic phase washed with water, dried over sodium sulfate and the solvent removed in vacuo. The residue is purified by chromatography to afford the title structure. Compound (105) is reported in WO 97/27169.

EXAMPLE 16

Preparation of (109), a Compound of Formula I via Scheme R

A solution of 30 mmols of (R)-N-ethyl mexiletine (105) in DMF with 10 mmols of 1,3,5-tri(bromoethyl)benzene (108) and 20 mmols of potassium carbonate is heated as necessary and the reaction followed by TLC. When judged complete, the mixture is partitioned between ethyl acetate and water and the organic phase washed with water, dried over sodium sulfate and the solvent removed in vacuo. The residue is purified by chromatography to afford the tide structure. Compound (105) is reported in WO 97/27169 and compound (108) is described in CAS 18226-42-1.

EXAMPLE 17

Preparation of (114), a Compound of Formula I via Scheme R

A solution of 20 mmols of (R)-mexiletine (110) in DMF with 20 mmols of 1,2-bis-(2-bromoethoxy)ethane (113) and 20 mmols of potassium carbonate is heated as necessary and the reaction followed by TLC. When judged complete, the mixture is partitioned between ethyl acetate and water and the organic phase washed with water, dried over sodium sulfate and the solvent removed in vacuo. The residue is purified by chromatography to afford the title structure. Compound (113) is described in CAS 31255-10-4.

EXAMPLE 18

Preparation of (120), a Compound of Formula I via Scheme R

A solution of 20 mmols of (S)-3-(4-bromo-2,6-dimethylphenoxymethyl)piperdine (118) in DMF with 10 mmols of 2-bromoethyl ether (119) and 20 mmols of potassium carbonate is heated as necessary and the reaction followed by TLC. When judged complete, the mixture is partitioned between ethyl acetate and water and the organic phase washed with water, dried over sodium sulfate and the solvent removed in vacuo. The residue is purified by chromatography to afford the title structure. Compound (118) is reported in EP 0869119 A1.

Scheme S illustrates the coupling of another monovalent compound with dihalide 3.

EXAMPLE 19

Preparation of (112), a Compound of Formula I via Scheme S

A solution of 20 mmols of (R)-mexiletine (110) in THF is treated with 20 mmols of trifluoroacetic anhydride and 20 mmols of triethylamine. After 1 hour, the solvent is removed in vacuo and the residue is partitioned between ethyl acetate and water. The organic layer is washed with additional water, dried over anhydrous sodium sulfate, filtered and the solvent removed under reduced pressure to afford the crude trifluoroacetamide of (R)-mexiletine.

A solution of the above crude trifluoroacetamide in anhydrous THF is cooled under nitrogen to −78 C and treated dropwise with 20 mL of 1 N LDA in THF. The temperature is raised to −20 C and a solution of 10 mmols of α',α'-dibromo-p-xylene (111) is added and the reaction followed by TLC. When judged complete, 30 mL of 1 N NaOH is added and the temperature is raised to 60 C until the trifluoroacetamide is removed as indicated by TLC. The reaction mixture is partitioned between ethyl acetate and water. The organic layer is washed with additional water, dried over anhydrous sodium sulfate, filtered, and concentrated under reduced pressure. The residue is purified by chromatography to afford the title structure.

Scheme T illustrates the coupling of two monovalent molecules with two diamine linkers 5 to a linkage involving two linkers.

EXAMPLE 20

Preparation of (117), a Compound of Formula I via Scheme T

A solution of 20 mmols of 2-(2-bromopropoxy)-1,3-dimethylbenzene (115) in DMF with 10 mmols of 1,4,10, 13-tetraoxa-7,16-diazacyclooctadecane (4,13-diaza-18-crown-6) (116) and 20 mmols of potassium carbonate is heated as necessary and the reaction followed by TLC. When judged complete, the mixture is partitioned between ethyl acetate and water and the organic phase washed with water, dried over sodium sulfate and the solvent removed in vacuo. The residue is purified by chromatography and separation of the stereoisomers by known technique to afford the title structure. Compound (115) is described in CAS 96656-46-1.

The following Examples 21–24 (as illustrated in FIG. 8) describe the syntheses of heterodimers comprising two nonidentical ligands.

EXAMPLE 21

Preparation of (122), a Compound of Formula I

A solution of 20 mmols of (R)-N-ethyl mexiletine (105) in DMF with 20 mmols of 1,4-dibromobutane (54) and 20 mmols of potassium carbonate is heated as necessary and the reaction followed by TLC. When judged complete, the mixture is partitioned between ethyl acetate and water and the organic phase washed with water, dried over sodium sulfate and the solvent removed in vacuo. The residue is purified by chromatography to afford the desired product (121).

A solution of 20 mmols of (S)-3-(4-bromo-2,6-dimethylphenoxymethyl)piperdine (118) in DMF with 20 mmols of the above product (121) and 20 mmols of potassium carbonate is heated as necessary and the reaction followed by TLC. When judged complete, the mixture is partitioned between ethyl acetate and water and the organic phase washed with water, dried over sodium sulfate and the solvent removed in vacuo. The residue is purified by chromatography to afford the title structure. Compound (105) is reported in WO 97/27169. Compound (118) is reported in EP 0869119 A1.

EXAMPLE 22

Preparation of (123), a Compound of Formula I

A solution of 20 mmols of 2-(2-bromopropoxy)-1,3-dimethylbenzene (115) in DMF with 20 mmols of (S)-3-(4-bromo-2,6-dimethylphenoxymethyl)piperidine (118) and 20 mmols of potassium carbonate is heated as necessary and the reaction followed by TLC. When judged complete, the mixture is partitioned between ethyl acetate and water and the organic phase washed with water, dried over sodium sulfate and the solvent removed in vacuo. The residue is purified by chromatography to afford the title structure. Compound (115) as described in CAS 96656-46-1 and compound (118) is reported in EP 0869119 A1.

EXAMPLE 23

Preparation of (126), a Compound of Formula I

A solution of 10 mmols of (67) in 20 mL DMF is treated sequentially with 15 mmols of diisopropylethylamine and 10 mmols of 1,4-diaminobutane (124). The solution is heated as necessary in a sealed vessel and the reaction followed by TLC. When it is judged complete, the mixture containing compound (125) is treated with 15 mmols additional diisopropylethylamine and 10 mmols of (80). The reaction is further heated as necessary and monitored by TLC until judged complete. The mixture is partitioned between ethyl acetate and water and the organic phase washed with water, dried over sodium sulfate and the solvent removed in vacuo. The residue is purified by chromatography to afford the title compound.
Compound (80) is described in WO 98/38174.

EXAMPLE 24

Preparation of (127), a Compound of Formula I

A solution of 10 mmols of (118) in 20 mL DMF is treated sequentially with 30 mmols diisopropylethylamine and 20 mmols of (80). The solution is heated as necessary in a sealed vessel and the reaction followed by TLC. When judged complete, the mixture is partitioned between ethyl acetate and water and the organic phase washed with water, dried over sodium sulfate and the solvent removed in vacuo. The residue is purified by chromatography to afford the title compound. Compound (118) is reported in EP 0869119 A1 and compound (80) is described in WO 98/38174.

EXAMPLES 25–53

The syntheses of starting materials and multibinding compounds are further described in the following Examples 25 through 53.

In general, unless noted otherwise, starting material (including di-amines, di-aldehydes, di-halides, amines, alkyl halides, aldehydes, and etc.) and solvents were purchased from commercial suppliers (Aldrich, Fluka, Sigma, and etc.), and used without further purification. Reactions were run under nitrogen atmosphere, unless noted otherwise such as in hydrogenation reaction. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; Reaction mixtures were worked up as described specifically in each reaction; commonly it was purified by flash column chromatography with silica gel. Other purification methods include preparative TLC, temperature-, and solvent-dependent crystallization, precipitation, and distillation. In addition, reaction mixtures were routinely purified by preparative HPLC: a general protocol is described below. Characterization of reaction products was routinely carried out by mass and $^1$H-NMR spectrometry. For NMR, samples were dissolved in deuterated solvent (CD$_3$OD, CDCl$_3$, or DMSO-d$_6$), and $^1$H-NMR spectra were acquired with a Varian Gemini 2000 instrument (300 MHz) under standard observe parameters. Mass spectrometric identification of compounds was performed by an electrospray ionization method (ESMS) with a Perkin Elmer instrument (PE SCIEX API 150 EX).

A general protocol for analytical HPLC: Each crude compound was dissolved in 50% MeCN/H$_2$O (with 0.1% TFA) at 0.5–1.0 mg/mL concentration, and was analyzed by using anal. HPLC: 1) reversed-phase analytical column, Bonus-RP (2.1×50 mm; ID=5 μm); 2) flow rate: 0.5 mL/min; 3) 10% MeCN/H$_2$O (0.1% TFA) (0–0.5 min), 10 to 70% (linear gradient; 0.5–5 min); 4) detection: 214, 254, and 280 nm.

A general protocol for preparative HPLC purification: Crude compounds were dissolved in 50% MeCN/H$_2$O (with 0.1% TFA) at 30–45 mg/mL concentration, filtered, and injected into a reversed-phase preparative column. Following represents a typical example among various purification conditions: 1) column; YMC Pack-Pro C18 (50a×20 mm; ID=5 μm); 2) linear gradient: 10 to 60% MeCN (0.1%

TFA)/H$_2$O (0.1% TFA) over 50 min; 3) flow rate: 40 mL/min; 4) detection: 214, 254, or 280 nm.

EXAMPLE 25

Synthesis of Mexiletine Dimers: Reductive Amination of Precursor Ketone 1 with bis-primary Amine via the Following Scheme

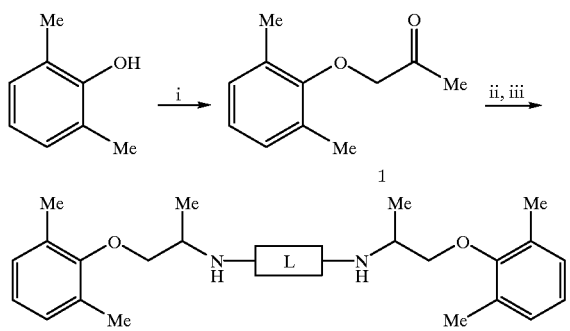

reagents and conditions: i) chloroacetone, K$_2$CO$_3$, KI, DMF, 80° C.; ii) H$_2$N-L-NH$_2$, EtOH rt; iii) NaBH$_4$, r.t.

To a stirred, suspension of 2,6-dimethylphenol (12.216 g, 100 mmol), potassium carbonate (14.0 g, 100 mmol), and potassium iodide (2.0 g, catalytic amount) in 400 mL of DMF at 80° C., was added dropwisely over 30 min 12.0 mL (150 mmol) of chloroacetone. After completion of the addition, the mixture was stirred and heated at 80° C. for 12 h. After cooling, the mixture was filtered, and concentrated in vacuo to give a tarry residue. It was partitioned between ethyl acetate and water. The organic phase was dried over Na$_2$SO$_4$, and concentrated to afford the oily residue. Treatment with hexanes caused precipitation of brown solid, which was filtered off. The filtrate was passed through a pad of basic alumna to remove remaining phenol. Filtrates were concentrated to provide the product ketone 1 as clear oil. $^1$H-NMR (CD$_3$OD, 299.96 MHz): δ (ppm) 7.06–6.95 (d, 2H), 6.90–6.84 (dd, 1H), 4.49 (s, 2H), 2.23 (s, 9H). Retention time (anal. HPLC: 2–90% MeCN/H$_2$O over 5 min)= 3.56 min.

Additional dimer compounds (1–72) having the following structure A with different linkers were synthesized using the above scheme.

(A)

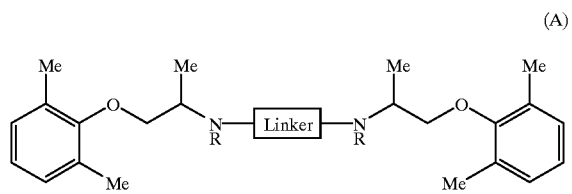

The following Table A lists 72 linkers that can be employed. For linkers 1–20 and 61–72, R of structure is H; for 21–46 R is a methyl group; and for 47–60 R is an ethyl group. Each numbered compound refers to a dimer that is linked by the linker in the table with the same number. For example, compound 1 would be linked by linker 1.

TABLE A

| No. | Linker | R |
|---|---|---|
| 1 | —(CH$_2$)$_2$—O—(CH$_2$)$_2$—O—(CH$_2$)$_2$— | H |
| 2 | —(CH$_2$)$_3$—O—(CH$_2$)$_3$— | H |
| 3 | —CH$_2$—Z—CH$_2$— where Z = 1,3-cyclohexyl | H |
| 4 | —CH$_2$—CH(OH)—CH$_2$— | H |
| 5 | —(CH$_2$)$_3$—N[(CH$_2$)$_2$—(CH$_2$)$_2$]N—(CH$_2$)$_3$— (piperazine) | H |
| 6 | —CH$_2$—Z—CH$_2$— where Z = 1,4-cyclohexyl | H |
| 7 | —(CH$_2$)$_5$— | H |
| 8 | —(CH$_2$)$_6$— | H |
| 9 | —(CH$_2$)$_2$—S—(CH$_2$)$_2$— | H |
| 10 | —(CH$_2$)$_3$—O—(CH$_2$)$_{10}$—O—(CH$_2$)$_3$— | H |
| 11 | —(CH$_2$)$_3$—Z—(CH$_2$)$_3$— where Z = 2,4,8,10-tetraoxa-spiro[5.5]undecan-3,9-yl | H |
| 12 | —(CH$_2$)$_3$—O—(CH$_2$)$_2$—O—(CH$_2$)$_2$—O—(CH$_2$)$_3$— | H |
| 13 | —(CH$_2$)$_3$—O—(CH$_2$)$_4$—O—(CH$_2$)$_3$— | H |
| 14 | —(CH$_2$)$_3$—N(CH$_3$)—(CH$_2$)$_3$— | H |
| 15 | —CH$_2$—Z—CH$_2$— where Z = trans-1,4-cyclohexyl | H |
| 16 | —CH$_2$—CH(CH$_3$)—CH$_2$—C(CH$_3$)$_2$—(CH$_2$)$_2$— | H |
| 17 | —Z— where Z = 2,7-[9H-fluorene] | H |
| 18 | —Z—C(CH$_3$)$_2$—Z—C(CH$_3$)$_2$—Z— where Z = 1,4-phenyl | H |
| 19 | —Z—CH$_2$—Z— where Z = 1,4-phenyl | H |
| 20 | —(CH$_2$)$_2$—N(CH$_3$)—(CH$_2$)$_2$— | H |
| 21 | —(CH$_2$)$_9$— | Me |
| 22 | —CH$_2$—Z—CH$_2$— where Z = 1,4-phenyl | Me |
| 23 | —(CH$_2$)$_2$—O—(CH$_2$)$_2$—O—(CH$_2$)$_2$— | Me |
| 24 | —CH$_2$—CH=CH—CH$_2$— (trans isomer) | Me |
| 25 | —CH$_2$—Z—CH$_2$— where Z = (–)-trans-2,2-dimethyl-[1,3]dioxolan-4,5-yl | Me |
| 26 | —(CH$_2$)$_{10}$— | Me |
| 27 | —(CH$_2$)$_{11}$— | Me |
| 28 | —(CH$_2$)$_{12}$— | Me |
| 29 | —(CH$_2$)$_{16}$— | Me |
| 30 | —CH$_2$—CH(OH)—CH$_2$— | Me |
| 31 | —CH$_2$—C≡C—CH$_2$— | Me |
| 32 | —(CH$_2$)$_7$— | Me |
| 33 | —(CH$_2$)$_8$— | Me |
| 34 | —CH$_2$—Z—CH$_2$— where Z = 2,3-quinoxalinyl | Me |
| 35 | —CH$_2$—CH(CH$_2$OH)— | Me |
| 36 | —CH$_2$—C(CH$_3$)$_2$—CH$_2$— | Me |
| 37 | —Z— where Z = 4,5-[1,3]dioxolan-2-one | Me |
| 38 | —CH$_2$—Z—CH$_2$— where Z = 1,3-phenyl | Me |
| 39 | —(CH$_2$)$_2$—O—CH$_2$—O—(CH$_2$)$_2$— | Me |
| 40 | —(CH$_2$)$_4$—O—(CH$_2$)$_4$— | Me |
| 41 | —(CH$_2$)$_2$—O—(CH$_2$)$_2$—O—(CH$_2$)$_2$—O—(CH$_2$)$_2$— | Me |
| 42 | —(CH$_2$)$_2$—O—C(O)—O—(CH$_2$)$_2$— | Me |
| 43 | —CH$_2$—CH[C(O)—O—CH$_2$CH$_3$]— | Me |
| 44 | —CH$_2$—C(O)—O—(CH$_2$)$_2$—O—C(O)—CH$_2$— | Me |
| 45 | —(CH$_2$)$_2$—NH—C(O)—C(O)—NH—(CH$_2$)$_2$— | Me |
| 46 | —(CH$_2$)$_3$— | Me |
| 47 | —(CH$_2$)$_2$—O—(CH$_2$)$_2$—O—(CH$_2$)$_2$— | Et |
| 48 | —CH$_2$—Z—CH$_2$— where Z = (–)-trans-2,2-dimethyl-[1,3]dioxolan-4,5-yl | Et |
| 49 | —(CH$_2$)$_{10}$— | Et |
| 50 | —(CH$_2$)$_{11}$— | Et |
| 51 | —(CH$_2$)$_{12}$— | Et |
| 52 | —(CH$_2$)$_{16}$— | Et |
| 53 | —(CH$_2$)$_7$— | Et |
| 54 | —CH$_2$—Z—CH$_2$— where Z = 1,3-phenyl | Et |
| 55 | —CH$_2$—Z—CH$_2$— where Z = 1,4-phenyl | Et |
| 56 | —(CH$_2$)$_2$—O—CH$_2$—O—(CH$_2$)$_2$— | Et |
| 57 | —(CH$_2$)$_4$—O—(CH$_2$)$_4$— | Et |
| 58 | —(CH$_2$)$_2$—O—(CH$_2$)$_2$—O—(CH$_2$)$_2$—O—(CH$_2$)$_2$— | Et |
| 59 | —CH$_2$—C(O)—O—(CH$_2$)$_2$—O—C(O)—CH$_2$— | Et |
| 60 | —(CH$_2$)$_3$— | Et |
| 61 | —CH$_2$—Z—CH$_2$— where Z = 2,5-thiophenyl | H |
| 62 | —CH$_2$—Z—O—(CH$_2$)$_2$—O—Z—CH$_2$— where Z = 1,2-phenyl | H |
| 63 | —CH$_2$—Z—O—(CH$_2$)$_6$—O—Z—CH$_2$— where Z = 1,2-phenyl | H |
| 64 | —CH$_2$—Z—O—(CH$_2$)$_3$—O—Z—CH$_2$— where Z = 1,2-phenyl | H |

TABLE A-continued

| No. | Linker | R |
|---|---|---|
| 65 | —CH₂—Z—CH₂— where Z = 2,3-thiophenyl | H |
| 66 | —CH₂—Z—CH₂— where Z = 2,6-pyridinyl | H |
| 67 | —CH₂—Z—CH₂— where Z = 2-hydroxy-5-methyl-phenyl-1,3-yl | H |
| 68 | —CH₂—Z—O—(CH₂)₂—O—Z—CH₂— where Z = 4-methoxy-phenyl-1,3-yl | H |
| 69 | —CH₂—Z—CH₂— where Z = 4-hydroxy-phenyl-1,3-yl | H |
| 70 | —CH₂—Z—CH₂— where Z = 2,2'-dihydroxy-3,3'-dimethoxy-biphenyl-5,5'-yl | H |
| 71 | —CH₂—Z—O—Z—CH₂— where Z = 1,2-phenyl | H |
| 72 | —CH₂—Z—CH₂— where Z = 1,3-phenyl | H |

General procedure for the synthesis of compound 1: To a solution of compound 1 (35.6 mg, 0.2 mmol) in 200 μL of anhydrous ethanol, was added a solution of 1,8-diamino-3,6-dioxaoctane (14.8 mg, 0.1 mmol) in 200 μL of anhydrous ethanol. The mixture was shaken for 12 h at 25° C., and followed by addition of a solution of NaBH₄ (15.2 mg, 0.4 mmol) in ethanol and shaking the mixture for 2 h at 25° C. The mixture was then quenched with a solution of 5% trifluoroacetic acid in 50% aqueous acetonitrile, and concentrated under reduced pressure. The residue was dissolved in 1 mL of a 1:1 mixture of acetonitrile and water (with 0.1% trifluoroacetic acid). The crude product was purified by preparative reversed phase HPLC. Retention time (anal. HPLC: 10–70% MeCN/H₂O over 5 min)=4.14 min. ESMS (C₂₈H₄₄N₂O₄): calcd. 472.67; obsd. 473.4 [M+H]⁺.

Compound 2 was prepared in an analogous manner from bis-(3-aminopropyl)ether. Retention time (anal. HPLC: 10–70% MeCN/H₂O over 5 min)=4.61 min. ESMS (C₂₈H₄₄N₂O₃): calcd. 456.67; obsd. 457.4 [M+H]⁺.

Compound 3 was prepared in an analogous manner from 1,3-cyclohexane-bis-(methylamine). Retention time (anal. HPLC: 10–70% MeCN/H₂O over 5 min) 4.60 min. ESMS (C₃₀H₄₆N₂O₂): calcd. 466. 71; obsd. 467.4 [M+H]⁺.

Compound 4 was prepared in an analogous manner from 1,3-diamino-2-propanol. Retention time (anal. HPLC: 10–70% MeCN/H₂O over 5 min)=4.12 min, 4.32 min. (mixture of diastereomers). ESMS (C₂₅H₃₈N₂O₃): calcd. 414.59; obsd. 415.4 [M+H]⁺.

Compound 5 was prepared in an analogous manner from 1,4-bis-(3-aminopropyl)piperazine. Retention time (anal. HPLC: 10–70% MeCN/H₂O over 5 min)=3.70 min. ESMS (C₂₅H₃₈N₂O₃): calcd. 524.79; obsd. 525.8 [M+H]⁺.

Compound 6 was prepared in an analogous manner from 1,4-cyclohexane-bis-methylamine. Retention time (anal. HPLC: 10–70% MeCN/H₂O over 5 min) 4.30 min, 4.53 min (mixture of isomers). ESMS (C₃₀H₄₆N₂O₂): calcd. 466.71; obsd. 467.4 [M+H]⁺.

Compound 7 was prepared in an analogous manner from 1,5-diaminopentane. Retention time (anal. HPLC: 10–70% MeCN/H₂O over 5 min)=4.18 min. 4.53 min (mixture of isomers). ESMS (C₂₇H₄₂N₂O₂): calcd. 426.64; obsd. 427.4 [M+H]⁺.

Compound 8 was prepared in an analogous manner from 1,6-diaminohexane. Retention time (anal. HPLC: 10–70% MeCN/H₂O over 5 min) 4.26 min, 4.53 min (mixture of isomers). ESMS (C₂₈H₄₄N₂O₂): calcd. 440.67; obsd. 441.4 [M+H]⁺.

Compound 9 was prepared in an analogous manner from 2,2'-thiobis(ethylamine). Retention time (anal. HPLC: 10–70% MeCN/H₂O over 5 min)=4.53 min. ESMS (C₂₆H₄₀N₂O₂S): calcd. 444.68; obsd. 441.4 [M+H]⁺.

Compound 10 was prepared in an analogous manner from 3,3'-(decamethylenedioxy)-bis-(propylamine). Retention time (anal. HPLC: 10–70% MeCN/H₂O over 5 min)=4.98 min. ESMS (C₃₈H₆₄N₂O₄): calcd. 612.94; obsd. 613.6 [M+H]⁺.

Compound 11 was prepared in an analogous manner from 3,9-bis(3-aminopropyl)-2,4,8,10-tetraoxapriro(5,5) undecane, Retention time (anal. HPLC: 10–70% MeCN/H₂O over 5 min)=4.53 nm. ESMS (C₃₅HN₂O₆): calcd. 598.82; obsd. 599.4 [M+H]⁺.

Compound 12 was prepared in an analogous manner from 4,7,10-trioxa-1,13-tridecanediamine. Retention time (anal. HPLC: 10–70% MeCN/H₂O over 5 min)=4.17 min. ESMS (C₃₂H₂N₂O₅): calcd. 544.78; obsd. 545.4 [M+H]⁺.

Compound 13 was prepared in an analogous manner from 4,9-dioxa-1,12-dodecaneamine. Retention Time (anal. HPLC: 10–70% MeCN/H₂O over 5 min)=4.22 min, 4.52 min (mixture of isomers). ESMS (C₃₂H₅₂N₂O₄): calcd. 528.78; obsd. 529.4 [M+H]⁺.

Compound 14 was prepared in an analogous manner from N,N-bis(3-aminopropyl)methylamine. Retention time (anal. HPLC: 10–70% MeCN/H₂O over 5 min)=3.85 min. ESMS (C₂₉H₄₇N₃O): calcd. 469.71; obsd. 470.2 [M+H]⁺.

Compound 15 was prepared in an analogous manner from trans-1,4-diaminocyclohexane. Retention time (anal. HPLC: 10–70% MeCN/H₂O over 5 min)=3.98 min. ESMS (C₂H₄₂N₂O₂): calcd. 438.65; obsd. 439.4 [M+H]⁺.

Compound 16 was prepared in an analogous manner from tri-methylhexamethylenediamine. Retention time (anal. HPLC: 10–70% MeCN/H₂O over 5 min) 4.55 min. ESMS (C₃₁H₅ON₂O₂): calcd. 482.75; obsd. 483.4 [M+H]⁺.

Compound 17 was prepared in an analogous manner from 2,7-diaminofluorene. Retention time (anal. HPLC: 10–70% MeCN/H₂O over 5 min)=5.2 min. ESMS (C₃₅H₄₀N₂O₂): calcd. 520.71; obsd. 521.4 [M+H]⁺.

Compound 18 was prepared in an analogous manner from 4,4'-(1,3-phenylenediisopropylidene)bisaniline. Retention time (anal. HPLC: 10–70% MeCN/H₂O over 5 min)=4.73 min. ESMS (C₄₆H₅₆N₂O₂): calcd. 668.96; obsd. 669.4 [M+H]⁺.

Compound 19 was prepared in an analogous manner from 4,4'-diaminodiphenylmethane. Retention time (anal. HPLC: 10–90% MeCN/H₂O over 5 min)=4.95 min. ESMS (C₃₅H₄₂N₂O₂): calcd. 522.73; obsd. 523.4 [M+H]⁺.

Compound 20 was prepared in an analogous manner from N,N-bis(3-aminoethyl)methylamine. Retention time (anal. HPLC: 10–70% MeCN/H₂O over 5 min)=3.96 min. ESMS (C₃₅H₄₂N₂O₂): calcd.441.66; obsd. 442.6 [M+H]⁺.

EXAMPLE 26

Synthesis of Intermediate Compounds 2 and 200 via the Following Scheme

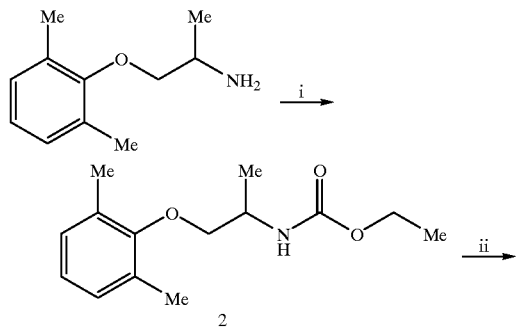

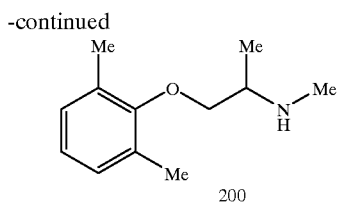

200 reagents and conditions: i) ethylchloroformate, EtOAc, 5N NaOH, 15° C.; ii) LiAlH$_4$, THF, 50° C.

The compounds were synthesized from mexiletine hydrochloride in accordance with the protocol described in Berger et. al., U.S. Pat. No. 5,688,830.

Compound 2: $^1$H-NMR (CD$_3$OD, 299.96 MHz): δ (ppm) 7.00–6.95 (d, 2H), 6.90–6.84 (dd, 1H), 4.20–3.90 (m, 3H), 3.72–3.66 (d, 2H), 2.24 (s, 6H), 1.34–1.30 (d, 3H), 1.28–1.20 (t, 3H).

Compound 200: $^1$H-NMR (CD$_3$OD, 299.96 MHz): δ (ppm) 7.04–6.95 (d, 2H), 6.90–6.83 (dd, 1H), 3.75–3.65 (d, 2H), 3.10–2.95 (m, 1H), 2.48 (s, 3H), 2.28 (s, 6H), 1.18–1.23 (d, 3H).

EXAMPLE 27

Synthesis of Dimers of Compound 200 via the Following Scheme

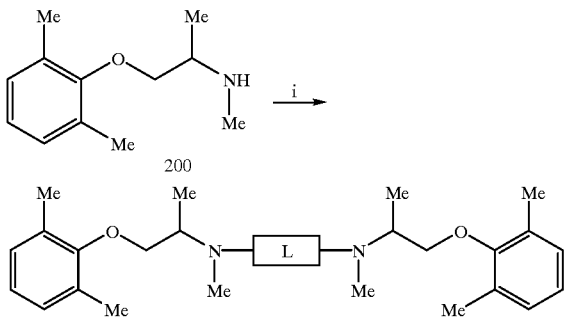

reagents and conditions: i) di-halide (X—L—X), diisopropylethylamine, DMF, 90° C.

General procedure for the synthesis of compound 21 of Table A: A solution of compound 200 (38.7 mg, 0.2 mmol) with diisopropylethylamine (54 μl, 0.3 mmol) in 200 μL of anhydrous DMF, was added to a solution of 1,9-diiodononane (38.0 mg, 0.1 mmol) in 200 μL anhydrous DMF. The mixture was shaken for 20 h at 90° C., then stripped of solvent under vacuum. The resulting tarry mixture was dissolved in 1 mL of a 1:1 mixture of acetonitrile and water (with 0.1% trifluoroacetic acid). The crude product was purified by preparative reversed phase HPLC. Retention time (anal. HPLC: 10 to 70% MeCN/H$_2$O over 6 min)=4.58 min.; ESMS (C$_{33}$H$_{54}$N$_7$O$_2$); calcd. 510.8; obsd. 511.6 [M+H]$^+$.

Compound 22 was prepared in an analogous manner from α,α'-dibromo-p-xylene. Retention time (anal. HPLC: 10 to 70% MeCN/H$_2$O over 6 min)=2.94 min. ESMS (C$_{32}$H$_{44}$N$_2$O$_2$); calcd. 488.71; obsd. 489.6 [M+H]$^+$.

Compound 23 was prepared in an analogous manner from bis-iodoethoxyethane. Retention time (anal. HPLC: 10 to 70% MeCN/H$_2$O over 6 min)=2.82 min. ESMS (C$_{30}$H$_{48}$N$_2$O$_4$); calcd. 500.7; obsd. 501.4 [M+H]$^+$.

Compound 24 was prepared in an analogous manner from 1,4-dibromo-2-butene. Retention time (anal. HPLC: 10 to 70% MeCN/H$_2$O over 6 min)=2.96 min. ESMS (C$_{28}$H$_{42}$N$_2$O$_2$); calcd. 438.7; obsd. 439.5 [M+H]$^+$.

Compound 25 was prepared in an analogous manner from (−)-trans-4,5-bis(iodomethyl)-2,2-dimethyl-1,3-dioxolane. Retention time (anal. HPLC: 10 to 70% MeCN/H$_2$O over 6 min)=4.40 min. ESMS (C$_{31}$H$_{48}$N$_2$O$_4$); calcd. 512.7; obsd. 513.4 [M+H]$^+$.

Compound 26 was prepared in an analogous manner from 1,10-diiododecane. Retention time (anal. HPLC: 10 to 70% MeCN/H$_2$O over 6 min)=4.72 min. ESMS (C$_{34}$H$_{56}$N$_2$O$_2$); calcd. 524.8; obsd. 525.4 [M+]$^+$.

Compound 27 was prepared in an analogous manner from 1,11-dibromoundecane. Retention time (anal. HPLC: 10 to 70% MeCN/H$_2$O over 6 min)=4.79 min. ESMS (C$_{35}$H$_{58}$N$_2$O$_2$); calcd. 538.9; obsd. 539.5 [M+H]$^+$.

Compound 28 was prepared in an analogous manner from 1,12-dibromododecane. Retention time (anal. HPLC: 10 to 70% MeCN/H$_2$O over 6 min)=4.91 min. ESMS (C$_{36}$H$_{60}$N$_2$O$_2$); calcd. 552.9; obsd. 553.6 [M+H]$^+$.

Compound 29 was prepared in an analogous manner from 1,16-dibromohexadecane. Retention time (anal. HPLC: 10 to 70% MeCN/H$_2$O over 6 min)=4.72 min. ESMS (C$_{40}$H$_{68}$N$_2$O$_2$); calcd. 609.0; obsd. 609.8 [M]$^+$.

Compound 30 was prepared in an analogous manner from 1,3-dibromo-2-propanol. Retention time (anal. HPLC: 10 to 70% MeCN/H$_2$O over 6 min)=4.18 min. ESMS (C$_{27}$H$_{42}$N$_2$O$_3$); calcd. 442.6; obsd. 443.5 [M+H]$^+$.

Compound 31 was prepared in an analogous manner from 1,4-dichloro-2-butyne, using a catalytic amount of NaI. Retention time (anal. HPLC: 10 to 70% MeCN/H$_2$O over 6 min)=4.11 min. ESMS (C$_{28}$H$_{40}$N$_2$O$_2$); calcd. 436.6; obsd. 437.5 [M+H]$^+$.

Compound 32 was prepared in an analogous manner from 1,7-dibromoheptane. Retention time (anal. HPLC: 10 to 70% MeCN/H$_2$O over 6 min)=4.36 min. ESMS (C$_{31}$H$_{52}$N$_2$O$_2$); calcd. 482.8; obsd. 483.4 [M+H]$^+$.

Compound 33 was prepared in an analogous manner from 1,8-dibromooctane. Retention time (anal. HPLC: 10 to 70% MeCN/H$_2$O over 6 min)=4.53 min. ESMS (C$_{32}$H$_{52}$N$_2$O$_2$); calcd. 496.8; obsd. 497.5 [M+H]$^+$.

Compound 34 was prepared in an analogous manner from 2,3-bis(bromomethyl)quinoxaline. Retention time (anal. HPLC: 10 to 70% MeCN/H$_2$O over 6 min)=4.84 min. ESMS (C$_{34}$H$_{44}$N$_4$O$_2$); calcd. 540.7; obsd. 541.3 [M+H]$^+$.

Compound 35 was prepared in an analogous manner from 2,3-dibromo-1-propanol. Retention time (anal. HPLC: 10 to 70% MeCN/H$_2$O over 6 min)=4.22 min. ESMS (C$_{27}$H$_{42}$N$_2$O$_3$); calcd. 442.6; obsd. 443.5: [M+H]$^+$.

Compound 36 was prepared in an analogous manner from 3chloro-2-chloromethyl-1-propene, using a catalytic amount of NaI. Retention time (anal. HPLC: 10 to 70% MeCN/H$_2$O over 6 min)=4.30 min. ESMS (C$_{28}$H$_{42}$N$_2$O$_2$); calcd. 438.7; obsd. 439.3 [M+H]$^+$.

Compound 37 was prepared in an analogous manner from 4,5-dichloro-1,3-dioxolan-2one. Retention time (anal. HPLC: 10 to 70% MeCN/H$_2$O over 6 min)=3.16 min. ESMS (C$_{27}$H$_{38}$N$_2$O$_5$); calcd. 470.6; obsd. 471.4 [M+H]$^+$.

Compound 38 was prepared in an analogous manner from alpha,alpha'-dibromo-p-xylene. Retention time (anal. HPLC: 10 to 70% MeCN/H$_2$O over 6 min)=4.30 min. ESMS (C$_{32}$H$_{44}$N$_2$O$_2$); calcd. 488.7; obsd. 489.4 [M+H]$^+$.

Compound 39 was prepared in an analogous manner from bis(2-chloroethoxymethane), using a catalytic amount of NaI. Retention time (anal. HPLC: 10 to 70% MeCN/H$_2$O over 6 min)=4.13 min. ESMS (C$_{29}$H$_{46}$N$_2$O$_4$); calcd. 486.7; obsd. 487.3 [M+H]$^+$.

Compound 40 was prepared in an analogous manner from bis(4-chlorobutyl)ether, using a catalytic amount of NaI. Retention time (anal. HPLC: 10 to 70% MeCN/H$_2$O over 6 min)=4.26 min. ESMS ($C_{32}H_{52}N_2O_3$); calcd. 512.8; obsd. 513.4 [M+H]$^+$.

Compound 41 was prepared in an analogous manner from bis[2-(2-chloroethoxy)ethyl]ether, using a catalytic amount of NaI. Retention time (anal. HPLC: 10 to 70% MeCN/H$_2$O over 6 min)=4.16 min. ESMS ($C_{32}H_{52}N_2O_5$); calcd. 544.8; obsd. 545.5 [M+H]$^+$.

Compound 42 was prepared in an analogous manner from carbonic acid bis(2-chloroethyl)ester, using a catalytic amount of NaI. Retention time (anal. HPLC: 10 to 70% MeCN/H$_2$O over 6 min)=4.13 min. ESMS ($C_{29}H_{44}N_2O_5$); calcd. 500.7; obsd. 501.4 [M+H]$^+$.

Compound 43 was prepared in an analogous manner from ethyl 2,3-dibromopropionate. Retention time (anal. HPLC: 10 to 70% MeCN/H$_2$O over 6 min)=4.78 min. ESMS ($C_{29}H_{44}N_2O_4$); calcd. 484.7; obsd. 485.5 [M+H]$^+$.

Compound 44 was prepared in an analogous manner from ethylene glycol dichloroacetate. Retention time (anal. HPLC: 10 to 70% MeCN/H$_2$O over 6 min)=4.09 min. ESMS ($C_{30}H_{44}N_2O_6$); calcd. 528.7; obsd. 529.3 [M+H]$^+$.

Compound 45 was prepared in an analogous manner from N,N'-bis(2-chloroethyl)oxamide, using a catalytic amount of NaI. Retention time (anal. HPLC: 10 to 70% MeCN/H$_2$O over 6 min)=3.96 min. ESMS ($C_{30}H_{46}N_4O_4$); calcd. 526.7; obsd. 527.5 [M+H]$^+$.

Compound 46 was prepared in an analogous manner from 1,3-iodopropane. Retention time (anal. HPLC: 10 to 70% MeCN/H$_2$O over 6 min)=4.09 min. ESMS ($C_{27}H_{42}N_2O_2$); calcd. 426.6; obsd. 427.3 [M+H]$^+$.

EXAMPLE 28

Synthesis of Compounds 3 and 300 via the Following Scheme

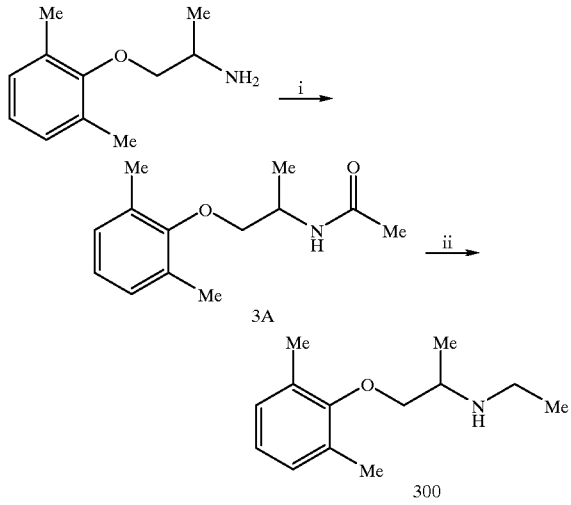

reagents and conditions: i) AcCl, EtOAc, 5N NaOH, 15° C.; ii) BH$_3$Me$_2$S, THF, reflux.

Compound 3A, and compound 300 were synthesized from mexiletine hydrochloride in accordance with the protocol described in Berger et. al. U.S. Pat. No. 5,688,830.

Compound 3: $^1$H-NMR (CD$_3$OD, 299.96 MHz): δ (ppm) 7.02–6.95 (d, 2H), 6.90–6.86 (dd, 1H), 4.31–4.20 (m, 1H), 3.72–3.66 (d, 2H), 2.24 (s, 6H), 1.97 (s, 3H), 1.38–1.29 (d, 3H).

Compound 300: Retention Time (anal. HPLC: 10–70% MeCN/H$_2$O over 5 min)=3.97min. ESMS ($C_{13}H_{21}NO$): calcd. 207.31, obsd. 208.1 [M+H]$^+$.

EXAMPLE 29

Synthesis of Dimers of Compound 300 via the Following Scheme

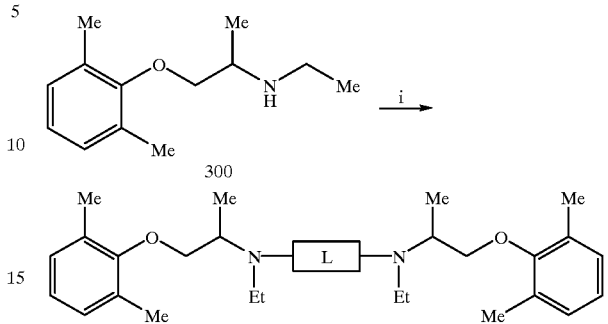

reagents and conditions: i) di-halide (X—L—X), diisopropylethylamine, DMF, 90° C.

General procedure for the synthesis of compound 47 of Table A: A solution of compound 300 (41.4 mg, 0.2 mmol) with diisopropylethylamine (54 μl, 0.3 mmol) in 200 μL anhydrous DMF, was added to a solution of bis-iodoethoxyethane (37.0 mg, 0.1 mmol) in 200 μL anhydrous DMF. The mixture was shaken for 20 h at 90° C., then stripped of solvent under vacuum. The resulting tarry mixture was dissolved in 1 mL of a 1:1 mixture of acetonitrile and water (with 0.1% trifluoroacetic acid). The crude product was purified by preparative reversed phase HPLC. Retention time (anal. HPLC: 10–70% MeCN/H$_2$O over 5 min)=3.79 min. ESMS ($C_{32}H_{52}N_2O_4$): calcd. 528.78, obsd. 529.4 [M++H]$^+$.

Compound 48 was prepared in an analogous manner from (−)-trans-4,5-bis(iodomethyl)-2,2-dimethyl-1,3-dioxolane. Retention time (anal. HPLC: 10–70% MeCN/H$_2$O over 5 min)=4.33 min ESMS ($C_{33}H_{52}N_2O_4$): calcd. 540.79 obsd. 541.5 [M+H]$^+$.

Compound 49 was prepared in an analogous manner from 1,10-diiododecane. Retention time (anal. HPLC: 10–70% MeCN/H$_2$O over 5 min)=4.49 min. ESMS ($C_{36}H_{60}N_2O_2$): calcd. 552.88, obsd. 553.5 [M+H]$^+$.

Compound 50 was prepared in an analogous manner from 1,11-dibromoundecane. Retention time (anal. HPLC: 10–70% MeCN/H$_2$O over 5 min)=4.61 min. ESMS ($C_{37}H_{62}N_2O_2$): calcd. 566.91, obsd. 567.5 [M+H]$^+$.

Compound 51 was prepared in an analogous manner from 1,12-dibromododecane. Retention time (anal. HPLC: 10–70% MeCN/H$_2$O over 5 min)=4.72 min. ESMS ($C_{38}H_{64}N_2O_2$): calcd. 580.94, obsd. 581.7 [M+H]$^+$.

Compound 52 was prepared in an analogous manner from 1,16-dibromohexadecane. Retention time (anal. HPLC: 10–90% MeCN/H$_2$O over 5 min)=4.90 min. ESMS ($C_{42}H_{72}N_2O_2$): calcd. 637.05, obsd. 637.7 [M+H]$^+$.

Compound 53 was prepared in an analogous manner from 1,7-dibromoheptane. Retention time (anal. HPLC: 10–70% MeCN/H$_2$O over 5 min)=4.09min. ESMS ($C_{33}H_{54}N_2O_2$): calcd. 510.8, obsd. 511.7 [M+H]$^+$.

Compound 54 was prepared in an analogous manner from α,α'-dibromo-m-xylene. Retention time (anal. HPLC: 10–70% MeCN/H$_2$O over 5 min)=4.05 min. ESMS ($C_{34}H_{48}N_2O_2$): calcd. 516.77, obsd. 517.6 [M+H]$^+$.

Compound 55 was prepared in an analogous manner from α,α'-dibromo-p-xylene. Retention time (anal. HPLC: 10–70% MeCN/H$_2$O over 5 min)=3.98 min. ESMS ($C_{34}H_{48}N_2O_2$): calcd. 516.77, obsd. 517.6 [M+H]$^+$.

Compound 56 was prepared in an analogous manner from bis(2-chloroethoxymethane). Retention time (anal. HPLC:

10–70% MeCN/H$_2$O over 5 min)=3.80 min. ESMS (C$_{31}$H$_{50}$N$_2$O$_4$): calcd. 514.75, obsd. 515.4 [M+H]$^+$.

Compound 57 was prepared in an analogous manner from bis(4-chlorobutyl)ether. Retention time (anal. HPLC: 10–70% MeCN/H$_2$O over 5 min)=3.98 min. ESMS (C$_{34}$H$_{56}$N$_2$O$_3$): calcd. 540.83, obsd. 541.5 [M+H]$^+$.

Compound 58 was prepared in an analogous manner from bis[2-(2-chloroethoxy)ethyl]ether. Retention time (anal. HPLC: 10–70% MeCN/H$_2$O over 5 min)=3.85 min. ESMS (C$_{34}$H$_{56}$N$_2$O$_5$): calcd. 572.83, obsd. 573.7 [M+H]$^+$.

Compound 59 was prepared in an analogous manner from ethylene glycol dichloroacetate. Retention time (anal. HPLC: 10–70% MeCN/H$_2$O over 5 min)=3.74 min. ESMS (C$_{32}$H$_{48}$N$_2$O$_6$): calcd. 556.74, obsd. 557.3 [M+H]$^+$.

Compound 60 was prepared in an analogous manner from 1,3-diodopropane. Retention time (anal. HPLC: 10–70% MeCN/H20 over 5 min)=3.80 min. ESMS (C$_{29}$H$_{46}$N$_2$O$_2$): calcd. 454.70, obsd. 455.3 [M+H]$^+$.

EXAMPLE 30

Synthesis of Dimers of Mexiletine: Reductive Alkylation via the Following Scheme

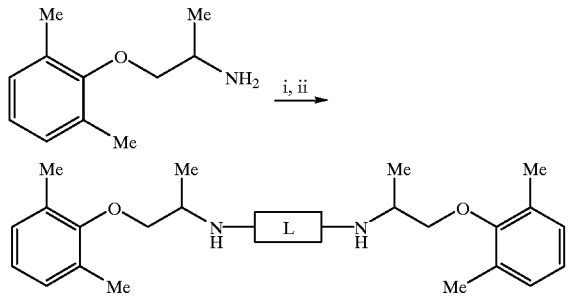

reagents and conditions: I) dialdehyde, EtOH, r.t., ii) NaBH$_4$, r.t.

General procedure for the synthesis of compound 61 of Table A: To a solution of mexiletine (neutral; 35.9 mg, 0.2 mmol) in 200 µL anhydrous ethanol, was added a solution of 2,5-thiophenedicarboxaldehyde (14.0 mg, 0.1 mmol) in 200 µL anhydrous ethanol. After shaking for 12 h at 25° C., the mixture was then treated with a solution of NaBH$_4$ (15.2 mg, 0.4 mmol) in ethanol. The final mixture was shaken for 2 h at 25° C., and then quenched with a solution of 5% trifluoroacetic acid in acetonitrile/water (1:1). After concentration of the mixture under reduced pressure, the residue was dissolved in 1 mL of a 1:1 mixture of acetonitrile and water (with 0.1% trifluoroacetic acid). This crude product was purified by preparative reversed phase HPLC. Retention Time (anal. HPLC: 10–70% MeCN/H$_2$O over 5 min)=4.28 min. ESMS (C$_{28}$H$_{38}$N$_2$O$_2$S): calcd. 466.69, obsd. 467.4 [M+H]$^+$.

Compound 62 was prepared in an analogous manner from 2,2'-(ethylenedioxy)dibenzaldehyde. Retention Time (anal. HPLC: 10–70% MeCN/H$_2$O over 5 min)=4.60 min. ESMS (C$_{38}$H$_{48}$N$_2$O$_4$): calcd. 596.81, obsd. 597.4 [M+H]$^+$.

Compound 63 was prepared in an analogous manner from 2,2'-(hexamethylenedioxy)dibenzaldehyde. Retention Time (anal. HPLC: 10–70% MeCN/H$_2$O over 5 min)=4.92 min. ESMS (C$_{42}$H$_{56}$N$_2$O$_4$): calcd. 652.92, obsd. 653.4 [M+H]$^+$.

Compound 64 was prepared in an analogous manner from 2,2'-(trimethylenedioxy)dibenzaldehyde. Retention Time (anal. HPLC: 10–70% MeCN/H$_2$O over 5 min)=4.75 min. ESMS (C$_{39}$H$_{50}$N$_2$O$_4$): calcd. 610.84, obsd. 611.4 [M+H]$^+$.

Compound 65 was prepared in an analogous manner from 2,3-thiophenedicarboxaldehyde. Retention Time (anal. HPLC: 10–70% MeCN/H$_2$O over 5 min)=4.64 min. ESMS (C$_{28}$H$_{38}$N$_2$O$_2$S): calcd. 466.69, obsd. 467.4 [M+H]$^+$.

Compound 66 was prepared in an analogous manner from 2,6-pyridinedicarboxaldehyde. Retention Time (anal. HPLC: 10–70% MeCN/H$_2$O over 5 min)=4.31 min. ESMS (C$_{29}$H$_{39}$N$_3$O$_2$): calcd. 461.65, obsd. 462.4 [M+H]$^+$.

Compound 67 was prepared in an analogous manner from 2-hydroxy-5-methylisophthalaldehyde. Retention Time (anal. HPLC: 10–70% MeCN/H$_2$O over 5 min)=4.59 min. ESMS (C$_{31}$H$_{42}$N$_2$O$_3$): calcd. 490.69, obsd. 491.4 [M+H]$^+$.

Compound 68 was prepared in an analogous manner from 3,3'-(ethylenedioxy)di-p-anisaldehyde. Retention Time (anal. HPLC: 10–70% MeCN/H$_2$O over 5 min)=4.83 min. ESMS (C$_{40}$H$_{52}$N$_2$O$_6$): calcd. 656.86, obsd. 657.6 [M+H]$^+$.

Compound 69 was prepared in an analogous manner from 5-formylsalicylaldehyde. Retention Time (anal. HPLC: 10–70% MeCN/H$_2$O over 5 min)=4.28 min. ESMS (C$_{30}$H$_{40}$N$_2$O$_3$): calcd. 476.65, obsd. 476.4 [M+H]$^+$.

Compound 70 was prepared in an analogous manner from 6,6'-dihydroxy-5,5'-dimethoxy-(1,1'-biphenyl)-3,3'-dicarboxaldehyde. Retention Time (anal. HPLC: 10–70% MeCN/H$_2$O over 5 min)=4.50 min. ESMS (C$_{38}$H$_{48}$N$_2$O$_6$): calcd. 628.81, obsd. 629.4 [M+H]$^+$.

Compound 71 was prepared i an analogous manner from bis(2-formylphenyl)ether. Retention Time (anal. HPLC: 10–70% MeCN/H$_2$O over 5 min)=4.66 min. ESMS (C$_{36}$H$_{44}$N$_2$O$_3$): calcd. 552.76, obsd. 553.4 [M+H]$^+$.

Compound 72 was prepared in an analogous manner from isophithalaldehyde. Retention Time (anal. HPLC: 10–70% MeCN/H$_2$O over 5 min)=4.39 min. ESMS (C$_{30}$H$_{40}$N$_2$O$_2$): calcd. 460.66, obsd. 461.2 [M+H]$^+$.

EXAMPLE 31

Synthesis of Compound 400 via the Following Scheme

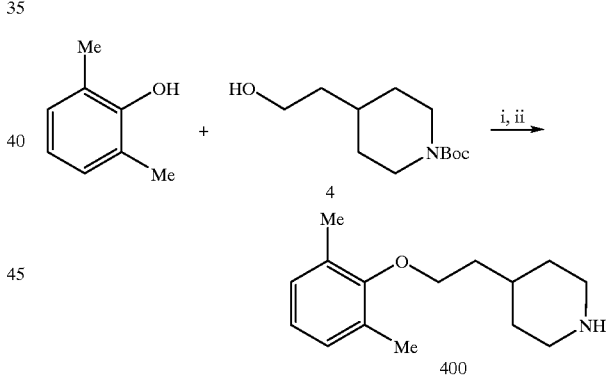

reagents and conditions: i) PPh$_3$, DEAD, THF, ii) TFA, CH$_2$Cl$_2$

To a stirred, cold solution of 2,6-dimethylphenol (11.25 g, 92.1 mmol), N-boc4-piperidinethanol (compound 4; 21.12 g, 92.1 mmol), and triphenylphosphine (27.30 g, 104.1 mmol) in 400 mL THF in ice bath, was added dropwisely over 30 min 14.6 mL (104.1 mmol) of diethyl azodicarboxylate (DEAD). The mixture was allowed to warm slowly to ambient temperature and stirred for 12 h. After concentration in vacuo, the residue was treated with hexane/dichloromethane to precipitate out triphenylphosphine oxide, which was filtered off. The filtrate was concentrated in vacuo, and the residue was chromatographed on silica gel. Evaporation of the appropriate fractions afforded boc-protected ether product.

Deprotection of N-Boc group of the ether product was done by using TFA. The above product (10 g) was dissolved in 300 mL of dichloromethane, cooled to 0° C., and treated with 50 mL of TFA, dropwisely over the period of 30 min. The mixture was warmed gradually to rt over 2 h, concentrated, and triturated with dichloromethane to give the desired amine product as an off-white solid. $^1$H-NMR (CD$_3$OD, 299.96 MHz): δ (ppm) 7.00–6.97 (d, 2H), 6.90–6.85 (dd, 1H), 3.86–3.82 (t, 2H), 3.42–3. 38 (d, 2H), 3.05–2.98 (t, 3H), 2.25 (s, 6H), 2.12–1.90 (m, 3H), 1.84–1.78 (q, 2H), 1.55–1.46 (m, 2H). ESMS (C$_{15}$H$_{23}$NO): calcd. 233.35; obsd. 234.2 [M+H]$^+$.

EXAMPLE 32

Synthesis of Dimers of Compound 400 via the Following Scheme

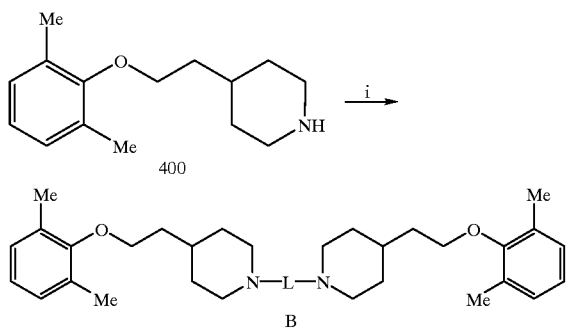

reagents and conditions: i) di-halide (X—L—X), diisopropylethylamine, DMF, 90° C.

Table 13 lists linkers 73–84 for dimers of structure B.

TABLE B

| No. | Linker |
|---|---|
| 73 | —CH$_2$-Z-CH$_2$-where Z = (−)-trans-2,2-dimethyl-[1,3]dioxolan-4,5-yl |
| 74 | —(CH$_2$)$_2$—O—(CH$_2$)$_2$—O—(CH$_2$)$_2$— |
| 75 | —CH$_2$—CH(OH)—CH$_2$— |
| 76 | —(CH$_2$)$_3$— |
| 77 | —(CH$_2$)$_6$— |
| 78 | —CH$_2$—C(CH$_2$)—CH$_2$— |
| 79 | —CH$_2$-Z-CH$_2$— where Z = 1,3-phenyl |
| 80 | —CH$_2$-Z-CH$_2$— where Z = 1,4-phenyl |
| 81 | —(CH$_2$)$_4$—O—(CH$_2$)$_4$— |
| 82 | —(CH$_2$)$_2$—O—(CH$_2$)$_2$—O—(CH$_2$)$_2$—O—(CH$_2$)$_2$— |
| 83 | —(CH$_2$)$_2$—NH—C(O)—C(O)—NH—(CH$_2$)$_2$— |
| 84 | —CH$_2$-Z-CH$_2$— where Z = 4,4'-biphenyl |

General procedure for synthesis of compound 75 of Table B: A solution of compound 400 (TFA salt; 69.5 mg, 0.2 mmol) with diisopropylethylamine (108 μl, 0.6 mmol) in 250 μL of anhydrous DMF, was added to a solution of 1,3-diiodo-2-propanol (31.8 mg, 0.1 mmol) in 250 μL of anhydrous DMF. The mixture was shaken for 20 h at 90° C., and concentrated under vacuum, yielding tarry mixture. It was dissolved in 1 mL of 50% aqueous acetonitrile (with 0.1% trifluoroacetic acid), and purified by reversed phase preparative HPLC. Retention time (anal. HPLC: 10–70% MeCN/H$_2$O over 5 min)=4.03 min. ESMS (C$_{33}$H$_{50}$N$_2$O$_3$): calcd. 522.78; obsd. 523.6 [M+H]$^+$.

Compound 73 was prepared in an analogous manner from (−)-trans-4,5-bis(iodomethyl)-2,2-dimethyl-1,3-dioxolane. Retention time (anal. HPLC: 10–90% MeCN/H$_2$O over 5 min)=4.40 min. ESMS (C$_{37}$H$_{56}$N$_2$O$_4$): calcd. 592.86; obsd. 593.4 [M+H]$^+$.

Compound 74 was prepared in an analogous manner from bis-iodoethoxyeffiane. Retention time (anal. HPLC: 10–70% MeCN/H$_2$O over 5 min)=4.13 min. ESMS (C$_{36}$H$_{56}$N$_2$O$_4$): calcd. 580.85; obsd. 581.6 [M+H]$^+$.

Compound 76 was prepared in an analogous manner from 1,3-diiodopropane. Retention time (anal. HPLC: 10–70% MeCN/H$_2$O over 5 min)=4.05 min. ESMS (C$_{33}$H$_{50}$N$_2$O$_2$): calcd. 506.77; obsd. 507.4 [M+H]$^+$.

Compound 77 was prepared in an analogous manner from 1,6-diiodohexane. Retention time (anal. HPLC: 10–70% MeCN/H$_2$O over 5 min)=4.26 min. ESMS (C$_{36}$H$_{56}$N$_2$O$_2$): calcd. 548.85; obsd. 549.6 [M+H]$^+$.

Compound 78 was prepared in an analogous manner from 3-chloro-2-chloromethyl-1-propene. Retention time (anal. HPLC: 10–70% MeCN/H$_2$O over 5 min)=4.22 min. ESMS (C$_{34}$H$_{50}$N$_2$O$_2$): calcd. 518.78; obsd. 519.6 [M+H]$^+$.

Compound 79 was prepared in an analogous manner from α,α'-dibromo-m-xylene. Retention time (anal. HPLC: 10–70% MeCN/H$_2$O over 5 min)=4.34 min. ESMS (C$_{38}$H$_{52}$N$_2$O$_2$): calcd. 568.84; obsd. 569.4 [M+H]$^+$.

Compound 80 was prepared in an analogous manner from α,α'-dibromo-p-xylene. Retention time (anal. HPLC: 10–70% MeCN/H$_2$O over 5 min)=4.28 min. ESMS (C$_{38}$H$_{52}$N$_2$O$_2$) calcd. 568.84; obsd. 569.4 [M+H]$^+$.

Compound 81 was prepared in an analogous manner from bis(4-chlorobutyl)ether. Retention time (anal. HPLC: 10–70% MeCN/H$_2$O over 5 min)=4.28 min. ESMS (C$_{38}$H$_{60}$N$_2$O$_3$): calcd. 592.91; obsd. 593.4 [M+H]$^+$.

Compound 82 was prepared in an analogous manner from bis[2-(2-chloroethoxy)ethyl]ether. Retention Time (anal. HPLC: 10–70%. MeCN/H$_2$O over 5 min)=4.14 min. ESMS (C$_{38}$H$_{60}$N$_2$O$_3$): calcd. 624.90; obsd. 625.6 [M+H]$^+$.

Compound 83 was prepared in an analogous manner from N,N'-bis(2-chloroethyl)oxamide. Retention time (anal. HPLC: 10–70% MeCN/H$_2$O over 5 min)=4.08 min. ESMS (C$_{36}$H$_{54}$N$_4$O$_4$): calcd. 606.84; obsd. 607.6 [M+H]$^+$.

Compound 84 was prepared in an analogous manner from 4,4-bis(chloromethyl)1,1-biphenyl. Retention time (anal. HPLC: 10–70% MeCN/H$_2$O over 5 min)=4.63 min. ESMS (C$_{44}$H$_{56}$N$_2$O$_2$): calcd. 644.94; obsd. 645.6 [M+H]$^+$.

EXAMPLE 33

Synthesis of Compound 1 of Table C via the Following Scheme

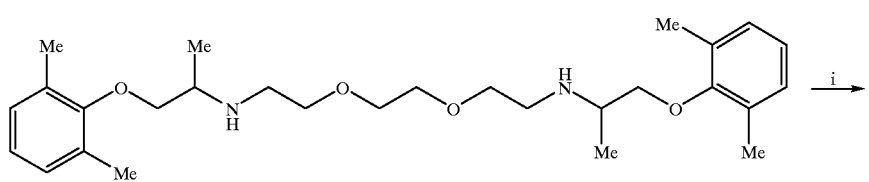

Table A, Compound 1

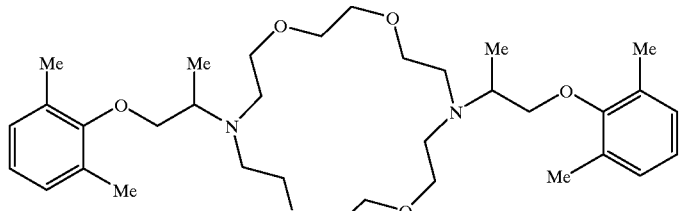

Table C, Compound 1 reagents and conditions: i) 1,2-bis-(2-iodoethoxy)ethane, Na$_2$CO$_3$, NaI, CH$_3$CN, 150°° C.

A suspension of acetonitrile (14 mL) containing Table C, compound 1 of Table A (43.4 mg, 0.092 mmol), 1,2-bis(2-iodoethoxy)ethane (21 μL, 0.115 mmol), potassium carbonate (63.6 mg, 0.46 mmol), and potassium iodide (7.6 mg, 0.046 mmol) in a thick-walled, sealed tube was heated at 150° C. for 12 h. The reaction mixture was cooled, filtered, and concentrated in vacuo. The resulting residue was dissolved in 1 mL of 50% aqueous acetonitrile (with 0.1% trifluoroacetic acid), and purified by reversed phase preparative HPLC. Retention time (anal. HPLC: 2–90% MeCN/H$_2$O over 5 min)=2.96 min (a mixture of diastereomers). ESMS (C$_{34}$H$_{54}$N$_2$O$_6$): calcd. 586.8; obsd. 587.4 [M+H]$^+$.

TABLE C

| No. | Molecule |
|---|---|
| 1 | |
| 2 | |
| 3 | |

TABLE C-continued

| No. | Molecule |
|---|---|
| 4 | 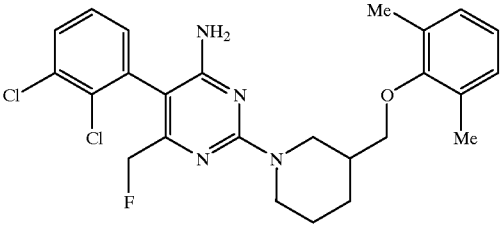 |
| 5 | 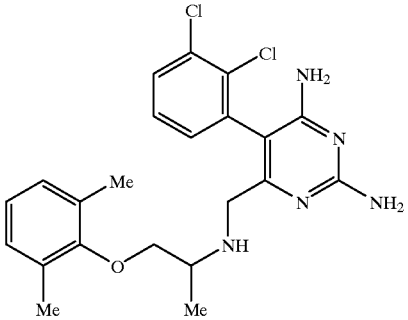 |

Table C lists linkers that can be employed in the above scheme.

EXAMPLE 34

Synthesis of Dimers via the Following Scheme

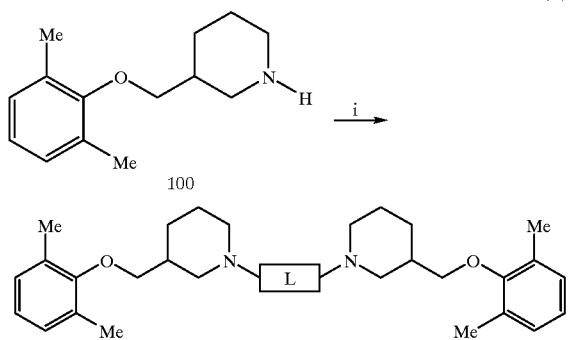

reagents and conditions: i) di-halide (X—L—X), diisopropylethylamine, DMF, 90° C.

Compound 100 was prepared in racemic form following procedures as described in L. A. Flippin, et al., EP0869119 A1.

Table D lists linkers 86–103 for dimer D.

TABLE D

| No. | Linker |
|---|---|
| 86 | —CH$_2$-Z-CH$_2$— where Z = 1,4-phenyl |
| 87 | —(CH$_2$)$_9$— |
| 88 | —CH$_2$—CH=CH—CH$_2$— (trans isomer) |
| 89 | —(CH$_2$)$_2$—O—(CH$_2$)$_2$—O—(CH$_2$)$_2$— |

TABLE D-continued

| No. | Linker |
|---|---|
| 90 | —CH$_2$-Z-CH$_2$— where Z = (−)-trans-2,2-dimethyl-[1,3]dioxolan-4,5-yl |
| 91 | —(CH$_2$)$_{10}$— |
| 92 | —(CH$_2$)$_{11}$— |
| 93 | —(CH$_2$)$_{12}$— |
| 94 | —(CH$_2$)$_{16}$— |
| 95 | —CH$_2$—CH(OH)—CH$_2$— |
| 96 | —CH$_2$—C≡C—CH$_2$— |
| 97 | —(CH$_2$)$_7$— |
| 98 | —(CH$_2$)$_8$— |
| 99 | —CH$_2$-Z-CH$_2$— where Z = 2,3-quinoxalinyl |
| 100 | —CH$_2$—CH(CO$_2$H)— |
| 101 | —CH$_2$—CH(CH$_3$)—CH$_2$— |
| 102 | —CH$_2$-Z-CH$_2$ where Z = 1,3-phenyl |
| 103 | —(CH$_2$)$_2$—O—CH$_2$—O—(CH$_2$)$_2$— |

General procedure for the synthesis of compound 86 of Table D: A solution of compound 100 (43.8 mg, 0.2 mmol) with diisopropylethylamine (54 µl, 0.3 mmol) in 200 µL of anhydrous DMF, was added to a solution of α,α'-dibromo-p-xylene (0.1 mmol) in 200 µL anhydrous DMF. The mixture was shaken for 20 h at 90° C., then stripped of solvent under vacuum. The resulting tarry mixture was dissolved in 1 mL of a 1:1 mixture of acetonitrile and water (with 0.1% trifluoroacetic acid). The crude product was purified by preparative reversed phase HPLC to afford 26.2 mg of the desired material as the TFA salt. ESMS (C$_{36}$H$_{48}$N$_2$O$_2$): calcd. 540.79; obsd. 541 [M+H]$^+$. Retention time (anal. HPLC: 2–90% MeCN/H$_2$O over 5 min)=4.7 min.

Compound 87 was prepared with 1,9-dibromononane (0.1 mmol) using the standard procedure to provide 16.3 mg of the desired material as the TFA salt. ESMS (C$_{37}$H$_{58}$N$_2$O$_2$): calcd. 562.8; obsd. 563 [M+H]$^+$. Retention time (anal. HPLC: 2–90% MeCN/H$_2$O over 5 min)=4.8 min.

Compound 88 was prepared with 1,4-dibromo-2-butene (0.1 mmol) using the standard procedure to provide the desired material as the TFA salt. ESMS (C$_{32}$H$_{46}$N$_2$O$_2$):

calcd. 490.72; obsd. 491 [M+H]+. Retention time (anal. HPLC: 2–90% MeCN/H₂O over 5 min)=4.76 min.

Compound 89 was prepared with 1,2-bis(2-iodoethoxy)ethane (0.1 mmol) using the standard procedure to provide 18.7 mg of the desired material as the TFA salt. ESMS (C₃₄H₅₂N₂O₄): calcd. 552.80; obsd. 553 [M+H]+. Retention time (anal. HPLC: 2–90% MeCN/H₂O over 5 min)=4.7 min.

Compound 90 was prepared with (−)-trans4,5-bis(idodomethyl))-2,2-dimethyl-1,3-dioxolane (0.1 mmol) using the standard procedure to provide 8.5 mg of the desired material as the TFA salt. ESMS (C₃₅H₅₂N₂O₄): calcd. 564.81; 565.3 [M+H]+. Retention time (anal. HPLC: 2–90% MeCN/H₂O over 5 min)=4.8 min.

Compound 91 was prepared with 1,10-diiododecane (0.1 mmol) using the standard procedure to provide 10.5 mg of the desired material as the TFA salt. ESMS (C₃₈H₆₀N₂O₂): calcd. 576.91; obsd. 577.6 [M+H]+. Retention time (anal. HPLC: 2–90% MeCN/H₂O over 5 min)=4.4 min.

Compound 92 was prepared with 1,11-dibromoundecane (0.1 mmol) using the standard procedure to provide 11.4 mg of the desired material as the TFA salt. ESMS (C₃₉H₆₂N₂O₂): calcd. 590.93; obsd. 591.5 [M+H]+. Retention time (anal. HPLC: 2–90% MeCN/H₂O over 5 min)=4.49 min.

Compound 93 was prepared with 1,12-dibromododecane (0.1 mmol) using the standard procedure to provide 13.2 mg of the desired material as the TFA salt. ESMS (C₄₀H₆₄N₂O₂): calcd. 604.96; obsd. 605.6 [M+H]+. Retention time (anal. HPLC: 2–90% MeCN/H₂O over 5 min)=4.58 min.

Compound 94 was prepared with 1,16-dibromohexadecane (0.1 mmol) using the standard procedure to provide 10.9 mg of the desired material as the TFA salt. ESMS (C₄₄H₇₂N₂O₂): calcd. 661.07; obsd. 661.7 [M]+. Retention time (anal. HPLC: 2–90% MeCN/H₂O over 5 min)=4.93 min.

Compound 95 was prepared with 1,3-dibromo-2-propanol (0.1 mmol) using the standard procedure to provide 7.5 mg of the desired material as the TFA salt. ESMS (C₃₁H₄₆N₂O₃): calcd. 494.72; obsd. 495.4 [M+H]+. Retention time (anal. HPLC: 2–90% MeCN/H₂O over 5 min)=3.95 min.

Compound 96 was prepared with 1,4-dichloro-2-butyne (0.1 mmol) using the standard procedure to provide 11.4 mg of the desired material as the TFA salt. ESMS (C₃₂H₄₄N₂O₂): calcd. 488.71; obsd. 489.4 [M+H]+. Retention time (anal. HPLC: 2–90% MeCN/H₂O over 5 min)=3.97 min.

Compound 97 was prepared with 1,7-dibromoheptane (0.1 mmol) using the standard procedure to provide 12.7 mg of the desired material as the TFA salt. ESMS (C₃₅H₅₄N₂O₂): calcd. 534.83; obsd. 535.5 [M+H]+. Retention time (anal. HPLC: 2–90% MeCN/H₂O over 5 min)=4.16min.

Compound 98 was prepared with 1,8-diiododecane (0.1 mmol) using the standard procedure to provide 16.3 mg of the desired material as the TFA salt. ESMS (C₃₆H₅₆N₂O₂) 548.85; obsd. 549.4 [M+H]+. Retention time (anal. HPLC: 2–90% MeCN/H₂O over 5 min)=4.22 min.

Compound 99 was prepared with 2,3-bis(bromomethyl)quinoxaline (0.1 mmol) using the standard procedure to provide the desired material as the TFA salt. ESMS (C₃₈H₄₈N₄O₂): calcd. 592.82; obsd. 593.6 [M+H]+. Retention time (anal. HPLC: 2–90% MeCN/H₂O over 5 min)=4.19 min.

Compound 100 was prepared with 2,3-dibromopropionic acid (0.1 mmol) using the standard procedure to provide 10.4 mg of the desired material as the TFA salt. ESMS (C₃₁H₄₄N₂O₄): calcd. 508.70; obsd. 509.5 [M+H]+. Retention time (anal. HPLC: 2–90% MeCN/H₂O over win)=4.23 min.

Compound 101 was prepared with 3chloro-2-chloromethyl-1-propene (0.1 mmol) using the standard procedure to provide 22.1 mg of the desired material as the TFA salt. ESMS (C₃₂H₄₆N₂O₂): calcd. 490.73; obsd. 491.4 [M+H]+. Retention time (anal. HPLC: 2–90% MeCN/H₂O over 5 min)=4.12 min.

Compound 102 was prepared with α,α'-dibromo-m-xylene (0.1 mmol) using the standard procedure to provide 22.5 mg of the desired material as the TFA salt. ESMS (C₃₆H₄₈N₂O₂): calcd. 540.79; obsd. 541.4 [M+H]+. Retention time (anal. HPLC: 2–90% MeCN/H₂O over 5 min)=4.12 min.

Compound 103 was prepared with bis(2-chloroethoxyethane) (0.1 mmol) using the standard procedure to provide 15.4 mg of the desired material as the TFA salt. ESMS (C₃₃H₅₀N₂O₄): calcd. 538.77; obsd. 539.4 [M+H]+. Retention time (anal. HPLC: 2–90% MeCN/H₂O over 5 min)=3.97 min.

EXAMPLE 35

Synthesis of Intermediate Compounds 9 to 12 via the Following Scheme

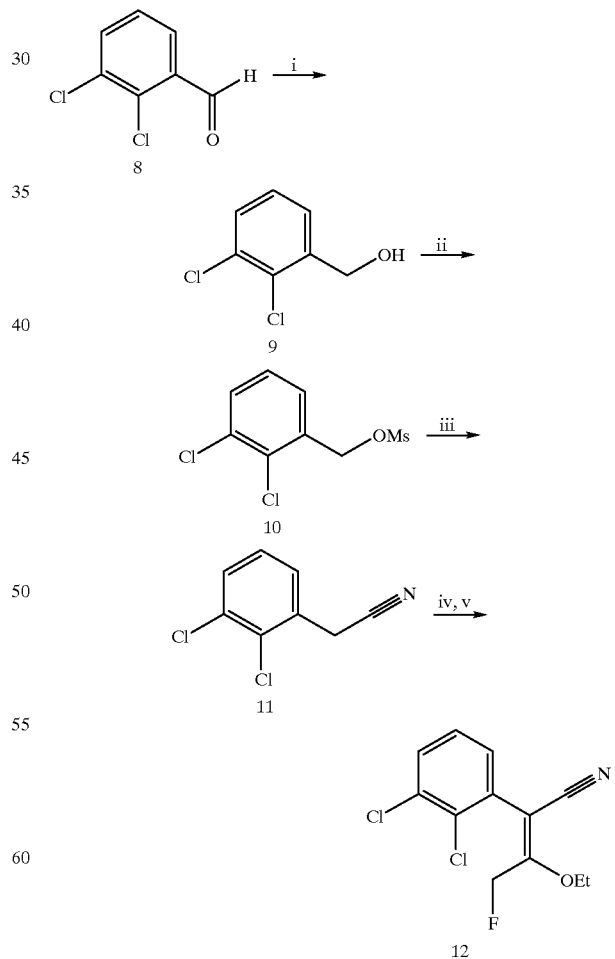

reagents and conditions i) NaBH₄, MeOH, 0° C.; ii) methanesulfonyl chloride, Et₃N, DMAP, toluene, 0° C.; iii) KCN, Bu₄NHSO₄, toluene water, rt; iv) FCH₂CO₂Et, NaOMe, MeOH, rt; v) Et-I, K₂CO₃, DMF, 75° C.

Compounds 9 to 12 were synthesized according to procedures described in Nobbs, et al., WO 97/09317 and Miller, et al., EP 0 372 934 B1.

Compound 9: To solution of MeOH (150 mL) containing 2,3-dichlorobenzaldehyde (20 g, 0.11 mole), cooled in ice bath, was added a solution of NaBH₄ (4.54 g, 0.12 mole) in 0.2 M NaOH (15 mL) slowly over 15 min under nitrogen atmosphere. After completion of the addition, the mixture was allowed to warm up gradually to rt, and stirred for 2.5 h at rt. The reaction was quenched by cooling the mixture and pouring it slowly to ice water (~700 mL). The mixing led to formation of white precipitates. After stirring for 30 min, the precipitates were collected on Bochner funnel; and the collected solid was dissolved in EtOAc (200 mL). The organic solution was washed with 0.1 M NaOH (150 mL), dried over Na₂SO₄, and concentrated to dryness in vacuo, yielding 2,3-dichlorobenzylalcohol as white solid (19.57 g, 97%). $R_f$=0.46 in EtOAc/hexane (1/3). ¹H-NMR (CD₃OD, 299.96 MHz): δ (ppm) 7.52–7.49 (dd, 1H), 7.45–7.42 (dd, 1H), 7.33–7.27 (t, 1H), 4.70 (s, 2H). Retention time (anal. HPLC: 10 to 70% MeCN/H₂O over 6 min)=4.00 min.

Compound 10: To a solution of toluene (100 mL) containing 2,3-dichlorobenzyl alcohol (18 g, 0.102 mole), Et₃N (12.4 g, 0.123 mole), and 4-dimethylaminopyridine (0.621 g, 5.08 mmole), cooled in ice bath, was added methanesulfonyl chloride (14 g, 0.122 mole) while stirring the mixture vigorously. The mixture was shaken at 0° C. for 1 h, prior to allowing it left in refrigerator over 2 days. The mixture was then diluted with EtOAc (100 mL) and brine (200 mL). After shaking in a separatory funnel, the organic phase was separated, and washed with sat. NaHCO₃ solution. Organic solution was dried over Na₂SO₄, and concentrated in vacuo to ~50 mL which was used directly in next step without further purification. ¹H-NMR (CD₃OD, 299.96 MHz): δ (ppm) 7.58–7.52 (dd, 1H), 7.51–7.48 (dd, 1H), 7.36–7.30(t, 1H), 5.36 (s, 2H), 3.14 (s, 3H). Retention time (anal. HPLC: 10 to 70% MeCN/H₂O over 6 min)=4.43 min.

Compound 11: Compound 10 (2,3-dichlorobenzyl mesylate), prepared above in toluene (~50 mL), was diluted to ~70 mL with toluene, and followed by addition of Bu₄NHSO₄ (7.0 g, 0.02 mole) in water (30 mL) and KCN (10 g, 0.15 mole) in water (40 mL). The mixture was stirred for 24 h at rt, and diluted with EtOAc (200 mL) prior to washing with 0.1 M NaOH (200 mL). The organic phase was washed again with 0.1 M NaOH and brine, dried over Na₂SO₄, and concentrated in vacuo, yielding a dark brown oily residue. The crude product was purified by flash silica column chromatography by eluting with hexane/EtOAc (3/1). The product was obtained as white to pale beige solid (16.35 g; 86% over two steps). $R_f$=0.58 in EtOAc/hexane (1/3). ¹H-NMR (CD₃OD, 299.96 MHz): δ (ppm) 7.56–7.53 (dd, 1H), 7.50–7.47 (dd, 1H), 7.36–7.31 (t, 1H), 4.03 (s, 2H). Retention time (anal. HPLC: 10 to 70% MeCN/H₂O over 6 min)=4.53 min.

Compound 12: To stirred suspension of compound 11 (16.6 g, 0.089 mole) in MeOH (100 mL) in water bath (rt) was added slowly NaOMe (12.05 g, 0.22 mole). After stirring for 10 min, ethyl fluoroacetate (11.36 g, 0.107 mole) was added to the mixture. The final mixture was stirred for 24 h at it. Reaction mixture was concentrated to oily residue, and the material was dissolved in water (150 mL). The aqueous layer was washed with ethyl ether (3×200 mL); white insoluble material was saved and pooled with the aqueous layer. The combined solution was acidified to pH 3 by using 6M HCl, and the aqueous solution was in extracted with ethyl ether (500 mL). The organic solution was dried over Na₂SO₄, and concentrated to yield product (4-fluoro-3-oxo-2-(2,3-dichlorophenyl)-butyronitrile) as pale yellow oily residue which slowly solidified. The crude product (11.29 g; 51.3%) was used in next step. $R_f$=0.76 in 5% MeOH/EtOAc/hexane (1/1). ¹H-NMR (CD₃OD, 299.96 MHz): δ (ppm) 7.57–7.54 (dd, 1H), 7.48–7.43 (dd, 1H), 7.35–7.32 (t, 1H), 5.36 & 5.20 (two s, 2H).

To a solution of DMF (200 mL) containing the above nitrite (11.2 g, 0.046 mole) was added K₂CO₃ (12.6 g, 0.091 mole) and ethyl iodide (14.2 g, 0.091 mole). The mixture was stirred overnight at 75° C. The reaction mixture was cooled down to rt, and diluted with EtOAc (500 mL) and followed by addition of water (300 mL). After shaking in a separatory funnel, the organic phase was separated and washed with brine solution (200 mL), dried over Na₂SO₄, and concentrated to oily residue. It was purified by flash silica column chromatography by eluting with hexane/EtOAc (4/1 to 2/1) to afford compound 12 as pale yellow oil (12.47 g; 49.1%). $R_f$=0.39 in 5% MeOH/EtOAc/hexane (1/1). ¹H-NMR (CD₃OD, 299.96 MHz): δ (ppm) 7.59–7.56 (t, 1H), 7.35–7.33 (m, 2H), 5.54 & 5.39 (two s, 2H), 4.25–4.18 (q, 2H), 1.22–1.17 (t, 3H).

EXAMPLE 36

Synthesis of bis-guanidines via the Following Scheme

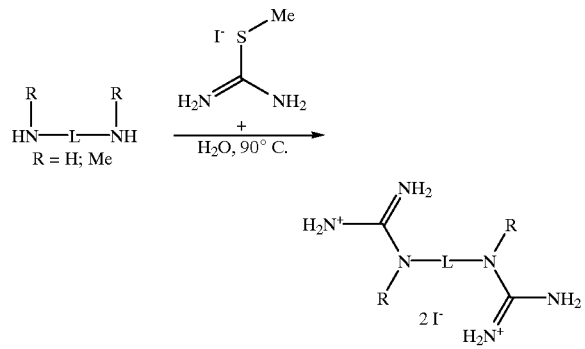

General procedure for the synthesis of compound 7 of Table E: To a solution of 1,5-diaminohexane (0.78 g, 7.63 mmole) in water (10 mL) was added methylmercaptocarboxamidine hydrogen iodide salt (5.0 g; 0.023 mole) at rt. The mixture was stirred, and heated at 90° C. for 24 h in well-ventilated hood. The reaction mixture was concentrated in vacuo, and white crystalline solid was obtained. It was suspended in 30 mL of i-PrOH/ether (1/1), collected on Büchner funnel, and further washed with 30 mL of i-PrOH/ether (1/1). The product was obtained as white solid (1.8 g; 52%) as hydrogen iodide salt. ¹H-NMR(D₂O, 299.96 MHz): δ (ppm) 3.03–3.09 (t, 4H), 1.49 (m,4H), 1.27 (m, 2H).

Table E lists linkers 1–18 for dimer E.

TABLE E

| No. | Linker | R |
|---|---|---|
| 1 | 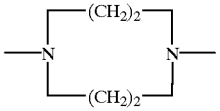 | — |
| 2 | —(CH$_2$)$_3$— | Me |
| 3 | —CH$_2$—CH=CH—CH$_2$— (trans isomer) | Me |
| 4 | —(CH$_2$)$_6$— | Me |
| 5 | —(CH$_2$)$_3$— | H |
| 6 | —CH$_2$—Z—CH$_2$— where Z = 1,4-phenyl | H |
| 7 | —(CH$_2$)$_5$— | H |
| 8 | —(CH$_2$)$_8$— | H |
| 9 | —(CH$_2$)$_7$— | H |
| 10 | —(CH$_2$)$_3$—O—(CH$_2$)$_4$—O—(CH$_2$)$_3$— | H |
| 11 | —(CH$_2$)$_2$—(CH$_2$)$_2$— | H |
| 12 | —(CH$_2$)$_{10}$— | H |
| 13 | —(CH$_2$)$_4$— | H |
| 14 | —CH$_2$—Z—CH$_2$— where Z = 1,3-phenyl | H |
| 15 | 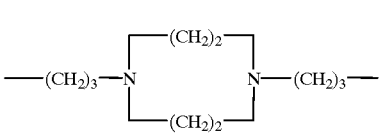 | H |
| 16 | —(CH$_2$)$_3$—O—(CH$_2$)$_3$— | H |
| 17 | —(CH$_2$)$_2$—O—(CH$_2$)$_2$—O—(CH$_2$)$_2$— | H |
| 18 | —(CH$_2$)$_3$—O—(CH$_2$)$_2$—O—(CH$_2$)$_2$—O—(CH$_2$)$_3$— | H |

Bis-guanidines below were prepared from corresponding di-amine's in an analogous manner as described above.

Compound 1: $^1$H-NMR (D$_2$O, 299.96 MHz): δ (ppm) 4.64 (s).

Compound 2: $^1$H-NMR (D$_2$O, 299.96 MHz): δ (ppm) 3.30–3.25 t, 4H), 2.92 (s, 6H), 1.94–1.92 (q, 2H).

Compound 3: $^1$H-NMR (D$_2$O, 299.96 MHz): δ (ppm) 5.59 (s, 2H), 3.92 (s, 4H), 2.94 (s, 6H).

Compound 4: $^1$H-NMR (D$_2$O, 299.96 MHz): δ (ppm) 3.22–3.18 (t, 4H), 2.89 (s, 6H), 1.55–1.46 (bra quin, 4H), 1.25–1.18 (bra quin, 4H).

Compound 5: $^1$H-NMR (D$_2$O, 299.96 MHz): δ (ppm) 3.18–3.1 (t, 4H), 1.8–1.7 (quin, 2H).

Compound 6: $^1$H-NMR (D$_2$O, 299.96 MHz): δ (ppm) 7.30 (s, 4H), 4.36 (s, 4H).

Compound 8: $^1$H-NMR (D$_2$O, 299.96 MHz): δ (ppm) 3.04–3.08 (t, 4H), 1.47 (m, 4H), 1.23 (m, 8H).

Compound 9: $^1$H-NMR (D$_2$O, 299.96 MHz): δ (ppm) 3.08–3.04 (t, 4H), 1.46–1.42 (t, 4H), 1.23 (m, 6H).

Compound 10: $^1$H-NMR (D$_2$O, 299.96 MHz): δ (ppm) 3.50–3.42 (m, 8H), 3.20–3.14 (t, 4H), 1.80–1.70 (quin, 4H), 1.55–1.48 m, 4H)., Compound 11: $^1$H-NMR (D$_2$O, 299.96 MHz) δ (ppm) 3.35–3.31 (t, 4H), 2.75 (m, 4H), 2.35 (s, 3H).

Compound 12: 1H-NMR (D$_2$O, 299.96 MHz): δ (ppm) 3.02–3.06 (t, 4H), 1.45 (m, 4H), 1.18 (m, 12H).

Compound 13: $^1$H-NMR (D$_2$O, 299.96 MHz): δ (ppm) 3.13 (t, 4H), 1.56 (t, 4H).

Compound 14: $^1$H-NMR (D$_2$O, 299.96 MHz): δ (ppm) 7.13–7.15 (d, 2H), 7.18 (s, 1H), 7.27–7.32 (t, 1H), 4.30 (s, 4H).

Compound 15: $^1$H-NMR (D$_2$O, 299.96 MHz): δ (ppm) 3.09–3.13 (t, 4H), 2.56 (m, 8H), 2.40–2.43 (t, 4H), 1.65–1.74 (quin, 4H).

Compound 16: $^1$H-NMR (D$_2$O, 299.96 MHz): δ (ppm) 3.45–3.49 (t, 4H), 3.14–3.18 (t, 4H), 1.71–1.79 (quin, 4H).

Compound 17: $^1$H-NMR (D$_2$O, 299.96 MHz): δ (ppm) 3.61 (s, 4H), 3.58–3.62 (t, 4H), 3.28–3.32 (t, 4H).

Compound 18: $^1$H-NMR (D$_2$O, 299.96 MHz): δ (ppm) 3.56 (s, 8H), 3.47–3.51 (t, 4H), 3.14–3.18 (t, 4H), 1.70–1.78 (quin, 4H).

EXAMPLE 37

Synthesis of Homodimers of 5-arylpyrimidine via the Following Scheme

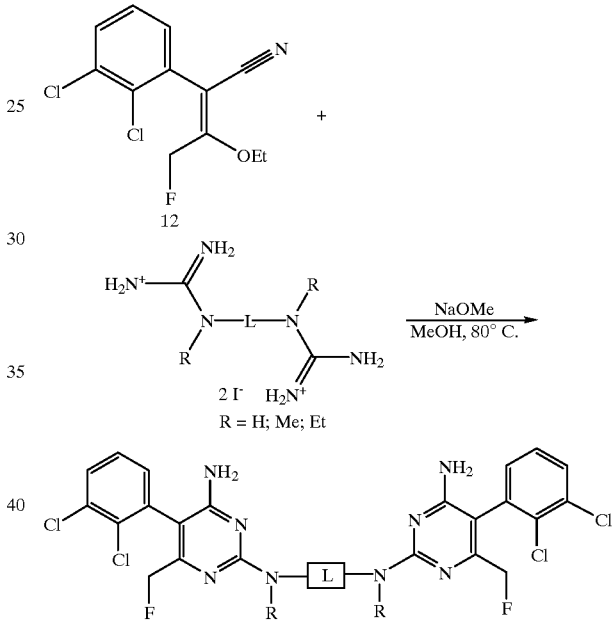

General procedure for the synthesis of compound 15 of Table F: R=Me, L=(CH$_2$)$_3$): To Table E, compound 2 (0.3 g, 0.678 mmole) in a vial was added NaOMe (100 mg/mL; 0.77 mL; 1.43 mmole) and compound 12 (500 mg/L MeOH; 1.116 mL, 2.04 mmole). The reaction vessel was well sealed with a screw cap, and shaken at 80° C. for 6 h. The mixture was then concentrated to dryness, and the dark brown residue was dissolved in 5 mL of 50% aqueous acetonitrile (with 5% TFA). After filtration, the crude product was purified by preparative reversed phase HPLC: 20 to 60% aqueous acetonitrile (0.1% TFA) over 40 min (linear gradient); 30 mL/min; 254 nm. The desired product was obtained as white solid (70 mg). ESMS (C$_{28}$H$_{30}$N$_8$O$_2$F$_2$Cl$_4$); calcd. 658.41; obsd. 659.3 [M+H]$^+$. $^1$H-NMR (CD$_3$OD, 299.96 MHz): δ (ppm) 7.72–7.70 (dd, 2H), 7.50–7.41 (dt, 2H), 4.32–7.29 (dt, 2H), 5.2–5.08 (q, 4H), 3.9–3.78 (m, 4H), 3.30 (s, 6H), 2.2–2.08 (quin, 2H). Retention time (anal. HPLC: 10 to 70% MeCN/H$_2$O over 6 min)=3.63 min.

Table F lists linkers 1–18 for tile following dimer.

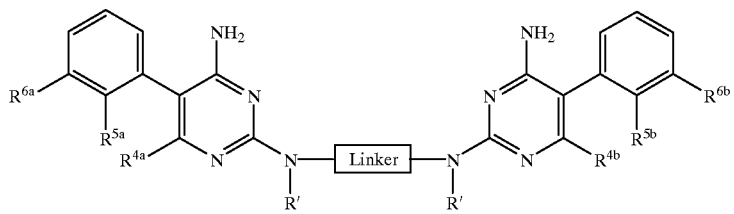

TABLE F

| No. | Linker | R | R$^{5a}$ | R$^{6a}$ | R$^{5b}$ | R$^{6b}$ | R$^{4a}$ | R$^{4b}$ |
|---|---|---|---|---|---|---|---|---|
| 1 | —(CH$_2$)$_3$— | H | Cl | Cl | Cl | Cl | —CH$_2$F | —CH$_2$F |
| 2 | —CH$_2$—Z—CH$_2$— where Z = 1,4-phenyl | H | Cl | Cl | Cl | Cl | —CH$_2$F | —CH$_2$F |
| 3 | —(CH$_2$)$_5$— | H | Cl | Cl | Cl | Cl | —CH$_2$F | —CH$_2$F |
| 4 | —(CH$_2$)$_8$— | H | Cl | Cl | Cl | Cl | —CH$_2$F | —CH$_2$F |
| 5 | —(CH$_2$)$_7$— | H | Cl | Cl | Cl | Cl | —CH$_2$F | —CH$_2$F |
| 6 | —(CH$_2$)$_3$—O—(CH$_2$)$_4$—O—(CH$_2$)$_3$— | H | Cl | Cl | Cl | Cl | —CH$_2$F | —CH$_2$F |
| 7 | —(CH$_2$)$_2$—N(CH$_3$)—(CH$_2$)$_2$— | H | Cl | Cl | Cl | Cl | —CH$_2$F | —CH$_2$F |
| 8 | —(CH$_2$)$_{10}$— | H | Cl | Cl | Cl | Cl | —CH$_2$F | —CH$_2$F |
| 9 | —(CH$_2$)$_4$— | H | Cl | Cl | Cl | Cl | —CH$_2$F | —CH$_2$F |
| 10 | —CH$_2$—Z—CH$_2$— where Z = 1,3-phenyl | H | Cl | Cl | Cl | Cl | —CH$_2$F | —CH$_2$F |
| 11 | —(CH$_2$)$_3$—N(piperazine)N—(CH$_2$)$_3$— | H | Cl | Cl | Cl | Cl | —CH$_2$F | —CH$_2$F |
| 12 | —(CH$_2$)$_3$—O—(CH$_2$)$_3$— | H | Cl | Cl | Cl | Cl | —CH$_2$F | —CH$_2$F |
| 13 | —(CH$_2$)$_2$—O—(CH$_2$)$_2$—O—(CH$_2$)$_2$— | H | Cl | Cl | Cl | Cl | —CH$_2$F | —CH$_2$F |
| 14 | —(CH$_2$)$_3$—O—(CH$_2$)$_2$—O—(CH$_2$)$_2$—O—(CH$_2$)$_3$— | H | Cl | Cl | Cl | Cl | —CH$_2$F | —CH$_2$F |
| 15 | —N(CH$_3$)—(CH$_2$)$_3$—N(CH$_3$)— | Me | Cl | Cl | Cl | Cl | —CH$_2$F | —CH$_2$F |
| 16 | —N(CH$_3$)—CH$_2$—CH=CH—CH$_2$—N(CH$_3$)— (trans isomer) | Me | Cl | Cl | Cl | Cl | —CH$_2$F | —CH$_2$F |
| 17 | —N(CH$_3$)—(CH$_2$)$_6$—N(CH$_3$)— | Me | Cl | Cl | Cl | Cl | —CH$_2$F | —CH$_2$F |
| 18 | —N(piperazine)N— | — | Cl | Cl | Cl | Cl | —CH$_2$F | —CH$_2$F |

Compound 1 was synthesized from Table E, compound 5 in an analogous way as described above. Retention time (anal. HPLC: 10 to 70% MeCN/H$_2$O over 6 min)=3.14. ESMS (C$_{25}$H$_{22}$Cl$_4$F$_2$N$_8$); calcd. 642.37; obsd. 643.1 [M+H]$^+$. $^1$H-NMR (CD$_3$OD, 299.96 MHz): δ (ppm) 7.72–7.69 (d, 4H), 7.46–7.42 (t, 2H), 7.33–7.31 (d, 4H), 4.98 (s, 2H), 4.82 (s, 2H), 4.30–4.24 (t, 4H), 2.38–2.36 (m, 2H).

Compound 2 was prepared from Table E, compound 6 in an analogous way as described above. ESMS (C$_{30}$H$_{24}$N$_8$F$_2$Cl$_4$); calcd. 676.4; obsd. 677.1 [M+H]$^+$. $^1$H-NMR (CD$_3$OD, 299.96 MHz): δ (ppm) 7.73–7.70 (dd, 2H), 7.50–7.42 (dt, 2H), 7.38–7.35 (dd, 2H), 7.34 (d, 4H), 5.49 (s, 4H), 5.03 & 4.88 (two s, 4H). Retention time (anal. HPLC: 10 to 70% MeCN/H$_2$O over 6 min)=3.48 min.

Compound 3 was synthesized from Table E, compound 7 in an analogous way as described above. Retention time (anal. HPLC: 10 to 70% MeCN/H$_2$O over 6 min)=3.02. ESMS (C$_{27}$H$_{26}$Cl$_4$F$_2$N$_8$); calcd. 642.37; obsd. 643.1 [M+H]$^+$. $^1$H-NMR (CD$_3$OD, 299.96 MHz): δ (ppm) 7.72–7.70 (d, 4H), 7.48–7.42 (t, 2H), 7.33–7.30 (d, 4H), 4.97 (s, 2H), 4.81 (s, 2H), 4.18–4.13 (t, 4H), 1.92–1.87 (m, 4H), 1.64–1.62 (m, 2H).

Compound 4 was synthesized from Table E, compound 8 in an analogous way as described above. Retention time (anal. HPLC: 10 to 70% MeCN/H$_2$O over 6 min)=3.24. ESMS (C$_{30}$H$_{32}$Cl$_4$F$_2$N$_8$); calcd. 684.45; obsd. 685.4 [M+H]$^+$. $^1$H-NMR (CD$_3$OD, 299.96 MHz): δ (ppm) 7.72–7.69 (d, 4H), 7.47–7.42 (t, 2H), 7.33–7.30 (d, 4H), 4.96 (s, 2H$_1$), 4.81 (s, 2H$_1$), 4.12–4.07 (t, 4H), 1.81 (m, 4H), 1.46–1.44(m, 8H).

Compound 5 was prepared from Table E, compound 9 in an analogous way as described above. ESMS (C$_{29}$H$_{30}$N$_8$F$_2$Cl$_4$); calcd. 670;4; obsd. 671.1 [M+H]$^+$. $^1$H-NMR (CD$_3$OD, 299.96. MHz): δ (ppm) 7.72–7.69 (dd, 2H), 7.48–7.42 (t, 2H), 7.33–7.30 (dd, 2H), 4.96 & 4.81 (two s, 4H), 4.14–4.09 (t, 4H), 1.81 (br, 4H), 1.48 (br,6H). Retention time (anal. HPLC: 10 to 70% MeCN/H$_2$O over 6 min)=3.58 min.

Compound 6 was prepared from Table E, compound 10 in an analogous way as described above. ESMS (C$_{32}$H$_{36}$N$_8$F$_2$Cl$_4$O); calcd. 744.5; obsd. 745.2 [M+H]$^+$. $^1$H-NMR (CD$_3$OD, 299.96 MHz): δ (ppm) 7.73–7.69 (dd, 2H), 7.48–7.42 (t, 2H), 7.33–7.30 (dd, 2H), 4.97 & 4.83 (two d, 4H), 4.23–4.19 (t, 4H), 3.61–3.57 (t, 4H0, 3.48 (br s, 4H), 2.15–2.11 (br m, 4H), 1.61 (br s, Retention time (anal. HPLC: 10 to 70% MeCN/H$_2$O over 6 min)=3.2 min.

Compound 7 was prepared from Table E, compound 11 in an analogous way as described above. ESMS (C$_{27}$H$_{27}$N$_9$F$_2$Cl$_4$); calcd. 657.4; obsd. 658.2 [M+H]$^+$. $^1$H-NMR (CD$_3$OD, 299.96 MHz): δ (ppm) 7.72–7.69 (dd, 2H), 7.48–7.43 (t, 2H), 7.36–7.33 (m, 2H), 4.99 & 4.83 (two s, 4H), 4.37–4.33 (t, 41), 3.10–3.0 (m, 4H), 2.56 (s, 3H). Retention time (anal. HPLC: 10 to 70% MeCN/H$_2$O over 6 min)=3.38 min.

Compound 8 was synthesized from Table E, compound 12 in an analogous way as described above. Retention time (anal. HPLC: 10 to 70% MeCN/H$_2$O over 6 min)=3.46. ESMS (C$_{32}$H$_{36}$Cl$_4$F$_2$N$_8$); calcd. 712.50; obsd. 713.3 [M+H]$^+$. $^1$H-NMR (CD$_3$OD, 299.96 MHz): δ (ppm) 7.72–7.69 (d, 4H), 7.47–7.42 (t, 2H), 7.33–7.30 (d, 4H), 4.96 (s, 2H), 4.80 (s, 2H), 4.12–4.06 (t, 4H), 1.79 (m, 4H), 1.36 (m, 4H).

Compound 9 was synthesized from Table E, compound 13 in an analogous way as described above. Retention time (anal. HPLC: 10 to 70% MeCN/H$_2$O over 6 min)=2.85. ESMS (C$_{26}$H$_{24}$Cl$_4$F$_2$N$_8$); calcd. 628.34; obsd. 629.0 [M+H]$^+$. $^1$H-NMR (CD$_3$OD, 299.96 MHz): δ (ppm) 7.73–7.69 (d, 4H), 7.48–7.43 (t, 2H), 7.34–7.32 (d, 4H), 4.97 (s, 2H), 4.81 (s, 2H), 4.18 (m, 4H), 1.99 (m, 4H).

Compound 10 was synthesized from Table E, compound 14 in an analogous way as described above. Retention time (anal. HPLC: 10 to 70% MeCN/H$_2$O over 6 min)=3.03. ESMS (C$_{30}$H$_{24}$Cl$_4$F$_2$N$_8$); calcd. 676.38; obsd. 677.0 [M+H]$^+$. $^1$H-NMR (CD$_3$OD, 299.96 MHz): δ (ppm) 7.73–7.72 (d, 4H), 7.59–7.54 (t, 1H), 7.47–7.44 (t, 2H), 7.39–7.37 (d, 2H), 7.32–7.30 (d, 4H), 6.94 (s, 1H), 5.51 (s 4H), 5.03 (s, 2H), 4.88 (s, 2H).

Compound 11 was synthesized from Table E, compound 15 in an analogous way as described above. Retention time (anal. HPLC: 10 to 70% MeCN/H$_2$O over 6 min)=2.66. ESMS (C$_{32}$H$_{36}$Cl$_4$F$_2$N$_{10}$); calcd. 740.51; obsd. 741.2 [M+H]$^+$. $^1$H-NMR (CD$_3$OD, 299.96 MHz): δ (ppm) 7.73–7.69 (d, 4H), 7.48–7.42 (t, 2H), 7.31–7.30 (d, 4H), 4.97 (s, 2H), 4.82 (s, 2H), 4.20–4.15 (t 14H), 3.11 (m, 8H), 2.21–2.16 (t, 4H), 1.87–1.84 (quin, 4H).

Compound 12 was synthesized from Table E, compound 16 in an analogous way as described above. Retention time (anal. HPLC: 10 to 70% MeCN/H$_2$O over 6 min)=1.44. ESMS (C$_{28}$H$_{28}$Cl$_4$F$_2$N$_8$O); calcd. 672.39; obsd. 673.1 [M+H]$^+$. $^1$H-NMR (CD$_3$OD, 299.96 MHz): δ (ppm) 7.73–7.70 (d, 4H), 7.48–7.42 (t, 2H), 7.33–7.30 (d, 4H), :4.97 (s, 2H), 4.82 (s, 2H), 4.23–4.19 (t, 4H), 3.74–3.70 (t, 4H), 3.64–3.60 (t, 2H), 2.16–2.08 (p, 2H), 1.88–1.84(p, 2H).

Compound 13 was synthesized from Table E, compound 17 in an analogous way as described above. Retention time (anal. HPLC: 10 to 70% MeCN/H$_2$O over 6 min)=2.41. ESMS. (C$_{28}$H$_{28}$Cl$_4$F$_2$N$_8$O$_2$); calcd. 688.39; obsd. 689.3 [M+H]$^+$. $^1$H-NMR (CD$_3$OD, 299.96 MHz): δ (ppm) 7.73–7.70 (d, 4H), 7.48–7.43 (t, 2H), 7.33–7.31 (d, 4H), 4.99 (s, 2H), 4.84 (s, 2H), 4.39–4.36 (t, 4H), 3.92–3.89 (t, 4H), 3.69 (s, 4H).

Compound 14 was prepared from Table E, compound in an analogous way as described above. Retention time (anal. HPLC: 10 to 70% MeCN/H$_2$O over 6 min)=1.49. ESMS (C$_{32}$H$_{36}$Cl$_4$F$_2$N$_8$O$_3$); calcd. 760.50; obsd. 761.2 [M+H]$^+$. $^1$H-NMR (CD$_3$OD, 299.96 MHz): δ (ppm) 7.73–7.70 (d, 4H), 7.48–7.42 (t, 2H), 7.33–7.31 (d, 4H), 4.96 (s, 2H), 4.81 (s, 2H), 4.24–4.20 (t, 4H), 3.74–3.70 (t, 2H), 3.65 (s, 8H), 3.69–3.61 (t, 2H), 2.20–2.12 (p, 2H), 1.87–1.84 (quin, 2H).

Compound 16 was prepared from Table E, compound 27 in an analogous way as described above. ESMS (C$_{29}$H$_{30}$N8F$_2$Cl$_4$); calcd. 670.4; obsd. 671.3 [M+H]$^+$. $^1$H-NMR (CD$_3$OD, 299.96 MHz): δ (ppm) 7.74–7.71 (dd, 2H), 7.49–7.44 (t, 2H), 7.33–7.31 (d, 2H), 5.86 (s, 2H), 5.20–5.10 (dd, 2H), 5.02–4.95 (dd, 2H), 4.48–4.35 (brt, 4H), 4.10 (s, 8H), 3.25 (s, 6H). Retention time (anal. HPLC: 10 to 70% MeCN/H$_2$O over 6 min)=3.68 min.

Compound 17 was synthesized from Table E, compound 4 in an analogous way as described above. Retention time (anal. HPLC: 10 to 70% MeCN/H$_2$O over 6 min)=3.51. ESMS (C$_{30}$H$_{32}$Cl$_4$F$_2$N$_8$); calcd. 684.44; obsd. 685.5 [M+H]$^+$. $^1$H-NMR (CD$_3$OD, 299.96 MHz): δ (ppm) 7.74–7.72 (d, 4H), 7.48–7.44 (t, 2H), 7.33–7.31 (d, 4H), 5.11 (m, 2H), 4.96 (m, 2H), 3.74 (m, 4H), 3.26 (s, 6H), 1.74 (m, 4H), 1.46 (m, 4H).

Compound 18 of Table F was prepared from Table E, compound 1 in an analogous way as described above. ESMS (C$_{26}$H$_{22}$N$_8$F$_2$Cl$_4$); calcd. 626.3; obsd. 627.2 [M+H]$^+$. $^1$H-NMR (CD$_3$OD, 299.96 MHz): δ (ppm) 7.75–7.72 (dd, 2H), 7.50–7.45 (t, 2H), 7.35–7.32 (dd, 2H), 5.21–5.10 (dd, 2H), 5.05–4.98 (dd, 2H), 4.10 (s, 8H). Retention time (anal. HPLC: 10 to 70% MeCN/H$_2$O over 6 min)=3.82 min.

EXAMPLE 38

Synthesis of Mexiletine-guaidines via the Following Scheme

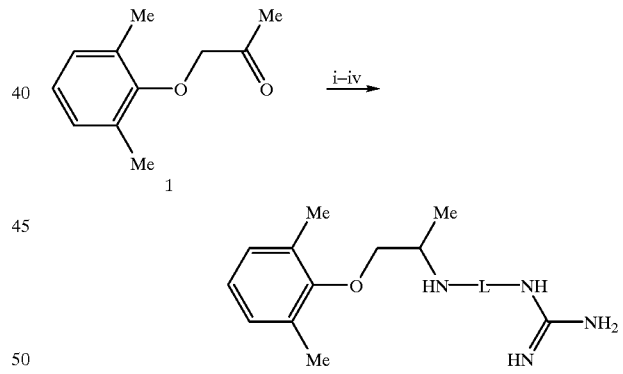

reagents and conditions: i) H$_2$N—L—NH$_2$, THF, rt; ii) 1-H-pyrazole-1-[N,N'-bis(tert-butoxycarbonyl)] carboxamidine, rt; iii) NaCNBH$_3$, rt; iv) TFA, CH$_2$Cl$_2$, 0° C.

General procedure for the synthesis of compound 1 of Table G: L=(CH$_2$)$_6$): (Step i): To a solution of 1,6-diaminohexane in TBF (10 mL) was, added 2,6-dimethylphenyloxyacetone (compound 1; 1.0 g, 5.6 mmole) in THF (5 mL). After stirring at rt for 1.5 h, mass spectrometric analysis of the reaction mixture indicated the formation of imine as a major species: ESMS (C$_{17}$H$_{28}$N$_2$O): calcd. 276.4; obsd. 277.3 [M+H]$^+$.

Table G lists linkers 1–15 for dimer G.

TABLE G

| No. | Linker |
|-----|--------|
| 1 | —(CH$_2$)$_6$— |
| 2 | —(CH$_2$)$_3$—N[—(CH$_2$)$_2$—][—(CH$_2$)$_2$—]N—(CH$_2$)$_3$— |
| 3 | —(CH$_2$)$_2$—O—(CH$_2$)$_2$—O—(CH$_2$)$_2$— |
| 4 | —(CH$_2$)$_5$— |
| 5 | —(CH$_2$)$_3$—O—(CH$_2$)$_2$—O—(CH$_2$)$_2$—O—(CH$_2$)$_3$— |
| 6 | —(CH$_2$)$_2$—N(CH$_3$)—(CH$_2$)$_2$— |
| 7 | —(CH$_2$)$_3$—O—(CH$_2$)$_3$— |
| 8 | —O—CH$_2$—CH(CH$_3$)—N[—(CH$_2$)$_2$—][—(CH$_2$)$_2$—]N— |
| 9 | —CH$_2$—Z—CH$_2$— where Z = 1,3-phenyl |
| 10 | —(CH$_2$)$_2$—S—(CH$_2$)$_2$— |
| 11 | —CH$_2$—Z—CH$_2$— where Z = 1,4-phenyl |
| 12 | —(CH$_2$)$_4$— |
| 13 | —(CH$_2$)$_2$—O—(CH$_2$)$_2$— |
| 14 | —(CH$_2$)$_2$— |
| 15 | —O—CH$_2$—CH[—CH$_2$—][—(CH$_2$)$_3$—]N— |

(Step ii): To the imine solution was added 1-H-pyrazole-1-[N,N'-bis(tert-butoxycarbonyl)carboxamidine] (2.10 g, 6.77 mole). The mixture was stirred at rt for 3 h. Again, mass analysis of the reaction mixture indicated formation of N,N'-bis-Boc-protected guanidine (ESMS: obsd. 519.5 [M+H]$^+$).

(Step iii): The mixture was then treated with NaCNBH$_3$ (0.423 g, 6.73 mmole) to reduce the imine functionality to amine. After stirring at rt or 1 h, the reaction was quenched by addition of water (1 mL). The reaction mixture was diluted with EtOAc (100 mL), washed with 0.1 M NaOH/brine solution, and dried over Na$_2$SO$_4$. The organic solution was evaporated in vacuo, yielding amine product as white solid. This crude product was used in next step without further purification. ESMS: calcd. 520.8; Obsd. 522.2 [M+H]$^+$.

(Step iv): The above product was dissolved in CH$_2$Cl$_2$ (15 mL), and then followed by addition of TFA (8 mL). The mixture was stirred overnight, and concentrated in vacuo, yielding colorless oily residue. The crude product was dissolved in 50% aqueous acetonitrile, and purified by preparative reversed phase HPLC: 10 to 40% aq. MeCN over 40 min (linear gradient); 40 mL/min; 214 nm. The product was obtained as colorless oil (500 mg; overall 16% to four steps). ESMS (C$_{18}$H$_{32}$N$_4$O$_1$); calcd. 320.5; obsd. 321.4 [M+H]$^+$. $^1$H-NMR (CD$_3$OD, 299.96 MHz): δ (ppm) 7.04–7.0 (d, 2H), 6.98–6.96 (t, 1H), 4.0–3.95 (m, 2H), 3.78–3.68 (m, 1H), 3.2–3.17 (m, 4H), 2.29 (s, 6H), 1.82–1.7 (br m, 2H), 1.64–1.58 (br m, 2H), 1.57–1.4 (m, 7H). Retention time (anal. HPLC: 10 to 70% MeCN/H$_2$O over 6 min)=2.01 min.

Compound 2 was prepared from N,N'-bis(3-amino-1-propyl)piperazine in an analogous manner as described above. ESMS (C$_{22}$H$_{40}$N$_6$O$_1$); calcd. 404.6; obsd. 405.4 [M+H]$^+$. $^1$H-NMR (CD$_3$OD, 299.96 MHz): δ (ppm) 7.05–7.0 (d, 2H), 6.98–6.9 (t, 1H), 3.98–3.96 (d, 2H), 3.8–3.70 (m, 1H), 3.55–3.46 (br s, 4H), 3.44–4.34 (br s, 4H), 3.32–3.20 (m, 4H), 3.18–3.05 (m, 4H), 2.29 (s, 6H), 2.30–2.15 (m, 2H), 2.05–1.95 (m, 2H).

Compound 3 was prepared from 1,8-diamino-3,6-dioxaoctane in an analogous manner as described above. ESMS (C$_{18}$H$_{32}$N$_4$O$_3$); calcd352.5; obsd. 353.2 [M+H]$^+$. $^1$H-NMR (CD$_3$OD, 299.96 MHz): δ (ppm) 7.04–7.0 (d, 2H), 6.98–6.9 (t, 1H), 3.99–3.96 (d, 2H), 3.85–3.83 (t, 2H), 3.82–3.75 (m, 1H), 3.72–3.68 (m, 4H), 3.65–3.51 (t, 2H), 3.45–3.40 (t, 2H), 3.47–3.45 (t, 2H), 2.29 (s, 6H), 1.53–1.51 (d, 3H).

Compound 4 was prepared from 1,5-diaminopeptane in an analogous manner as described above. ESMS (C$_{17}$H$_{30}$N$_4$O$_1$); calcd. 306.8; obsd. 307.3 [M+H]$^+$. $^1$H-NMR (CD$_3$OD, 299.96 MHz): δ (ppm) 7.02–7.0 (d, 2H), 6.97–6.91 (t, 1H), 4.0–3.9 (m, 2H), 3.79–3.65 (br m, 1H), 3.21–3.15 (m, 4H), 2.28 (s, 6H), 1.84–1.78 (br m, 2H), 1.7–1.6 (quin, 2H), 1.58–1.5 (m, 5H). Retention time (anal. HPLC: 10 to 70% MeCN/H$_2$O over 6 min)=2.2 min.

Compound 5 was prepared from 1,13-diamino-4,7,10-trioxatridecane in an analogous manner as described above. ESMS (C$_{22}$H$_{40}$N$_4$O$_4$); calcd. 424.6; obsd. 425.2 [M+H]$^+$. $^1$H-NMR (CD$_3$OD, 299.96 MHz): δ (ppm) 7.03–7.0 (d, 2H), 6.98–6.91 (t, 1H), 4.0–3.9 (m, 2H), 3.80–3.78 (m, 1H), 3.75–3.65 (t, 2H), 3.62–3.58 (m, 4H), 3.56–3.5 (m, 6H), 3.40–3.21 (m, 4H), 2.30 (s, 6H), 2.05–2.01 (quin, 2H), 1.83–1.78 (quin, 2H), 1.50–1.48 (d, 3H). Retention time (anal. HPLC: 10 to 70% MeCN/H$_2$O over 6 min)=2.51 min.

Compound 6 was prepared from N,N-bis(2-aminoethyl)methylamine in an analogous manner as described above. Retention time (anal. HPLC: 10 to 70% MeCN/H$_2$O over 6 min)=0.38. ESMS (C$_{17}$H$_{31}$N$_5$O); calcd. 321.46; obsd. 322.2 [M+H]$^+$.

Compound 7 was prepared from 1,7-diamino-4-oxaheptane in an analogous manner as described above. Retention time (anal. HPLC: 10 to 70% MeCN/H$_2$O over 6 min)=0.59. ESMS (C$_{18}$H$_{32}$N$_4$O$_2$); calcd. 336.47; obsd. 337.5 [M+H]$^+$.

Compound 8 was prepared from piperazine in an analogous manner as described above. ESMS (C$_{16}$H$_{26}$N$_4$O$_1$); calcd. 290.4; obsd. 291.1 [M+H]$^+$. Retention time (anal. HPLC: 10 to 70% MeCN/H$_2$O over 6 min)=1.76 min.

Compound 9 was prepared from α,α'-diamino-m-xylene in an analogous manner as described above. ESMS (C$_{20}$H$_{28}$N$_4$O$_1$); calcd. 340.5; obsd. 341.2 [M+H]$^+$. Retention time (anal. HPLC: 10 to 70% MeCN/H$_2$O over 6 min)=2.15 min.

Compound 10 was prepared from 1,5-diamino-3-mercaptopentane m an analogous manner as described above. ESMS (C$_{16}$H$_{28}$N$_4$O$_1$S$_1$); calcd. 324.5; obsd. 325.3 [M+H]$^+$. Retention time (anal. HPLC: 10 to 70% MeCN/H$_2$O over 6 min)=2.05 min.

Compound 11 was prepared from α,α'-di-amino-p-xylene in an analogous manner as described above. Retention time (anal. HPLC: 10 to 70% MeCN/H$_2$O over 6 min)=1.07. ESMS (C$_{20}$H$_{28}$N$_4$O); calcd. 340.46; obsd. 341.4 [M+H]$^+$.

Compound 12 was prepared from 1,4-diaminobutane in an analogous manner as described above. Retention time (anal. HPLC: 10 to 70% MeCN/H$_2$O over 6 min)=1.70. ESMS (C$_{16}$H$_{28}$N$_4$O); calcd. 292.42; obsd. 293.1 [M+H]$^+$.

Compound 13 was prepared from 1,5-diamino-3-oxapentane in an analogous manner as described above. Retention time (anal. HPLC: 10 to 70% MeCN/H$_2$O over 6 min)=1.68. ESMS (C$_{16}$H$_{28}$N$_4$O$_2$); calcd. 308.48; obsd. 309.3 [M+H]$^+$. $^1$H-NMR (CD$_3$OD, 299.96 MHz): δ (ppm)

7.04–7.02 (d, 2H), 6.97–6.92 (t, 1H), 3.99–3.97 (d, 2H), 3.87–3.84 (t, 4H), 3.71–3.69 (t, 4H), 3.47–3.40 (p, 1H), 2.30 (s, 6H), 1.53–1.51 (d, 3H).

Compound 14 was prepared from 1,2-diaminoethane in an analogous manner as described above. Retention time (anal. HPLC: 10 to 70% MeCN/H$_2$O over 6 min)=1.54. ESMS (C$_{14}$H$_{24}$N$_4$O); calcd. 264.37; obsd. 265.2 [M+H]$^+$.

EXAMPLE 39

Synthesis of dimers of 5-arylpyrimidine and Mexiletine via the Following Scheme

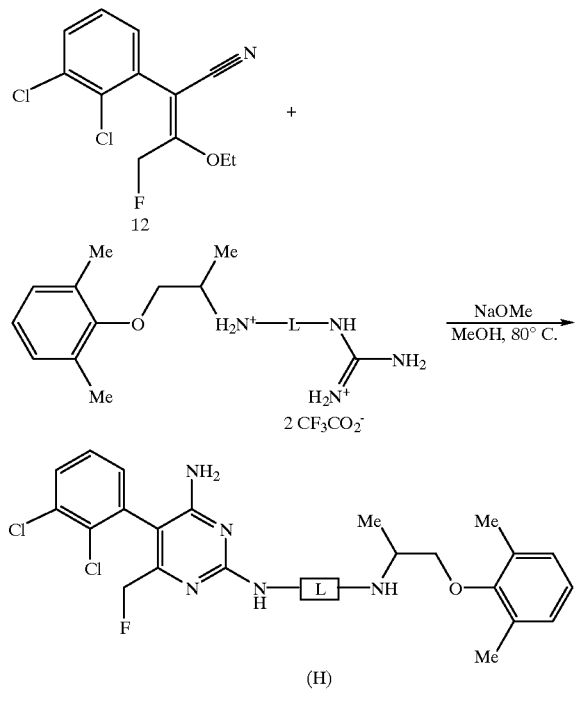

General procedure for synthesis of compound 4 of Table H: L=(CH$_2$)$_5$: To Table G, compound 4 (0.488 g, 0.912 mmole) in a vial was added NaOMe (100 mg/mL; 1.0 mL, 1.85 mmole) and compound 12 (500 mg/mL MeOH; 0.5 mL, 0.912 mmole). The reaction vessel was well sealed with a screw cap, and shaken at 80° C. for 12 h. The mixture was then concentrated to dryness, and the dark brown residue was dissolved in 5 mL of 50% aqueous acetonitrile (with 5% TFA). After filtration, the crude product was purified by preparative reversed phase HPLC: 20 to 60% aqueous acetonitrile (0.1% TFA) over 50 min (linear gradient); 40 mL/min; 254 nm. The desired product was obtained as white solid (80 mg). ESMS (C$_{27}$H$_{34}$N$_5$OFCl$_2$); calcd. 534.5; obsd. 534.2 [M]$^+$. $^1$H-NMR (CD$_3$OD, 299.96 MHz): δ (ppm) 7.78–7.7 (dd, 1H), 7.5–7.4 (t, 1H), 7.38–7.3 (dd, 1H), 7.05–7.01 (d, 2H), 6.97–6.9 (t, 1H), 4.96 & 4.81 (two s, 2H), 4.18–4.05 (t, 2H), 4.01–3.9 (m, 2H), 3.8–3.7 (m, 1H), 3.25–3.2 (t, 2H), 2.29 (s, 6H), 1.95–1.79 (br m, 4H), 1.65–1.58 (br m, 2H), 1.52–1.50 (d, 3H). Retention time (anal. HPLC: 10 to 70% MeCN/H$_2$O over 6 min)=3.48 min.

Table H lists linkers 1–14 from dimer H

TABLE H

| No. | Linker |
|---|---|
| 1 | —(CH$_2$)$_6$— |
| 2 | —(CH$_2$)$_3$—N[(CH$_2$)$_2$—(CH$_2$)$_2$]N—(CH$_2$)$_3$— |
| 3 | —(CH$_2$)$_2$—O—(CH$_2$)$_2$—O—(CH$_2$)$_2$— |
| 4 | —(CH$_2$)$_5$— |
| 5 | —(CH$_2$)$_3$—O—(CH$_2$)$_2$—O—(CH$_2$)$_2$—O—(CH$_2$)$_3$— |
| 6 | —(CH$_2$)$_2$—N(CH$_3$)—(CH$_2$)$_2$— |
| 7 | —(CH$_2$)$_3$—O—(CH$_2$)$_3$— |
| 8 | —N[(CH$_2$)$_2$—(CH$_2$)$_2$]N— |
| 9 | —CH$_2$—Z—CH$_2$— where Z = 1,3-phenyl |
| 10 | —(CH$_2$)$_2$—S—(CH$_2$)$_2$— |
| 11 | —CH$_2$—Z—CH$_2$— where Z = 1,4-phenyl |
| 12 | —(CH$_2$)$_4$— |
| 13 | —(CH$_2$)$_2$—O—(CH$_2$)$_2$— |
| 14 | —(CH$_2$)$_2$— |

Compound 1 was prepared from compound 1 of Table G in an analogous way as described above. ESMS (C$_{28}$H$_{36}$N$_5$OFCl$_2$); calcd. 548.5; obsd. 548.3 [M]$^+$. $^1$H-NMR (CD$_3$OD, 299.96 MHz): δ (ppm) 7.72–7.69 (dd, 1H), 7.56–7.42 (t, 1H), 7.33–7.3 (dd, 1H), 7.02–7.0 (d, 2H), 6.98–6.9 (dd, 1H), 4.96 & 4.81 (two s, 2H), 4.18–4.1 (t, 2H), 4.02–3.9 (m, 2H), 3.78–3.7(m, 1H), 3.21–3.17 (t, 2H), 2.29 (s, 6H), 1.9–1.75 (br m, 4H), 1.6–1.5 (m, 7H). Retention time (anal. HPLC: 10 to 70% MeCN/H$_2$O over 6 min)=3.14 min.

Compound 2 was prepared from compound 2 of Table G in an analogous way as described above. ESMS (C$_{32}$H$_{44}$N$_7$OFCl$_2$); calcd. 632.7; obsd. 632.4 [M]$^+$. $^1$H-NMR (CD$_3$OD, 299.96. MHz): δ (ppm) 7.75–7.7 (dd, 1H), 7.5–7.4 (t, 1H), 7.38–7.35 (dd, 1H), 7.05–7.0 (d, 2H), 6.98–6.9 (dd, 1H), 4.98 & 4.82 (two s, 2H), 4.2–4.15 (t, 2H), 4.0–3.97 (m, 2H), 3.8–3.75 (m, 1H), 3.35–3.2 (m, 6H), 3.19–3.1 (m, 6H), 2.95–2.88 (t, 2H), 2.30 (s, 6H), 2.2–2.18 (m, 4H), 1.52–1.49 (d, 3H). Retention time (anal. HPLC: 10 to 70% MeCN/H$_2$O over 6 min)=3.13 min.

Compound 3 was prepared from compound 3 Table G in an analogous way as described above. ESMS (C$_{28}$H$_{36}$N$_5$O$_3$FCl); calcd.580.5; obsd. 580.4 [M]$^+$. $^1$H-NMR (CD$_3$OD, 299.96 MHz): δ (ppm) 7.73–7.70 (dd, 1H), 7.45–7.4 (t, 1H), 7.35–7.3 (dd, 1H), 7.05–7.0 (d, 2H), 6.98–6.95 (dd, 1H), 4.96 & 4.81 (two s, 2H), 4.4 (br m, 2H), 4.40–3.95 (m, 3H), 3.8–3.7 (m, 8H), 3.42–3.4 (t, 2H), 2.29 (s, 6H), 1.52–1.49 (d, 3H). Retention time (anal. HPLC: 10 to 70% MeCN/H$_2$O over 6 min)=3.40 min.

Compound 5 was prepared from compound 5 of Table G in an analogous way as described above. ESMS (C$_{32}$H$_{44}$N$_5$O$_4$FCl$_2$); calcd. 652.6; obsd. 652.5 [M]$^+$. $^1$H-NMR (CD$_3$OD, 299.96 MHz): δ (ppm) 7.71–7.7 (dd, 1H), 7.48–7.41 (t, 1H), 7.35–7.32 (dd, 1H), 7.02–7.0 (d, 2H), 6.98–6.9 (dd, 1H$_1$), 4.97 & 4.82 (two 4.2–4.14 (t, 2H), 4.0–3.9 (m, 3H), 3.8–3.5 (m, 12H), 3.2–3.15 (m, 2H), 6H), 2.18–2.01 (m, 4H), 1.50–1.47 (d, 3H). Retention time (anal. HPLC: 10 to 70% MeCN/H$_2$O over 6 min)=3.46 min.

Compound 6 was synthesized from compound 6 of Table G in an analogous way as described above. Retention time (anal. HPLC: 10 to 70% MeCN/H$_2$O over 6 min)=1.48. ESMS (C$_{27}$H$_{35}$Cl$_2$FN$_6$O); calcd. 549.52; obsd. 550.4 [M+H]$^+$. $^1$H-NMR (CD$_3$OD, 299.96 MHz): δ (ppm) 7.73–7.70 (d, 1H), 7.46–7.42 (t, 1H), 7.32–7.30 (d, 1H), 7.05–7.02 (d, 2H), 6.97–6.92 (t, 1H), 4.98 (s, 1H), 4.82 (s, 1H), 4.33–4.30 (t, 2H), 3.99–3.96 (m, 2H), 3.78–3.74 (p, 1H), 3.04–3.01 (t, 4H), 2.97–2.92 (t, 2H), 2.47 (s, 3H), 2.29 (s, 6H), 1.52–1.50 (d, 3H).

Compound 7 was synthesized from compound 7 of Table G in an analogous way as described above. Retention time (anal. HPLC: 10 to 70% MeCN/H$_2$O over 6 min)=1.56. ESMS (C$_{28}$H$_{36}$Cl$_2$FN$_5$O$_2$); calcd. 564.53; obsd. 565.2 [M+H]$^+$. $^1$H-NMR (CD$_3$OD, 299.96 MHz): δ (ppm) 7.73–7.71 (d, 1H), 7.48–7.43 (t, 1H), 7.32–7.29 (d, 1H), 7.04–7.01 (d, 2H), 6.97–6.92 (t, 1), 5.16–5.07 (m, 1H), 5.01–4.92 (m, 1H), 4.03–3.90 (m, 2H), 3.82–3.76 (p, 1H), 3.70–3.67 (t, 2H), 3.62–3.58 (t, 2H), 3.55–3.50 (t, 2H), 2.30 (s, 6H), 2.12–2.03 (quin, 2H), 1.95–1.86 (quin, 2H), 1.50–1.48 (d, 3H).

Compound 8 was prepared from compound 8 of Table G in an analogous way as described above. ESMS (C$_{26}$H$_{30}$N$_5$OFCl$_2$); calcd. 518.5; obsd. 518.2 [M]$^+$. $^1$H-NMR (CD$_3$OD, 299.96 MHz): δ (ppm) 7.64 (dd, 1H), 7.42 (t, 1H), 7.27 (dd, 1H), 7.06–7.0 (dd, 2H), 6.99–6.92 (dd, 1H), 5.03 & 4.87 (two m, 2H), 4.18–4.10 (m, 3H), 4.0–3.93 (m, 2H), 3.62 (br s, 6H), 2.31 (s, 6H), 1.60–1.57 (d, 3H). Retention time (anal. HPLC: 10 to 70% MeCN/H$_2$O over 6 min)=3.94 min.

Compound 9 was prepared from compound 9 of Table G in an analogous way as described above. ESMS (C$_{30}$H$_{32}$N$_5$OFCl$_2$); calcd. 568.5; obsd. 568.3 [M]$^+$. $^1$H-NMR (CD$_3$OD, 299.96 MHz): δ (ppm) 7.7–7.65 (dd, 1H), 7.62–7.56 (m, 2H), 7.42–7.39 (m, 2H), 7.38–7.3 (m, 2H), 7.02–7.0 (d, 2H), 6.98–6.9 (dd, 1H), 5.54 (s, 2H), 5.03 & 4.87 (two s, 2H), 4.44 (s, 2H), 4.03–4.01 (d, 2H), 3.8–3.7 (br m, 1H), 2.30 (s, 6H), 1.59–1.56 (d, 3H). Retention time (anal. HPLC: 10 to 70% MeCN/H$_2$O over 6 min)=3.48 min.

Compound 10 was prepared from compound 10 of Table G in an analogous way as described above. ESMS (C$_{26}$H$_{32}$N$_5$OFCl$_2$S); calcd.552.5; obsd. 552.2 [M+H]$^+$. $^1$H-NMR (CD$_3$OD, 299.96 MHz): δ (ppm) 7.73–7.68 (dd, 1H), 7.5–7.4 (t, 1H), 7.35–7.3 (dd, 1H), 7.02–7.0 (d, 2H), 6.98–6.95 (dd, 1H), 4.97 & 4.82 (two s, 2H), 4.46 (t, 2H), 3.99–3.97 (d, 2H), 3.81–3.78 (m, 1H), 3.5–3.42 (t, 2H), 3.20–3.1 (t, 2H), 3.08–3.02 (t, 2H), 2.29 (s, 6H), 1.53–1.51 (d, 3H). Retention time (anal. HPLC: 10 to 70% MeCN/H$_2$O over 6 min)=3.46 min.

Compound 11 was synthesized from compound 11 of Table G in an analogous way as described above. Retention time (anal. HPLC: 10 to 70% MeCN/H$_2$O over 6 min)=3.11. ESMS (C$_{30}$H$_{32}$Cl$_2$FN$_5$O); calcd. 568.52; obsd. 569.3 [M+H]$^+$. $^1$H-NMR (CD$_3$OD, 299.96 MHz): δ (ppm) 7.73–7.72 (d, 1H), 7.68–7.66 (d, 1H), 7.49–7.44 (t, 1H), 7.37–7.34 (d, 2H), 7.38–7.36 (d, 2H), 7.04–7.02 (d, 2H), 6.97–6.92 (t, 1H), 5.53 (s, 2H), 5.04 (s, 1H), 4.88 (s, 1H), 4.44 (s, 1H), 4.02–4.01 (d, 2H), 3.75–3.73 (m, 1H), 2.29 (s, 6H), 1.57–1.55 (d, 3H).

Compound 12 was synthesized from compound 12 of Table G in an analogous way as described above. Retention time (anal. HPLC: 10 to 70% MeCN/H$_2$O over 6 min)=3.06. ESMS (C$_{26}$H$_{32}$Cl$_2$FN$_5$O); calcd. 526.48; obsd. 521.3 [M+H]$^+$. $^1$H-NMR (CD$_3$OD, 299.96 MHz): δ (ppm) 7.72–7.70 (d, 1H), 7.48–7.42 (t, 1H), 7.33–7.31 (d, 1H), 7.05–7.02 (d, 2H), 6.97–6.92 (t, 1H), 4.978 (s, 1H), 4.81 (s, 1H), 4.18 (m, 2H), 4.01–3.92 (m, 2H), 3.78–3.70 (m, 1H), 3.26–3.22 (m, 2H), 2.97 (s, 6H), 1.94 (m, 4H), 1.53–1.51 (d, 3H).

Compound 13 was synthesized from compound 13 of Table G in an analogous way as described above. Retention time (anal. HPLC: 10 to 70% MeCN/H$_2$O over 6 min)=3.12. ESMS (C$_{26}$H$_{32}$Cl$_2$FN$_5$O$_2$); calcd. 536.48; obsd. 537.2 [M+H]$^+$. $^1$H-NMR (CD$_3$OD, 299.96 MHz): δ (ppm) 7.72–7.69 (d, 1H), 7.46–7.40 (t, 1H), 7.31–7.29 (d, 1H), 7.04–7.02 (d, 2H), 6.97–6.92 (t, 1H), 4.96 (s, 1H), 4.80 (s, 1H), 4.45–4.42 (t, 2H), 3.99–3.96 (t, 2H), 3.99–3.97 (d, 2H), 3.92–3.89 (t, 2H), 3.85–3.77 (m, 1H), 3.46–3.43 (t, 2H), 2.29 (s, 6H), 1.52–1.50 (d, 3H).

Compound 14 was synthesized from compound 14 of Table G in an analogous way as described above. Retention time (anal. HPLC: 10 to 70% MeCN/H$_2$O over 6 min)=3.30. ESMS (C$_{27}$H$_{35}$Cl$_2$FN$_6$O); calcd. 492.42; obsd. 493.2 [M+H]$^+$. $^1$H-NMR (CD$_3$OD, 299.96 MHz): δ (ppm) 7.72–7.70 (d, 1H), 7.47–7.42 (t, 1H), 7.32–7:30 (d, 1H), 7.03–7.01 (d, 2H), 6.96–6.91 (t, 1H), 4.99 (s, 1H), 4.83 (s, 1H), 4.61–4.56 (t, 2H), 4.00–3.93 (m, 2H), 3.80–3.76 (m, 1H), 3.69–3.65 (t, 2H), 2.29 (s, 6H), 1.51–1.49 (d, 3H).

EXAMPLE 40

Synthesis of Dimers of 5-arylpyrimidine and Mexiletine via the Following Scheme

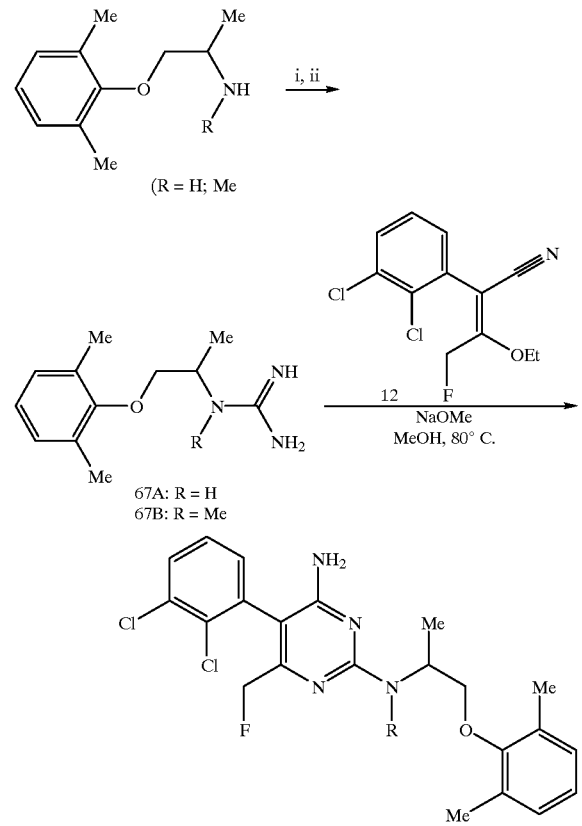

Table C Compound 2: R = H
Table C Compound 3: R = Me reagents and conditions: i) 1-H-pyrazole-1-[N,N'-bis(tert-butoxycarbonyl)]-carboxamidine, MeCN, 80° C.; ii) TFA, CH$_2$Cl$_2$, rt General procedure for the synthesis of the above compound 67A: To a pyrazole-1-N,N'-bis(tert-butoxycarbonyl)carboxamidine (2.0 g, 6.44 mole). The mixture was stirred at 80° C. for 14 h. The reaction mixture was concentrated in vacuo, and the oily residue was dissolved in ethyl ether (100 mL), followed by washing with brine solution. The organic phase was dried over $MgSO_4$, and evaporated to yield a pale yellow oily residue (2.8 g). %): $R_f$=0.74 in 10% MeOH/EtOAc/hexane (1/1). It was dissolved in $CH_2Cl_2$ (25 mL), and then followed by slow addition of TFA (13 mL) while stirring the mixture. After stirring overnight at rt, the reaction mixture was concentrated in vacuo, yielding colorless oily residue. The crude product was dissolved in 50% aqueous acetonitrile, and purified by preparative reversed phase. HPLC: 10 to 40% aq MeCN over 50 min (linear gradient); 40 mL/min; 214 nm. Compound 67 was obtained as colorless oil (1.0 g; overall 45% to two steps). ESMS ($C_{12}H_{19}N_3O$); calcd. 221.3; obsd. 222.0 [M+H]+. $^1$H-NMR ($CD_3OD$, 299.96 MHz): δ (ppm) 7.01–6.99 (d, 2H), 6.93–6.9 (dd, 1H), 4.1–3.98 (m, 1H), 3.9–3.85 (dd, 1H), 3.7–3.65 (dd, 1H), 2.26 (s, 6H), 1.39–1.37 (d, 3H). Retention time (anal. HPLC: 10 to 70% $MeCN/H_2O$ over 6 min)=2.91 mm.

Compound 68A was prepared from N-methyl-mexiletine in an analogous way as described above. ESMS ($C_{13}H_{21}N_3O$); calcd. 235.3; obsd. 236.1 [M+H]+. $^1$H-NMR ($CD_3OD$, 299.96 MHz): δ (ppm) 7.01–6.99 (d, 2H), 6.93–6.89 (dd, 1H), 4.45–3.35 (m, 1H), 3.98–3.95 (dd, 1H), 3.81–3.78 (dd, 1H), 3.05 (s, 3H), 2.25 (s, 6H), 1.34–1.31 (d, 3H). Retention time (anal. HPLC: 10 to 70% $MeCN/H_2O$ over 6 min)=2.91 min.

Synthesis compound 2 of Table C: To compound 67 (TFA salt; 0.459 g, 1.37 mmole) in a glass vial was added NaOMe (100 mg/mL; 0.75 mL, 1.39 mmole) and compound 12 (500 mg/mL MeOH; 1 mL, 1.82 mmole). The reaction vessel was sealed well with a screw cap, and shaken at 80° C. for 12 h. The mixture was then concentrated to dryness, and the dark brown residue was dissolved in 5 mL of 50% aqueous acetonitrile (with 5% TFA). After filtration, the crude product was purified by preparative reverse phase HPLC: 20 to 60% aqueous acetonitrile (0.1% TFA) over 50 min (linear gradient); 40 mL/min; 254 nm. The desired product was obtained as white solid (80 mg). ESMS ($C_{22}H_{23}N_4OFCl_2$); calcd. 449.4; obsd. 449.3 [M]+. $^1$H-NMR ($CD_3OD$, 299.96 MHz): δ (ppm) 7.75–7.71 (dd, 1H), 7.5–7.4 (dt, 1H), 7.38–7.32 (dd, 1H), 7.01–6.98 (d, 2H), 6.95–6.88 (dd, 1H), 5.25–4.9 (two dd, 2H), 4.6 (br m, 1H), 4.0–3.8 (m, 2H), 2.27 (s, 6H), 1.51–1.49 (d, 3H). Retention time (anal. HPLC: 10 to 70% $MeCN/H_2O$ over 6 min)=4.41 min.

Compound 3 of Table C was synthesized from compound 68 in an analogous manner as described above. ESMS ($C_{23}H_{25}N_4OFCl_2$); calcd. 463.4; obsd. 463.1 [M]+. $^1$H-NMR ($CD_3OD$, 299.96 MHz): δ (ppm) 7.75–7.7 (dd, 1H), 7.5–7.42 (dt, 1H), 7.38–7.35 (dd, 1H), 7.0–6.97 (d, 2H), 6.95–6.88 (dd, 1H), 5.21–4.95 (m, 2H), 4.16–4.0 (dd, 2H), 3.9–3.81 (m, 1H), 3.3 (s, 3H), 2.25 (s, 6H), 1.42–1.4 (d, 3H), Retention time (anal. HPLC: 10 to 70% $MeCN/H_2O$ over 6 min)=4.21 min.

EXAMPLE 41

Synthesis Compound 4 of Table C via the Following Scheme

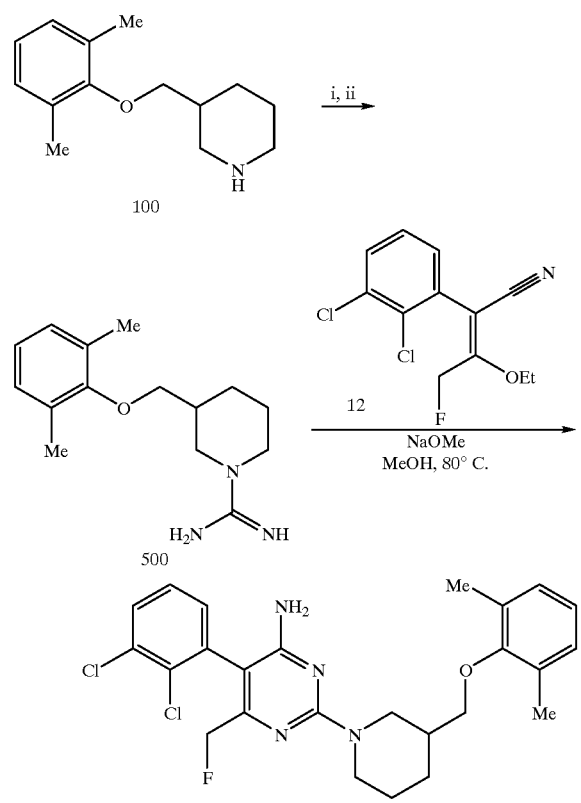

Table C, Compound 4 reagents and conditions: i) 1-H-pyrazole-1-[N,N'-bis(tert-butoxycarbonyl)]carboxamidine, MeCN, 80° C.; ii) TFA, $CH_2Cl_2$, rt Synthesis of Compound 500: To a solution of compound 100 (TFA salt; 1.0 g, 3.0 mmole) in MeOH (5 mL) was added NaOMe (0.5 M, 6.31 mL). The mixture was concentrated to dryness in vacuo. The oily residue was solubilized in THF (15 mL), and followed by addition of 1-H-pyrazole-1-[N,N'-bis(tert-butoxycarbonyl)carboxamidine] (0.979 g, 3.15 mmole). After stirring at 80° C. overnight, the reaction mixture was diluted with EtOAc (150 mL) and then washed with brine solution. The organic phase was dried over $Na_2SO_4$, and evaporated to yield colorless oily residue. It was dissolved in $CH_2Cl_2$ (15 mL), and then followed by slow addition of TFA (10 mL). The mixture was stirred overnight at rt, and was concentrated in vacuo, yielding colorless oily residue. The crude product was dissolved in 50% aqueous acetonitrile, and purified by preparative reversed phase HPLC: 10 to 40% aq. MeCN over 40 min (linear gradient); 40 mL/min; 214 nm. Compound 69 was obtained as colorless oil. ESMS ($C_{15}H_{23}N_3O$); calcd. 261.4; obsd. 262.2 [M+H]+. $^1$H-NMR ($CD_3OD$, 299.96 MHz): δ (ppm) 7.01–6.98 (d, 2H), 6.91–6.85 (dd, 1H), 4.1–4.04 (br d, 1H), 3.85–3.78 (br d, 1H), 3.71–3.65 (m, 2H), 3.21–3.1 (m, 2H), 2.2–1.95 (m, 2H), 1.89–1.82 (m, 1H), 1.7–1.55 (m, 2H). Retention time (anal. HPLC: 10 to 70% $MeCN/H_2O$ over 6 min)=3.35 min.

Synthesis of Table C, compounds 4: To compound 500 (TFA salt; 0.13 g, 0.346 mmole) in a glass vial was added NaOMe (100 mg/mL; 0.22 mL, 0.407 mmole) and compound 12 (500 mg/mL MeOH; 0.38 mL, 0.693 mmole). The reaction vessel was sealed well with a screw cap, and shaken at 80° C. for 12 h. The mixture was then concentrated in vacuo, yielding the dark brown residue. It was dissolved in 3 mL of 50% aqueous acetonitrile (with 5% TFA), filtered, and purified by preparative reversed phase HPLC: 20 to 60% aqueous acetonitrile (0.1% TFA) over 50 min (linear gradient); 40 mL/min; 254 nm. ESMS ($C_{25}H_{27}N_4OFCl_2$); calcd. 489.5; obsd. 489.2 [M]+. Retention time (anal. HPLC: 10 to 70% MeCN/$H_2O$ over 6 min)=4.5 min.

EXAMPLE 42

Synthesis of Compounds 71, 72, and 73 via the Following Scheme

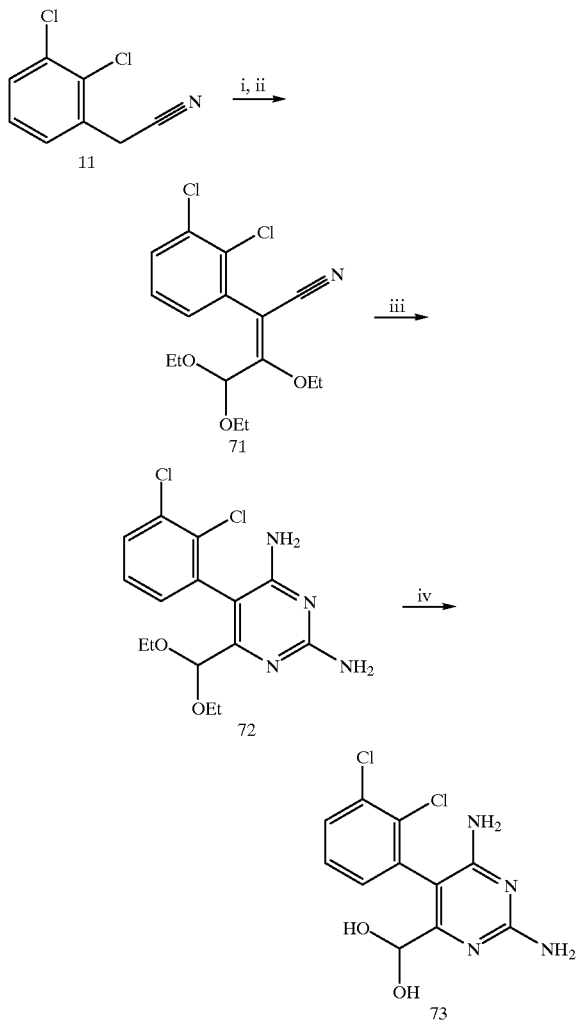

reagents and conditions: i) $(EtO)_2CHCO_2Et$, KO$^t$BU, EtOH, rt; ii) Et-I; iii) guanidine hydrochloride, NaOMe, MeOH, 80° C.; iv) 1,2-dimethoxyethane, 3M HCl, 90° C., 5 h.

Compounds 71, 72, and 73 were synthesized generally in accordance with procedures described in Nobbs, et al., WO 97/09317 and Miller, et al., EP 0 372 934B1.

Compound 71: To a stirred solution of compound 11 (10 g, 53.6 mmole) in 1,2-diethoxyethane (75 mL) was added ethyl 2,2-diethoxyacetate (14.4 mL, 80.5 mmole) and then KO$^t$Bu (7.2 g, 64.2 mmole) in ice bath. The reaction mixture was gradually warmed to rt over 10 min, and then heated at 90° C. for 6 h. After cooling the mixture to rt, ethyl iodide (8.6 mL, 0.108 mole) was added, and followed by heating at 65° C. overnight. Reaction mixture was concentrated to brown solid, which was then partitioned between EtOAc (300 mL) and brine (200 mL). After shaking in a separatory funnel, organic phase was collected, washed with brine solution, and dried over $Na_2SO_4$. Evaporation of the organic phase afforded compound 71 as dark orange oil. ESMS ($C_{16}H_{19}N_1O_3Cl_2$); calcd. 344.2; obsd. 345.1 [M]+. $^1$H-NMR (CD$_3$OD, 299.96 MHz): δ (ppm) 7.42–7.4 (dd, 1H), 7.31–7.28 (dd, 1H), 7.18–7.14 (t, 1H), 5.34 (s, 1H), 3.8–3.6 (m, 6H), 1.33–1.19 (m, 9H).

Compound 72: To EtOH (80 mL) cooled in ice bath was added in small portions NaOEt (6 g, 88.2 mmole) under stream of nitrogen, and then followed by addition of guanidine hydrochloride (8.3 g, 86.9 mmole). After stirring at 0° C. for 10 min, compound 71 (15 g, 43.5 mmole) in EtOH (70 mL) was added to it. The mixture was warmed to rt over 2 h, and heated at 65° C. overnight. After concentration to brown oily residue, it was treated with cold water (200 mL) to yield brown precipitate. The supernatant was decanted, and the oily residue was washed with water (200 mL). The residue was dissolved in EtOAc (500 mL), washed with brine solution, and dried over NaSO$_4$. Evaporation of the organic phase afforded crude compound 7 as dark orange oil, which solidified slowly over several days. The solid material was suspended in i-PrOH/hexane (1/1), and collected on Büchner funnel. This product was used in next step without further purification. ESMS ($C_{15}H_{18}N_4O_2Cl_2$); calcd. 357.6; obsd. 357.1 [M]+. $^1$H-NMR (CD$_3$OD, 299.96 MHz): δ (ppm) 7.61–7.58 (dd, 1H), 7.38–7.35 (t, 1H), 7.23–7.21 (d, 1H), 4.78 (s, 1H), 3.78–3.35 (m, 4H), 1.25–1.02 (m, 6H). Retention time (anal. HPLC: 10 to 70% MeCN/$H_2O$ over 6 min)=3.3 min.

Compound 73: To a solution of compound 72 (3 g, 8.39 mmole) in 1,2-dimethoxymethane (70 mL) was added 70 mL of 3 M HCl, and the mixture was heated at 90° C. for 5 h. The reaction mixture was concentrated, and dissolved in 50% aqueous acetonitrile prior to purification by using preparative reversed phase HPLC: 10 to 60% MeCN over 50 min; 40 ml/min; 254 nm. Compound 73 (TFA salt) was obtained as pale beige solid. ESMS ($C_{11}H_{10}N_4O_2Cl_2$); calcd. 301.3; obsd. 301.4 [M]+. $^1$H-NMR (CD$_3$OD, 299.96 MHz): δ (ppm) 7.71–7.35 (dd, 1H), 7.48–7.41 (t, 1H), 7.35–7.29 (m, 1H), 5.09 & 5.03 (two s, 1H). Retention time (anal. HPLC: 10 to 70% MeCN/$H_2O$ over 6 min)=0.90 min.

EXAMPLE 43

Synthesis of Compound 1 of Table I and Compound 5 of Table C via the Following Scheme

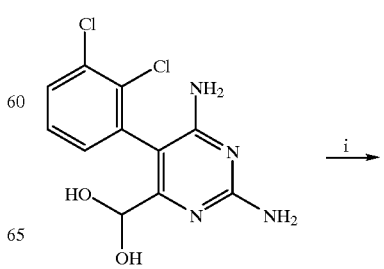

-continued

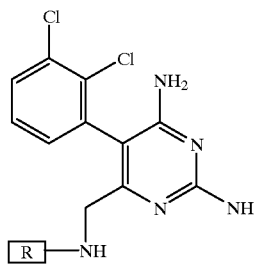

reagents and condition: i) RNH$_2$, EtOH, 70° C.; then NaCNBH$_3$, rt

Table C, Compound 5:

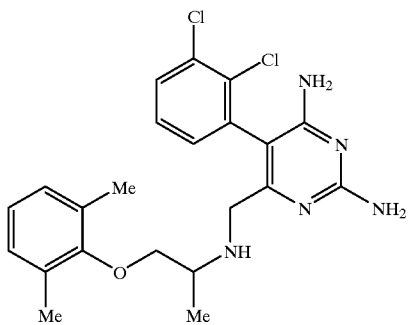

TABLE I

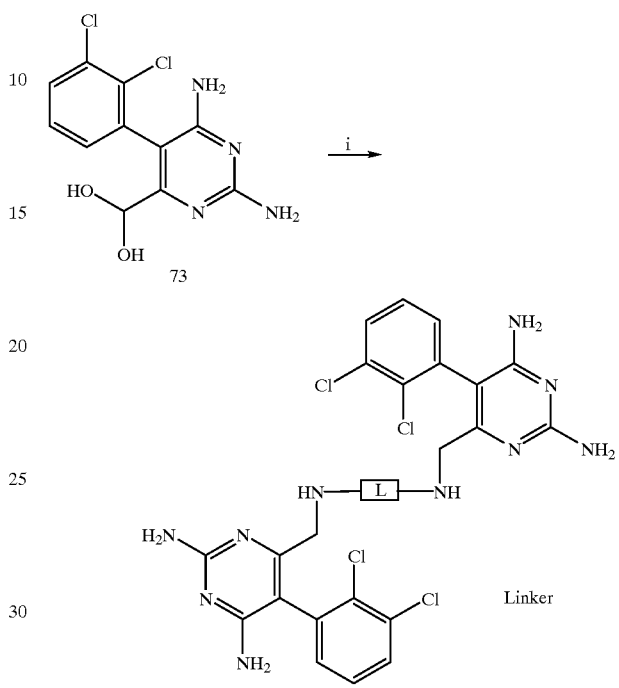

| No. | Linker | R | R' | R$^{5a}$ | R$^{6a}$ | R$^{5b}$ | R$^{6b}$ |
|---|---|---|---|---|---|---|---|
| 1 | —(CH$_2$)$_2$—O—(CH$_2$)$_2$— | H | H | Cl | Cl | Cl | Cl |

General procedure synthesis compound 1 of Table I: To a solution of mexiletine (28 mg, 0.16 mmole) in EtOH (1 mL) was added compound 73 (TFA salt; 41.5 mg, 0.1 mmole). The reaction mixture was stirred at 70° C. for 6 h, and cooled to rt prior to addition of NaCNBH$_3$ (13 mg, 0.21 mmole). After stirring for 2 h at rt, and concentration in vacuo, the crude product was dissolved in aqueous acetonitrile and purified by reversed phase HPLC: 10 to 50% MeCN over 50 min; 10 mL/min; 254 nm. ESMS (C$_{22}$H$_{25}$N$_5$OCl$_2$); calcd. 446.4; obsd. 460.0 [M]$^+$. Retention time (anal. HPLC: 10 to 70% MeCN/H$_2$O over 6 min)=3.20 min. $^1$H-NMR (CD$_3$OD, 299.96 MHz): δ (ppm) 7.69–7.66 (d, 1H), 7.46–7.35 (m, 1H), 7.34–7.32 (d, 1H), 7.01–7.69 (d, 2H), 6.95–6.90 (t, 1H), 4.03–4.01 (d, 1H), 3.96–3.95 (d, 1H), 3.89–3.88 (d, 2H), 3.75–3.69 (p, 1H), 2.17 (s, 6H), 1.42–1.40 (d, 3H).

Compound 5 of Table C was prepared from N-[1-(5-guanidino-3-oxa)pentyl]mexiletine in an analogous manner as described above. Retention time (anal. HPLC: 10 to 70% MeCN/H$_2$O over 6 min)=3.21. ESMS (C$_{26}$H$_{34}$Cl$_2$N$_6$O$_2$); calcd. 533.49; obsd. 534.2 [M+H]$^+$.

EXAMPLE 44

Synthesis Compounds 1 to 5 of Table J via the Following Scheme reagents condition: i) H$_2$N—L—NH$_2$, EtOH, 70° C.; then NaCNBH$_3$, rt

TABLE J

| No. | Linker |
|---|---|
| 1 | —(CH$_2$)$_3$— |
| 2 | —(CH$_2$)$_3$—O—(CH$_2$)$_3$— |
| 3 | —CH$_2$—C(CH$_3$)$_2$—CH$_2$— |
| 4 | —CH$_2$-Z-CH$_2$— where Z = 1,4-cyclohexyl |
| 5 | —CH$_2$-Z-CH$_2$— where Z = 1,3-phenyl |
| 6 | —(CH$_2$)$_4$— |
| 7 | —(CH$_2$)$_2$—O—(CH$_2$)$_2$—O—(CH$_2$)$_2$— |
| 8 | —CH$_2$-Z-CH$_2$— where Z = trans-1,4-cyclohexyl |

Compound 1 of Table J: To a solution of 1,3-diaminopropane (3.4 mg, 0.05 mmole) in EtOH (1 mL) was added compound 73 (TFA salt; 41.5 mg, 0:1 mmole). The reaction mixture was stirred at 70° C. for 6 h, and cooled to rt prior to addition of NaCNBH$_3$ (13 mg, 0.21 mmole). After stirring for 2 h at rt, and, concentration in vacuo, the crude product was dissolved in aqueous acetonitrile and purified by reversed phase HPLC. ESMS (C$_{25}$H$_{26}$N$_{10}$Cl$_4$); calcd. 608.4; obsd. 609.0 [M+H]$^+$.

Compound 2 was prepared from 1,7-dimamino-4-oxaheptnane in a analogous manner as described above. ESMS (C$_{28}$H$_{32}$N$_{10}$OCl$_4$); calcd. 666.4; obsd. 667.1 [M+H]$^+$.

Compound 3 was prepared from 2,2-dimethyl-1,3-diaminopropane in an analogous manner as described above. ESMS (C$_{27}$H$_{30}$N$_{10}$Cl$_4$); calcd. 636.4; obsd. 637.4 [M+H]$^+$.

Compound 4 was prepared from cyclohexane-1,4-dimethylamine in an analogous manner as described above. ESMS (C$_{30}$H$_{34}$N$_{10}$Cl$_4$); calcd. 676.5; obsd. 677.1 [M+H]$^+$.

147

Compound 5 was prepared from α,α'-dimamino-m-xylene in an analogous manner as described above. ESMS ($C_{30}H_{28}N_{10}Cl_4$); calcd. 670.4; obsd. 671 [M+H]$^+$.

Compound 6 was prepared from 1,4-dimaminobutane in an analogous manner as described above. Retention time (anal. HPLC: 10 to 70% MeCN/H$_2$O over 6 min)=1.87. ESMS ($C_{26}H_{28}Cl_4N_{10}$); calcd. 622.38; obsd. 623.2 [M+H]$^+$.

Compound 7 was prepared from trans-1,4-diaminocyclohexane in an analogous manner as described above. Retention time (anal. HPLC: 10 to 70% MeCN/H$_2$O over 6 min)=2.91. ESMS ($C_{28}H_{30}Cl_4N_{10}$); calcd. 648.42; obsd. 649.0 [M+H]$^+$.

Compound 8 was prepared from trans-1,4-diaminocyclohexane in an analogous manner as described above. Retention time (anal. HPLC: 10 to 70% MeCN/H$_2$O over 6 min)=2.91. ESMS ($C_{28}H_{32}Cl_4N_{10}O_2$); calcd. 682.43; obsd.683.2 [M+H]$^+$.

EXAMPLE 45

Synthesis of Compound A1 via the Following Scheme

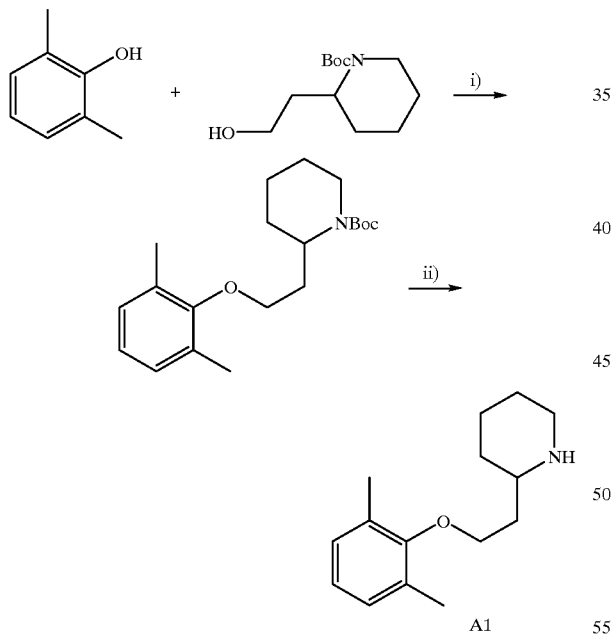

reagents and conditions: i) Ph$_3$P, DEAD, THF, ii) DCM, TFA

148

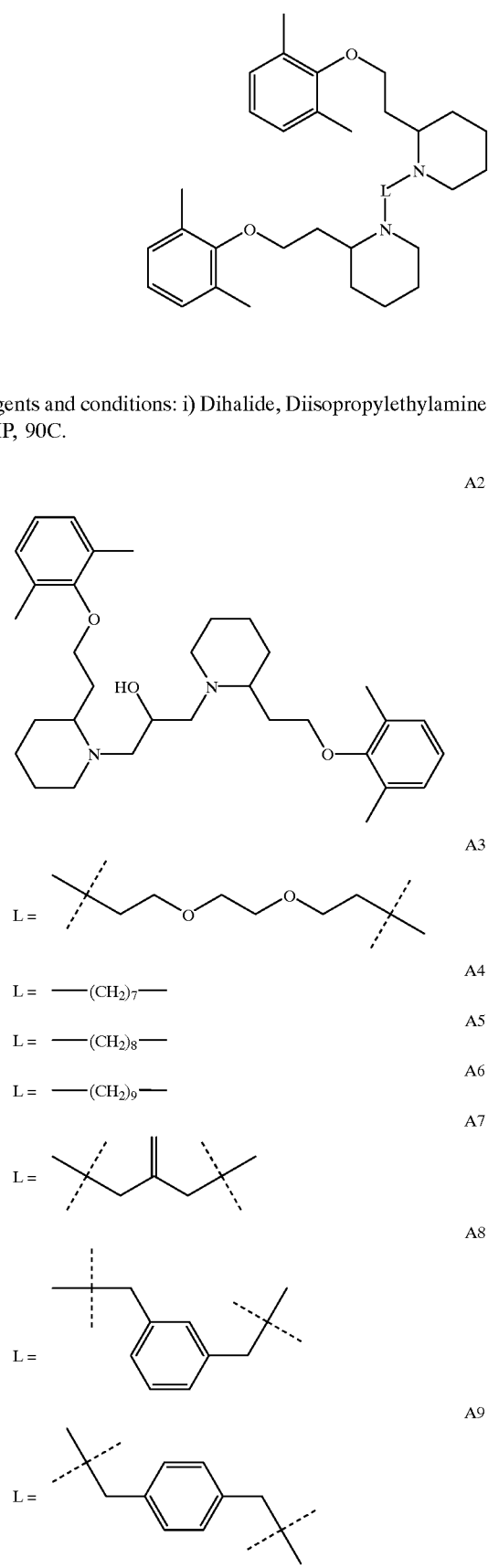

reagents and conditions: i) Dihalide, Diisopropylethylamine, DMP, 90C.

-continued

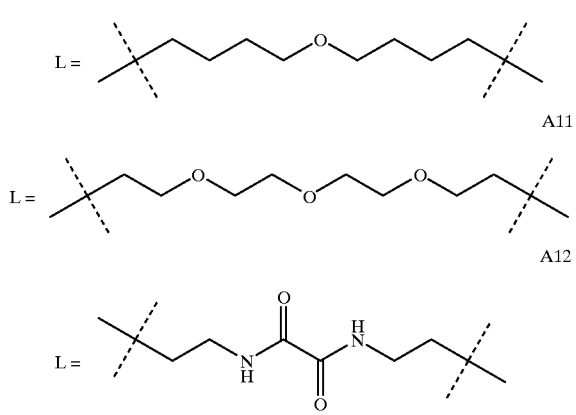

To a stirring, 0° C. solution of 2,6-dimethylphenol (12.2 g, 100 mmol), N-Boc-2-piperidineethanol (22.9 g, 100 mmol), and triphenylphosphene (29.6 g, 113 mmol) in 400 mL THF, was added dropwise over 30 min 19.7 mL (113 mmol) DEAD. The mixture was mixed slowly and allowed to warm to ambient temperature and stirred for 12 hours. The mixture was concentrated in vacuo, and Hexane/DCM was added to precipitate out triphenylphosphene oxide, which was filtered off. The filtrate was concentrated in vacuo, and the residue was flash chromatographed on silica gel, the appropriate fractions were combined to give the desired boc-amino ether. 10 g of this material was dissolved in 300 mL of DCM, cooled to 0° C., and 50 mL of TFA was added dropwise over the period of 30 minutes. The mixture was allowed to warm to room temperature over 2 hours, then was concentrated, then titrated with DCM to give the desired amine as an off-white solid.

Compound A1

1H-NMR (CD$_3$OD, 299.96 MHz): δ (ppm) 7.09–6.97 (d, 2H), 6.88–6.78 (dd, 1H), 3.98–3.71 (m, 2H), 3.50–3.38 (d, 2H), 3.10–2.97 (t, 1H), 2.29–2.10 (m, 7H), 2.05–1.85 (m, 3H), 1.75–1.49 (m, 3H). ESMS (C$_{15}$H$_{23}$NO): calcd. 233.35, obsd. 234.0 [M+H]+.

Synthesis of Dimers of Compounds A1

A general Procedure (synthesis of Compound A2 which is a dimer of A1): A solution of Compound A1 (69.5 mg of the TFA salt, 0.2 mmol) with diisopropylethylamine (108 μl, 0.6 mmol) in 250 μL anhydrous DMF, was added to a solution of 1,3-diiodo-2propanol (31.8 mg, 0.1 mmol) in 250 μL anhydrous DMF. The mixture was shaken for 20 h at 90° C., then stripped of solvent under vacuum. The resulting tarry mixture was dissolved in 1 mL of a 1:1 mixture of acetonitrile and water, with 0.1% trifluoroacetic acid. This mixture was separated by preparative HPLC.

Compounds A2

Retention Time (anal. HPLC: 5–55% MeCN/H$_2$O over 5 min)=4.90 min. ESMS (C$_{33}$H$_{50}$N$_2$O$_3$): calcd. 522.78, obsd. 523.6 [M+H]+.

Synthesis of Compounds A3–A12 Which Have Different Linkers L Identified Above

Compound A3 was prepared in an analogous manner from bis-iodoethoxyethane

Retention Time (anal. HPLC: 5–55% MeCN/H$_2$O over 5 min)=4.85 min. ESMS (C$_{36}$H$_{56}$N$_2$O$_4$): calcd. 580.85, obsd. 581.6 [M+H]+.

Compound A4 was prepared in an analogous manner from 1,7-dibromoheptane

Retention Time (anal. HPLC: 5–90% MeCN/H$_2$O over 5 min)=3.99 min. ESMS (C$_{36}$H$_{56}$N$_2$O$_4$): calcd. 562.88, obsd. 563.6 [M+H]+.

Compound A5 was prepared in analogous manner from 1,8-dibromooctane

Retention Time (anal. HPLC: 5–90% MeCN/H$_2$O over 5 min)=4.06 min. ESMS (C$_{36}$H$_{56}$N$_2$O$_4$): calcd. 576.91, obsd. 577.6 [M+H]+.

Compound A6 was prepared in an analogous manner from 1,9-dibromononane

Retention Time (anal. HPLC: 5–90% MeCN/H$_2$O over 5 min)=4.14 min. ESMS (C$_{36}$H$_{56}$N$_2$O$_4$): calcd. 590.93, obsd. 591.6 [M+H]+.

Compound A7 was prepared in an analogous manner from 3-chloro-2-chloromethyl-1-propene, using a catalytic amount of NaI.

Retention Time (anal. HPLC: 5–90% MeCN/H$_2$O over 5 min)=3.97 min. ESMS (C34H50N2O2): calcd. 518.78, obsd. 519.6 [M+H]+.

Compound A8 was prepared in an analogous manner from 1,3-dibromo-m-xylene.

Retention Time (anal. HPLC: 5–90% MeCN/H$_2$O over 5 min)=3.96 min. ESMS (C$_{38}$H$_{52}$N$_2$O$_2$): calcd. 568.84, obsd. 569.4 [M+H]+.

Compound A9 was prepared in an analogous manner from 1,3-dibromo-p-xylene.

Retention Time (anal. HPLC: 5–90% MeCN/H$_2$O over 5 min)=3.90 min. ESMS (C$_{38}$H$_{52}$N$_2$O$_2$): calcd. 568.84, obsd. 569.4 [M+H]+.

Compound A10 was prepared in an analogous manner from bis(4-chlorobutyl)ether, using a catalytic amount of NaI.

Retention Time (anal. HPLC: 5–90% MeCN/H$_2$O over 5 min)=3.94 min. ESMS (C$_{38}$H$_{60}$N$_2$O$_3$): calcd. 592.91, obsd. 593.6 [M+H]+.

Compound A11 was prepared in an analogous manner from bis[2-(2-chloroethoxy)ethyl]ether, using a catalytic amount of NaI.

Retention Time (anal. HPLC: 5–90% MeCN/H$_2$O over 5 min)=3.85 min. ESMS (C$_{38}$H$_{60}$N$_2$O$_3$): cald. 624.90, obsd. 625.6 [M+H]+.

Compound A12 was prepared in an analogous manner from N,N'-bis(2-chloroethyl)oxamide, using a catalytic amount of NaI.

Retention Time (anal. HPILC: 5–90% MeCN/H$_2$O over 5 min)=3.66 min. ESMS (C$_{36}$H$_{54}$N$_4$O$_4$): calcd. 606.84, obsd. 607.6 [M+H]+.

EXAMPLE 46

Synthesis of Compound A13 via the Following Scheme

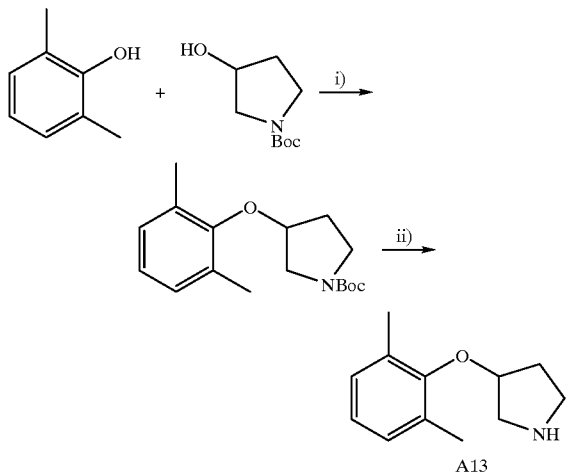

reagents and conditions: i) Ph₃P, DEAD, THF, ii) DCM, TFA

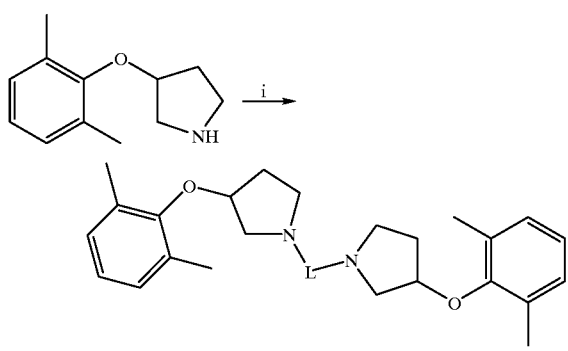

reagents and conditions: i) Dihalide, Diisopropylethylamine, DMF, 90C.

A14

A15

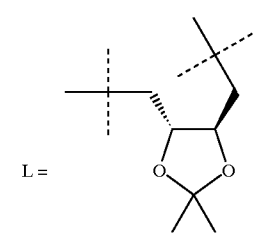

A16

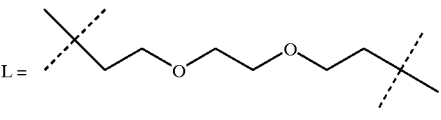

A17

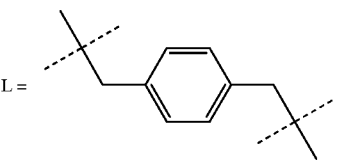

A18

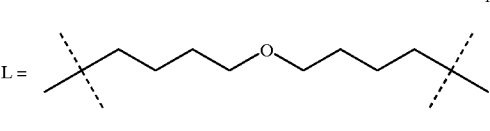

A19

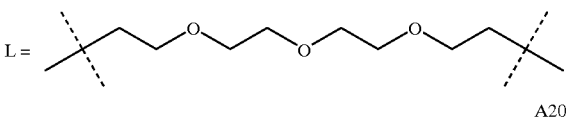

A20

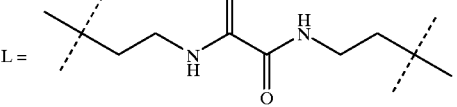

A21

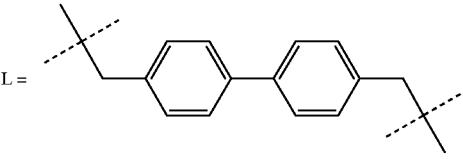

A22

L = —(CH₂)₃—

To a stirring, 0° C. solution of 2,6-dimethylphenol (11.86 g, 97.1 mmol), N-Boc-3-pyrrolidinol (18.18 g, 97.1 mmol), and triphenylphosphene (28.85 g, 110 mmol) in 400 mL THF, was added dropwise over 30 min 15.4 mL (110 mmol) DEAD. The mixture was mixed slowly and allowed to warm to ambient temperature and stirred for 12 hours. The mixture was concentrated in vacuo, and Hexane/DCM was added to precipitate out triphenylphosphene oxide, which was filtered off. The filtrate was concentrated in vacuo, and the residue was flash chromatographed on silica gel, the appropriate fractions were combined to give the desired boc-amino ether. 11.14 g of this material was dissolved in 300 mL of DCM, cooled to 0° C., and 5 mL of TFA was added dropwise over the period of 30 minutes. The mix was allowed to warm to room temperature over 2 hours, then was concentrated, then titrated with DCM to give the desired amine as red oil.

Compound A13

1H-NMR (CD$_3$OD, 299.96 MHz): δ (ppm) 7.06–7.00 (d, 2H), 6.98–6.90 (dd, 1H), 4.82–4.76 (m, 1H), 3.64–3.43 (m, 4H), 2.37–2.25 (m, 7H), 2.20–2.08 (m, 1H). ESMS (C$_{12}$H$_{17}$NO): calcd. 191.27, obsd. 192.0 [M+H]+.

Synthesis of Dimers of Compound A13

A general procedure (synthesis of Compound A14 which is a dimer of A13): A solution of Compound A13 (61.1 mg of the TFA salt, 0.2 mmol) with diisopropylethylamine (108 µl, 0.6 mmol) in 250 µL anhydrous DMF, was added to a solution of 1,3-diiodo-2propanol (31.8 mg, 0.1 mmol) in 250 µL anhydrous DMF. The mixture was shaken for 20 h at 90° C., then stripped of solvent under vacuum. The resulting tarry mixture was dissolved in 1 mL of a 1:1 mixture of acetonitrile and water, with 0.1% trifluoroacetic acid. This mixture was separated by preparative HPLC.

Compound A14

Retention Time (anal. HPLC: 10–70% MeCN/H$_2$O over 5 min)=3.54 min. ESMS (C$_{27}$H$_{38}$N$_2$O$_3$): calcd. 438.61, obsd. 439.5 [M+H]+.

Synthesis of Compounds A15–A22 Which Have Different Linkers L Identified Above Compound A15 was prepared in an analogous manner from (−)-trans-4,5-bis(iodomethyl)-2,2-dimethyl-1,3-dioxolane Retention Time (anal. HPLC: 10–60% MeCN/H$_2$O over 5 min)=4.12 min. ESMS (C$_{31}$H$_{44}$N$_2$O$_4$): calcd. 508.71, obsd. 509.4 [M+H]+.

Compound A16 was prepared in an analogous manner from bis-iodoethoxyethane

Retention Time (anal. HPLC: 10–60% MeCN/H$_2$O over 5 min)=3.84 min. ESMS (C$_{30}$H$_{44}$N$_2$O$_4$): calcd. 496.69, obsd. 497.4 [M+H]+.

Compound A17 was prepared in an analogous manner from 1,3-dibromo-p-xylene.

Retention Time (anal. HPLC: 10–60% MeCN/H$_2$O over 5 min)=4.01 min. ESMS (C$_{32}$H$_{40}$N$_2$O$_2$): calcd. 484.68, obsd. 485.4 [M+H]+.

Compound A18 was prepared in an analogous manner from bis(4-chlorobutyl)ether, using a catalytic amount of NaI.

Retention Time (anal. HPLC: 10–60% MeCN/H$_2$O over 5 min)=4.06 min. ESMS (C$_{32}$H$_{48}$N$_2$O$_3$): calcd. 508.74, obsd. 509.4 [M+H]+.

Compound A19 was prepared in an analogous manner from bis[2-(2-chloroethoxy)ethyl]ether, using a catalytic amount of NaI.

Retention Time (anal. HPLC: 10–90% MeCN/H$_2$O over 5 min)=3.27 min. ESMS (C$_{32}$H$_{48}$N$_2$O$_5$): calcd. 540.74, obsd. 541.4 [M+H]+.

Compound A20 was prepared in an analogous manner from N,N'-bis(2-chloroethyl)oxamide, using a catalytic amount of NaI.

Retention Time (anal. HPLC: 10–60% MeCN/H$_2$O over 5 min)=3.77 min. ESMS (C$_{30}$H$_{42}$N$_4$O$_4$): calcd. 522.69, obsd. 523.4 [M+H]+.

Compound A21 was prepared in an analogous manner from 4,4-bis(chloromethyl)1,1-biphenyl, using a catalytic amount of NaI.

Retention Time (anal. HPLC: 10–60% MeCN/H$_2$O over 5 min)=4.59 min. ESMS (C$_{38}$H$_{44}$N$_2$O$_2$): calcd. 560.78, obsd. 561.4 [M+]+.

Compound A22 was prepared in an analogous manner from 1,3-diiodopropane

Retention Time (anal. HPLC: 10–70% MeCN/H$_2$O over 5 min)=3.54 min. ESMS (C$_{27}$H$_{38}$N$_2$O$_2$): calcd. 422.61, obsd. 423.4 [M+H]+.

EXAMPLE 47

Synthesis of Compound A23 via the Following Scheme

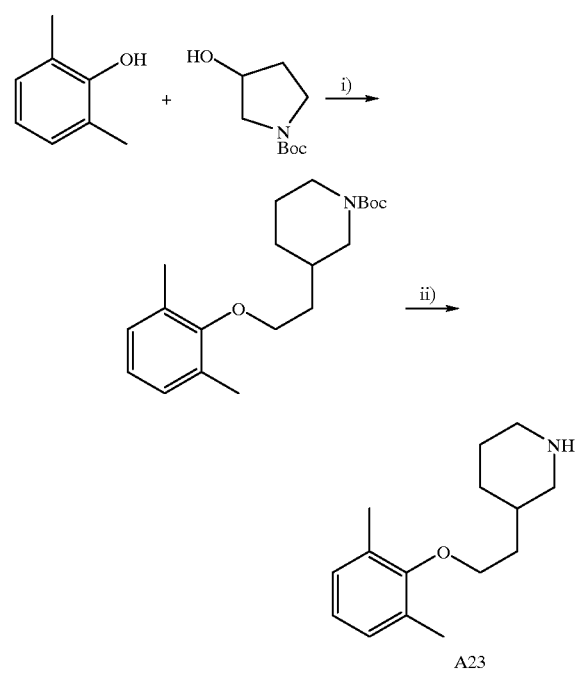

reagent and conditions: i) Ph$_3$P, DEAD, TBF, ii) DCM, TFA

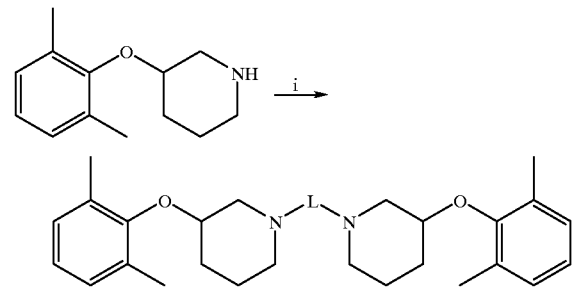

reagents and conditions: i) Dihalide, Diisopropylethylamine, DMF, 90C.

A24

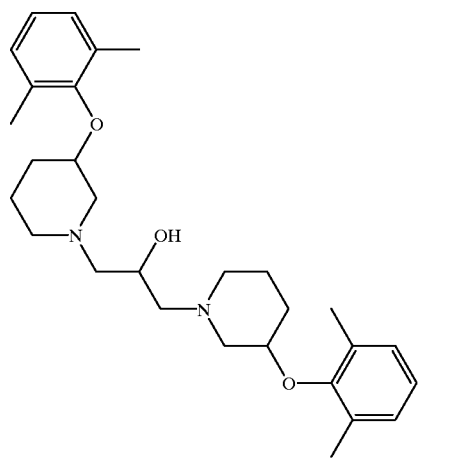

A25

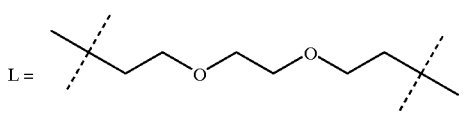

A26

L = —(CH₂)₃—

A27

L = —(CH₂)₆—

A28

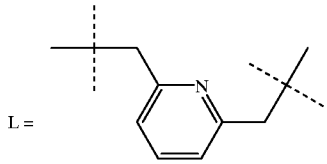

A29

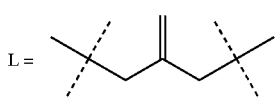

A30

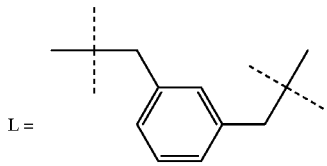

A31

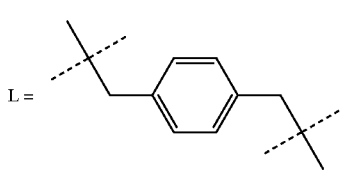

A32

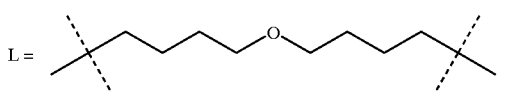

A33

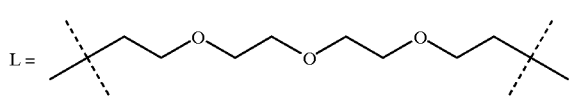

-continued

A34

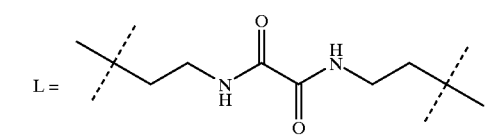

To a stirring, 0° C. solution of 2,6-dimethylphenol (3.15 g, 25.8 mmol) N-Boc-3-hydroxypiperidine (5.2 g, 25.8 mmol), and triphenylphosphene (7.64 g, 29.15 mmol) in 100 mL TBF, was added dropwise over 30 min 4.08 mL (29.15 mmol) DEAD; The mixture was mixed slowly and allowed to warm to ambient temperature and stirred for 12 hours. The mixture was concentrated in vacuo, and Hexane/DCM was added to precipitate out triphenylphosphene oxide, which was filtered off. The filtrate was concentrated in vacuo, and the residue was flash chromatographed on silica gel, the appropriate fractions were combined to give the desired boc-amino ether. 1.8 g of this material was dissolved in 300 mL of DCM, cooled to 0° C., and 50 mL of TFA was added dropwise over the period of 30 minutes. The mixture was allowed to warm to room temperature over 2 hours, then was concentrated, then titrated with DCM to give the desired amine as a clear oil.

Compound A23

1H-NMR (CD₃OD, 299.96 MHz): δ (ppm) 7.06–7.00 (d, 2H), 6.96–6.88 (dd, 1H), 4.18–4.10 (m, 1H), 3.47–3.32 (m, 2H), 3.22–3.10 (m, 2H), 2.32–2.27 (s, 6H), 2.27–2.14 (m, 1H), 2.01–1.70 (m, 3H). ESMS ($C_{13}H_{19}NO$): calcd. 205.30, obsd. 206.1 [M+H]+.

Synthesis of Dimers of Compound A23

A general procedure (synthesis of Compound A24 which is a dimer of A23): A solution of Compound A23 (63.8 mg of the TFA salt, 0.2 mmol) with diisopropylethylamine (108 μl, 0.6 mmol) in 250 μL anhydrous DMF, was added to a solution of 1,3-diiodo-2propanol (31.8 mg, 0.1 mmol) in 250 μL anhydrous DMF. The mixture was shaken for 20 h at 90° C., then stripped of solvent under vacuum. The resulting tarry mixture was dissolved in 1 mL of a 1:1 mixture of acetonitrile and water, with 0.1% trifluoroacetic acid. This mixture was separated by preparative HPLC.

Compound A24

Retention Time (anal. HPLC: 10–70% MeCN/H₂O over 5 min)=3.92 min. ESMS ($C_{29}H_{42}N_2O_3$): calcd. 466.66, obsd. 467.4 [M+H]+.

Synthesis of Compounds A25–A34 Which Have Different Linkers L Identified Above

Compound A25 was prepared in an analogous manner from bisiodoethoxyethane

Retention Time (anal. HPLC: 10–70% MeCN/H₂O over 5 min)=3.86 min. ESMS ($C_{32}H_{48}N_2O_4$): calcd. 524.74, obsd. 525.4 [M+H]+.

Compound A26 was prepared in an analogous manner from 1,3-dilodopropane

Retention Time (anal. HPLC: 10–70% MeCN/H₂O over 5 min)=3.88 min. ESMS ($C_9H_{42}N_2O_2$): calcd. 450.66, obsd. 451.2 [M+H]+.

Compound A27 was prepared in an analogous manner from 1,6-diiodohexane

Retention Time (anal. HPLC: 10–70% MeCN/H$_2$O over 5 min)=3.99 min. ESMS (C$_{32}$H$_4$N$_2$O$_2$): calcd. 492.74, obsd. 493.4 [M+H]+.

Compound A28 was prepared in an analogous manner from 2,6-bis (bromomethyl) pyridine Retention Time (anal. HPLC: 10–70% MeCN/H$_2$O over 5 min)=3.94 min. ESMS (C$_{53}$H$_{43}$N$_3$O$_2$): calcd. 513.72, obsd. 514.4 [M+H]+.

Compound A29 was prepared in an analogous manner from 3-chloro-2-chloromethyl-1-propene, using a catalytic amount of NaI.

Retention Time (anal. HPLC: 10–70% MeCN/H$_2$O over 5 min)=4.09 min. ESMS (C$_{30}$H$_{42}$N$_2$O$_2$): calcd. 462.67, obsd. 463.2 [M+H]+.

Compound A30 was prepared in an analogous manner from 1,3-dibromo-m-xylene.

Retention Time (anal. HPLC: 10–70% MeCN/H$_2$O over 5 min)=4.04 min. ESMS (C$_{34}$H$_{44}$N$_2$O$_2$): calcd. 512.73, obsd. 513.4 [M+H]+.

Compound A31 was prepared in an analogous manner from 1,3-dibromo-p-xylene.

Retention Time (anal. HPLC: 10–70% MeCN/H$_2$O over 5 min)=3.94 min. ESMS (C$_{34}$H$_{44}$N$_2$O$_2$): calcd. 512.73, obsd. 513.4 [M+H]+.

Compound A32 was prepared in an analogous manner from bis (4-chlorobutyl) ether, using a catalytic amount of NaI.

Retention Time (anal. HPLC: 10–70% MeCN/H$_2$O over 5 min)=4.00 min. ESMS (C$_{34}$H$_{62}$N$_2$O$_3$): calcd. 536.80, obsd. 537.4 [M+H]+.

Compound A33 was prepared in an analogous manner from bis [2-(2-chloroethoxy) ethyl] ether, using a catalytic amount of NaI.

Retention Time (anal. HPLC: 10–70% MeCN/H$_2$O over 5 min)=3.84 min. ESMS (C$_{34}$H$_{52}$N$_2$O$_2$): calcd. 568.80, obsd. 569.4 [M+H]+.

Compound A34 was prepared in an analogous manner from N,N'-bis (2-chloroethyl) oxamide, using a catalytic amount of NaI.

Retention Time (anal. HPLC: 10–70% MeCN/H$_2$O over 5 min)=3.77 min. ESMS (C$_{32}$H$_{46}$N$_4$O$_4$): calcd. 550.74, obsd. 551.4 [M+H]+.

EXAMPLE 48

Synthesis of Compound A35 via the Following Scheme

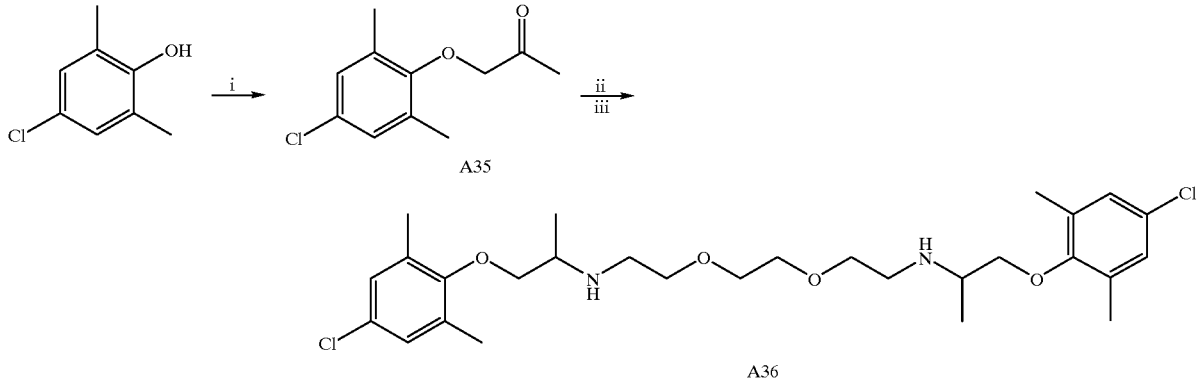

reagents and conditions: i) chloroacetone, K$_2$CO$_3$, KI, DMF, 150C, ii) Toluene, bisiodoethioxyethane, 75C iii) NaBH$_3$CN, r.t.

To a stirring, 150° C. solution of 4-chloro-2,6-dimethylphenol (15.66 g, 100 mmol), potassium carbonate (14.0 g, 100 mmol), and potassium iodide (2.0 g, catalytic amount) in 400 mL DMEF, was added dropwise over 30 min 12.0 mL (150 mmol) chloroacetone. The mixture was continuously heated at 150° C. and stirred for 12 hours. The mixture was filtered, and then concentrated in vacuo to give a tarry residue that was taken up in ethyl acetate and water washed. This solution was concentrated and the residue diluted with hexanes, which caused a brown precipitate to form, which was filtered off. The filtrate was filtered through a pad of basic alumna to remove unreacted phenol. The filtrate was concentrated to provide the desired ketone as a pale yellow solid.

Compound A35

1H-NMR (CD$_3$OD, 299.96 MHz): δ (ppm) 7.03 (s, 2H), 4.49 (s, 2H), 2.23 (s, 9H).

Retention Time (anal. HPLC: 10–70% MeCN/H$_2$O over 5 min)=3.96 min.

Synthesis of Compound A36

To a solution of compound A35 (212.7 mg, 1.0 mmol) in 2 mL anhydrous toluene, was added 2,2'-(ethylenedioxy)bis (ethylamine) (73 μL, 0.5 mmol), followed by 4A molecular sieves and 50 mg sodium sulfate. The mixture was shaken for 12 h at 75° C., then a solution of NaBH3CN (125.7 mg, 2.0 mmol) in ethanol was added, and the mixture shaken for 2 hours at 25° C. The mix was then quenched with water, concentrated under reduced pressure, then dissolved in 1 mL of a 1:1 mixture of acetonitrile and water, with 0.1% trifluoroacetic acid. This mixture was separated by preparative HPLC.

Compound A36

Retention Time (anal. HPLC: 10–70% MeCN/H$_2$O over 5 min)=3.00 min. ESMS (C$_{28}$H$_{42}$C$_1$N$_2$O$_4$): calcd. 541.55, obsd. 542.2 [M+H]+.

EXAMPLE 49

Synthesis of Compound A38 via the Following Scheme

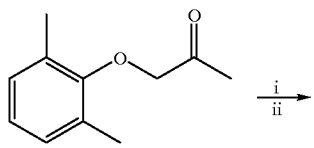

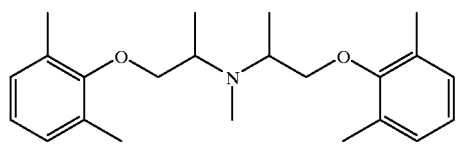

reagents and conditions: i) Toluene, N-Me Mexiletine, 75C, ii) NaBH$_3$CN, r.t.

To a solution of compound 1 (178 mg, 1 mmol) in 2 mL anhydrous toluene, was added a solution of neutral N-methyl mexiletine (193.3 mg, 1 mmol) in 2 mL anhydrous toluene, followed by, 4A molecular sieves and 50 mg sodium sulfate. The mixture was shaken for 12 h at 75° C., then a solution of NaBH3CN (125.7 mg, 2.0 mmol) in ethanol was added, and the mix shaken for 2 hours at 25° C. The mix was then quenched with water, concentrated under reduced pressure, then dissolved in 1 mL of a 1:1 mixture of acetonitrile and water, with 0.1% trifluoroacetic acid. This mixture was separated by preparative HPLC.

Compound A37

Retention Time (anal. HPLC: 10–70% MeCN/H$_2$O over 5 min)=3.92 min. ESMS (C$_{23}$H$_{33}$NO$_2$): calcd. 355.52, obsd. 356.4 [M+H]+.

EXAMPLE 50

Synthesis of Compound A39 via the Following Scheme

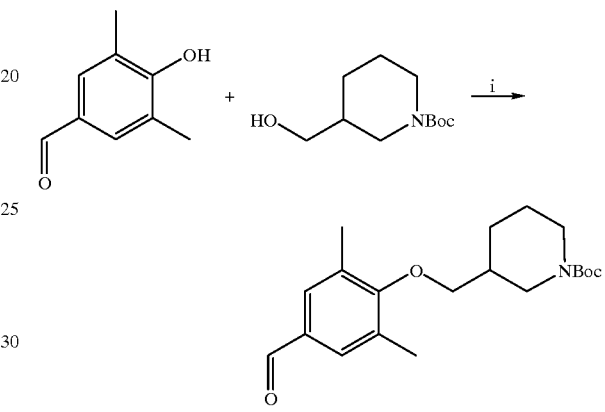

reagents and conditions: i) Ph$_3$P, DEAD

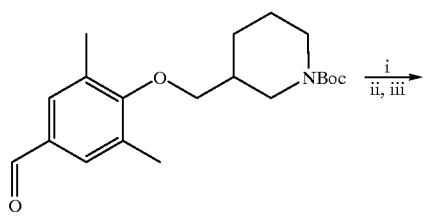

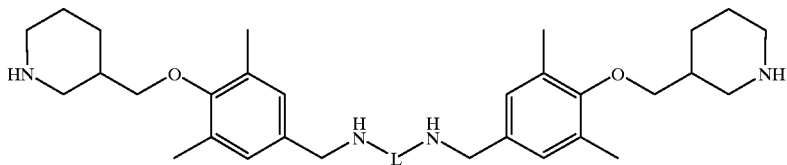

reagents and conditions: i) ethanol, diamine, ii) NaBH₃CN, ii) TFA/DCM phene (2.964 g, 11.3 mmol) in 40 mL THF, was added dropwise over 10 min 1.78 mL (11.3 mmol) DEAD the

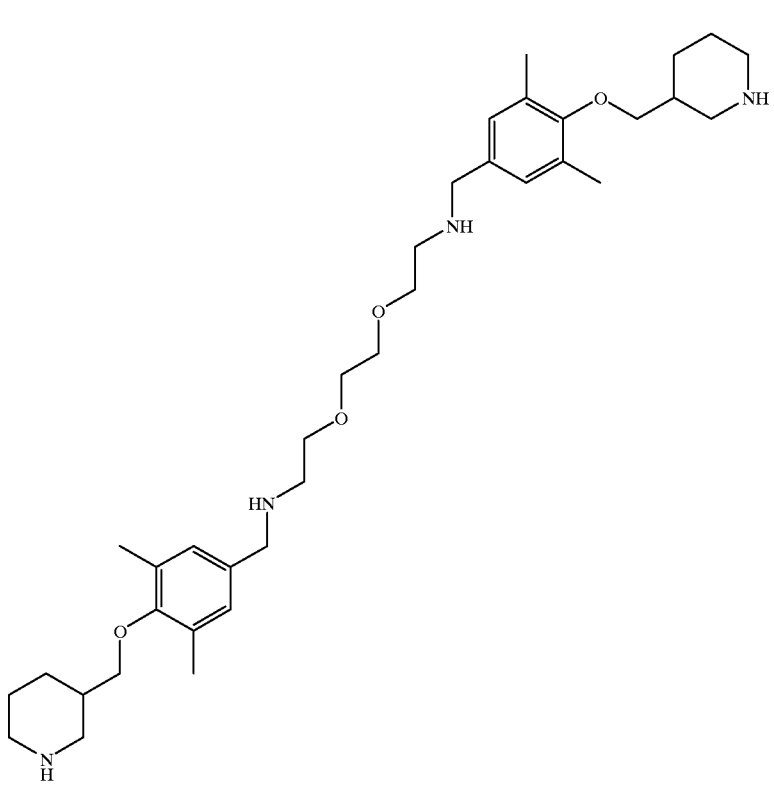

A40

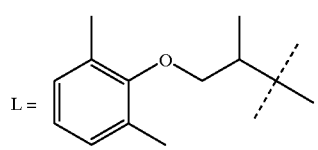

A41

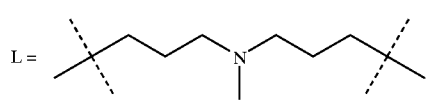

A42

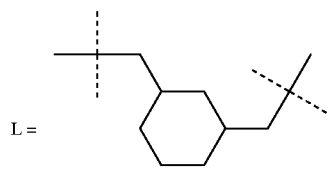

A43

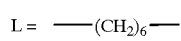

L = —(CH₂)₆—

A44

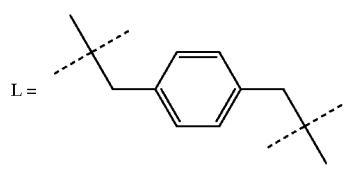

A45

To a stirring, 0° C. solution of 3,5-dimethyl-4-hydroxybenzaldehyde (1.5018 g, 10 mmol), N-Boc-3-piperidineethanol (2.153 g, 10 mmol), and triphenylphosmixture was mixed slowly and allowed to warm to ambient temperature and stirred for 12 hours. The mixture was concentrated in vacuo, and Hexane/DCM was added to precipitate out triphenylphosphene oxide, which was filtered off. The filtrate was concentrated in vacuo, and the residue was flash chromatographed on silica gel, the appropriate fractions combined to give the desired boc-amino ether.

Compound A39

1H-NMR (CD$_3$OD, 299.96 MHz): δ (ppm) 9.82 (s, 1H), 7.60 (s, 21), 4.29–4.20 (dd, 1H), 3.90–3.98 (d, 1H), 3.0–2.78 (m, 2H), 2.35 (s, 6H), 2.09–2.0 (m, 2H), 1.95–1.87 (m, 1H), 1.78–1.65 (m, 1H), 1.58–1.40 (m, 10H). ESMS (C$_{20}$H$_{29}$NO$_4$): calcd. 347.45, obsd. 348.2 [M+H]+.

Synthesis of Dimers of Compound A39

A general procedure (synthesis of Compound A40 which is a dimer of A39): A solution of compound A39 (69.5 mg, 0.2 mmol) in 250 µL anhydrous EtOH, was added 1,8-diamino-3,6-dioxaoctane (14.8 mg, 0.1 mmol). The mixture was shaken for 12 h at 23° C., then a solution of NaBH4 (15.2 mg, 0.4 mmol) in ethanol was added, and the mix shaken for 2 hours at 25° C. The mix was then quenched with a solution of 5% trifluoroacetic acid in acetonitrile/water (1:1), concentrated under reduced pressure, then dissolved in 1 mL of a 10:1 mixture of dichloromethane/trifluoroacetic acid, and shaken for 12 hours. This was then concentrated under reduced pressure, then dissolved in 1 mL of a 1:1 mixture of acetonitrile and water, with 0.1% trifluoroacetic acid. This mixture was separated by preparative HPLC.

Compound A40

Retention Time (anal. HPLC: 10–70% MeCN/H$_2$O over 5 min)=2.84 min. ESMS (C$_{36}$H$_{58}$N$_4$O$_4$): calcd. 610.88, obsd. 611.6 [M+H]+.

Synthesis of Compounds A41–A45 Which Have Different Linkers L Identified Above

Compound A41 was prepared in an analogous manner from neutral mexiletine.

Retention Time (anal. HPLC: 10–70% MeCN/H$_2$O over 5 min)=3.45 min. ESMS (C$_{26}$H$_{38}$N$_2$O$_2$): calcd. 410.6, obsd. 411.2 [M+H]+.

Compound A42 was prepared in an analogous manner from N,N'-bis(3-aminopropyl) methylamine.

Retention Time (anal. HPLC: 10–70% MeCN/H$_2$O over 5 min)=2.27 min. ESMS (C$_{37}$H$_{61}$N$_5$O$_2$): calcd. 607.92, obsd. 608.4 [M+H]+.

Compound A4 was prepared m an analogous manner from 1,3-cyclohexane-bis(methylamine).

Retention Time (anal. HPLC: 10–70% MeCN/H$_2$O over 5 min)=2.73 min. ESMS (C$_{38}$H$_{60}$N$_4$O$_2$): calcd. 604.92, obsd. 605.6 [M+H]+.

Compound A44 was prepared in an analogous manner from 1,6-hexanediamine.

Retention Time (anal. HPLC: 10–70% MeCN/H$_2$O over 5 min)=2.63 min. ESMS (C$_{36}$H$_{58}$N$_4$O$_2$): calcd. 578.88, obsd. 579.6 [M+H]+.

Compound A45 was prepared in an analogous manner from p-xylenediamine.

Retention Time (anal. HPLC: 10–70% MeCN/H$_2$O over 5 min)=2.66 min. ESMS (C$_{38}$H$_{54}$N$_4$O$_2$): calcd. 598.87, obsd. 599.4 [M+H]+.

EXAMPLE 51

Synthesis of Compound A46 via the Following Scheme

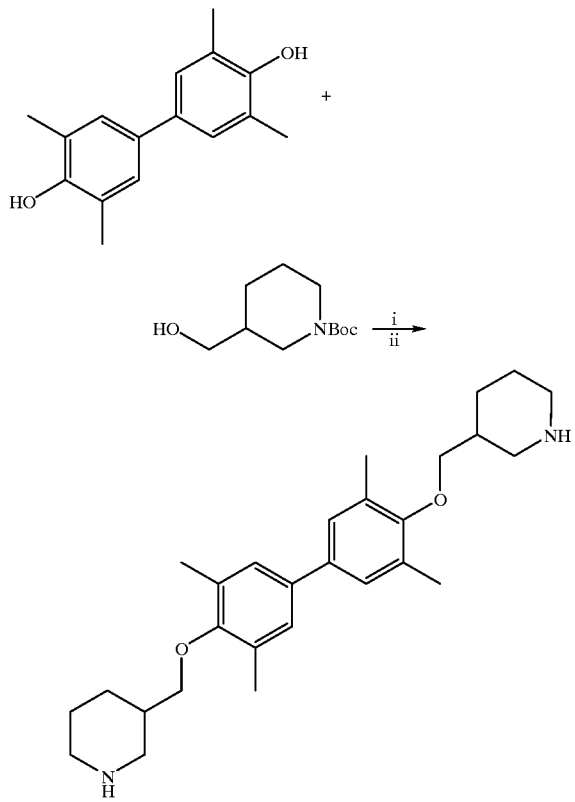

A46 reagents and conditions: i) Ph$_3$P, DEAD ii) TFA/DCM

To a stirring, 0° C. solution of 3,3',5,5'-tetramethyl-[1,1'-biphenyl]-4,4'-diol (1.2116 g, 5.0 mmol), N-Boc-3-piperidineethanol (2.153 g, 10 mmol), and triphenylphosphene (2.964 g, 11.3 mmol) in 40 mL THF, was added dropwise over 10 min 1.78 mL (11.3 mmol) DEAD. Mix slowly allowed to warm to ambient temperature and stirred for 12 hours. The mixture was concentrated in vacuo, and Hexane/DCM was added to precipitate out triphenylphosphene oxide, which was filtered off. The filtrate was concentrated in vacuo, and the residue was flash chromatographed on silica gel, the appropriate fractions combined to give the desired boc-amino ether. This compound (3.0 g, 4.7 mmol) was dissolved in 100 mL Dichloromethane and cooled to 0° C. in an ice bath. 10 mL of trifluoroacetic acid was added dropwise with stirring over 20 minutes, and the mixture was slowly brought to room temperature. The mixture was concentrated in vacuo and the excess TFA was removed by toluene azeotroping to give the product as a white solid.

Compound A46

Retention Time (anal. HPLC: 10–70% MeCN/H$_2$O over 5 min)=2.83 min. ESMS (C$_{28}$H$_{40}$N$_2$O$_2$): calcd. 436.64, obsd. 437.5 [M+H]+.

EXAMPLE 52

Heterodimer Starting Material (compounds B1–B8)

Compound B1:
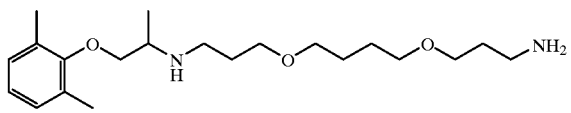

Compound B2:
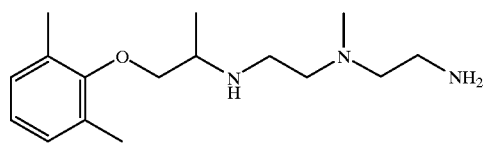

Compound B3:
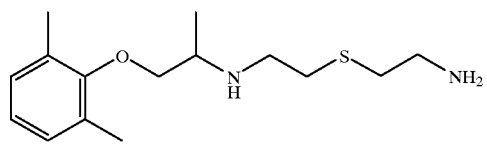

Compound B4:
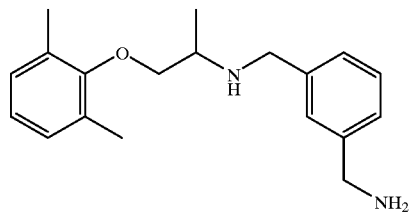

Compound B5:
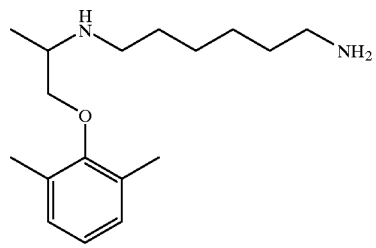

Compound B6:
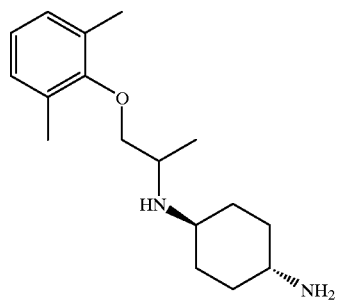

-continued

Compound B7:
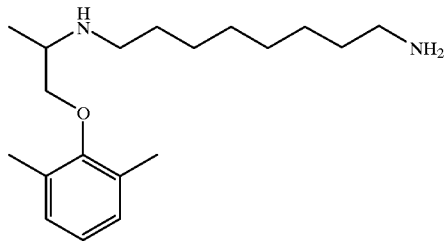

Compound B8:
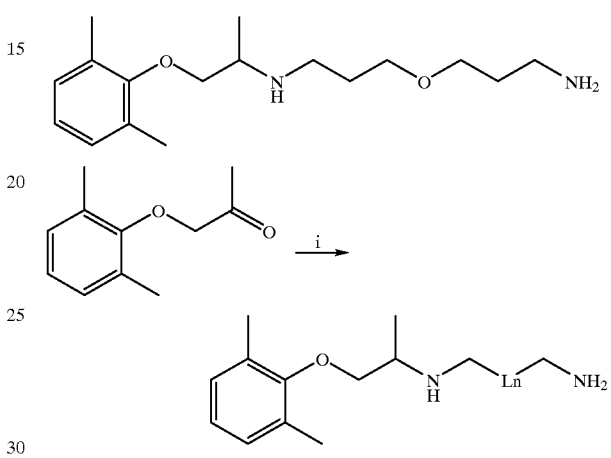

reagent and conditions: i) $H_2N$—Ln—$NH_2$, EtOH, molecular seives $NaSO_4$, 70° C.; then $NaCNBH_3$, rt General procedure synthesis compound B1 via the above schemes. To a solution of 4,9-Dioxa-1,12-dodecanediamine (1.192 ml, 5.61 mmole) in EtOH (1.5 ml) was added compound SM1 (1.0 g, 5.61 mmole), molecular sieves (~10 sieves), and $Na_2SO_4$ (20.0 mg). The reaction was stirred at 70° C. for 6 h and then cooled to room temperature prior to addition of $NaCNBH_3$ (529.1 mg, 8.42 mmole). After stirring for 2 h at rt, and concentrating in vacuo, the crude product was dissolved in aqueous acetonitrile and purified by reversed phase HPLC: 10 to 50% MeCN over 60 min; 40 ml/min; 214 nm. Retention time (anal. HPLC: 10 to 70% MeCN/$H_2O$ over 6 min)=2.15. ESMS ($C_{21}H_{38}N_2O_3$); calcd. 366.54; obsd. 367.2 [M+H]$^+$.

Compound B2 was prepared from N-Methyl-2,2'diaminodiethylamine in an analogous manner as described above. Retention time (anal. HPLC: 10 to 70% MeCN/$H_2O$ over 6 min)=1.52. ESMS ($C_{16}H_{29}N_3O$); calcd. 279.42; obsd. 280.2 [M+H]$^+$.

Compound B3 was prepared from 2,2'-Tiobis(ethylamine) in an analogous manner as described above. Retention time (anal. HPLC: 10 to+70% MeCN/$H_2O$ over 6 min)=1.61. ESMS ($C_{15}H_{26}N_2OS$); calcd. 282.45; obsd. 283.2 [N+H]$^+$.

Compound B4 was prepared from m-Xylylenediamine in an analogous manner as described above. Retention time (anal. HPLC: 10 to 70% MeCN/$H_2O$ over 6 min)=2.00. ESMS ($C_{19}H_{26}N_2O$); calcd. 298.42; obsd. 299.1 [M+H]$^+$.

Compound B5 was prepared from 1,6-Diaminohexane in an analogous manner as described above. Retention time (anal. HPLC: 10 to 70% MeCN/H$_2$O over 6 min)=. ESMS (C$_{17}$H$_{30}$N$_2$O); calcd. 278.43; obsd. [M+H]$^+$.

Compound B6 was prepared from Trans-1,4-cyclohexanediamine in an analogous manner as described above. Retention time (anal. HPLC: 10 to 70% MeCN/H$_2$O over 6 min)=. ESMS (C$_{17}$H$_{28}$N$_2$O); calcd. 276.42; obsd. [M+H]$^+$.

Compound B7 was prepared from 1,8-Diaminooctane in an analogous manner as described above. Retention time (anal. HPLC: 10 to 70% MeCN/H$_2$O over 6 min)=. ESMS (C$_{19}$H$_{34}$N$_2$O); calcd. 306.49; obsd. [M+H]$^+$.

Compound B8 was prepared from Bis (3-aminopropyl) ether in an analogous manner as described above. Retention time (anal. HPLC: 10 to 70% MeCN/H$_2$O over 6 min)=. ESMS (C$_{17}$H$_{30}$N$_2$O$_2$); calcd. 294.43; obsd. [M+H]$^+$.

EXAMPLE 53

Synthesis of Heterodimers 6–13

Compound 6:

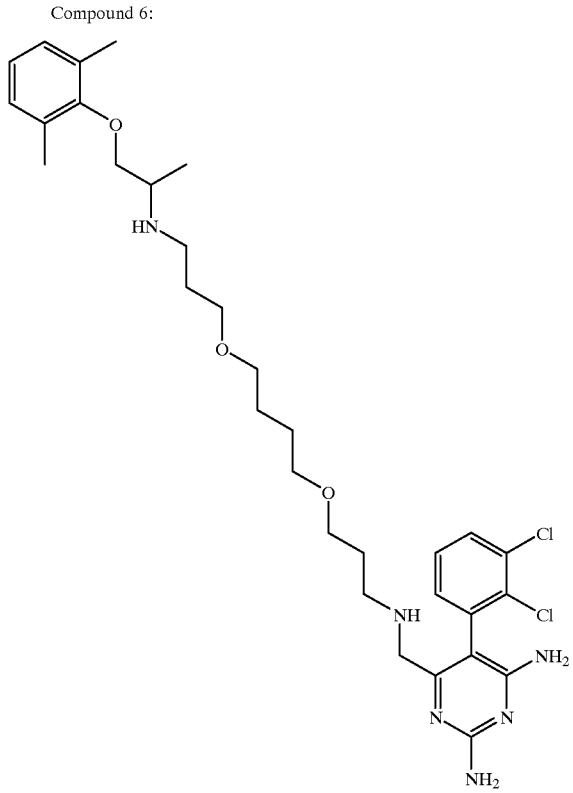

Compound 7:

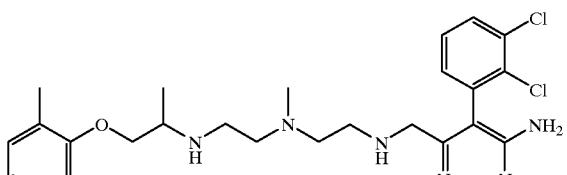

Compound 8:

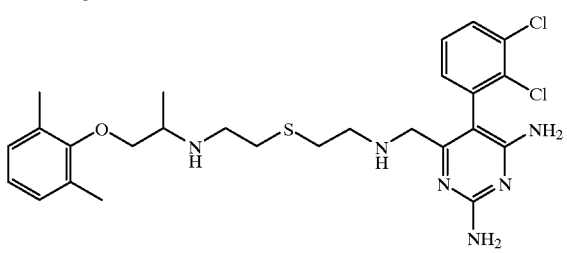

Compound 9:

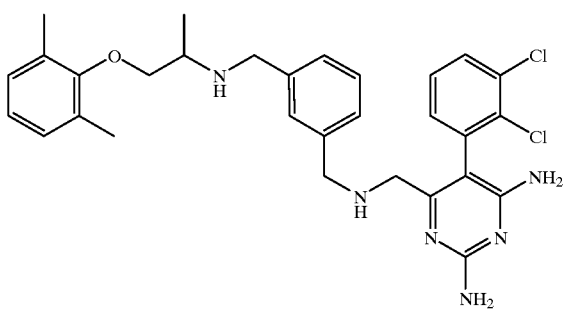

Compound 10:

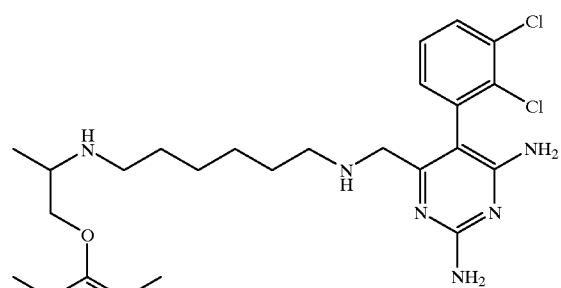

Compound 11:

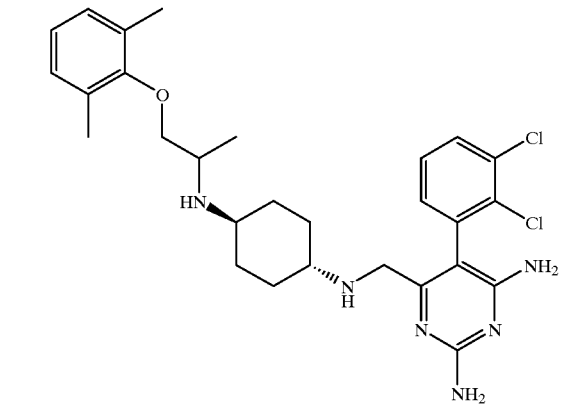

-continued

Compound 12:

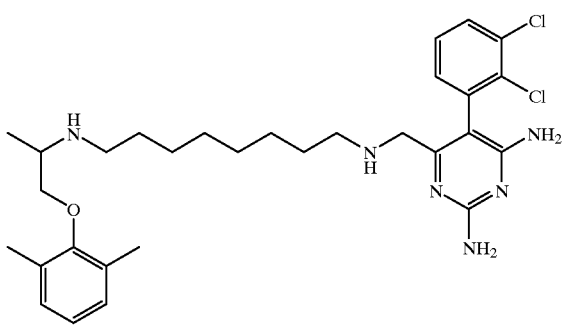

Compound 13:

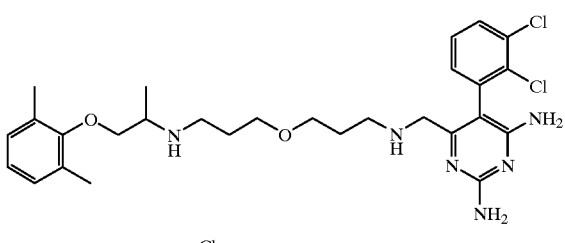

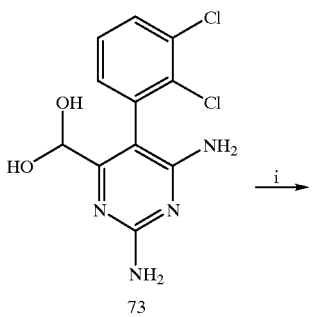
73

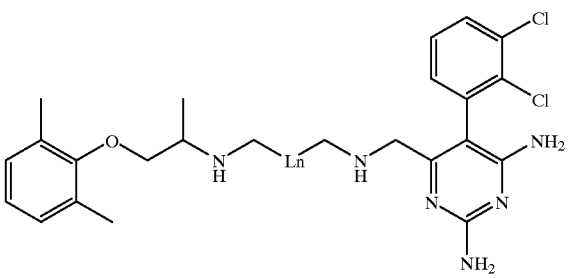

reagents and conditions: i) Mex—Ln—NH₂, EtOH, molecular seives, NA₂SO₄, 70° C.; the NaCNBH₃, rt General procedure synthesis compound 6 via the above scheme; To a solution of N-[1-(12-amino-4,9-dioxa) dodecyl]mexiletine (65.4 mg, 0.11 mmole) in EtOH (1 ml) was added compound 73 (TFA salt; 40.0 mg, 0.096 mmole), molecular sieves (6 sieves), and NaSO₄ (10.0 mg). The reaction was stirred at 70° C. for 6 h and then cooled to room temperature prior to addition of NaCNBH₃ (78.6 mg, 0.125 mmole). After stirring for 2 h at rt, and concentrating in vacuo, the crude product was dissolved in aqueous acetonitrile and purified by reversed phase HPLC: 10 to 50% MeCN over 50 min; 10 ml/min; 254 nm. Retention time (anal. HPLC: 10 to 70% MeCN/H₂O over 6 min)=3.46. ESMS ($C_{32}H_{46}Cl_2N_6O_3$); calcd. 633.66; obsd. 634.4 [M+H]⁺.

Compound 7 was prepared from N-[1-(2-amino-N-methyl)ethyl]mexiletine in an analogous manner as described above. Retention time (anal. HPLC: 10 to 70% MeCN/H₂O over 6 min)=3.32. ESMS ($C_{27}H_{37}Cl_2N_7O$); calcd. 546.54; obsd. 547.3 [M+H]⁺.

Compound 8 was prepared from N-[1-(5-amino-3-thio) pentyl]mexiletine in an analogous manner as described above. Retention time (anal. HPLC: 10 to 70% MeCN/H₂O over 6 min)=3.33. ESMS ($C_{26}H_{34}Cl_2N_6OS$); calcd. 549.57; obsd. 550.3 [M+H]⁺.

Compound 9 was prepared from N-[1(2-amino-m-xyleyl) methyl]mexiletine in an analogous manner as described above. Retention time (anal. HPLC: 10 to 70% MeCN/H₂O over 6 min)=3.46. ESMS ($C_{30}H_{34}Cl_2N_6O$); calcd. 565.55; obsd. 566.2 [M+H]⁺.

Compound 10 was prepared from N-[1-(6-amino)hexyl] mexiletine in an analogous manner as described above. Retention time (anal. HPLC: 10 to 70% MeCN/H₂O over 6 min)=3.38. ESMS ($C_{28}H_{38}Cl_2N_6O$); calcd. 545.56; obsd. 546.1 [M+H]⁺.

Compound 11 was prepared from N-[1-(4-amino) cyclohexyl]mexiletine in an analogous manner as described above. Retention time (anal. HPLC: 10 to 70% MeCN/H₂O over 6 min)=3.25. ESMS ($C_{28}H_{36}Cl_2N_6O$); calcd. 543.54; obsd. 544.3 [M+H]⁺.

Compound 12 was prepared from N-[1-(8-amino)octyl] mexiletine in an analogous manner as described above. Retention time (anal. HPLC: 10 to 70% MeCN/H₂O over 6 min)=3.63. ESMS ($C_{30}H_{42}Cl_2N_6O$); calcd. 573.61; obsd. 574.2 [M+H]⁺.

Compound 13 was prepared from N-[1-(7-amino-4-oxa) heptyl]mexiletine in an analogous manner as described above. Retention time (anal. HPLC: 10 to 70% MeCN/H₂O over 6 min)=3.25. ESMS ($C_{28}H_{38}Cl_2N_6O_2$); calcd. 561.55; obsd. 562.1 [M+H]⁺.

Isolation and Purification of the Compounds

Isolation and purification of the compounds and intermediates described herein can be effected, if desired, by any suitable separation or purification such as, for example, filtration, extraction, crystallization, column chromatography, thin-layer chromatography, thick-layer chromatography, preparative low or high-pressure liquid chromatography or a combination of these procedures. Characterization is preferably by NMR and mass spectroscopy.

Utility and Testing

The multibinding compounds of this invention can be used to modulate sodium channels in various tissues including neurons, heart, and muscle. They will typically be used for the treatment of diseases and conditions in mammals that involve or are mediated by Na⁺ channels, such as pathophysiological disorders, including hypertension, cardiac arrhythmogenesis, insulin-dependent diabetes, non-insulin dependent diabetes mellitus, diabetic neuropathy, seizures, tachycardia, ischemic he disease, cardiac failure, angina, myocardial infarction, transplant rejection, autoimmune disease, sickle cell anemia, muscular dystrophy, gastrointestinal disease, mental disorder, sleep disorder, anxiety disorder, eating disorder, neurosis, alcoholism, inflammation, cerebrovascular ischemia, CNS diseases, epilepsy, Parkinson's disease, asthma, incontinence, urinary dysfunction, micturition disorder, irritable bowel syndrome, restenosis, subarachnoid hemorrhage, Alzheimers disease, drug dependence/addiction, schizophrenia, Huntington's chorea, tension-type headache, trigeminal neuralgia, cluster headache, migraine (acute and prophylaxis), depression, and they mediate the transmission of pain impulses by peripheral nerves, and the like.

The multibinding compounds of this invention can be tested in well-known and reliable assays and their activities are compared with those of the corresponding unlinked (i.e., monovalent) ligands.

I. BIOASSAY OF THE EFFECT OF COMPOUNDS ON PAIN

A. Acute Pain (the Formalin Test)

The formalin test is used as an animal model of acute injury. As described by Dubuisson and Dennis (1977, Pain 4:161), a standard dose of formalin is injected into the dorsal portion of the front paw of a rat. Bach rat is placed into a clear plastic cage for observation. The animals are observed and ratings, based on pain responses, are taken at 30 and 60 minutes. Elevation, favoring, or excessive licking and biting of the injected paw indicate a pain response. Analgesic response or protection from compounds is indicated if both paws are resting on the floor with no obvious favoring, excessive licking or biting of the injected paw.

Determining the number of pain responses occurring per minute quantitates the analgesic effect of the test compounds. The concentration of test compound resulting in a 50% decrease in pain-responses/minute is the $ED_{50}$.

B. Chronic Pain

Modifications of the method of Hunter, J. C., et al., (1997, Eur. J Pharmacol. 324:153) are used in the following models of chronic pain.

1. Constriction Injury

Adult male Spraque-Dawley rats weighing 150 g–180 g are placed two per cage and allowed free access to food and water. The cages are housed in temperature and humidity controlled rooms and maintained on a 12-h light/dark cycle.

Rats are anesthetized with sodium pentobarbital (70 mg/kg). Chronic constriction injury is produced by exposing the common right sciatic nerve at mid-thigh level and proximal to the trifarcation of the sciatic. Four loose ligatures (4.0 chromic gut), with about 1-mm spacing, are tied around the nerve. The desired degree of constriction retards but does not block circulation through the epineurial vasculatore. In every animal, an identical (sham) procedure is performed on the opposite side (left) with the exception that the sciatic nerve is not ligated. All operations are completed by closing the muscle in layers, applying wound clips to close the skin incision, and allowing the animals to recover for a period of 5–7 days.

A cold water test is performed, after the recovery phase. The cold water test is performed by placing each animal onto a metal stage submerged to a depth of 2.5 cm in ice-cold water (0° C.) contained within a square Perspex chamber (21×21 cm). The animals respond by lifting the paw on the ligated side out of the water. The latency to paw withdrawal (mean±standard error) is measured at 6.8±0.8 s (n=28). At no time does any animal withdraw the paw on the sham side from the cold water. In each experiment, animals are first pre-screened twice with 20-min interval between tests, in order to select for animals displaying clear signs of cold allodynia, i.e. animals with a paw withdrawal latency on the ligated side of <13 s in both trials. The animals are then randomly assigned to groups consisting of 8–10 animals per group The animals are treated with experimental compounds. The ability of the compounds to extend the latency to paw withdrawal is determined at 1, 3 and/or 5 h posttreatment.

2. Spinal nerve (L5/L6) Ligation

Adult male Spraque-Dawley rats weighing 150 g–180 g are used in all experiments. Animals are placed two per cage and allowed free access to food and water. The cages are housed in rooms that are temperature and humidity controlled and maintained on a 12-h light/dark cycle.

Spinal nerve ligation is performed on rats anesthetized with sodium pentobarbital (70 mg/kg, ip). L5 and L6 spinal nerves are ligated with a 6.0 silk suture distal to the dorsal root ganglia. The muscle is then closed in layers using wound clips and the animals allowed to recover for a period of at least 5 days before testing.

Tactile allodynia is evaluated in spinal nerve ligated animals with a calibrated series of eight von Frey filaments as follows. The rats are placed in clear plastic cages (H: 5', L: 10", W: 4⅝") fitted with a wire mesh floor and allowed to acclimate for 15 min. The following filaments (log 10 of the bending force (g)) are employed to test for allodynia: 0.4, 0.7, and 1. 2, 2.0, 3.6, 5.5 8.5 and 15.1 g. Filaments of greater force are not used since these alone would physically lift the paw. Each filament is applied once to the mid-plantar surface of the affected hindpaw in a perpendicular fashion aid depressed slowly (4–6 s) until bending occurred. From the overall pattern of responses a 50% gram withdrawal threshold is calculated according to the following formula:

$$50\% \text{ withdrawal threshold } (g) = 10(10[^{xf-kd}]/10000$$

where xf is the value (in log units) of the final von Frey hair used: k is the pattern value and d is the mean difference in log units) between filaments: 0.223.

For each experiment, animals are first pre-screened in order to select for animals displaying clear signs of tactile allodynia, i.e. animals with a 50% gram paw threshold of <4-g on the ligated side. The animals are then randomly assigned to groups consisting of 8–10 animals per group. The 50% gram paw withdrawal threshold is then determined 60 min post-treatment.

Model of Nocioceptive Pain (The "Tail Flick" assay)

The "tail flick" assay is a modification of the method of Ther, L., et al (1963. Zur pharmakodynamischen Wirkiiung der optischen isomeren des methadons Dtsh Apoth Zig, 103;514). Adult male Spraque-Dawley rats weighing 150–180 g are used in experiments. Animals are housed two per cage and allowed free access to food and water. The cages are housed in rooms that are temperature and humidity controlled and maintained on a 12-h light/dark cycle.

Each experimental group consists of 8–10 animals (180 g–220 g). The animals are loosely wrapped, individually, in a thin cotton towel with the head covered and tail exposed.

Each animal is placed on a platform with the tail position in a shallow groove and a focused beam of light directed at the tail from above, approximately 2.5-cm from the tip. Movement of the tail from the groove allows the beam of light to hit a sensor, formerly covered by the tail, which then automatically switches off the beam and stops the timer. The duration of time required for the tail response after exposure to the thermal stimulus is considered the tail response latency time. The maximum time allowed is 10 s in order to prevent tissue damage. Rats are tested once to determine the pre-dose tail response latency following which they are then dosed and again tested for their tail response latency at 60 min post-dose.

II. CENTRAL NERVOUS SYSTEM, (CNS) DISORDERS

A. Depression

Antidepressant activity of compounds is tested in rats following the method of Porsolt, R D., et al (1978, Eur. J. Pharmacol. 47:379. Adult male Spraque-Dawley rats weighing 150 g–180 g are used in experiments. Animals are placed two per cage and allowed free access to food and water. The cages are housed in temperature and humidity controlled rooms and maintained on a 12-h light/dark cycle.

The rats (150 g–180 g) are forced to swim in an escape-proof cylinder. After an initial period of vigorous activity they adopt a readily identified immobile posture which is used as a model of human depression. The ability of experimental compounds to increase the period of time elapsing before animals become immobile is determined.

B. Bipolar Disorder

Current antidepressant therapy, which is based on the inhibition of biogenic amine uptake, can be evaluated in vitro. Both rat brain synaptosomes and washed human platelets are used in these studies. The inhibition of 5-HT, dopamine, and noradrenaline uptake in these systems is a measure of the efficacy of the therapeutic compounds.

1. Cells

The effect of test compounds on 5-HT transport in washed human platelets is evaluated following the method of Southam, E., et al (1998, Eur. J. Pharmacol. 358:19). Human blood is obtained from volunteers and platelets isolated by centrifugation, washed, and resuspended ($3 \times 10^5$/ul) in cold (4° C.) HEPES buffer (pH 7.4) consisting of 5.0 mM HEPES containing 140 mM NaCl, 2.82 mM KCL, 0.74 mM $KH_2PO_4$, 5.5 mM $NaHCO_3$, 1 mM $CaCl_2$, 0.5 mM $MgSO_4$ and 5.1 mM glucose. 10 uM pargyline is added to inhibit monamine oxidase activity.

Cells are obtained from adult male Lister hooded rat cortex (5-HT and noradrenaline uptake) or striatum (dopamine uptake). The cortex and striatum are homogenized in 0.32 M sucrose solution and syntaptosomes isolated by centrifugation before being gently suspended in cold ($4_0$C) pre-gassed (5% $CO_2$, 95% $O_2$) Krebs solution containing 115 mM NaCl, 4.97 KCL, 1.2 mM $KH_2PO_4$, 5.5 mM $NaHCO_3$, 1.0 mM $CaCl_2$, 1.22 mM $MgSO_4$, 11.1 mM glucose, 0,01 mM pargyline. The protein concentration (0.2–0.5 mg/ml of the crude synaptosomal preparation, is determined following the method of Bradford (Bradford, M M., 1976. Anal. Biochem. 72:248).

Biogenic Amine Uptake.

190 ul of either the platelet or synaptosome preparation are added to solutions containing 800 ul of one of three tritiated biogenic amines: 1) [$^3$H] 5-HT (final concentration 20 mM): or 2) [$^3$H] noradrenaline (50 nM); or 3) [$^3$H] dopamine (20 nM). Test compounds are added and the mixtures incubated for 10 min at 37° C. The mixture of cells, biogenic amines, and test substances are individually filtered through pre-wetted Whatman GF/B filter paper. Then the filter paper was washed 3 times with ice-cold buffer to stop the uptake of the tritiated amines. Liquid scintillation counting assesses the radioactivity captured on the filter paper. Non-specific uptake is determined and subsequently subtracted from counts. Data points represent the mean±SEM of at least four different assays. Each assay point is performed in triplicate and expressed as a percentage of controls (also performed in triplicate). $IC_{50}$s are generated by calculating the geometric mean (number (n) and 95% confidence interval ($CI_{95}$) indicated in parentheses) of values estimated by fitting a sigmoidal model of the following form using a non-linear curve fit based on the algorithm of Marquard (1963, J. Soc. Indust. Appl. Math. 11:431):

$$Y = \frac{(a-d)}{1+(x/c)b}$$

where, y=raw counts: x=concentration of compound: a=lower asymptote: d=upper asymptote, b=Hill slope and c=$IC_{50}$. The assumption is that uptake will be depressed to non-specific levels at infinitely high concentrations.

Neurodegeneration

The neuroprotective effect of the compounds is tested in vitro in a model of neurodegeneration. In this model cytotoxicity is induced by glutamate as described by Huettner, J E and Baughman, R W. (1986. J. Neurosci. 6:3044). Briefly, rat pups aging from newborn to 1 day weighing from 6 g to 8 g are anesthetized with chloral hydrate. The cortices with hippocami attached are removed and placed in Cl free dissociation medium supplemented with 1-mM kynurenic acid and 10 mM $MgSO_4$. The tissue is cleared of meninges, washed, and incubated for 20 min at 37° C. in dissociation medium containing 10 units/ml papain (Wortington), a digestive enzyme. The tissue is then incubated for three 5-min periods at 37° C. in isotonic. medium containing 10-mg/ml trypsin inhibitor to stop the reaction.

The cells are dissociated by trituration and resuspended in growth medium (GM) consisting of Eagles minimum essential medium (MEM) supplemented with 5% fetal bovine serum, 5% defined supplemented calf serum (hyclone), 50 mM glucose, 50 U/ml penicillin/streptomycin and serum extender (Collaborative Research). The cells ($5 \times 10^5$/ml) are aliquoted (0.1 ml/well) into the wells of 96 well plates pre-coated with poly-D-ysine (0.5 mg/ml) and laminin (2 ug/nl) (Collaborative Research) so that a final density of $5 \times 10^4$ cells per well 1s achieved. The cells are maintained at 37° C. in a humidified incubator in an atmosphere of 5% $CO_2$ in air.

Fresh media is added to the cultures by removing one half of the media and adding the equivalent volume of new media twice weekly for 15–16 days.

Experiments are performed on cultures in which the neurons are at a uniform density. Cultures are washed three times in a modification of the medium used by Choi et al (1987, J. Neurosci. 7:257) consisting of HEPES-buffered control salt solution (CSS) containing 10 mM HEPES buffered at pH 7.4. In all experiments the cells are incubated with a neurotoxic concentration of glutamate (500 uM). Test compounds, diluted in CSS are added to the cultures in 2-fold serial dilutions. Control cultures are incubated with CSS alone, or serial dilutions of test compounds in CSS alone, or 500 uM glutamate. The wells are washed three times with CSS and 100 ul aliquots of glucose enriched MED are added to all wells. The plates are maintained overnight at 37° C. in an atmosphere of 5% $CO_2$ in air.

Glutamate-induced death of neurons is measured by determining the levels of lactate dehydrogenase (LDH) released into the medium by dead and dying neurons 24–48 hours following glutamate insult (Koh and Choi, 1987, J. Neurosci. Methods, 20:83). Media samples are collected from all wells and assayed for LDH according to the protocol suggested by Molecular Devices Applications Bulletin, 012-A using the Molecular Devices Kinetic Microplate Reader. Results are normalized to the LDH values obtained in the. glutamate alone controls.

The concentration of test compound resulting in a 50% inhibition of release of LDH is the $ED_{50}$.

Cerebrovascular Ischemia

Following the method of O=Neill, M J et al. (1997, Eur. J. Pharmacol. 332:121) male Mongolian gerbils, at least 3 months old and weighing in excess of 60 g, are used in these in vivo experiments. The animals are maintained in standard lighting conditions and food and water are. available ad libitum. The animals are anesthetized with 5% halothane/oxygen mixture and maintained using 2% halothane delivered with oxygen at 1 L/min via a face mask throughout the operation. Through a midline cervical incision, both common carotid arteries are exposed and freed from surrounding connective tissue. In animals to be rendered ischemic both common carotid arteries are clamped for 5 min. to occlude the blood flow. At the end of the occlusion period blood flow was re-established. In sham operated animals the arteries are exposed but not occluded. The wound is then sutured and the animals allowed to recover. Throughout the surgery body temperature is maintained at 37° C. using a "K-TEMP" temperature controller/heating pad (International Market Supply) and brain temperature are maintained using a heating lamp. After surgery the animals are placed in a four compartment thermacage (Beta Medical and Scientific) which maintained the environmental temperature at 28° C. and rectal temperatures are measured for a 6 h period after occlusion.

The doses of compounds were selected based on previous work and administered a various times prior to during and after the occlusion. 5 days after surgery the animals are perfused transcardially with 30 ml of 0.9% saline followed by 100 ml of 10% buffered formalin solution. The brains are removed and placed in 10% formalin for 3 days processed and embedded in paraffin wax. 5 um coronal sections are taken 1.5–1.9 mm caudal to the bregma in the anterior hippocampus using a sledgemicrotome (Leitz 1400). The slices were stained with hemoatoxylin and eosin and the neuronal density in the CA1 subfield of the hippocampus was measured using a microscope with grid lines (0.05 mm×0.05 mm). The neuronal density is expressed as neuronal density per mm CA1 hippocampus.

Epilepsy: Bioassays of the Effect of Compounds on Experimentally Induced Seizures and Convulsions.

Following the method of Dalby, N., et al (1997, Epilepsy Research 28:63). Groups of animals (10 animals/group) receive ip injections of either vehicle or test compounds at a variety of concentrations prior to inducing seizures or convulsions as described below.

1. Seizures Induced by Maximal Electroshock

Male NMRI mice (20±2 g) of either sex are maintained in groups of 40. The cages (59×38×20 cm) are placed in a room at 22° C. with a relative humidity of 55% in a 12 h/12 h normal light/dark cycle with ad libitum access to food and water. The mice are stimulated by corneal electrodes from a Hugo Sachs stimulator (type 207) with 50 mA, 60 Hz AC, for 0.2 s. The animals are observed for tonic hindlimb extension following 10 s after stimulation. An $ED_{50}$ value is determined as the dose of ligand protecting 50% of the animals against tonic hindlimb extension.

2. Seizures Induced by Sound.

DBA/2 mice of either sex (8+1 g) 18–21 days old are individually exposed to a 111 db sinusoidal tone at 14 kHz for 30 s and observed for the presence of clonic and tonic convulsions during this period. An $ED_{50}$ value is determined as the dose of ligand (umol/kg) protecting 50% of the animals from clonic or/and tonic convulsions.

3. Pentylentetrazol (PTZ) Induced Convulsions

Male NMRI mice (20±2 g) are injected subcutaneously with 160 mg/kg of PTZ to induce tonic convulsions. The mice are observed for the following 15 min and time to tonic convulsions is noted for each animal. For PTZ induced clonic convulsions, a dose of PTZ (120 mg/kg) is administered subcutaneously, and the animals observed for the following 30 min and time to clonic convulsions is noted for each animal. $ED_{50}$ values are determined as the dose of ligand which protects 50% of the animals against clonic or tonic convulsion.

4. 6.7-dimethoxy-4ethyl-β-carboline-3-carboxylate (DMCM) Induced Convulsions.

Male NMRI mice (20±2 g) receive DMCM (18 mg/kg) and are observed for 15 min following injection for the presence of clonic and tonic convulsions and death. An $ED_{50}$ value is determined as the dose of ligand protecting 50% of the animals against clonic or/and toxic convulsions.

Schizophrenia

Subjects diagnosed with schizophrenia are selected from a group of inpatients. All subjects give written informed consents to participate.

After a 2 week baseline assessment period, subjects are randomly assigned to receive, under double-blind conditions, either experimental compounds (dissolved in water) or placebo (glucose in water). Each patient undergoes a 2-week adjunctive treatment washout period after which he/she crossed over to the alternative substance for a further 6 weeks. Experimental compounds are administered at a variety of concentrations. The only other medications allowed during the study was trilexyphenidyl (2–5 mg/day) for treatment of extrapyramidal symptoms and chloral hydrate (250–750 mg/day on PRN basis) for treatment of insomnia or agitation. For patients needing antiparkinsonian medication, trihexyphenidyl dose was kept constant throughout the study.

Symptoms and extrapyramidal side effects are assessed starting from week-2, biweekly throughout the study, using Positive and Negative Symptom Scale (PANSS), the Simpson-Angus Scale for Extrapyramidal Symptoms (SAS) and Abnormal Involuntary Movement Scale (AIMS). Patients requiring, at any point during the study, neuroleptic dose increases are withdrawn and appropriate treatment instituted. Withdrawl decisions are based on clinical evaluations and coincide with an increase of at least 30% on the PANSS score.

Physical complaints and status are monitored daily. Hematology, blood chemistry, liver and kidney function, laboratory measures are assessed biweekly. Blood samples for the assessment of serum levels of experimental compounds are obtained at baseline and at the end of study weeks 6 and 14. Blood drawings are performed before breakfast and first daily administration of medication. Serum compound levels were determined by HPLC.

The anti-anxiety effects of compounds are studied in vivo following the method of Costall, B., et al (1987, Neuropharmacol. 26:195). Briefly, mice that tend to explore a novel environment, are placed I n a two-chambered system in which they can freely move between a brightly lit open field and a dark corner. The animals are averse to moving into the bright area. The ability of compounds to suppress anxiety about moving into the bright light is determined.

Briefly, naïve male albino mice with a weight between 18 g and 25 g are placed into a testing apparatus consisting of a light and dark chamber divided by a photocell-equipped zone. A polypropylene animal cage, 44×21×21 cm is darkened with black spray over one-third of its surface. A partition containing a 13-cm long×5-cm high opening separates the dark one third from the bright two thirds of the cage. The cage rests on an Animex activity monitor which counts total locomoter activity. An electronic system using four sets of photocells across the partition automatically count movements through the partition and clocks the time spent in the light and dark compartments. The animals are treated 30 min before the experiment with the test drugs or the vehicle intra peritoneal and are then observed for 10 min.

Dose-response curves are obtained and the number of crossings throughout the partition between the light and dark chamber are compared with total activity counts during the 10 minutes.

Migraine: Plasma Extravasation Model

Plasma extravasation is a sequela of neurogenic inflammation within the dura mater and the mechanism involved in the production of migrane headache. Plasma extravasation may be experimentally produced in the dura by electrical stimulation of the trigeminal ganglion. The protective effect of therapeutic compounds on extravasation can be evaluated in such models.

Thus, following the method of Shepheard, S L, et al., (1995, Neuropharmacology, 34(3):255) male Sprague-Dawley rats (180 g–230 g) are anaesthetized with pentobarbitone sodium (60 mg $kg^{-1}$, ip) and anaethesia maintained by giving supplementary doses (10 mg $kg^{-1}$, iv) as required. A femoral vein and artery are cannulated for iv injections and monitoring of arterial blood pressure respectively. Rats are placed in a sterotaxic frame and burr holes drilled 3.2 mm posterior and 2.8 mm lateral from bregma to allow placement of bipolar concentric stimulating electrodes (NE 200X, Clark Electromedical). Test compounds dissolved in $H_2O$ or $H_2O$ alone are administered (n=8–10 per group) at time t=0 min. The radioactive plasma marker, $^{125}I$ bovine serum albumen (70 uCi $kg^{-1}$) was administered at t=5 min. The electrodes are lowered 9.5 mm below the surface of the dura and at t=10 min the right trigeminal ganglion is stimulated with 0.6 mA constant current, 5 mSec duration square wave pulse, 5 Hz for 5 min. At t=20 min the animals are killed by exsanguination and the dura dissected from both sides of the skull. The area of dura immediately surrounding the sites of electrode penetration is discarded. Correct electrode placement is confirmed by the presence of electrode marks in the trigeminal ganglion. Samples of extracranial tissues (conjunctiva, eyelid and lip) innervated by the trigeminal nerve are also taken. Tissues are rinsed, dried overnight weighed and then counted for radioactivity.

The counts $mg^{-1}$ dry weight of tissue samples from the stimulated and unstimulated sides are calculated and results expressed as an extravasation ratio, ie the ratio of the stimulated to unstimulated sides. For calculation of an $ID_{50}$ value, (dose producing 50% extravasation) an inhibition curve is fitted to the data using "Grafit" curve-fitting software (Erithacus software, UK).

STATISTICS

Pain Models

All group comparison data are analyzed using a Kruskal-Wallis one way analysis of variance (ANOVA) followed by a pairwise comparison between vehicle and each drug-treated group with a Dunnett=s t-test on the ranked data Ligand effects are considered to be statistically significant only if they are different from both the pre-dose data and the vehicle data (at that time point) at the $P<0.05$ level.

Seizure and Convulsion Models $ED_{50}$ values and 95% confidence intervals ($CI_{95\%}$) in all tests are obtained using log-probit method.

In Vivo Model of Ischemia

Statistical analysis of histological data is carried out using ANOVA followed by Student=s t-test with Bonferoni corrections using $P<0.05$ as the level of significance.

Schizophrenia

To assess treatment responses to compounds, rmANOVA. In order to assess the possibility that treatment order affected overall results, rmNAOVA of negative symptoms by treatment phase and week are covaried for treatment order.

Pharmaceutical Formulations

When employed as pharmaceuticals, the compounds of formula I are usually administered in the form of pharmaceutical compositions. This invention therefore provides pharmaceutical compositions which contain, as the active ingredient, one or more of the compounds of Formula I above or a pharmaceutically acceptable salt thereof and one or more pharmaceutically acceptable excipients, carriers, diluents, permeation enhancers, solubilizers and adjuvants. The compounds may be administered alone or in combination with other therapeutic agents (e.g., other antihypertensive drugs, diuretics and the like). Such compositions are prepared in a manner well known in the pharmaceutical art (see, e.g., *Remington's Pharm. Sci.*, Mack Publishing Co., Philadelphia, Pa., $17^{th}$ Ed. (1985) and "*Modem Pharm.*," Marcel Dekker, Inc., $3^{rd}$ Ed. (G. S. Banker & C. T. Rhodes, Eds.).

The compounds of Formula I may be administered by any of the accepted modes of administration of agents having similar utilities, for example, by oral, parenteral, rectal, buccal, intranasal or transdermal routes. The most suitable route will depend on the nature and severity of the condition being treated. Oral administration is a preferred route for the compounds of this invention. In making the compositions of this invention; the active ingredient is usually diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to, 10% by weight of the active compound, soft and hard gelatin capsules, suppositories, sterile injectable solutions, and sterile packaged powders. Pharmaceutically acceptable salts of the active agents may be prepared using standard procedures known to those skilled in the art of synthetic organic chemistry and described, e.g., by J. March, *Advanced Organic Chem. Reactions, Mechanisms and Structure*, 4$^{th}$ Ed. (N.Y.: Wiley-Interscience, 1992).

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another preferred formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The active compound is effective over a wide dosage range and is generally administered in a pharmaceutically effective amount. Preferably, for oral administration, each dosage unit contains from 1–250 mg of a compound of Formula I, and for parenteral administration, preferably from 0.1 to 60 mg of a compound of Formula I or a pharmaceutically acceptable salt thereof. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 |
| Starch | 45.0 |
| Microcrystalline cellulose | 35.0 |
| Polyvinylpyrrolidone (as 10% solution in sterile water) | 4.0 |
| Sodium carboxymethyl starch | 4.5 |
| Magnesium stearate | 0.5 |
| Talc | 1.0 |
| Total | 120.0 |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 |
| Starch | 109.0 |
| Magnesium stearate | 1.0 |
| Total | 150.0 |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25.0 mg |
| Saturated fatty acid glycerides to | 2,000.0 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
| --- | --- |
| Active Ingredient | 5.0 mg |
| Corn Oil | 1.0 mL |

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

What is claimed is:
1. A compound of the formula:

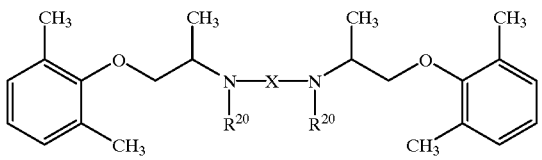

and pharmaceutically acceptable salts thereof;
wherein each $R^{20}$ is independently hydrogen, methyl or ethyl; and
X is a linker of the formula:

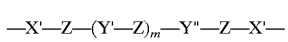

in which:
m is an integer of from 0 to 20;
X' at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;
Z at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;
Y' and Y" at each separate occurrence are selected from the group consisting of:

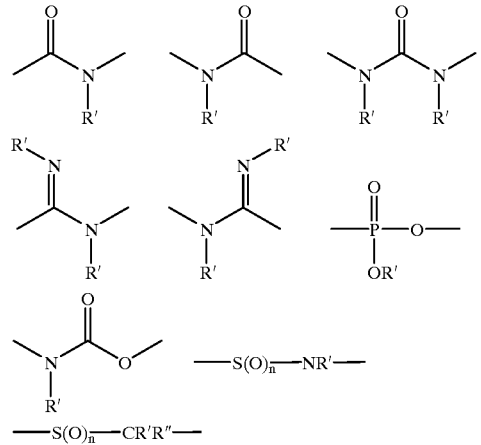

—S—S— and a covalent bond;
in which:
n is 0, 1 or 2; and
R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

2. The compound of claim 1, wherein each $R^{20}$ is hydrogen.
3. The compound of claim 1, wherein each $R^{20}$ is methyl.
4. The compound of claim 1, wherein each $R^{20}$ is ethyl.

5. A compound of the formula:

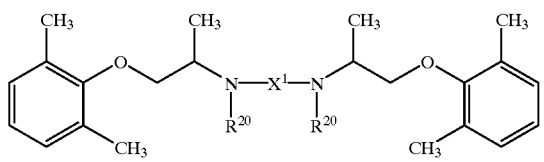

and pharmaceutically acceptable salts thereof;
wherein each $R^{20}$ is independently hydrogen, methyl or ethyl; and
$X^1$ is a linker of the formula:

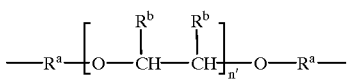

wherein
each $R^a$ is independently selected from the group consisting of a covalent bond, alkylene, substituted alkylene and arylene;
each $R^b$ is independently selected from the group consisting of hydrogen, alkyl and substituted alkyl; and
n' is an integer ranging from 1 to about 20.

6. The compound of claim 5, wherein each $R^{20}$ is hydrogen.

7. The compound of claim 5, wherein each $R^{20}$ is methyl.

8. The compound of claim 5, wherein each $R^{20}$ is ethyl.

9. A compound of the formula:

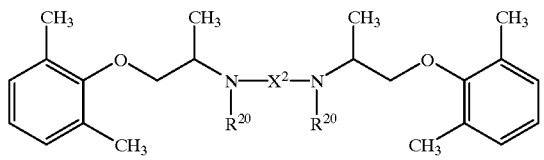

and pharmaceutically acceptable salts thereof;
wherein said compound is selected from the group consisting of compounds wherein $X^2$ and $R^{20}$ are as follows:

| $X^2$ | $R^{20}$ |
|---|---|
| —(CH$_2$)$_2$—O—(CH$_2$)$_2$—O—(CH$_2$)$_2$— | H; |
| —(CH$_2$)$_3$—O—(CH$_2$)$_3$— | H; |
| —CH$_2$—Z—CH$_2$— where Z = 1,3-cyclohexyl | H; |
| —CH$_2$—CH(OH)—CH$_2$— | H; |
| —(CH$_2$)$_3$—N[(CH$_2$)$_2$—]$_2$N—(CH$_2$)$_3$— (piperazine) | H; |
| —CH$_2$—Z—CH$_2$— where Z = 1,4-cyclohexyl | H; |
| —(CH$_2$)$_5$— | H; |
| —(CH$_2$)$_6$— | H; |
| —(CH$_2$)$_2$—S—(CH$_2$)$_2$— | H; |
| —(CH$_2$)$_3$—O—(CH$_2$)$_{10}$—O—(CH$_2$)$_3$— | H; |
| —(CH$_2$)$_3$—Z—(CH$_2$)$_3$— where Z = 2,4,8,10-tetraoxa-spiro[5.5]undecan-3,9-yl | H; |
| —(CH$_2$)$_3$—O—(CH$_2$)$_2$—O—(CH$_2$)$_2$—O—(CH$_2$)$_3$— | H; |
| —(CH$_2$)$_3$—O—(CH$_2$)$_4$—O—(CH$_2$)$_3$— | H; |
| —(CH$_2$)$_3$—N(CH$_3$)—(CH$_2$)$_3$— | H; |
| —CH$_2$—Z—CH$_2$— where Z = trans-1,4-cyclohexyl | H; |
| —CH$_2$—CH(CH$_3$)—CH$_2$—C(CH$_3$)$_2$—(CH$_2$)$_2$— | H; |
| —Z— where Z = 2,7-[9H-fluorene] | H; |
| —Z—C(CH$_3$)$_2$—Z—C(CH$_3$)$_2$—Z— where Z = 1,4-phenyl | H; |
| —Z—CH$_2$—Z— where Z = 1,4-phenyl | H; |
| —(CH$_2$)$_2$—N(CH$_3$)—(CH$_2$)$_2$— | H; |
| —(CH$_2$)$_9$— | Me; |
| —CH$_2$—Z—CH$_2$— where Z = 1,4-phenyl | Me; |
| —(CH$_2$)$_2$—O—(CH$_2$)$_2$—O—(CH$_2$)$_2$— | Me; |
| —CH$_2$—CH=CH—CH$_2$— (trans isomer) | Me; |
| —CH$_2$—Z—CH$_2$— where Z = (-)trans-2,2-dimethyl-[1,3]dioxolan-4,5-yl | Me; |
| —(CH$_2$)$_{10}$— | Me; |
| —(CH$_2$)$_{11}$— | Me; |
| —(CH$_2$)$_{12}$— | Me; |
| —(CH$_2$)$_{16}$— | Me; |
| —CH$_2$—CH(OH)—CH$_2$— | Me; |
| —CH$_2$—C≡C—CH$_2$— | Me; |
| —(CH$_2$)$_7$— | Me |
| —(CH$_2$)$_8$— | Me |
| —CH$_2$—Z—CH$_2$— where Z = 2,3-quinoxalinyl | Me |
| —CH$_2$—CH(CH$_2$OH)— | Me |
| —CH$_2$—C(CH$_2$)—CH$_2$— | Me |
| —Z— where Z = 4,5-[1,3]dioxolan-2-one | Me |
| —CH$_2$—Z—CH$_2$— where Z = 1,3-phenyl | Me |
| —(CH$_2$)$_2$—O—CH$_2$—O—(CH$_2$)$_2$— | Me |
| —(CH$_2$)$_4$—O—(CH$_2$)$_4$— | Me |
| —(CH$_2$)$_2$—O—(CH$_2$)$_2$—O—(CH$_2$)$_2$—O—(CH$_2$)$_2$— | Me |
| —(CH$_2$)$_2$—O—C(O)—O—(CH$_2$)$_2$— | Me |
| —CH$_2$—CH[C(O)—O—CH$_2$CH$_3$]— | Me |
| —CH$_2$—C(O)—O—(CH$_2$)$_2$—O—C(O)—CH$_2$— | Me |
| —(CH$_2$)$_2$—NH—C(O)—C(O)—NH—(CH$_2$)$_2$— | Me |
| —(CH$_2$)$_3$— | Me |
| —(CH$_2$)$_2$—O—(CH$_2$)$_2$—O—(CH$_2$)$_2$— | Et; |
| —CH$_2$—Z—CH$_2$— where Z = (-)trans-2,2-dimethyl-[1,3]dioxolan-4,5-yl | Et; |
| —(CH$_2$)$_{10}$— | Et; |
| —(CH$_2$)$_{11}$— | Et; |
| —(CH$_2$)$_{12}$— | Et; |
| —(CH$_2$)$_{16}$— | Et; |
| —(CH$_2$)$_7$— | Et; |
| —CH$_2$—Z—CH$_2$— where Z = 1,3-phenyl | Et; |
| —CH$_2$—Z—CH$_2$— where Z = 1,4-phenyl | Et; |
| —(CH$_2$)$_2$—O—CH$_2$—O—(CH$_2$)$_2$— | Et; |
| —(CH$_2$)$_4$—O—(CH$_2$)$_4$— | Et; |
| —(CH$_2$)$_2$—O—(CH$_2$)$_2$—O—(CH$_2$)$_2$—O—(CH$_2$)$_2$— | Et; |
| —CH$_2$—C(O)—O—(CH$_2$)$_2$—O—C(O)—CH$_2$— | Et; |
| —(CH$_2$)$_3$— | Et; |
| —CH$_2$—Z—CH$_2$— where Z = 2,5-thiophenyl | H; |
| —CH$_2$—Z—O—(CH$_2$)$_2$—O—Z—CH$_2$— where Z = 1,2-phenyl | H; |
| —CH$_2$—Z—O—(CH$_2$)$_6$—O—Z—CH$_2$— where Z = 1,2-phenyl | H; |
| —CH$_2$—Z—O—(CH$_2$)$_3$—O—Z—CH$_2$— where Z = 1,2-phenyl | H; |
| —CH$_2$—Z—CH$_2$— where Z = 2,3-thiophenyl | H; |
| —CH$_2$—Z—CH$_2$— where Z = 2,6-pyridinyl | H; |
| —CH$_2$—Z—CH$_2$— where Z = 2-hydroxy-5-methyl-phenyl-1,3-yl | H; |
| —CH$_2$—Z—O—(CH$_2$)$_2$—O—Z—CH$_2$— where Z = 4-methoxy-phenyl-1,3-yl | H; |
| —CH$_2$—Z—CH$_2$— where Z = 4-hydroxy-phenyl-1,3-yl | H; |
| —CH$_2$—Z—CH$_2$— where Z = 2,2'-dihydroxy-3,3'-dimethoxy-biphenyl-5,5'-yl | H; |
| —CH$_2$—Z—O—Z—CH$_2$— where Z = 1,2-phenyl | H; and |
| —CH$_2$—Z—CH$_2$— where Z = 1,3-phenyl | H. |

10. The compound of claim 9, wherein each $R^{20}$ is hydrogen, and $X^2$ is —CH$_2$—Z—CH$_2$— where Z is pyrridin-2,6-diyl.

11. A pharmaceutical composition comprising a pharmaceutically acceptable excipient and a therapeutically effective amount of a compound of any of claims 1–10, or a pharmaceutically acceptable salt thereof.

12. A method of treating pain in a mammal, the method comprising administering to said mammal an effective amount of a pharmaceutical composition according to claim 11.

13. A method of modulating the activity of a sodium channel in a biological tissue, the method comprising contacting a biological tissue having a sodium channel with a sodium channel modulating amount of a compound of any of claims 1–10, or a pharmaceticall acceptable salt thereof.

* * * * *

UNITED STATES PATENT AND TRADEMARK OFFICE
CERTIFICATE OF CORRECTION

PATENT NO. : 6,420,354 B1
APPLICATION NO. : 09/458107
DATED : July 16, 2002
INVENTOR(S) : Marquess et al.

It is certified that error appears in the above-identified patent and that said Letters Patent is hereby corrected as shown below:

On title page, item (75),
after "La Honda," insert -- S. Derek Turner, Pacifica; --

Column 186
lines 15 and 36, "(-)trans" should read -- (-)-trans --.
line 65, "pyrridin" should read -- pyridin --.

Signed and Sealed this

Third Day of October, 2006

JON W. DUDAS
*Director of the United States Patent and Trademark Office*